(12) United States Patent
Münch et al.

(10) Patent No.: US 8,119,135 B2
(45) Date of Patent: Feb. 21, 2012

(54) ANTIBODIES WHICH BIND TO EPITOPES OF GLYCOPROTEIN VI

(75) Inventors: Götz Münch, München (DE); Meinrad Gawaz, Tübingen (DE); Andreas Bültmann, Planegg (DE); Elisabeth Kremmer, Freising (DE)

(73) Assignees: Helmhotz Zentrum Munchen, Deutsches Forschungszentrum fur Gesundheit und Umwelt (GmbH), Neuherberg (DE); Corimmun GmbH, Martinsreid (DE)

(*) Notice: Subject to any disclaimer, the term of this patent is extended or adjusted under 35 U.S.C. 154(b) by 293 days.

(21) Appl. No.: 12/355,689

(22) Filed: Jan. 16, 2009

(65) Prior Publication Data

US 2010/0003244 A1 Jan. 7, 2010

Related U.S. Application Data

(63) Continuation of application No. 11/446,537, filed on Jun. 2, 2006, now abandoned, which is a continuation-in-part of application No. 11/009,106, filed on Dec. 10, 2004, now Pat. No. 7,531,178, which is a continuation-in-part of application No. 10/489,053, filed as application No. PCT/EP03/05929 on Jun. 5, 2003, now Pat. No. 7,514,543, application No. 12/355,689, which is a continuation-in-part of application No. PCT/EP2004/013779, filed on Dec. 3, 2004.

(30) Foreign Application Priority Data

| Jun. 7, 2002 | (EP) | ..................................... 02012742 |
| Dec. 3, 2003 | (EP) | ..................................... 03027772 |
| Jun. 7, 2005 | (GB) | ................................... 0511590.2 |

(51) Int. Cl.
*A61K 39/395* (2006.01)

(52) U.S. Cl. ............... 424/141.1; 424/133.1; 424/144.1; 514/13.8; 435/326

(58) Field of Classification Search ........................ None
See application file for complete search history.

(56) References Cited

U.S. PATENT DOCUMENTS

| 5,116,964 | A | | 5/1992 | Capon et al. |
| 5,525,491 | A | | 6/1996 | Huston et al. |
| 5,693,762 | A | * | 12/1997 | Queen et al. ............... 530/387.3 |
| 6,245,527 | B1 | | 6/2001 | Busfield et al. |
| 6,383,779 | B1 | | 5/2002 | Busfield et al. |
| 6,406,697 | B1 | | 6/2002 | Capon et al. |
| 6,989,144 | B1 | * | 1/2006 | Busfield et al. ............ 424/130.1 |
| 2004/0152628 | A9 | | 8/2004 | Tandon et al. |
| 2004/0157300 | A1 | | 8/2004 | Burger et al. |
| 2005/0079541 | A1 | | 4/2005 | Massberg et al. |

FOREIGN PATENT DOCUMENTS

| EP | 0 832 971 | A1 | 4/1998 |
| EP | 0 383 799 | B1 | 5/1998 |
| EP | 0 314 317 | B1 | 8/1998 |
| EP | 1 224 942 | A1 | 7/2002 |
| EP | 1 228 768 | A1 | 8/2002 |
| EP | 1 369 128 | A | 12/2003 |
| EP | 1 369 128 | A1 | 12/2003 |
| EP | 1 538 165 | A | 6/2005 |
| WO | WO 99/50281 | A2 | 10/1999 |
| WO | WO 99/58572 | A1 | 11/1999 |
| WO | WO 00/68377 | A1 | 11/2000 |
| WO | WO 01/00810 | | 1/2001 |
| WO | WO 01/00810 | A1 | 1/2001 |
| WO | WO 0100810 | A1 * | 1/2001 |
| WO | WO 01/16321 | | 3/2001 |
| WO | WO 01/16321 | A1 | 3/2001 |
| WO | WO 02/080968 | A1 | 10/2002 |
| WO | WO 02/096926 | A1 | 12/2002 |
| WO | WO 03/008454 | A2 | 1/2003 |
| WO | WO 03/054020 | A2 | 7/2003 |
| WO | WO 03/055516 | A1 | 7/2003 |
| WO | WO 03/097875 | A1 | 11/2003 |
| WO | WO 03/103662 | A2 | 12/2003 |

OTHER PUBLICATIONS

Janeway et al., Immunobilogy, 3rd ed., 1997, Garland Publishing Inc., pp. 3:1-3:11.*
Rudikoff et al., Proc Natl Acad Sci U S A. Mar. 1982;79(6):1979-83.*
William E. Paul, M.D., editor, Fundamental Immunology, 3d ed. Raven Press, 1993, p. 242.*
Portolano et al., J Immunol. Feb. 1, 1993;150(3):880-7.*
Capon et al., "Designing CD4 immunoadhesins for AIDS therapy," *Nature* 337:525-531, 1989.
Chamow and Ashkenazi eds., *Antibody Fusion Proteins*, Wiley-Liss, Inc., 312 pp., New York 1999.
Clemetson et al., "The Platelet Collagen Receptor Glycoprotein VI is a Member of the Immunoglobulin Superfamily Closely Related to FcαR and the Natural Killer Receptors," *The Journal of Biological Chemistry* 274(41):29019-29024, 1999.
European Search Report corresponding to Application No. 02012742.9 mailed Sep. 19, 2003.
Ezumi et al., "Molecular Cloning, Genomic Structure, Chromosomal Localization, and Alternative Splice Forms of the Platelet Collagen Receptor Glycoprotein VI," *Biochemical and Biophysical Research Communication* 277:27-36, 2000.
GenBank Accession No. AB043819 including UniGene Cluster No. Hs.272216, Nov. 2, 2000.
GenBank Accession No. AX046772, Dec. 15, 2000.
Gibbins et al., "Glycoprotein VI is the collagen receptor in platelets which underlies tyrosine phosphorylation of the Fc receptor γ-chain," *FEBS Letters* 413:255-259, 1997.
Goto et al., "Involvement of Glycoprotein VI in Platelet Thrombus Formation of Both Collagen and von Willebrand Factor Surfaces Under Flow Conditions," *Circulation* 106:266-272, 2002.
Grüner et al., "Relative antithrombotic effect of soluble GPVI dimer versus anti-GPVI antibodies in mice," *Blood First Edition Paper*, prepublished online Oct. 26, 2004, pp. 1-29.

(Continued)

Primary Examiner — Michael Szperka
(74) Attorney, Agent, or Firm — Klarquist Sparkman, LLP

(57) ABSTRACT

The present invention provides anti-thrombotic agents, methods for screening for said anti-thrombotics agents and methods of treating thrombotic and other cardiovascular disorders.

27 Claims, 57 Drawing Sheets

OTHER PUBLICATIONS

Harlow et al. "Antibodies," A Laboratory Manual, Cold Spring Harbor Press, pp. 76, 1988.

International Search Report corresponding to Application No. PCT/EP2003/05929 mailed Aug. 6, 2005.

International Search Report corresponding to Application No. PCT/EP2004/013779 mailed Mar. 4, 2004.

International Search Report issued in PCT Patent Application No. PCT/EP2006/062908, dated Feb. 21, 2007.

Jandrot-Perrus et al., "Adhesion and Activation of Human Platelets Induced by Convulxin Involve Glycoprotein VI and Integrin $\alpha_2\beta_1$," *The Journal of Biological Chemistry* 272(43):27035-27041, 1997.

Jandrot-Perrus et al., "Cloning, characterization, and functional studies of human and mouse glycoprotein VI: a platelet-specific collagen receptor from the immunoglobulin superfamily," *Blood* 96(5):1798-1807, 2000.

Joutsi-Korhonen et al., "The low-frequency allele of the platelet collagen signaling receptor glycoprotein VI is associated with reduced functional responses and expressions," *Blood* 101(11):4372-4379, 2003.

Konishi et al., "Platelets Activated by Collagen Through Immunoreceptor Tyrosine-Based Activation Motif Play Pivotal Role in Initiation and Generation of Neointimal Hyperplasia After Vascular Injury," *Circulation* 105:912-916, 2002.

Kuby, Immunology, W.H. Freeman and Company, pp. 125, 1991.

Lecut et al., "Identification of Residues within Human Glycoprotein VI Involved in the Binding to Collagen," *J. Biological Chemistry* 279(5):52293-52299, 2004.

Lecut et al., "Inhibition of Platelet-Collagen Interactions by Specific Anti-Human GPVI Monoclonal Antibodies," *Supplement J. Thrombosis and Haemostasis* Jul. 2001 Abstract Only.

Massberg et al., "Effects of a dimeric, soluble form of glycoprotein VI on platelet adhesion following vascular injury in vivo," *ESC Congress 2004*, Munich, Germany, Sep. 26, 2004 (Abstract only).

Massberg et al., "Platelet-Endothelial Cell Interactions During Ischemia/Reperfusion: The Role of P-Selectin," *Blood* 92(2)507-515, 1998.

Massberg et al., "Soluble glycoprotein VI dimer inhibits platelet adhesion and aggregation to the injured vessel wall in vivo," *The FASEB Journal Express Article*, published online Dec. 4, 2003.

Massberg et al., "Soluble glycoprotein VI dimer inhibits platelet adhesion and aggregation to the injured vessel wall in vivo," *The FASEB Journal* 18:397-399, 2004.

Massberg, S., "Glycoprotein VI—platelet adhesion molecule and therapeutic target," *Gesellschaft fur Mikrozirkulation and Vaskulare Biologie e.V. Annual Meeting 2004, Berlin, Final Program* p. 29, Oct. 8, 2004, Abstract Only.

Miura et al., "Analysis of the Interaction of Platelet Collagen Receptor Glycoprotein VI (GPVI) with Collagen," *The Journal of Biological Chemistry* 277(38):46197-46204, 2002.

Moroi et al., "A new monoclonal antibody, mAb 204-11, that influences the binding of platelet GPVI to fibrous collagen," *Thromb Haemost* 89:996-1003, 2003.

Nieswandt and Watson, "Platelet-collagen interaction: is GPVI the central receptor?" *Blood* 102(2):449-461, Jul. 15, 2003.

Nieswandt et al., "Glycoprotein VI but not $\alpha 2\beta 1$ integrin is essential for platelet interaction with collagen," *The EMBO Journal* 20(9):2120-2130, 2001.

Nieswandt et al., "Long-term Antithrombotic Protection by In Vivo Depletion of Platelet Glycoprotein VI in Mice," *J. Exp. Med.* 193(4):459-469, 2001.

Penz et al., "Human atheromatous plaques stimulate thrombus formation by activating platelet glycoprotein VI," *FASEB J.* 19:898-909, 2005.

Robinson and Sauer, "Optimizing the stability of single-chain proteins by linker length and composition mutagenesis," *Proc. Natl. Acad. Sci. USA*, vol. 95, pp. 5929-5934, May 1998.

Rosenfeld et al., "Animal Models of Spontaneous Plaque Rupture: The Holy Grail of Experimental Atherosclerosis Research," *Current Atherosclerosis Reports* 4:238-242, 2002.

Smethurst et al., "Identification of the primary collagen-binding surface on human glycoprotein VI by site-directed mutagenesis and by a blocking phage antibody," *Blood* 103(3):903-911, Feb. 1, 2004.

Vinik et al., "Diabetes and macrovascular disease," *Journal of Diabetes and Its Complications* 16:235-24, 2002.

Vinik et al., "Platelet Dysfunction in Type 2 Diabetes," *Diabetes Care* 24(8): 1476-141485, 2001.

\* cited by examiner

FIG. 1C
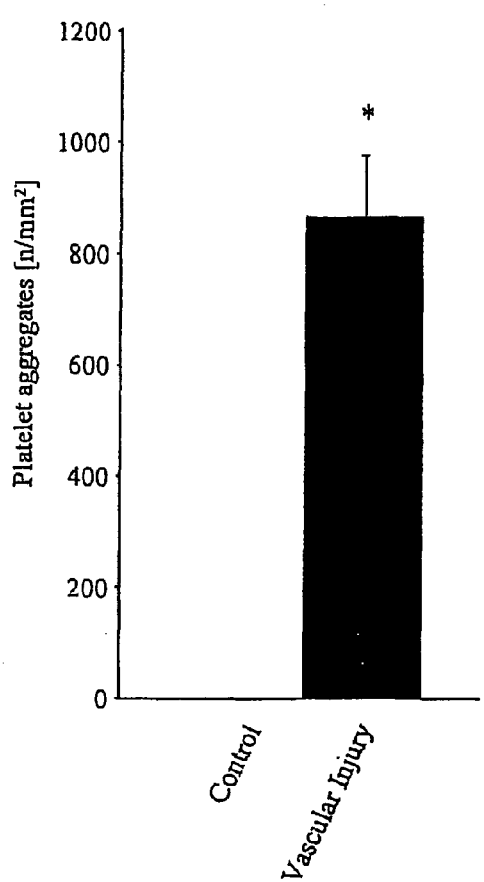
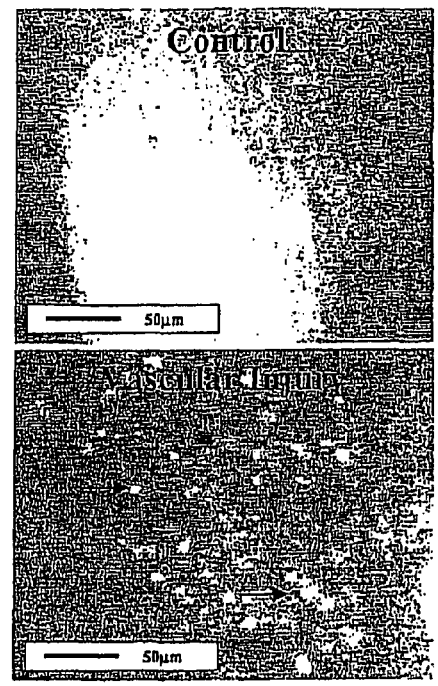

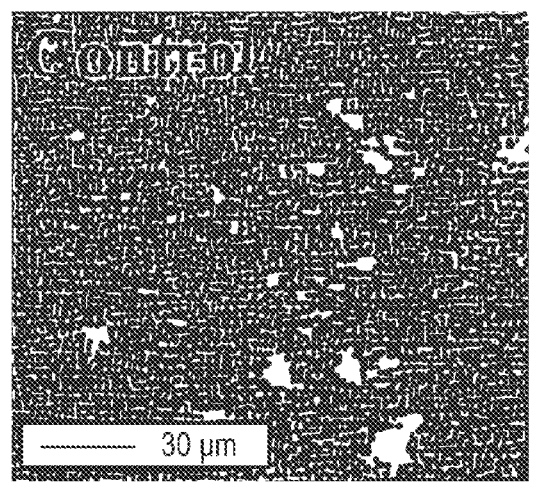 Control
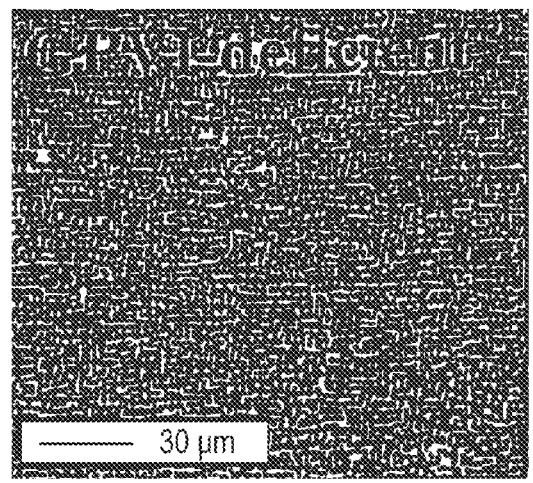 GPVI deficient
FIG. 3F

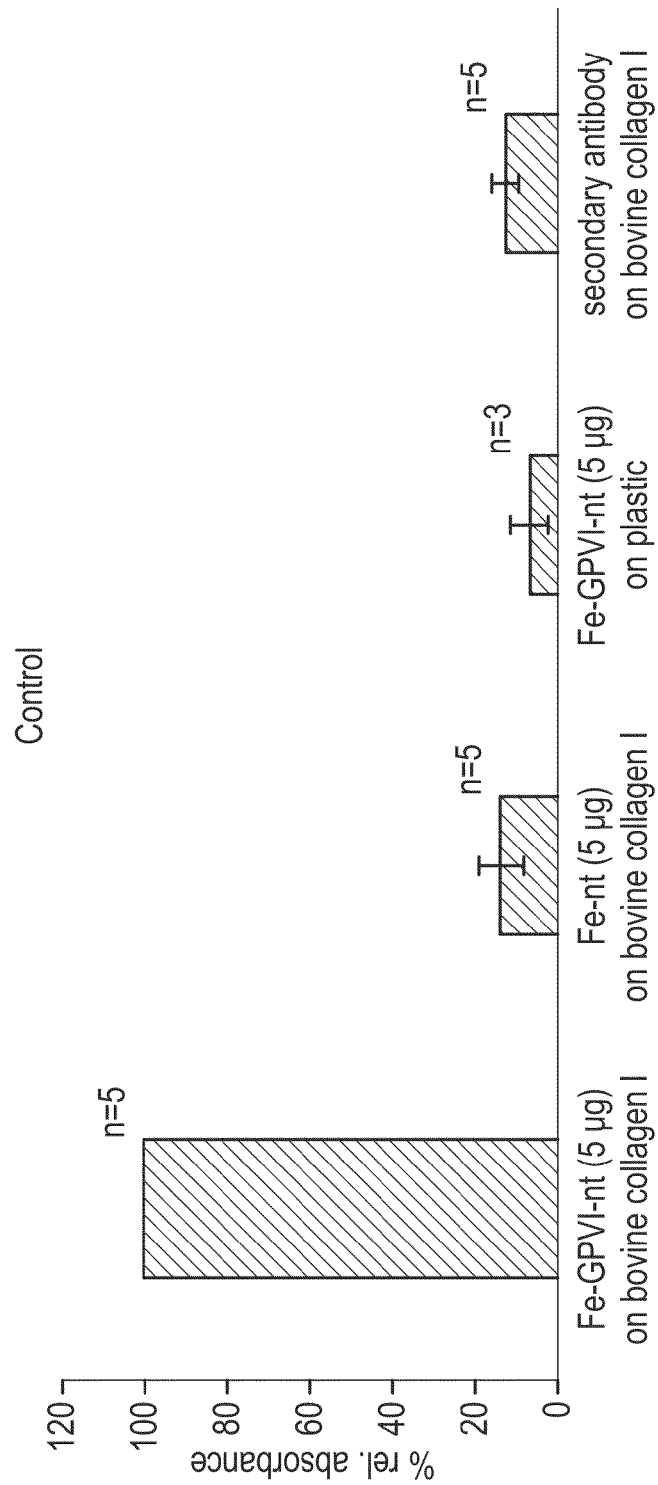

```
  1  MSPSPTALFC  LGLCLGRVPA  QSGPLPKPSL  QALPSSLVPL  EKPVTLRCQG
 51  PPGVDLYRLE  KLSSSRYQDQ  AVLFIPAMKR  SLAGRYRCSY  QNGSLWSLPS
101  DQLELVATGV  FAKPSLSAQP  GPAVSSGGDV  TLQCQTRYGF  DQFALYKEGD
151  PAPYKNPERW  YRASFPIITV  TAAHSGTYRC  YSFSSRDPYL  WSAPSDPLEL
201  VVTGTSVTPS  RLPTEPPSSV  AEFSEATAEL  TVSFTNKVFT  TETSRSITTS
251  PKESDSPAGP  ARQYYTKGNG  GRESKSCDKT  HTCPPCPAPE  LLGGPSVFLF
301  PPKPKDTLMI  SRTPEVTCVV  VDVSHEDPEV  KFNWYVDGVE  VHNAKTKPRE
351  EQYNSTYRVV  SVLTVLHQDW  LNGKEYKCKV  SNKALPAPIE  KTISKAKGQP
401  REPQVYTLPP  SRDELTKNQV  SLTCLVKGFY  PSDIAVEWES  NGQPENNYKT
451  TPPVLDSDGS  FFLYSKLTVD  KSRWQQGNVF  SCSVMHEALH  NHYTQKSLSL
501  SPGK*
```

FIG. 7

```
   1 ATGTCTCCAT CCCCGACCGC CCTCTTCTGT CTTGGGCTGT GTCTGGGGCG
  51 TGTGCCAGCG CAGAGTGGAC CGCTCCCCAA GCCCTCCCTC CAGGCTCTGC
 101 CCAGCTCCCT GGTGCCCCTG GAGAAGCCAG TGACCCTCCG GTGCCAGGGA
 151 CCTCCGGGCG TGGACCTGTA CCGCCTGGAG AAGCTGAGTT CCAGCAGGTA
 201 CCAGGATCAG GCAGTCCTCT TCATCCCGGC CATGAAGAGA AGTCTGGCTG
 251 GACGCTACCG CTGCTCCTAC CAGAACGGAA GCCTCTGGTC CCTGCCCAGC
 301 GACCAGCTGG AGCTCGTTGC CACGGGAGTT TTTGCCAAAC CCTCGCTCTC
 351 AGCCCAGCCC GGCCCGGCGG TGTCGTCAGG AGGGGACGTA ACCCTACAGT
 401 GTCAGACTCG GTATGGCTTT GACCAATTTG CTCTGTACAA GGAAGGGGAC
 451 CCTGCGCCCT ACAAGAATCC CGAGAGATGG TACCGGGCTA GTTTCCCCAT
 501 CATCACGGTG ACCGCCGCCC ACAGCGGAAC CTACCGATGC TACAGCTTCT
 551 CCAGCAGGGA CCCATACCTG TGGTCGGCCC CCAGCGACCC CCTGGAGCTT
 601 GTGGTCACAG GAACCTCTGT GACCCCCAGC CGGTTACCAA CAGAACCACC
 651 TTCCTCGGTA GCAGAATTCT CAGAAGCCAC CGCTGAACTG ACCGTCTCAT
 701 TCACAAACAA AGTCTTCACA ACTGAGACTT CTAGGAGTAT CACCACCAGT
 751 CCAAAGGAGT CAGACTCTCC AGCTGGTCCT GCCCGCCAGT ACTACACCAA
 801 GGGCAACGGC GGCCGCGAGT CCAAATCTTG TGACAAAACT CACACATGCC
 851 CACCGTGCCC AGCACCTGAA CTCCTGGGGG GACCGTCAGT CTTCCTCTTC
 901 CCCCCAAAAC CCAAGGACAC CCTCATGATC TCCCGGACCC CTGAGGTCAC
 951 ATGCGTGGTG GTGGACGTGA GCCACGAAGA CCCTGAGGTC AAGTTCAACT
1001 GGTACGTGGA CGGCGTGGAG GTGCATAATG CCAAGACAAA GCCGCGGGAG
1051 GAGCAGTACA ACAGCACGTA CCGTGTGGTC AGCGTCCTCA CCGTCCTGCA
1101 CCAGGACTGG CTGAATGGCA AGGAGTACAA GTGCAAGGTC TCCAACAAAG
1151 CCCTCCCAGC CCCCATCGAG AAAACCATCT CCAAAGCCAA AGGGCAGCCC
1201 CGAGAGCCAC AGGTGTACAC CCTGCCCCCA TCCCGGGATG AGCTGACCAA
1251 GAACCAGGTC AGCCTGACCT GCCTGGTCAA AGGCTTCTAT CCCAGCGACA
1301 TCGCCGTGGA GTGGGAGAGC AATGGGCAGC CGGAGAACAA CTACAAGACC
1351 ACGCCTCCCG TGCTGGACTC CGACGGCTCC TTCTTCCTCT ACAGCAAGCT
1401 CACCGTGGAC AAGAGCAGGT GGCAGCAGGG GAACGTCTTC TCATGCTCCG
1451 TGATGCATGA GGCTCTGCAC AACCACTACA CGCAGAAGAG CCTCTCCCTG
1501 TCTCCGGGTA AATGA
```

FIG. 8

FIG. 9
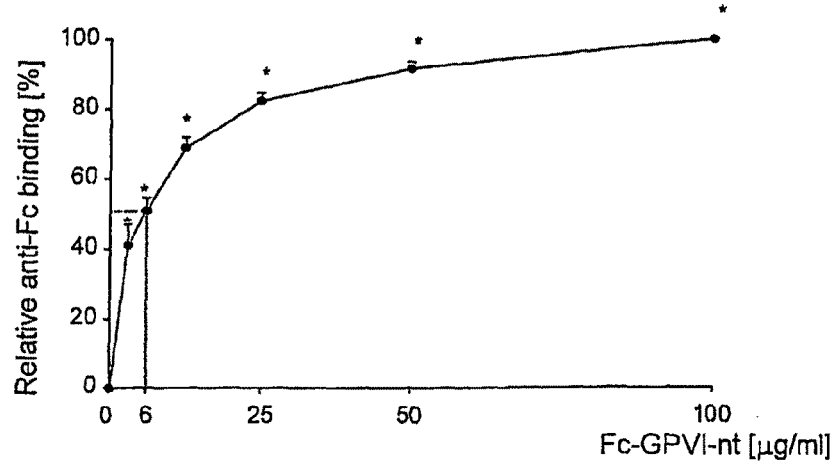
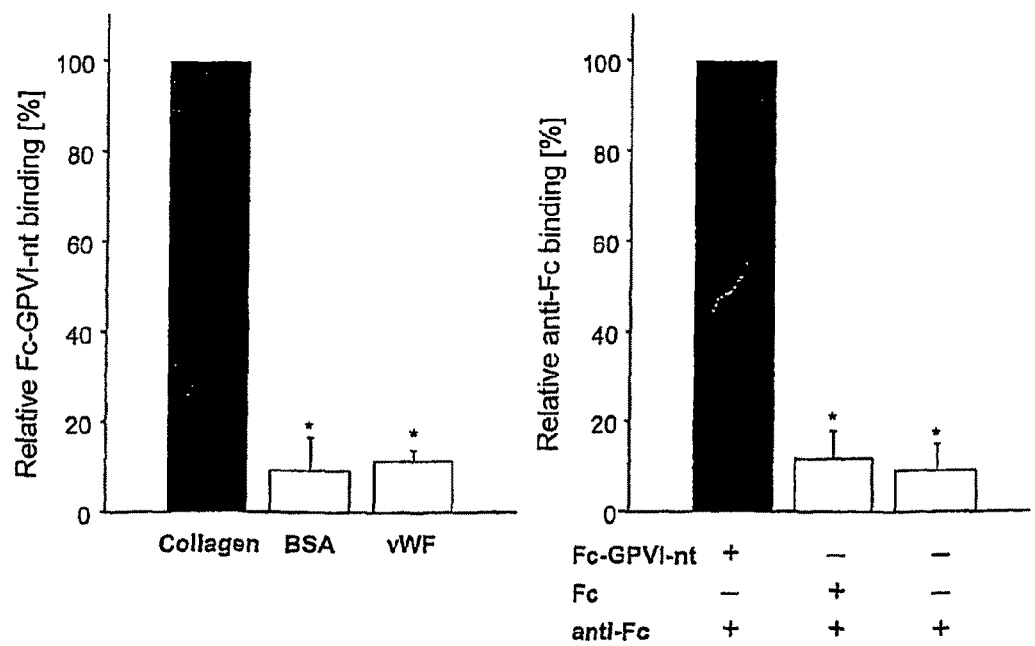

C

FIG. 13
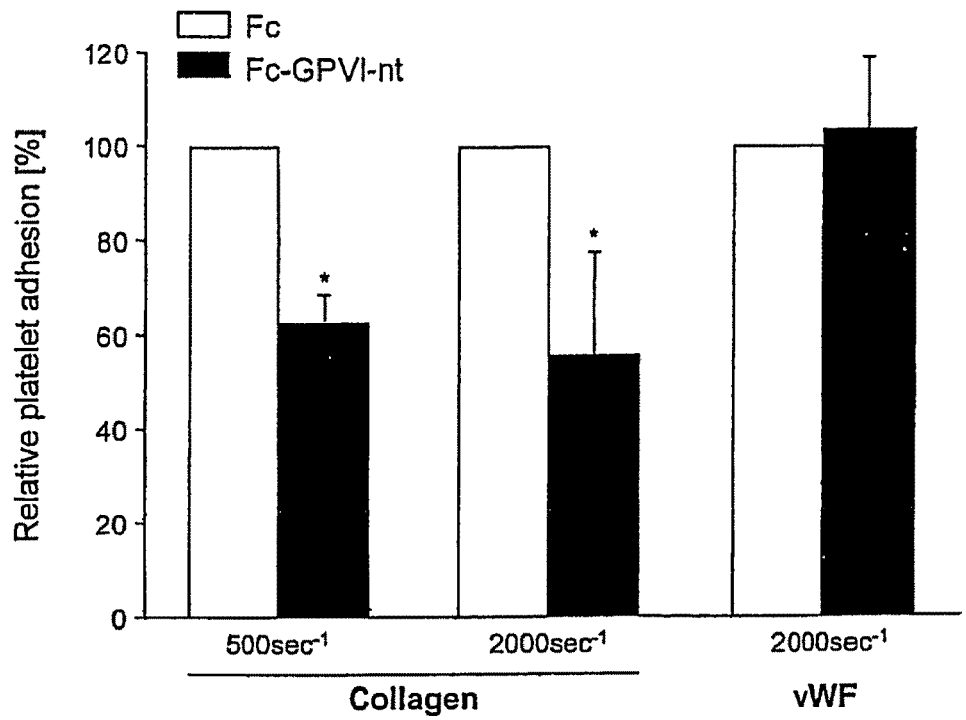
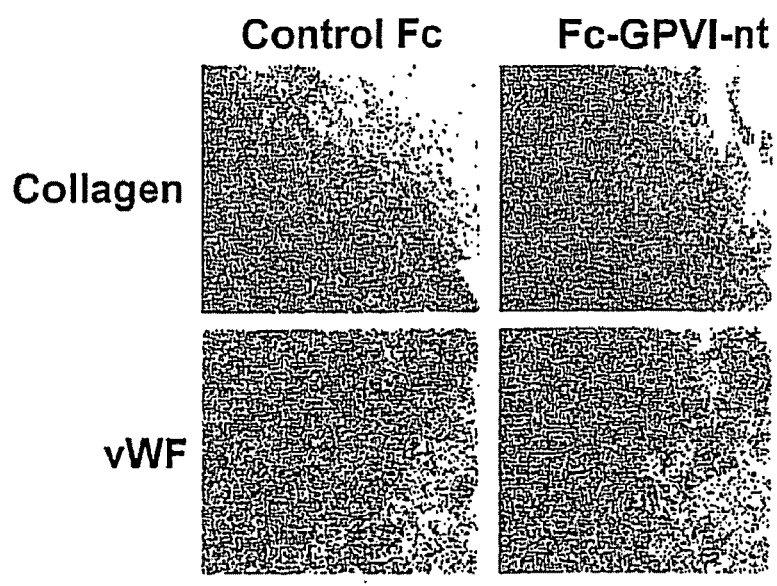

FIG. 14
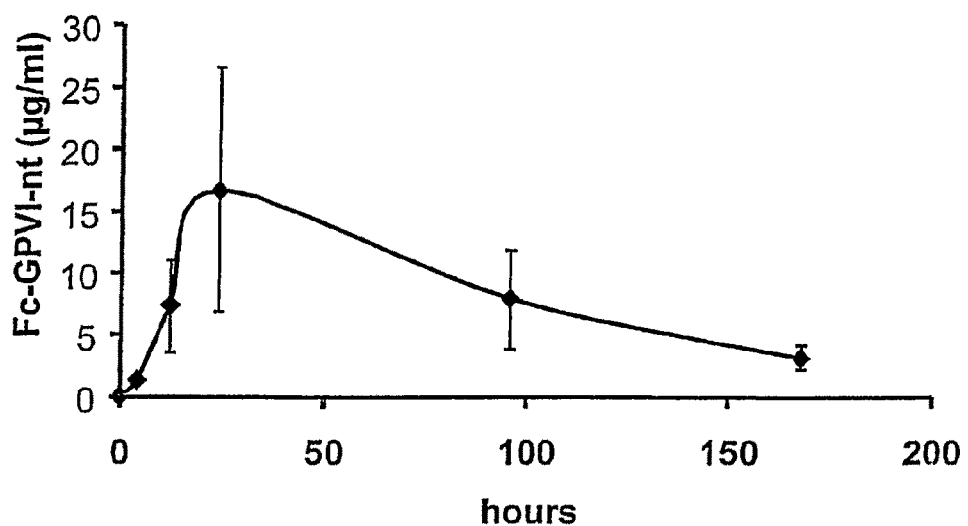
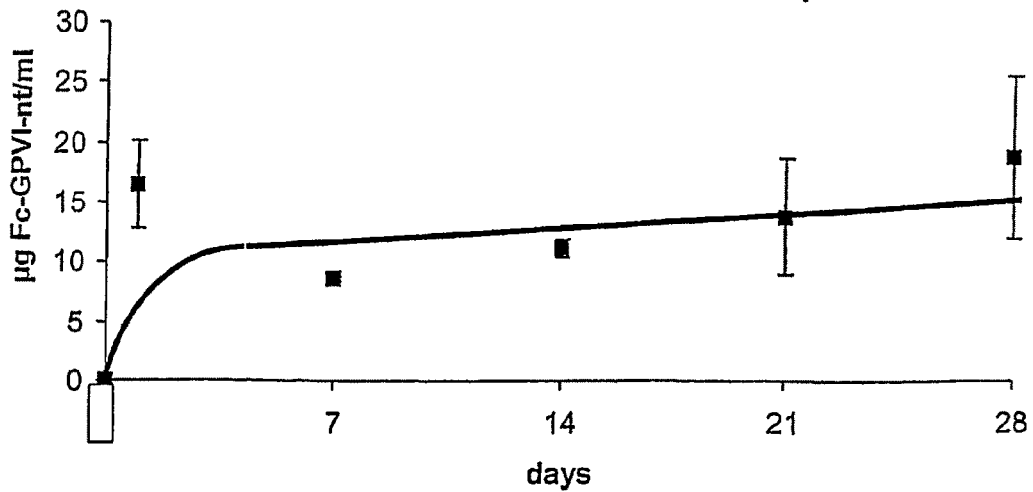

FIG. 15
*b*
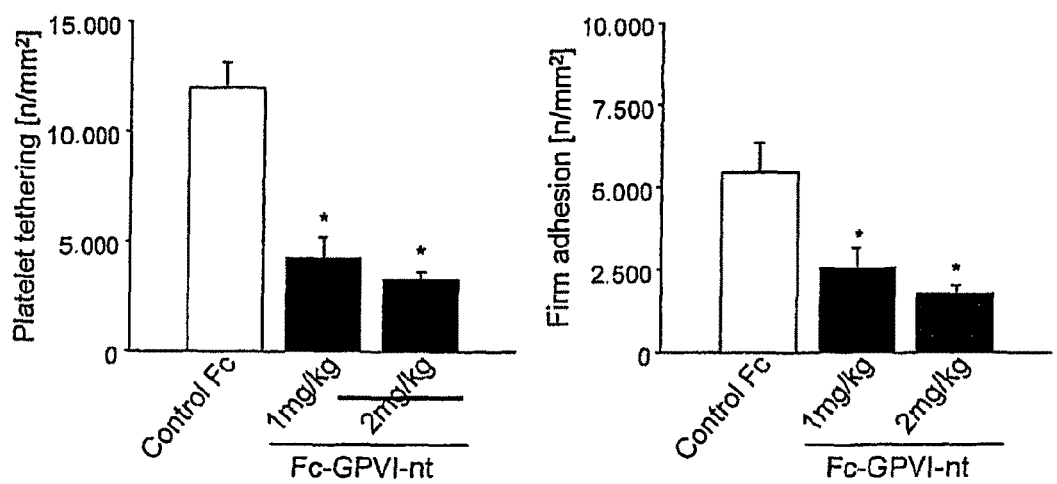
*c*
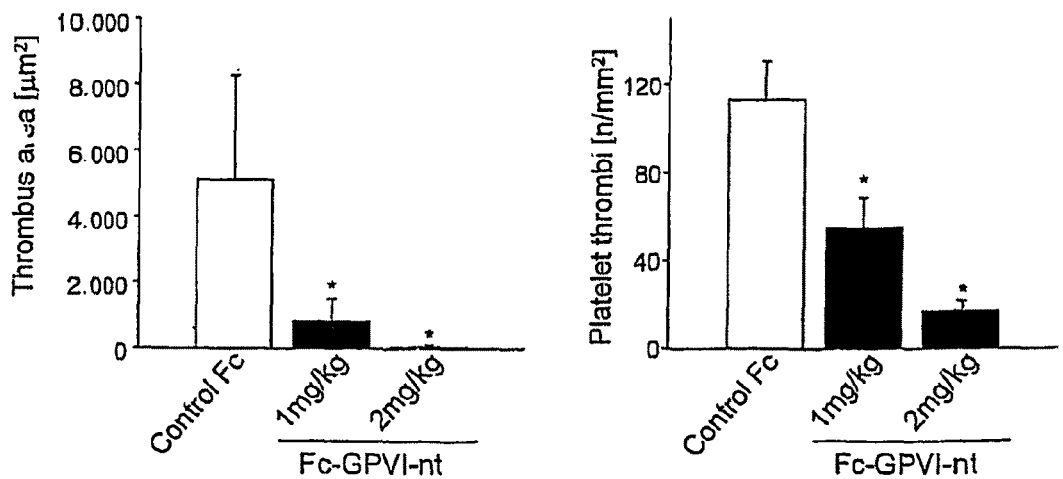

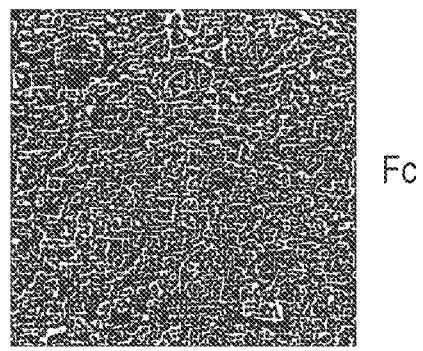
FIG. 15e
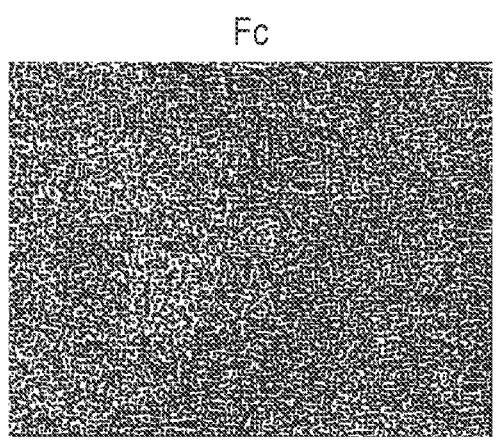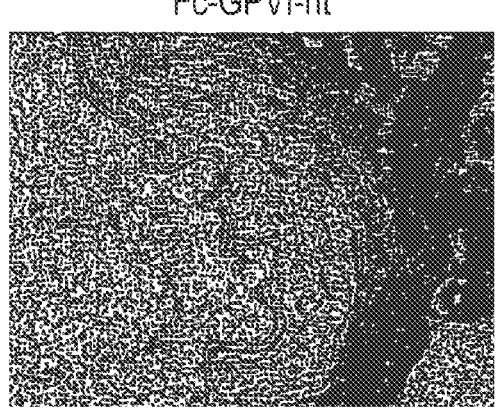
FIG. 15f

FIG. 17
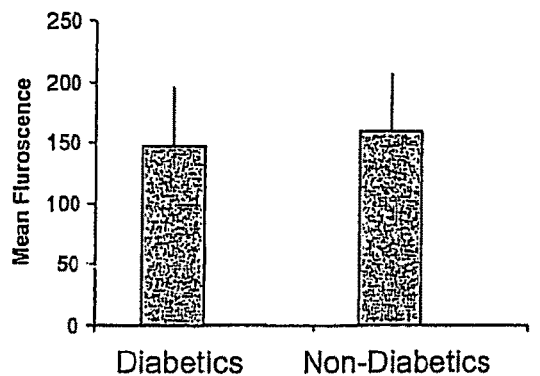
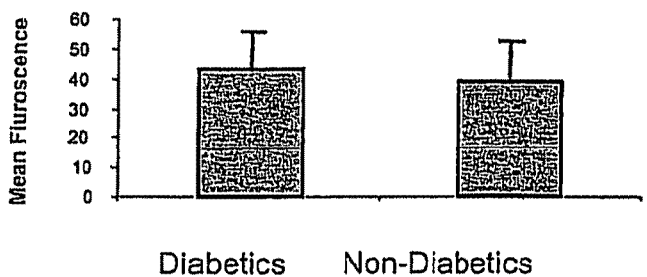
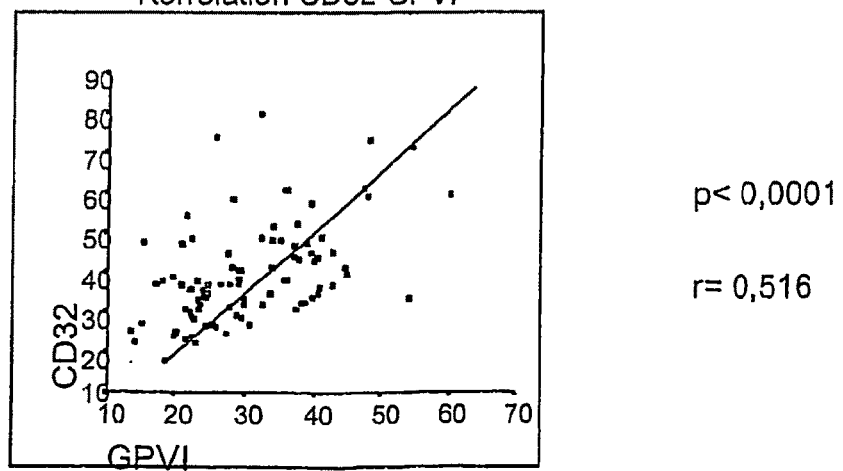
p< 0,0001
r= 0,516

FIG. 18

MSPSPTALFCLGLCLGRVPAQSGPLPKPSLQALPSSLVPLEKPVTLRCQGPPGVDLYRLEKLSSSRYQDQ
AVLFIPAMKRSLAGRYRCSYQNGSLWSLPSDQLELVATGVFAKPSLSAQPGPAVSSGGDVTLQCQTRYG
FDQFALYKEGDPAPYKNPERWYRASFPIITVTAAHSGTYRCYSFSSRDPYLWSAPSDPLELVVTGTSVTP
SRLPTEPPSSVAEFSEATAELTVSFTNKVFTTETSRSITTSPKESDSPAGPARQYYTKGN*GGRP*APELLGG
PSVFLFPPKPKDTLMISRTPEVTCVVVDVSHEDPEVKFNWYVDGVEVHNAKTKPREEQYNSTYRVVSVLT
VLHQDWLNGKEYKCKVSNKALPAPIEKTISKAKGQPREPQVYTLPPSRDELTKNQVSLTCLVKGFYPSDIA
VEWESNGQPENNYKTTPPVLDSDGSFFLYSKLTVDKSRWQQGNVFSCSVMHEALHNHYTQKSLSLSPG
K

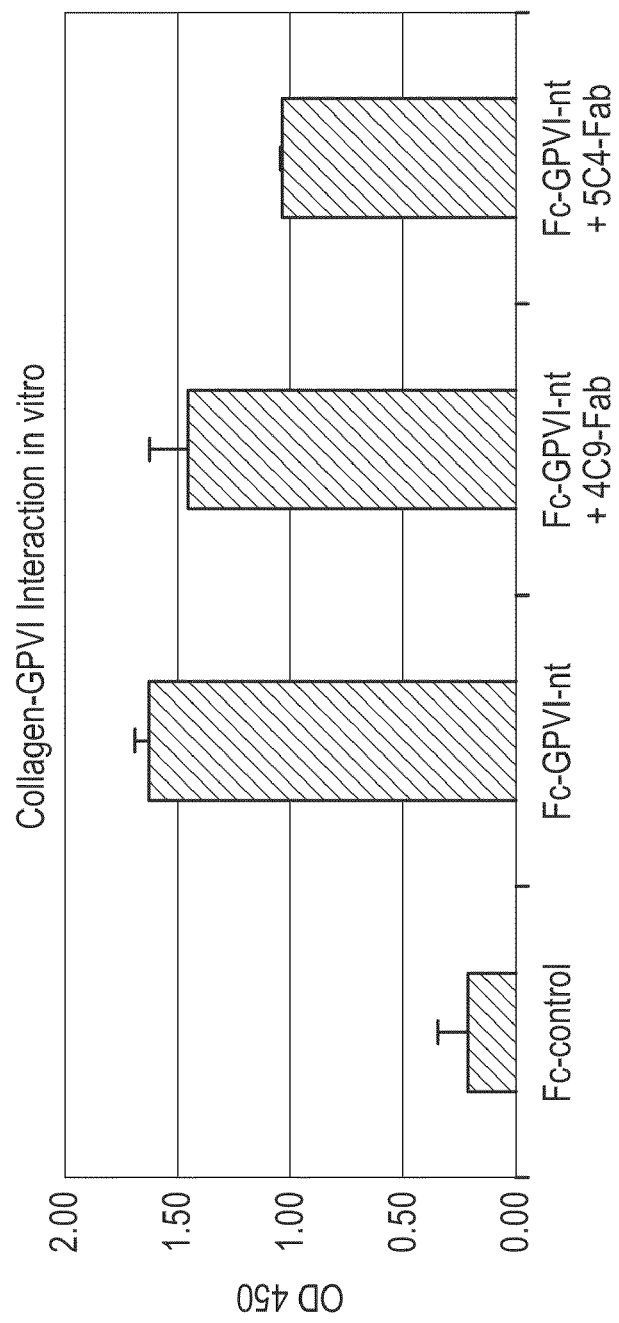

FIG. 28 a) Amino acid sequence of hGP 5C4 heavy chain variable domain (γ2a)

SEQ ID No.: 149

```
  1  EVKLQESGGG LVQPGRSLKL SCTASGFTFS DYFMSWVRQA PTRGLEWVAS
 51  ISSGGASAYW RDSVKGRFTI SRDNAKSALY LQMDSLRSED TATYFCARGE
101  LDFDYWGQGV MVAVSSAETT PPSVYP
``` b) Nucleotide acid sequence of 5C4 heavy chain variable domain (γ2a)

SEQ ID No.: 150

GAGGTGAAGCTGCAGGAGTCAGGGGGAGGCTTAGTGCAGCCTGGAAGGTCCTTGAAACTCTCCTGTACAGCCTCA
GGATTCACTTTCAGTGACTATTTCATGTCCTGGGTCCGCCAGGCTCCAACGCGTGGTCTGGAGTGGGTCGCATCC
ATTAGTTCTGGTGGTGCTAGCGCTTACTGGCGAGACTCCGTGAAGGGCCGATTCACTATCTCCAGAGATAATGCA
AAAAGCGCCCTATACCTGCAAATGGACAGTCTGAGGTCTGAGGACACGGCCACTTATTTCTGTGCAAGAGGGGAG
CTCGACTTTGATTACTGGGGCCAAGGAGTCATGGTCGCAGTCTCCTCTGCTGAAACGACACCCCCATCTGTCTAT
CCG

FIG. 29 a) Amino acid sequence of hGP 5C4 light chain variable domain (κ)

1   ADPNSTLLSA SVGDRVTLNC TASQNVYKNL AWYQQKLGEA PRLLLYSANS

51  QTGIPSRFS GSGSGPDFTL TISSLQPEDV ASYFCQQYYS GNTFGAGTKL

101 ELKRADAAPT VSIF

SEQ ID No.: 151 b) Nucleotide acid sequence of hGP 5C4 light chain variable domain (κ)

GCTGACCCAAACTCCACTCTCCTGTCTGCATCTGTGGGAGACAGAGTCACTCTCAAC
TGCACAGCAAGTCAGAATGTTTATAAGAACTTAGCCTGGTATCAGCAAAAGCTTGGAGAAGC
TCCCAGACTCCTGCTTTATAGTGCCAACAGTTTGCAAACGGGCATCCCATCACGGTTCAGTG
GCAGTGGATCTGGTCCAGATTTCACACTCACCATCAGCAGCCTGCAGCCTGAAGATGTTGCC
TCATATTTCTGCCAGCAGTATTATAGCGGGAACACGTTTGGAGCTGGGACCAAGCTGGAACT
CAAACGGGCTGATGCTGCACCAACTGTATCTATCTTC

SEQ ID No.: 152

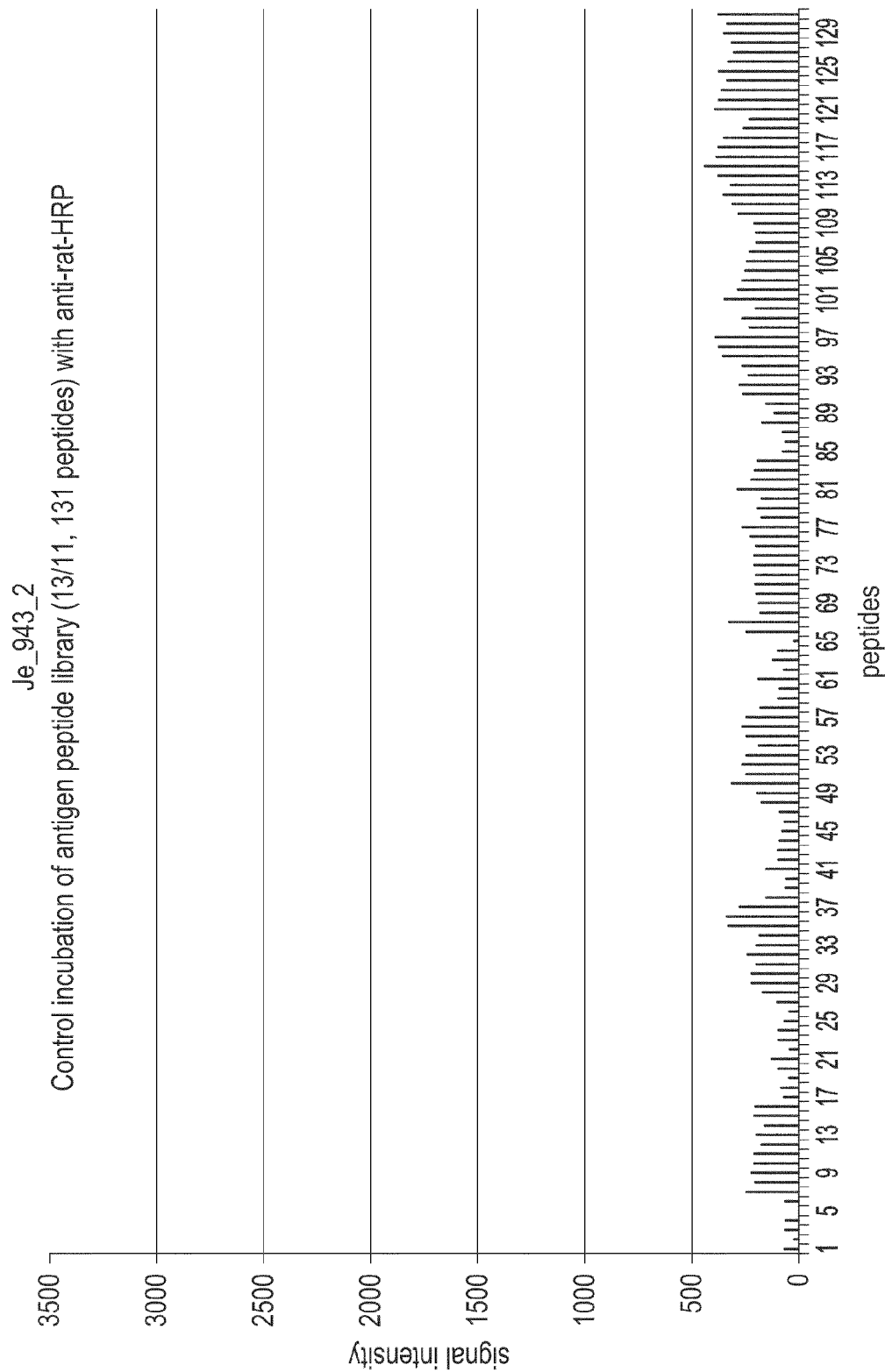

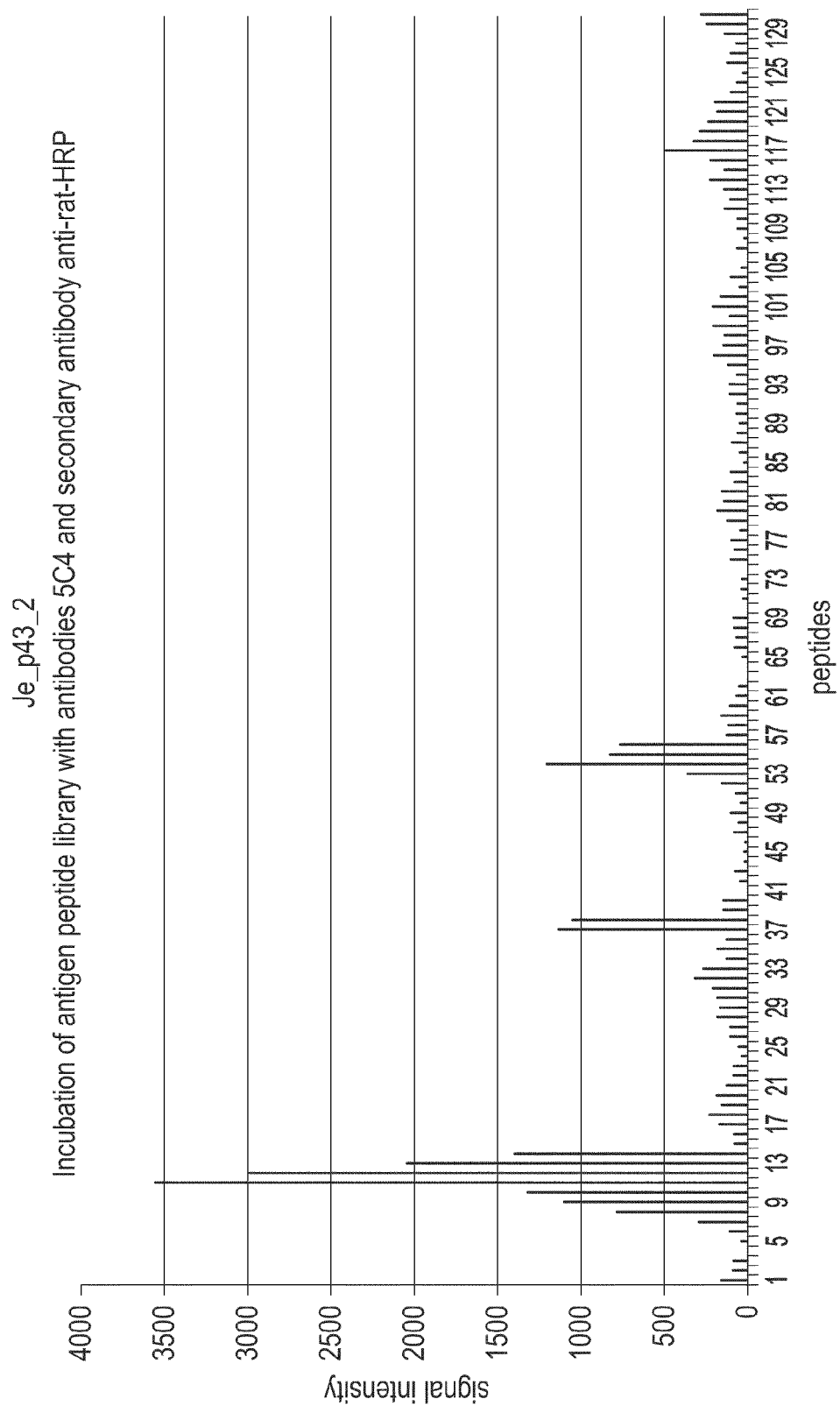

```
1    mspsptalfc lglclgrvpa qsgplpkpsl qalpsslvpl ekpvtlrcqg ppgvdlyrle
61   klsssryqdq avlfipamkr slagryrcsy qngslwslps dqlelvatgv fakpslsaqp
121  gpavssggdv tlqcqtrygf dqfalykegd papyknperw yrasfpiitv taahsgtyrc
181  ysfssrdpyl wsapsdplel vvtgtsvtps rlpteppssv aefseatael tvsftnkvft
241  tetsrsitts pkesdspagp arqyytkgnl vriclgavil iilagflaed whsrrkrlrh
301  rgravqrplp plpplpqtrk shggqdggrq dvhsrglcs
```

```
   1  acagagctca ggacagggct gaggaaccat gtctccatcc ccgaccgccc tcttctgtct
  61  tgggctgtgt ctggggcgtg tgccagcgca gagtggaccg ctccccaagc cctccctcca
 121  ggctctgccc agctccctgg tgccctgga gaagccagtg accctccggt gccagggacc
 181  tccgggcgtg gacctgtacc gcctggagaa gctgagttcc agcaggtacc aggatcaggc
 241  agtcctcttc atcccggcca tgaagagaag tctggctgga cgctaccgct gctcctacca
 301  gaacggaagc ctctggtccc tgcccagcga ccagctggag ctcgttgcca cgggagtttt
 361  tgccaaaccc tcgctctcag cccagcccgg cccggcggtg tcgtcaggag gggacgtaac
 421  cctacagtgt cagactcggt atggctttga ccaatttgct ctgtacaagg aaggggaccc
 481  tgcgccctac aagaatcccg agagatggta ccgggctagt ttccccatca tcacggtgac
 541  cgccgcccac agcggaacct accgatgcta cagcttctcc agcagggacc catacctgtg
 601  gtcggccccc agcgaccccc tggagcttgt ggtcacagga acctctgtga ccccagccg
 661  gttaccaaca gaaccacctt cctcggtagc agaattctca gaagccaccg ctgaactgac
 721  cgtctcattc acaaacaaag tcttcacaac tgagacttct aggagtatca ccaccagtcc
 781  aaaggagtca gactctccag ctggtcctgc ccgccagtac tacaccaagg gcaacctggt
 841  ccggatatgc ctcggggctg tgatcctaat aatcctggcg gggtttctgg cagaggactg
 901  gcacagccgg aggaagcgcc tgcggcacag gggcagggct gtgcagaggc cgcttccgcc
 961  cctcccgccc ctcccgcaga cccggaaatc acacgggggt caggatggag gccgacagga
1021  tgttcacagc cgcgggttat gttcatgacc gctgaacccc aggcacggtc gtatccaagg
1081  gagggatcat ggcatgggag gcgactcaaa gactggcgtg tgtggagcgt ggaagcagga
1141  gggcagaggc tacagctgtg gaaacgaggc catgctgcct cctcctggtg ttccatcagg
1201  gagccgttcg gccagtgtct gtctgtctgt ctgcctctct gtctgagggc accctccatt
1261  tgggatggaa ggaatctgtg gagacccat cctcctccct gcacactgtg gatgacatgg
1321  taccctggct ggaccacata ctggcctctt tcttcaacct ctctaatatg ggctccagac
1381  ggatctctaa ggttcccagc tctcagggtt gactctgttc catcctctgt gcaaaatcct
1441  cctgtgcttc cctttggccc tctgtgctct tgtctggttt tccccagaaa ctctcaccct
1501  cactccatct cccactgcgg tctaacaaat ctccttcgt ctctcagaac gggtcttgca
1561  ggcagtttgg gtatgtcatt cattttcctt agtgtaaaac tagcacgttg cccgcttccc
1621  ttcacattag aaaacaagat cagcctgtgc aacatggtga aacctcatct ctaccaacaa
1681  aacaaaaaaa cacaaaaatt agccaggtgt ggtggtgcat ccctatactc ccagcaactc
1741  gggggctga ggtgggagaa tggcttgagc ctgggaggca gaggttgcag tgagctgaga
1801  tcacaccact gcactctagc tcgggtgacg aagcctgacc ttgtctcaaa aaatacaggg
1861  atgaatatgt caattaccct gatttgatca tagcacgttg tatacatgta ctgcaatatt
1921  gctgtccacc ccataaatat gtacaattat gtatacattt ttaaaatcat aaaaataaga
```

FIG. 36B 1981 taatgcaccg tctccacccc tctcatattt actttctgaa ggaaatgtta ggtcttctca
2041 aggtaaagtt ctatatttat tatagcgttt aggcatttct tgaccatcta atgagtgtaa
2101 aactgtacca ctgggccaag tgcagtggat catgtctgta atcctagcac tgtgggaggc
2161 caaggcagga ggatcgcttg agcccaggag ttcaagacca gcctgggcaa catagtgaga
2221 ccccatctct acttaaaata aagaagtaaa aattgttta aaa

SEQUENCE LISTING

<160> NUMBER OF SEQ ID NOS: 171

<210> SEQ ID NO 1
<211> LENGTH: 13
<212> TYPE: PRT
<213> ORGANISM: Artificial
<220> FEATURE:
<223> OTHER INFORMATION: Epitope mapping peptide

<400> SEQUENCE: 1

Met Ser Pro Ser Pro Thr Ala Leu Phe Cys Leu Gly Leu
1               5                   10

<210> SEQ ID NO 2
<211> LENGTH: 13
<212> TYPE: PRT
<213> ORGANISM: Artificial
<220> FEATURE:
<223> OTHER INFORMATION: Epitope mapping peptide

<400> SEQUENCE: 2

Pro Ser Pro Thr Ala Leu Phe Cys Leu Gly Leu Cys Leu
1               5                   10

<210> SEQ ID NO 3
<211> LENGTH: 13
<212> TYPE: PRT
<213> ORGANISM: Artificial
<220> FEATURE:
<223> OTHER INFORMATION: Epitope mapping peptide

<400> SEQUENCE: 3

Pro Thr Ala Leu Phe Cys Leu Gly Leu Cys Leu Gly Arg
1               5                   10

<210> SEQ ID NO 4
<211> LENGTH: 13
<212> TYPE: PRT
<213> ORGANISM: Artificial
<220> FEATURE:
<223> OTHER INFORMATION: Epitope mapping peptide

<400> SEQUENCE: 4

Ala Leu Phe Cys Leu Gly Leu Cys Leu Gly Arg Val Pro
1               5                   10

<210> SEQ ID NO 5
<211> LENGTH: 13
<212> TYPE: PRT
<213> ORGANISM: Artificial
<220> FEATURE:
<223> OTHER INFORMATION: epitope mapping peptide

<400> SEQUENCE: 5

Phe Cys Leu Gly Leu Cys Leu Gly Arg Val Pro Ala Gln
1               5                   10

<210> SEQ ID NO 6
<211> LENGTH: 13
<212> TYPE: PRT
<213> ORGANISM: Artificial
<220> FEATURE:
<223> OTHER INFORMATION: epitope mapping peptide

<400> SEQUENCE: 6

Leu Gly Leu Cys Leu Gly Arg Val Pro Ala Gln Ser Gly

```
1               5                   10

<210> SEQ ID NO 7
<211> LENGTH: 13
<212> TYPE: PRT
<213> ORGANISM: Artificial
<220> FEATURE:
<223> OTHER INFORMATION: epitope mapping peptide

<400> SEQUENCE: 7

Leu Cys Leu Gly Arg Val Pro Ala Gln Ser Gly Pro Leu
1               5                   10

<210> SEQ ID NO 8
<211> LENGTH: 13
<212> TYPE: PRT
<213> ORGANISM: Artificial
<220> FEATURE:
<223> OTHER INFORMATION: epitope mapping peptide

<400> SEQUENCE: 8

Leu Gly Arg Val Pro Ala Gln Ser Gly Pro Leu Pro Lys
1               5                   10

<210> SEQ ID NO 9
<211> LENGTH: 13
<212> TYPE: PRT
<213> ORGANISM: Artificial
<220> FEATURE:
<223> OTHER INFORMATION: epitope mapping peptide

<400> SEQUENCE: 9

Arg Val Pro Ala Gln Ser Gly Pro Leu Pro Lys Pro Ser
1               5                   10

<210> SEQ ID NO 10
<211> LENGTH: 13
<212> TYPE: PRT
<213> ORGANISM: Artificial
<220> FEATURE:
<223> OTHER INFORMATION: epitope mapping peptide

<400> SEQUENCE: 10

Pro Ala Gln Ser Gly Pro Leu Pro Lys Pro Ser Leu Gln
1               5                   10

<210> SEQ ID NO 11
<211> LENGTH: 13
<212> TYPE: PRT
<213> ORGANISM: Artificial
<220> FEATURE:
<223> OTHER INFORMATION: epitope mapping peptide

<400> SEQUENCE: 11

Gln Ser Gly Pro Leu Pro Lys Pro Ser Leu Gln Ala Leu
1               5                   10

<210> SEQ ID NO 12
<211> LENGTH: 13
<212> TYPE: PRT
<213> ORGANISM: Artificial
<220> FEATURE:
<223> OTHER INFORMATION: epitope mapping peptide

<400> SEQUENCE: 12

Gly Pro Leu Pro Lys Pro Ser Leu Gln Ala Leu Pro Ser
1               5                   10
```

<210> SEQ ID NO 13
<211> LENGTH: 13
<212> TYPE: PRT
<213> ORGANISM: Artificial
<220> FEATURE:
<223> OTHER INFORMATION: epitope mapping peptide

<400> SEQUENCE: 13

Leu Pro Lys Pro Ser Leu Gln Ala Leu Pro Ser Ser Leu
1               5                   10

<210> SEQ ID NO 14
<211> LENGTH: 13
<212> TYPE: PRT
<213> ORGANISM: Artificial
<220> FEATURE:
<223> OTHER INFORMATION: epitope mapping peptide

<400> SEQUENCE: 14

Lys Pro Ser Leu Gln Ala Leu Pro Ser Ser Leu Val Pro
1               5                   10

<210> SEQ ID NO 15
<211> LENGTH: 13
<212> TYPE: PRT
<213> ORGANISM: Artificial
<220> FEATURE:
<223> OTHER INFORMATION: epitope mapping peptide

<400> SEQUENCE: 15

Ser Leu Gln Ala Leu Pro Ser Ser Leu Val Pro Leu Glu
1               5                   10

<210> SEQ ID NO 16
<211> LENGTH: 13
<212> TYPE: PRT
<213> ORGANISM: Artificial
<220> FEATURE:
<223> OTHER INFORMATION: epitope mapping peptide

<400> SEQUENCE: 16

Gln Ala Leu Pro Ser Ser Leu Val Pro Leu Glu Lys Pro
1               5                   10

<210> SEQ ID NO 17
<211> LENGTH: 13
<212> TYPE: PRT
<213> ORGANISM: Artificial
<220> FEATURE:
<223> OTHER INFORMATION: epitope mapping peptide

<400> SEQUENCE: 17

Leu Pro Ser Ser Leu Val Pro Leu Glu Lys Pro Val Thr
1               5                   10

<210> SEQ ID NO 18
<211> LENGTH: 13
<212> TYPE: PRT
<213> ORGANISM: Artificial
<220> FEATURE:
<223> OTHER INFORMATION: epitope mapping peptide

<400> SEQUENCE: 18

Ser Ser Leu Val Pro Leu Glu Lys Pro Val Thr Leu Arg
1               5                   10

<210> SEQ ID NO 19

```
<211> LENGTH: 13
<212> TYPE: PRT
<213> ORGANISM: Artificial
<220> FEATURE:
<223> OTHER INFORMATION: epitope mapping peptide

<400> SEQUENCE: 19

Leu Val Pro Leu Glu Lys Pro Val Thr Leu Arg Cys Gln
1               5                   10

<210> SEQ ID NO 20
<211> LENGTH: 13
<212> TYPE: PRT
<213> ORGANISM: Artificial
<220> FEATURE:
<223> OTHER INFORMATION: epitope mapping peptide

<400> SEQUENCE: 20

Pro Leu Glu Lys Pro Val Thr Leu Arg Cys Gln Gly Pro
1               5                   10

<210> SEQ ID NO 21
<211> LENGTH: 13
<212> TYPE: PRT
<213> ORGANISM: Artificial
<220> FEATURE:
<223> OTHER INFORMATION: epitope mapping peptide

<400> SEQUENCE: 21

Glu Lys Pro Val Thr Leu Arg Cys Gln Gly Pro Pro Gly
1               5                   10

<210> SEQ ID NO 22
<211> LENGTH: 13
<212> TYPE: PRT
<213> ORGANISM: Artificial
<220> FEATURE:
<223> OTHER INFORMATION: epitope mapping peptide

<400> SEQUENCE: 22

Pro Val Thr Leu Arg Cys Gln Gly Pro Pro Gly Val Asp
1               5                   10

<210> SEQ ID NO 23
<211> LENGTH: 13
<212> TYPE: PRT
<213> ORGANISM: Artificial
<220> FEATURE:
<223> OTHER INFORMATION: epitope mapping peptide

<400> SEQUENCE: 23

Thr Leu Arg Cys Gln Gly Pro Pro Gly Val Asp Leu Tyr
1               5                   10

<210> SEQ ID NO 24
<211> LENGTH: 13
<212> TYPE: PRT
<213> ORGANISM: Artificial
<220> FEATURE:
<223> OTHER INFORMATION: epitope mapping peptide

<400> SEQUENCE: 24

Arg Cys Gln Gly Pro Pro Gly Val Asp Leu Tyr Arg Leu
1               5                   10

<210> SEQ ID NO 25
<211> LENGTH: 13
<212> TYPE: PRT
```

```
<213> ORGANISM: Artificial
<220> FEATURE:
<223> OTHER INFORMATION: epitope mapping peptide

<400> SEQUENCE: 25

Gln Gly Pro Pro Gly Val Asp Leu Tyr Arg Leu Glu Lys
1               5                   10

<210> SEQ ID NO 26
<211> LENGTH: 13
<212> TYPE: PRT
<213> ORGANISM: Artificial
<220> FEATURE:
<223> OTHER INFORMATION: epitope mapping peptide

<400> SEQUENCE: 26

Pro Pro Gly Val Asp Leu Tyr Arg Leu Glu Lys Leu Ser
1               5                   10

<210> SEQ ID NO 27
<211> LENGTH: 13
<212> TYPE: PRT
<213> ORGANISM: Artificial
<220> FEATURE:
<223> OTHER INFORMATION: epitope mapping peptide

<400> SEQUENCE: 27

Gly Val Asp Leu Tyr Arg Leu Glu Lys Leu Ser Ser Ser
1               5                   10

<210> SEQ ID NO 28
<211> LENGTH: 13
<212> TYPE: PRT
<213> ORGANISM: Artificial
<220> FEATURE:
<223> OTHER INFORMATION: epitope mapping peptide

<400> SEQUENCE: 28

Asp Leu Tyr Arg Leu Glu Lys Leu Ser Ser Ser Arg Tyr
1               5                   10

<210> SEQ ID NO 29
<211> LENGTH: 13
<212> TYPE: PRT
<213> ORGANISM: Artificial
<220> FEATURE:
<223> OTHER INFORMATION: epitope mapping peptide

<400> SEQUENCE: 29

Tyr Arg Leu Glu Lys Leu Ser Ser Ser Arg Tyr Gln Asp
1               5                   10

<210> SEQ ID NO 30
<211> LENGTH: 13
<212> TYPE: PRT
<213> ORGANISM: Artificial
<220> FEATURE:
<223> OTHER INFORMATION: epitope mapping peptide

<400> SEQUENCE: 30

Leu Glu Lys Leu Ser Ser Ser Arg Tyr Gln Asp Gln Ala
1               5                   10

<210> SEQ ID NO 31
<211> LENGTH: 13
<212> TYPE: PRT
<213> ORGANISM: Artificial
<220> FEATURE:
```

<223> OTHER INFORMATION: epitope mapping peptide

<400> SEQUENCE: 31

Lys Leu Ser Ser Ser Arg Tyr Gln Asp Gln Ala Val Leu
1               5                   10

<210> SEQ ID NO 32
<211> LENGTH: 13
<212> TYPE: PRT
<213> ORGANISM: Artificial
<220> FEATURE:
<223> OTHER INFORMATION: epitope mapping peptide

<400> SEQUENCE: 32

Ser Ser Ser Arg Tyr Gln Asp Gln Ala Val Leu Phe Ile
1               5                   10

<210> SEQ ID NO 33
<211> LENGTH: 13
<212> TYPE: PRT
<213> ORGANISM: Artificial
<220> FEATURE:
<223> OTHER INFORMATION: epitope mapping peptide

<400> SEQUENCE: 33

Ser Arg Tyr Gln Asp Gln Ala Val Leu Phe Ile Pro Ala
1               5                   10

<210> SEQ ID NO 34
<211> LENGTH: 13
<212> TYPE: PRT
<213> ORGANISM: Artificial
<220> FEATURE:
<223> OTHER INFORMATION: epitope mapping peptide

<400> SEQUENCE: 34

Tyr Gln Asp Gln Ala Val Leu Phe Ile Pro Ala Met Lys
1               5                   10

<210> SEQ ID NO 35
<211> LENGTH: 13
<212> TYPE: PRT
<213> ORGANISM: Artificial
<220> FEATURE:
<223> OTHER INFORMATION: epitope mapping peptide

<400> SEQUENCE: 35

Asp Gln Ala Val Leu Phe Ile Pro Ala Met Lys Arg Ser
1               5                   10

<210> SEQ ID NO 36
<211> LENGTH: 13
<212> TYPE: PRT
<213> ORGANISM: Artificial
<220> FEATURE:
<223> OTHER INFORMATION: epitope mapping peptide

<400> SEQUENCE: 36

Ala Val Leu Phe Ile Pro Ala Met Lys Arg Ser Leu Ala
1               5                   10

<210> SEQ ID NO 37
<211> LENGTH: 13
<212> TYPE: PRT
<213> ORGANISM: Artificial
<220> FEATURE:
<223> OTHER INFORMATION: epitope mapping peptide

```
<400> SEQUENCE: 37

Leu Phe Ile Pro Ala Met Lys Arg Ser Leu Ala Gly Arg
1               5                   10

<210> SEQ ID NO 38
<211> LENGTH: 13
<212> TYPE: PRT
<213> ORGANISM: Artificial
<220> FEATURE:
<223> OTHER INFORMATION: epitope mapping peptide

<400> SEQUENCE: 38

Ile Pro Ala Met Lys Arg Ser Leu Ala Gly Arg Tyr Arg
1               5                   10

<210> SEQ ID NO 39
<211> LENGTH: 13
<212> TYPE: PRT
<213> ORGANISM: Artificial
<220> FEATURE:
<223> OTHER INFORMATION: epitope mapping peptide

<400> SEQUENCE: 39

Ala Met Lys Arg Ser Leu Ala Gly Arg Tyr Arg Cys Ser
1               5                   10

<210> SEQ ID NO 40
<211> LENGTH: 13
<212> TYPE: PRT
<213> ORGANISM: Artificial
<220> FEATURE:
<223> OTHER INFORMATION: epitope mapping peptide

<400> SEQUENCE: 40

Lys Arg Ser Leu Ala Gly Arg Tyr Arg Cys Ser Tyr Gln
1               5                   10

<210> SEQ ID NO 41
<211> LENGTH: 13
<212> TYPE: PRT
<213> ORGANISM: Artificial
<220> FEATURE:
<223> OTHER INFORMATION: epitope mapping peptide

<400> SEQUENCE: 41

Ser Leu Ala Gly Arg Tyr Arg Cys Ser Tyr Gln Asn Gly
1               5                   10

<210> SEQ ID NO 42
<211> LENGTH: 13
<212> TYPE: PRT
<213> ORGANISM: Artificial
<220> FEATURE:
<223> OTHER INFORMATION: epitope mapping peptide

<400> SEQUENCE: 42

Ala Gly Arg Tyr Arg Cys Ser Tyr Gln Asn Gly Ser Leu
1               5                   10

<210> SEQ ID NO 43
<211> LENGTH: 13
<212> TYPE: PRT
<213> ORGANISM: Artificial
<220> FEATURE:
<223> OTHER INFORMATION: epitope mapping peptide

<400> SEQUENCE: 43
```

```
Arg Tyr Arg Cys Ser Tyr Gln Asn Gly Ser Leu Trp Ser
1               5                   10

<210> SEQ ID NO 44
<211> LENGTH: 13
<212> TYPE: PRT
<213> ORGANISM: Artificial
<220> FEATURE:
<223> OTHER INFORMATION: epitope mapping peptide

<400> SEQUENCE: 44

Arg Cys Ser Tyr Gln Asn Gly Ser Leu Trp Ser Leu Pro
1               5                   10

<210> SEQ ID NO 45
<211> LENGTH: 13
<212> TYPE: PRT
<213> ORGANISM: Artificial
<220> FEATURE:
<223> OTHER INFORMATION: epitope mapping peptide

<400> SEQUENCE: 45

Ser Tyr Gln Asn Gly Ser Leu Trp Ser Leu Pro Ser Asp
1               5                   10

<210> SEQ ID NO 46
<211> LENGTH: 13
<212> TYPE: PRT
<213> ORGANISM: Artificial
<220> FEATURE:
<223> OTHER INFORMATION: epitope mapping peptide

<400> SEQUENCE: 46

Gln Asn Gly Ser Leu Trp Ser Leu Pro Ser Asp Gln Leu
1               5                   10

<210> SEQ ID NO 47
<211> LENGTH: 13
<212> TYPE: PRT
<213> ORGANISM: Artificial
<220> FEATURE:
<223> OTHER INFORMATION: epitope mapping peptide

<400> SEQUENCE: 47

Gly Ser Leu Trp Ser Leu Pro Ser Asp Gln Leu Glu Leu
1               5                   10

<210> SEQ ID NO 48
<211> LENGTH: 13
<212> TYPE: PRT
<213> ORGANISM: Artificial
<220> FEATURE:
<223> OTHER INFORMATION: epitope mapping peptide

<400> SEQUENCE: 48

Leu Trp Ser Leu Pro Ser Asp Gln Leu Glu Leu Val Ala
1               5                   10

<210> SEQ ID NO 49
<211> LENGTH: 13
<212> TYPE: PRT
<213> ORGANISM: Artificial
<220> FEATURE:
<223> OTHER INFORMATION: epitope mapping peptide

<400> SEQUENCE: 49

Ser Leu Pro Ser Asp Gln Leu Glu Leu Val Ala Thr Gly
1               5                   10
```

```
<210> SEQ ID NO 50
<211> LENGTH: 13
<212> TYPE: PRT
<213> ORGANISM: Artificial
<220> FEATURE:
<223> OTHER INFORMATION: epitope mapping peptide

<400> SEQUENCE: 50

Pro Ser Asp Gln Leu Glu Leu Val Ala Thr Gly Val Phe
1               5                   10

<210> SEQ ID NO 51
<211> LENGTH: 13
<212> TYPE: PRT
<213> ORGANISM: Artificial
<220> FEATURE:
<223> OTHER INFORMATION: epitope mapping peptide

<400> SEQUENCE: 51

Asp Gln Leu Glu Leu Val Ala Thr Gly Val Phe Ala Lys
1               5                   10

<210> SEQ ID NO 52
<211> LENGTH: 13
<212> TYPE: PRT
<213> ORGANISM: Artificial
<220> FEATURE:
<223> OTHER INFORMATION: epitope mapping peptide

<400> SEQUENCE: 52

Leu Glu Leu Val Ala Thr Gly Val Phe Ala Lys Pro Ser
1               5                   10

<210> SEQ ID NO 53
<211> LENGTH: 13
<212> TYPE: PRT
<213> ORGANISM: Artificial
<220> FEATURE:
<223> OTHER INFORMATION: epitope mapping peptide

<400> SEQUENCE: 53

Leu Val Ala Thr Gly Val Phe Ala Lys Pro Ser Leu Ser
1               5                   10

<210> SEQ ID NO 54
<211> LENGTH: 13
<212> TYPE: PRT
<213> ORGANISM: Artificial
<220> FEATURE:
<223> OTHER INFORMATION: epitope mapping peptide

<400> SEQUENCE: 54

Ala Thr Gly Val Phe Ala Lys Pro Ser Leu Ser Ala Gln
1               5                   10

<210> SEQ ID NO 55
<211> LENGTH: 13
<212> TYPE: PRT
<213> ORGANISM: Artificial
<220> FEATURE:
<223> OTHER INFORMATION: epitope mapping peptide

<400> SEQUENCE: 55

Gly Val Phe Ala Lys Pro Ser Leu Ser Ala Gln Pro Gly
1               5                   10
```

```
<210> SEQ ID NO 56
<211> LENGTH: 13
<212> TYPE: PRT
<213> ORGANISM: Artificial
<220> FEATURE:
<223> OTHER INFORMATION: epitope mapping peptide

<400> SEQUENCE: 56

Phe Ala Lys Pro Ser Leu Ser Ala Gln Pro Gly Pro Ala
1               5                   10

<210> SEQ ID NO 57
<211> LENGTH: 13
<212> TYPE: PRT
<213> ORGANISM: Artificial
<220> FEATURE:
<223> OTHER INFORMATION: epitope mapping peptide

<400> SEQUENCE: 57

Lys Pro Ser Leu Ser Ala Gln Pro Gly Pro Ala Val Ser
1               5                   10

<210> SEQ ID NO 58
<211> LENGTH: 13
<212> TYPE: PRT
<213> ORGANISM: Artificial
<220> FEATURE:
<223> OTHER INFORMATION: epitope mapping peptide

<400> SEQUENCE: 58

Ser Leu Ser Ala Gln Pro Gly Pro Ala Val Ser Ser Gly
1               5                   10

<210> SEQ ID NO 59
<211> LENGTH: 13
<212> TYPE: PRT
<213> ORGANISM: Artificial
<220> FEATURE:
<223> OTHER INFORMATION: epitope mapping peptide

<400> SEQUENCE: 59

Ser Ala Gln Pro Gly Pro Ala Val Ser Ser Gly Gly Asp
1               5                   10

<210> SEQ ID NO 60
<211> LENGTH: 13
<212> TYPE: PRT
<213> ORGANISM: Artificial
<220> FEATURE:
<223> OTHER INFORMATION: epitope mapping peptide

<400> SEQUENCE: 60

Gln Pro Gly Pro Ala Val Ser Ser Gly Gly Asp Val Thr
1               5                   10

<210> SEQ ID NO 61
<211> LENGTH: 13
<212> TYPE: PRT
<213> ORGANISM: Artificial
<220> FEATURE:
<223> OTHER INFORMATION: epitope mapping peptide

<400> SEQUENCE: 61

Gly Pro Ala Val Ser Ser Gly Gly Asp Val Thr Leu Gln
1               5                   10

<210> SEQ ID NO 62
<211> LENGTH: 13
```

```
<212> TYPE: PRT
<213> ORGANISM: Artificial
<220> FEATURE:
<223> OTHER INFORMATION: epitope mapping peptide

<400> SEQUENCE: 62

Ala Val Ser Ser Gly Gly Asp Val Thr Leu Gln Cys Gln
1               5                   10

<210> SEQ ID NO 63
<211> LENGTH: 13
<212> TYPE: PRT
<213> ORGANISM: Artificial
<220> FEATURE:
<223> OTHER INFORMATION: epitope mapping peptide

<400> SEQUENCE: 63

Ser Ser Gly Gly Asp Val Thr Leu Gln Cys Gln Thr Arg
1               5                   10

<210> SEQ ID NO 64
<211> LENGTH: 13
<212> TYPE: PRT
<213> ORGANISM: Artificial
<220> FEATURE:
<223> OTHER INFORMATION: epitope mapping peptide

<400> SEQUENCE: 64

Gly Gly Asp Val Thr Leu Gln Cys Gln Thr Arg Tyr Gly
1               5                   10

<210> SEQ ID NO 65
<211> LENGTH: 13
<212> TYPE: PRT
<213> ORGANISM: Artificial
<220> FEATURE:
<223> OTHER INFORMATION: epitope mapping peptide

<400> SEQUENCE: 65

Asp Val Thr Leu Gln Cys Gln Thr Arg Tyr Gly Phe Asp
1               5                   10

<210> SEQ ID NO 66
<211> LENGTH: 13
<212> TYPE: PRT
<213> ORGANISM: Artificial
<220> FEATURE:
<223> OTHER INFORMATION: epitope mapping peptide

<400> SEQUENCE: 66

Thr Leu Gln Cys Gln Thr Arg Tyr Gly Phe Asp Gln Phe
1               5                   10

<210> SEQ ID NO 67
<211> LENGTH: 13
<212> TYPE: PRT
<213> ORGANISM: Artificial
<220> FEATURE:
<223> OTHER INFORMATION: epitope mapping peptide

<400> SEQUENCE: 67

Gln Cys Gln Thr Arg Tyr Gly Phe Asp Gln Phe Ala Leu
1               5                   10

<210> SEQ ID NO 68
<211> LENGTH: 13
<212> TYPE: PRT
<213> ORGANISM: Artificial
```

<220> FEATURE:
<223> OTHER INFORMATION: epitope mapping peptide

<400> SEQUENCE: 68

Gln Thr Arg Tyr Gly Phe Asp Gln Phe Ala Leu Tyr Lys
1               5                   10

<210> SEQ ID NO 69
<211> LENGTH: 13
<212> TYPE: PRT
<213> ORGANISM: Artificial
<220> FEATURE:
<223> OTHER INFORMATION: epitope mapping peptide

<400> SEQUENCE: 69

Arg Tyr Gly Phe Asp Gln Phe Ala Leu Tyr Lys Glu Gly
1               5                   10

<210> SEQ ID NO 70
<211> LENGTH: 13
<212> TYPE: PRT
<213> ORGANISM: Artificial
<220> FEATURE:
<223> OTHER INFORMATION: epitope mapping peptide

<400> SEQUENCE: 70

Gly Phe Asp Gln Phe Ala Leu Tyr Lys Glu Gly Asp Pro
1               5                   10

<210> SEQ ID NO 71
<211> LENGTH: 13
<212> TYPE: PRT
<213> ORGANISM: Artificial
<220> FEATURE:
<223> OTHER INFORMATION: epitope mapping peptide

<400> SEQUENCE: 71

Asp Gln Phe Ala Leu Tyr Lys Glu Gly Asp Pro Ala Pro
1               5                   10

<210> SEQ ID NO 72
<211> LENGTH: 13
<212> TYPE: PRT
<213> ORGANISM: Artificial
<220> FEATURE:
<223> OTHER INFORMATION: epitope mapping peptide

<400> SEQUENCE: 72

Phe Ala Leu Tyr Lys Glu Gly Asp Pro Ala Pro Tyr Lys
1               5                   10

<210> SEQ ID NO 73
<211> LENGTH: 13
<212> TYPE: PRT
<213> ORGANISM: Artificial
<220> FEATURE:
<223> OTHER INFORMATION: epitope mapping peptide

<400> SEQUENCE: 73

Leu Tyr Lys Glu Gly Asp Pro Ala Pro Tyr Lys Asn Pro
1               5                   10

<210> SEQ ID NO 74
<211> LENGTH: 13
<212> TYPE: PRT
<213> ORGANISM: Artificial
<220> FEATURE:
<223> OTHER INFORMATION: epitope mapping peptide

<400> SEQUENCE: 74

Lys Glu Gly Asp Pro Ala Pro Tyr Lys Asn Pro Glu Arg
1               5                   10

<210> SEQ ID NO 75
<211> LENGTH: 13
<212> TYPE: PRT
<213> ORGANISM: Artificial
<220> FEATURE:
<223> OTHER INFORMATION: epitope mapping peptide

<400> SEQUENCE: 75

Gly Asp Pro Ala Pro Tyr Lys Asn Pro Glu Arg Trp Tyr
1               5                   10

<210> SEQ ID NO 76
<211> LENGTH: 13
<212> TYPE: PRT
<213> ORGANISM: Artificial
<220> FEATURE:
<223> OTHER INFORMATION: epitope mapping peptide

<400> SEQUENCE: 76

Pro Ala Pro Tyr Lys Asn Pro Glu Arg Trp Tyr Arg Ala
1               5                   10

<210> SEQ ID NO 77
<211> LENGTH: 13
<212> TYPE: PRT
<213> ORGANISM: Artificial
<220> FEATURE:
<223> OTHER INFORMATION: epitope mapping peptide

<400> SEQUENCE: 77

Pro Tyr Lys Asn Pro Glu Arg Trp Tyr Arg Ala Ser Phe
1               5                   10

<210> SEQ ID NO 78
<211> LENGTH: 13
<212> TYPE: PRT
<213> ORGANISM: Artificial
<220> FEATURE:
<223> OTHER INFORMATION: epitope mapping peptide

<400> SEQUENCE: 78

Lys Asn Pro Glu Arg Trp Tyr Arg Ala Ser Phe Pro Ile
1               5                   10

<210> SEQ ID NO 79
<211> LENGTH: 13
<212> TYPE: PRT
<213> ORGANISM: Artificial
<220> FEATURE:
<223> OTHER INFORMATION: epitope mapping peptide

<400> SEQUENCE: 79

Pro Glu Arg Trp Tyr Arg Ala Ser Phe Pro Ile Ile Thr
1               5                   10

<210> SEQ ID NO 80
<211> LENGTH: 13
<212> TYPE: PRT
<213> ORGANISM: Artificial
<220> FEATURE:
<223> OTHER INFORMATION: epitope mapping peptide

<400> SEQUENCE: 80

```
Arg Trp Tyr Arg Ala Ser Phe Pro Ile Ile Thr Val Thr
1               5                   10
```

<210> SEQ ID NO 81
<211> LENGTH: 13
<212> TYPE: PRT
<213> ORGANISM: Artificial
<220> FEATURE:
<223> OTHER INFORMATION: epitope mapping peptide

<400> SEQUENCE: 81

```
Tyr Arg Ala Ser Phe Pro Ile Ile Thr Val Thr Ala Ala
1               5                   10
```

<210> SEQ ID NO 82
<211> LENGTH: 13
<212> TYPE: PRT
<213> ORGANISM: Artificial
<220> FEATURE:
<223> OTHER INFORMATION: epitope mapping peptide

<400> SEQUENCE: 82

```
Ala Ser Phe Pro Ile Ile Thr Val Thr Ala Ala His Ser
1               5                   10
```

<210> SEQ ID NO 83
<211> LENGTH: 13
<212> TYPE: PRT
<213> ORGANISM: Artificial
<220> FEATURE:
<223> OTHER INFORMATION: epitope mapping peptide

<400> SEQUENCE: 83

```
Phe Pro Ile Ile Thr Val Thr Ala Ala His Ser Gly Thr
1               5                   10
```

<210> SEQ ID NO 84
<211> LENGTH: 13
<212> TYPE: PRT
<213> ORGANISM: Artificial
<220> FEATURE:
<223> OTHER INFORMATION: epitope mapping peptide

<400> SEQUENCE: 84

```
Ile Ile Thr Val Thr Ala Ala His Ser Gly Thr Tyr Arg
1               5                   10
```

<210> SEQ ID NO 85
<211> LENGTH: 13
<212> TYPE: PRT
<213> ORGANISM: Artificial
<220> FEATURE:
<223> OTHER INFORMATION: epitope mapping peptide

<400> SEQUENCE: 85

```
Thr Val Thr Ala Ala His Ser Gly Thr Tyr Arg Cys Tyr
1               5                   10
```

<210> SEQ ID NO 86
<211> LENGTH: 13
<212> TYPE: PRT
<213> ORGANISM: Artificial
<220> FEATURE:
<223> OTHER INFORMATION: epitope mapping peptide

<400> SEQUENCE: 86

```
Thr Ala Ala His Ser Gly Thr Tyr Arg Cys Tyr Ser Phe
```

<210> SEQ ID NO 87
<211> LENGTH: 13
<212> TYPE: PRT
<213> ORGANISM: Artificial
<220> FEATURE:
<223> OTHER INFORMATION: epitope mapping peptide

<400> SEQUENCE: 87

Ala His Ser Gly Thr Tyr Arg Cys Tyr Ser Phe Ser Ser
1               5                   10

<210> SEQ ID NO 88
<211> LENGTH: 13
<212> TYPE: PRT
<213> ORGANISM: Artificial
<220> FEATURE:
<223> OTHER INFORMATION: epitope mapping peptide

<400> SEQUENCE: 88

Ser Gly Thr Tyr Arg Cys Tyr Ser Phe Ser Ser Arg Asp
1               5                   10

<210> SEQ ID NO 89
<211> LENGTH: 13
<212> TYPE: PRT
<213> ORGANISM: Artificial
<220> FEATURE:
<223> OTHER INFORMATION: epitope mapping peptide

<400> SEQUENCE: 89

Thr Tyr Arg Cys Tyr Ser Phe Ser Ser Arg Asp Pro Tyr
1               5                   10

<210> SEQ ID NO 90
<211> LENGTH: 13
<212> TYPE: PRT
<213> ORGANISM: Artificial
<220> FEATURE:
<223> OTHER INFORMATION: epitope mapping peptide

<400> SEQUENCE: 90

Arg Cys Tyr Ser Phe Ser Ser Arg Asp Pro Tyr Leu Trp
1               5                   10

<210> SEQ ID NO 91
<211> LENGTH: 13
<212> TYPE: PRT
<213> ORGANISM: Artificial
<220> FEATURE:
<223> OTHER INFORMATION: epitope mapping peptide

<400> SEQUENCE: 91

Tyr Ser Phe Ser Ser Arg Asp Pro Tyr Leu Trp Ser Ala
1               5                   10

<210> SEQ ID NO 92
<211> LENGTH: 13
<212> TYPE: PRT
<213> ORGANISM: Artificial
<220> FEATURE:
<223> OTHER INFORMATION: epitope mapping peptide

<400> SEQUENCE: 92

Phe Ser Ser Arg Asp Pro Tyr Leu Trp Ser Ala Pro Ser
1               5                   10

<210> SEQ ID NO 93
<211> LENGTH: 13
<212> TYPE: PRT
<213> ORGANISM: Artificial
<220> FEATURE:
<223> OTHER INFORMATION: epitope mapping peptide

<400> SEQUENCE: 93

Ser Arg Asp Pro Tyr Leu Trp Ser Ala Pro Ser Asp Pro
1               5                   10

<210> SEQ ID NO 94
<211> LENGTH: 13
<212> TYPE: PRT
<213> ORGANISM: Artificial
<220> FEATURE:
<223> OTHER INFORMATION: epitope mapping peptide

<400> SEQUENCE: 94

Asp Pro Tyr Leu Trp Ser Ala Pro Ser Asp Pro Leu Glu
1               5                   10

<210> SEQ ID NO 95
<211> LENGTH: 13
<212> TYPE: PRT
<213> ORGANISM: Artificial
<220> FEATURE:
<223> OTHER INFORMATION: epitope mapping peptide

<400> SEQUENCE: 95

Tyr Leu Trp Ser Ala Pro Ser Asp Pro Leu Glu Leu Val
1               5                   10

<210> SEQ ID NO 96
<211> LENGTH: 13
<212> TYPE: PRT
<213> ORGANISM: Artificial
<220> FEATURE:
<223> OTHER INFORMATION: epitope mapping peptide

<400> SEQUENCE: 96

Trp Ser Ala Pro Ser Asp Pro Leu Glu Leu Val Val Thr
1               5                   10

<210> SEQ ID NO 97
<211> LENGTH: 13
<212> TYPE: PRT
<213> ORGANISM: Artificial
<220> FEATURE:
<223> OTHER INFORMATION: epitope mapping peptide

<400> SEQUENCE: 97

Ala Pro Ser Asp Pro Leu Glu Leu Val Val Thr Gly Thr
1               5                   10

<210> SEQ ID NO 98
<211> LENGTH: 13
<212> TYPE: PRT
<213> ORGANISM: Artificial
<220> FEATURE:
<223> OTHER INFORMATION: epitope mapping peptide

<400> SEQUENCE: 98

Ser Asp Pro Leu Glu Leu Val Val Thr Gly Thr Ser Val
1               5                   10

<210> SEQ ID NO 99

```
<211> LENGTH: 13
<212> TYPE: PRT
<213> ORGANISM: Artificial
<220> FEATURE:
<223> OTHER INFORMATION: epitope mapping peptide

<400> SEQUENCE: 99

Pro Leu Glu Leu Val Val Thr Gly Thr Ser Val Thr Pro
1               5                   10

<210> SEQ ID NO 100
<211> LENGTH: 13
<212> TYPE: PRT
<213> ORGANISM: Artificial
<220> FEATURE:
<223> OTHER INFORMATION: epitope mapping peptide

<400> SEQUENCE: 100

Glu Leu Val Val Thr Gly Thr Ser Val Thr Pro Ser Arg
1               5                   10

<210> SEQ ID NO 101
<211> LENGTH: 13
<212> TYPE: PRT
<213> ORGANISM: Artificial
<220> FEATURE:
<223> OTHER INFORMATION: epitope mapping peptide

<400> SEQUENCE: 101

Val Val Thr Gly Thr Ser Val Thr Pro Ser Arg Leu Pro
1               5                   10

<210> SEQ ID NO 102
<211> LENGTH: 13
<212> TYPE: PRT
<213> ORGANISM: Artificial
<220> FEATURE:
<223> OTHER INFORMATION: epitope mapping peptide

<400> SEQUENCE: 102

Thr Gly Thr Ser Val Thr Pro Ser Arg Leu Pro Thr Glu
1               5                   10

<210> SEQ ID NO 103
<211> LENGTH: 13
<212> TYPE: PRT
<213> ORGANISM: Artificial
<220> FEATURE:
<223> OTHER INFORMATION: epitope mapping peptide

<400> SEQUENCE: 103

Thr Ser Val Thr Pro Ser Arg Leu Pro Thr Glu Pro Pro
1               5                   10

<210> SEQ ID NO 104
<211> LENGTH: 13
<212> TYPE: PRT
<213> ORGANISM: Artificial
<220> FEATURE:
<223> OTHER INFORMATION: epitope mapping peptide

<400> SEQUENCE: 104

Val Thr Pro Ser Arg Leu Pro Thr Glu Pro Pro Ser Ser
1               5                   10

<210> SEQ ID NO 105
<211> LENGTH: 13
<212> TYPE: PRT
```

```
<213> ORGANISM: Artificial
<220> FEATURE:
<223> OTHER INFORMATION: epitope mapping peptide

<400> SEQUENCE: 105

Pro Ser Arg Leu Pro Thr Glu Pro Pro Ser Ser Val Ala
1               5                   10

<210> SEQ ID NO 106
<211> LENGTH: 13
<212> TYPE: PRT
<213> ORGANISM: Artificial
<220> FEATURE:
<223> OTHER INFORMATION: epitope mapping peptide

<400> SEQUENCE: 106

Arg Leu Pro Thr Glu Pro Pro Ser Ser Val Ala Glu Phe
1               5                   10

<210> SEQ ID NO 107
<211> LENGTH: 13
<212> TYPE: PRT
<213> ORGANISM: Artificial
<220> FEATURE:
<223> OTHER INFORMATION: epitope mapping peptide

<400> SEQUENCE: 107

Pro Thr Glu Pro Pro Ser Ser Val Ala Glu Phe Ser Glu
1               5                   10

<210> SEQ ID NO 108
<211> LENGTH: 13
<212> TYPE: PRT
<213> ORGANISM: Artificial
<220> FEATURE:
<223> OTHER INFORMATION: epitope mapping peptide

<400> SEQUENCE: 108

Glu Pro Pro Ser Ser Val Ala Glu Phe Ser Glu Ala Thr
1               5                   10

<210> SEQ ID NO 109
<211> LENGTH: 13
<212> TYPE: PRT
<213> ORGANISM: Artificial
<220> FEATURE:
<223> OTHER INFORMATION: epitope mapping peptide

<400> SEQUENCE: 109

Pro Ser Ser Val Ala Glu Phe Ser Glu Ala Thr Ala Glu
1               5                   10

<210> SEQ ID NO 110
<211> LENGTH: 13
<212> TYPE: PRT
<213> ORGANISM: Artificial
<220> FEATURE:
<223> OTHER INFORMATION: epitope mapping peptide

<400> SEQUENCE: 110

Ser Val Ala Glu Phe Ser Glu Ala Thr Ala Glu Leu Thr
1               5                   10

<210> SEQ ID NO 111
<211> LENGTH: 13
<212> TYPE: PRT
<213> ORGANISM: Artificial
<220> FEATURE:
```

<223> OTHER INFORMATION: epitope mapping peptide

<400> SEQUENCE: 111

Ala Glu Phe Ser Glu Ala Thr Ala Glu Leu Thr Val Ser
1               5                   10

<210> SEQ ID NO 112
<211> LENGTH: 13
<212> TYPE: PRT
<213> ORGANISM: Artificial
<220> FEATURE:
<223> OTHER INFORMATION: epitope mapping peptide

<400> SEQUENCE: 112

Phe Ser Glu Ala Thr Ala Glu Leu Thr Val Ser Phe Thr
1               5                   10

<210> SEQ ID NO 113
<211> LENGTH: 13
<212> TYPE: PRT
<213> ORGANISM: Artificial
<220> FEATURE:
<223> OTHER INFORMATION: epitope mapping peptide

<400> SEQUENCE: 113

Glu Ala Thr Ala Glu Leu Thr Val Ser Phe Thr Asn Lys
1               5                   10

<210> SEQ ID NO 114
<211> LENGTH: 13
<212> TYPE: PRT
<213> ORGANISM: Artificial
<220> FEATURE:
<223> OTHER INFORMATION: epitope mapping peptide

<400> SEQUENCE: 114

Thr Ala Glu Leu Thr Val Ser Phe Thr Asn Lys Val Phe
1               5                   10

<210> SEQ ID NO 115
<211> LENGTH: 13
<212> TYPE: PRT
<213> ORGANISM: Artificial
<220> FEATURE:
<223> OTHER INFORMATION: epitope mapping peptide

<400> SEQUENCE: 115

Glu Leu Thr Val Ser Phe Thr Asn Lys Val Phe Thr Thr
1               5                   10

<210> SEQ ID NO 116
<211> LENGTH: 13
<212> TYPE: PRT
<213> ORGANISM: Artificial
<220> FEATURE:
<223> OTHER INFORMATION: epitope mapping peptide

<400> SEQUENCE: 116

Thr Val Ser Phe Thr Asn Lys Val Phe Thr Thr Glu Thr
1               5                   10

<210> SEQ ID NO 117
<211> LENGTH: 13
<212> TYPE: PRT
<213> ORGANISM: Artificial
<220> FEATURE:
<223> OTHER INFORMATION: epitope mapping peptide

```
<400> SEQUENCE: 117

Ser Phe Thr Asn Lys Val Phe Thr Thr Glu Thr Ser Arg
1               5                   10

<210> SEQ ID NO 118
<211> LENGTH: 13
<212> TYPE: PRT
<213> ORGANISM: Artificial
<220> FEATURE:
<223> OTHER INFORMATION: epitope mapping peptide

<400> SEQUENCE: 118

Thr Asn Lys Val Phe Thr Thr Glu Thr Ser Arg Ser Ile
1               5                   10

<210> SEQ ID NO 119
<211> LENGTH: 13
<212> TYPE: PRT
<213> ORGANISM: Artificial
<220> FEATURE:
<223> OTHER INFORMATION: epitope mapping peptide

<400> SEQUENCE: 119

Lys Val Phe Thr Thr Glu Thr Ser Arg Ser Ile Thr Thr
1               5                   10

<210> SEQ ID NO 120
<211> LENGTH: 13
<212> TYPE: PRT
<213> ORGANISM: Artificial
<220> FEATURE:
<223> OTHER INFORMATION: epitope mapping peptide

<400> SEQUENCE: 120

Phe Thr Thr Glu Thr Ser Arg Ser Ile Thr Thr Ser Pro
1               5                   10

<210> SEQ ID NO 121
<211> LENGTH: 13
<212> TYPE: PRT
<213> ORGANISM: Artificial
<220> FEATURE:
<223> OTHER INFORMATION: epitope mapping peptide

<400> SEQUENCE: 121

Thr Glu Thr Ser Arg Ser Ile Thr Thr Ser Pro Lys Glu
1               5                   10

<210> SEQ ID NO 122
<211> LENGTH: 13
<212> TYPE: PRT
<213> ORGANISM: Artificial
<220> FEATURE:
<223> OTHER INFORMATION: epitope mapping peptide

<400> SEQUENCE: 122

Thr Ser Arg Ser Ile Thr Thr Ser Pro Lys Glu Ser Asp
1               5                   10

<210> SEQ ID NO 123
<211> LENGTH: 13
<212> TYPE: PRT
<213> ORGANISM: Artificial
<220> FEATURE:
<223> OTHER INFORMATION: epitope mapping peptide

<400> SEQUENCE: 123
```

Arg Ser Ile Thr Thr Ser Pro Lys Glu Ser Asp Ser Pro
1               5                   10

<210> SEQ ID NO 124
<211> LENGTH: 13
<212> TYPE: PRT
<213> ORGANISM: Artificial
<220> FEATURE:
<223> OTHER INFORMATION: epitope mapping peptide

<400> SEQUENCE: 124

Ile Thr Thr Ser Pro Lys Glu Ser Asp Ser Pro Ala Gly
1               5                   10

<210> SEQ ID NO 125
<211> LENGTH: 13
<212> TYPE: PRT
<213> ORGANISM: Artificial
<220> FEATURE:
<223> OTHER INFORMATION: epitope mapping peptide

<400> SEQUENCE: 125

Thr Ser Pro Lys Glu Ser Asp Ser Pro Ala Gly Pro Ala
1               5                   10

<210> SEQ ID NO 126
<211> LENGTH: 13
<212> TYPE: PRT
<213> ORGANISM: Artificial
<220> FEATURE:
<223> OTHER INFORMATION: epitope mapping peptide

<400> SEQUENCE: 126

Pro Lys Glu Ser Asp Ser Pro Ala Gly Pro Ala Arg Gln
1               5                   10

<210> SEQ ID NO 127
<211> LENGTH: 13
<212> TYPE: PRT
<213> ORGANISM: Artificial
<220> FEATURE:
<223> OTHER INFORMATION: epitope mapping peptide

<400> SEQUENCE: 127

Glu Ser Asp Ser Pro Ala Gly Pro Ala Arg Gln Tyr Tyr
1               5                   10

<210> SEQ ID NO 128
<211> LENGTH: 13
<212> TYPE: PRT
<213> ORGANISM: Artificial
<220> FEATURE:
<223> OTHER INFORMATION: epitope mapping peptide

<400> SEQUENCE: 128

Asp Ser Pro Ala Gly Pro Ala Arg Gln Tyr Tyr Thr Lys
1               5                   10

<210> SEQ ID NO 129
<211> LENGTH: 13
<212> TYPE: PRT
<213> ORGANISM: Artificial
<220> FEATURE:
<223> OTHER INFORMATION: epitope mapping peptide

<400> SEQUENCE: 129

Pro Ala Gly Pro Ala Arg Gln Tyr Tyr Thr Lys Gly Asn
1               5                   10

```
<210> SEQ ID NO 130
<211> LENGTH: 13
<212> TYPE: PRT
<213> ORGANISM: Artificial
<220> FEATURE:
<223> OTHER INFORMATION: epitope mapping peptide

<400> SEQUENCE: 130

Gly Pro Ala Arg Gln Tyr Tyr Thr Lys Gly Asn Gly Gly
1               5                   10

<210> SEQ ID NO 131
<211> LENGTH: 13
<212> TYPE: PRT
<213> ORGANISM: Artificial
<220> FEATURE:
<223> OTHER INFORMATION: epitope mapping peptide

<400> SEQUENCE: 131

Ala Arg Gln Tyr Tyr Thr Lys Gly Asn Gly Gly Arg Glu
1               5                   10

<210> SEQ ID NO 132
<211> LENGTH: 5
<212> TYPE: PRT
<213> ORGANISM: Homo sapiens

<400> SEQUENCE: 132

Leu Pro Lys Pro Ser
1               5

<210> SEQ ID NO 133
<211> LENGTH: 5
<212> TYPE: PRT
<213> ORGANISM: Homo sapiens

<400> SEQUENCE: 133

Pro Leu Pro Lys Pro
1               5

<210> SEQ ID NO 134
<211> LENGTH: 5
<212> TYPE: PRT
<213> ORGANISM: Homo sapiens

<400> SEQUENCE: 134

Gly Pro Leu Pro Lys
1               5

<210> SEQ ID NO 135
<211> LENGTH: 5
<212> TYPE: PRT
<213> ORGANISM: Homo sapiens

<400> SEQUENCE: 135

Pro Lys Pro Ser Leu
1               5

<210> SEQ ID NO 136
<211> LENGTH: 5
<212> TYPE: PRT
<213> ORGANISM: Homo sapiens

<400> SEQUENCE: 136

Lys Pro Ser Leu Gln
```

<210> SEQ ID NO 137
<211> LENGTH: 5
<212> TYPE: PRT
<213> ORGANISM: Homo sapiens

<400> SEQUENCE: 137

Ala Met Lys Arg Ser
1               5

<210> SEQ ID NO 138
<211> LENGTH: 5
<212> TYPE: PRT
<213> ORGANISM: Homo sapiens

<400> SEQUENCE: 138

Pro Ala Met Lys Arg
1               5

<210> SEQ ID NO 139
<211> LENGTH: 5
<212> TYPE: PRT
<213> ORGANISM: Homo sapiens

<400> SEQUENCE: 139

Met Lys Arg Ser Leu
1               5

<210> SEQ ID NO 140
<211> LENGTH: 5
<212> TYPE: PRT
<213> ORGANISM: Homo sapiens

<400> SEQUENCE: 140

Lys Arg Ser Leu Ala
1               5

<210> SEQ ID NO 141
<211> LENGTH: 5
<212> TYPE: PRT
<213> ORGANISM: Homo sapiens

<400> SEQUENCE: 141

Arg Ser Leu Ala Gly
1               5

<210> SEQ ID NO 142
<211> LENGTH: 5
<212> TYPE: PRT
<213> ORGANISM: Homo sapiens

<400> SEQUENCE: 142

Lys Pro Ser Leu Ser
1               5

<210> SEQ ID NO 143
<211> LENGTH: 5
<212> TYPE: PRT
<213> ORGANISM: Homo sapiens

<400> SEQUENCE: 143

Ala Lys Pro Ser Leu
1               5

```
-continued

<210> SEQ ID NO 144
<211> LENGTH: 5
<212> TYPE: PRT
<213> ORGANISM: Homo sapiens

<400> SEQUENCE: 144

Phe Ala Lys Pro Ser
1               5

<210> SEQ ID NO 145
<211> LENGTH: 5
<212> TYPE: PRT
<213> ORGANISM: Homo sapiens

<400> SEQUENCE: 145

Pro Ser Leu Ser Ala
1               5

<210> SEQ ID NO 146
<211> LENGTH: 5
<212> TYPE: PRT
<213> ORGANISM: Homo sapiens

<400> SEQUENCE: 146

Ser Leu Ser Ala Gln
1               5

<210> SEQ ID NO 147
<211> LENGTH: 504
<212> TYPE: PRT
<213> ORGANISM: Artificial
<220> FEATURE:
<223> OTHER INFORMATION: GPVI-Fc fusion protein of Figure 7

<400> SEQUENCE: 147

Met Ser Pro Ser Pro Thr Ala Leu Phe Cys Leu Gly Leu Cys Leu Gly
1               5                   10                  15

Arg Val Pro Ala Gln Ser Gly Pro Leu Pro Lys Pro Ser Leu Gln Ala
            20                  25                  30

Leu Pro Ser Ser Leu Val Pro Leu Glu Lys Pro Val Thr Leu Arg Cys
        35                  40                  45

Gln Gly Pro Pro Gly Val Asp Leu Tyr Arg Leu Glu Lys Leu Ser Ser
    50                  55                  60

Ser Arg Tyr Gln Asp Gln Ala Val Leu Phe Ile Pro Ala Met Lys Arg
65                  70                  75                  80

Ser Leu Ala Gly Arg Tyr Arg Cys Ser Tyr Gln Asn Gly Ser Leu Trp
                85                  90                  95

Ser Leu Pro Ser Asp Gln Leu Glu Leu Val Ala Thr Gly Val Phe Ala
            100                 105                 110

Lys Pro Ser Leu Ser Ala Gln Pro Gly Pro Ala Val Ser Ser Gly Gly
        115                 120                 125

Asp Val Thr Leu Gln Cys Gln Thr Arg Tyr Gly Phe Asp Gln Phe Ala
    130                 135                 140

Leu Tyr Lys Glu Gly Asp Pro Ala Pro Tyr Lys Asn Pro Glu Arg Trp
145                 150                 155                 160

Tyr Arg Ala Ser Phe Pro Ile Ile Thr Val Thr Ala Ala His Ser Gly
                165                 170                 175

Thr Tyr Arg Cys Tyr Ser Phe Ser Ser Arg Asp Pro Tyr Leu Trp Ser
            180                 185                 190

Ala Pro Ser Asp Pro Leu Glu Leu Val Val Thr Gly Thr Ser Val Thr
        195                 200                 205
```

| | | | | | | | | | | | | |
|---|---|---|---|---|---|---|---|---|---|---|---|---|
| Pro | Ser | Arg | Leu | Pro | Thr | Glu | Pro | Ser | Ser | Val | Ala | Glu | Phe | Ser |
| | | 210 | | | | 215 | | | | 220 | | |

Pro Ser Arg Leu Pro Thr Glu Pro Ser Ser Val Ala Glu Phe Ser
210 215 220

Glu Ala Thr Ala Glu Leu Thr Val Ser Phe Thr Asn Lys Val Phe Thr
225 230 235 240

Thr Glu Thr Ser Arg Ser Ile Thr Thr Ser Pro Lys Glu Ser Asp Ser
245 250 255

Pro Ala Gly Pro Ala Arg Gln Tyr Tyr Thr Lys Gly Asn Gly Gly Arg
260 265 270

Glu Ser Lys Ser Cys Asp Lys Thr His Thr Cys Pro Pro Cys Pro Ala
275 280 285

Pro Glu Leu Leu Gly Gly Pro Ser Val Phe Leu Phe Pro Pro Lys Pro
290 295 300

Lys Asp Thr Leu Met Ile Ser Arg Thr Pro Glu Val Thr Cys Val Val
305 310 315 320

Val Asp Val Ser His Glu Asp Pro Glu Val Lys Phe Asn Trp Tyr Val
325 330 335

Asp Gly Val Glu Val His Asn Ala Lys Thr Lys Pro Arg Glu Glu Gln
340 345 350

Tyr Asn Ser Thr Tyr Arg Val Val Ser Val Leu Thr Val Leu His Gln
355 360 365

Asp Trp Leu Asn Gly Lys Glu Tyr Lys Cys Lys Val Ser Asn Lys Ala
370 375 380

Leu Pro Ala Pro Ile Glu Lys Thr Ile Ser Lys Ala Lys Gly Gln Pro
385 390 395 400

Arg Glu Pro Gln Val Tyr Thr Leu Pro Pro Ser Arg Asp Glu Leu Thr
405 410 415

Lys Asn Gln Val Ser Leu Thr Cys Leu Val Lys Gly Phe Tyr Pro Ser
420 425 430

Asp Ile Ala Val Glu Trp Glu Ser Asn Gly Gln Pro Glu Asn Asn Tyr
435 440 445

Lys Thr Thr Pro Pro Val Leu Asp Ser Asp Gly Ser Phe Phe Leu Tyr
450 455 460

Ser Lys Leu Thr Val Asp Lys Ser Arg Trp Gln Gln Gly Asn Val Phe
465 470 475 480

Ser Cys Ser Val Met His Glu Ala Leu His Asn His Tyr Thr Gln Lys
485 490 495

Ser Leu Ser Leu Ser Pro Gly Lys
500

<210> SEQ ID NO 148
<211> LENGTH: 1515
<212> TYPE: DNA
<213> ORGANISM: Artificial
<220> FEATURE:
<223> OTHER INFORMATION: DNA encoding GPVI-Fc fusion protein of Figure 7

<400> SEQUENCE: 148
atgtctccat ccccgaccgc cctcttctgt cttgggctgt gtctggggcg tgtgccagcg      60
cagagtggac cgctccccaa gccctccctc aggctctgc ccagctccct ggtgcccctg     120
gagaagccag tgaccctccg gtgccaggga cctccgggcg tggacctgta ccgcctggag     180
aagctgagtt ccagcaggta ccaggatcag gcagtcctct tcatcccggc catgaagaga     240
agtctggctg acgctaccg ctgctcctac cagaacggaa gcctctggtc cctgcccagc     300
gaccagctgg agctcgttgc cacgggagtt tttgccaaac cctcgctctc agcccagccc     360

```
ggcccggcgg tgtcgtcagg aggggacgta accctacagt gtcagactcg gtatggcttt    420
gaccaatttg ctctgtacaa ggaagggac cctgcgccct acaagaatcc cgagagatgg      480
taccgggcta gtttccccat catcacggtg accgccgccc acagcggaac ctaccgatgc    540
tacagcttct ccagcaggga cccatacctg tggtcggccc ccagcgaccc cctggagctt    600
gtggtcacag gaacctctgt gaccccagc cggttaccaa cagaaccacc ttcctcggta     660
gcagaattct cagaagccac cgctgaactg accgtctcat tcacaaacaa agtcttcaca    720
actgagactt ctaggagtat caccaccagt ccaaaggagt cagactctcc agctggtcct    780
gcccgccagt actacaccaa gggcaacggc ggccgcgagt ccaaatcttg tgacaaaact    840
cacacatgcc caccgtgccc agcacctgaa ctcctggggg gaccgtcagt cttcctcttc    900
cccccaaaac ccaaggacac cctcatgatc tcccggaccc ctgaggtcac atgcgtggtg    960
gtggacgtga gccacgaaga ccctgaggtc aagttcaact ggtacgtgga cggcgtggag   1020
gtgcataatg ccaagacaaa gccgcgggag gagcagtaca acagcacgta ccgtgtggtc   1080
agcgtcctca ccgtcctgca ccaggactgg ctgaatggca aggagtacaa gtgcaaggtc   1140
tccaacaaag ccctcccagc ccccatcgag aaaaccatct ccaaagccaa agggcagccc   1200
cgagagccac aggtgtacac cctgccccca tcccgggatg agctgaccaa gaaccaggtc   1260
agcctgacct gcctggtcaa aggcttctat cccagcgaca tcgccgtgga gtgggagagc   1320
aatgggcagc cggagaacaa ctacaagacc acgcctcccg tgctggactc cgacggctcc   1380
ttcttcctct acagcaagct caccgtggac aagagcaggt ggcagcaggg gaacgtcttc   1440
tcatgctccg tgatgcatga ggctctgcac aaccactaca cgcagaagag cctctccctg   1500
tctccgggta aatga                                                    1515
```

<210> SEQ ID NO 149
<211> LENGTH: 126
<212> TYPE: PRT
<213> ORGANISM: Rattus sp.

<400> SEQUENCE: 149

```
Glu Val Lys Leu Gln Glu Ser Gly Gly Gly Leu Val Gln Pro Gly Arg
1               5                   10                  15

Ser Leu Lys Leu Ser Cys Thr Ala Ser Gly Phe Thr Phe Ser Asp Tyr
            20                  25                  30

Phe Met Ser Trp Val Arg Gln Ala Pro Thr Arg Gly Leu Glu Trp Val
        35                  40                  45

Ala Ser Ile Ser Ser Gly Gly Ala Ser Ala Tyr Trp Arg Asp Ser Val
    50                  55                  60

Lys Gly Arg Phe Thr Ile Ser Arg Asp Asn Ala Lys Ser Ala Leu Tyr
65                  70                  75                  80

Leu Gln Met Asp Ser Leu Arg Ser Glu Asp Thr Ala Thr Tyr Phe Cys
                85                  90                  95

Ala Arg Gly Glu Leu Asp Phe Asp Tyr Trp Gly Gln Gly Val Met Val
            100                 105                 110

Ala Val Ser Ser Ala Glu Thr Thr Pro Pro Ser Val Tyr Pro
        115                 120                 125
```

<210> SEQ ID NO 150
<211> LENGTH: 378
<212> TYPE: DNA
<213> ORGANISM: Rattus sp.

<400> SEQUENCE: 150

```
gaggtgaagc tgcaggagtc aggggaggc ttagtgcagc ctggaaggtc cttgaaactc      60
tcctgtacag cctcaggatt cactttcagt gactatttca tgtcctgggt ccgccaggct    120
ccaacgcgtg gtctggagtg ggtcgcatcc attagttctg gtggtgctag cgcttactgg    180
cgagactccg tgaagggccg attcactatc tccagagata tgcaaaaag cgccctatac     240 ctgcaaatgg acagtctgag gtctgaggac acggccactt atttctgtgc aagaggggag    300
ctcgactttg attactgggg ccaaggagtc atggtcgcag tctcctctgc tgaaacgaca    360
cccccatctg tctatccg                                                  378
```

<210> SEQ ID NO 151
<211> LENGTH: 113
<212> TYPE: PRT
<213> ORGANISM: Rattus sp.

<400> SEQUENCE: 151

```
Ala Asp Pro Asn Ser Thr Leu Leu Ser Ala Ser Val Gly Asp Arg Val
1               5                   10                  15

Thr Leu Asn Cys Thr Ala Ser Gln Asn Val Tyr Lys Asn Leu Ala Trp
            20                  25                  30

Tyr Gln Gln Lys Leu Gly Glu Ala Pro Arg Leu Leu Leu Tyr Ser Ala
        35                  40                  45

Asn Ser Gln Thr Gly Ile Pro Ser Arg Phe Ser Gly Ser Gly Ser Gly
    50                  55                  60

Pro Asp Phe Thr Leu Thr Ile Ser Ser Leu Gln Pro Glu Asp Val Ala
65                  70                  75                  80

Ser Tyr Phe Cys Gln Gln Tyr Tyr Ser Gly Asn Thr Phe Gly Ala Gly
                85                  90                  95

Thr Lys Leu Glu Leu Lys Arg Ala Asp Ala Ala Pro Thr Val Ser Ile
            100                 105                 110

Phe
```

<210> SEQ ID NO 152
<211> LENGTH: 342
<212> TYPE: DNA
<213> ORGANISM: Rattus sp.

<400> SEQUENCE: 152

```
gctgacccaa actccactct cctgtctgca tctgtgggag acagagtcac tctcaactgc      60
acagcaagtc agaatgttta taagaactta gcctggtatc agcaaaagct tggagaagct    120
cccagactcc tgctttatag tgccaacagt ttgcaaacgg gcatcccatc acggttcagt    180
ggcagtggat ctggtccaga tttcacactc accatcagca gcctgcagcc tgaagatgtt    240
gcctcatatt tctgccagca gtattatagc gggaacacgt ttggagctgg gaccaagctg    300
gaactcaaac gggctgatgc tgcaccaact gtatctatct tc                       342
```

<210> SEQ ID NO 153
<211> LENGTH: 339
<212> TYPE: PRT
<213> ORGANISM: Homo sapiens

<400> SEQUENCE: 153

```
Met Ser Pro Ser Pro Thr Ala Leu Phe Cys Leu Gly Leu Cys Leu Gly
1               5                   10                  15

Arg Val Pro Ala Gln Ser Gly Pro Leu Pro Lys Pro Ser Leu Gln Ala
            20                  25                  30

Leu Pro Ser Ser Leu Val Pro Leu Glu Lys Pro Val Thr Leu Arg Cys
```

```
                  35                  40                  45
Gln Gly Pro Pro Gly Val Asp Leu Tyr Arg Leu Glu Lys Leu Ser Ser
 50                  55                  60

Ser Arg Tyr Gln Asp Gln Ala Val Leu Phe Ile Pro Ala Met Lys Arg
 65                  70                  75                  80

Ser Leu Ala Gly Arg Tyr Arg Cys Ser Tyr Gln Asn Gly Ser Leu Trp
                 85                  90                  95

Ser Leu Pro Ser Asp Gln Leu Glu Leu Val Ala Thr Gly Val Phe Ala
                100                 105                 110

Lys Pro Ser Leu Ser Ala Gln Pro Gly Pro Ala Val Ser Ser Gly Gly
                115                 120                 125

Asp Val Thr Leu Gln Cys Gln Thr Arg Tyr Gly Phe Asp Gln Phe Ala
130                 135                 140

Leu Tyr Lys Glu Gly Asp Pro Ala Pro Tyr Lys Asn Pro Glu Arg Trp
145                 150                 155                 160

Tyr Arg Ala Ser Phe Pro Ile Ile Thr Val Thr Ala Ala His Ser Gly
                165                 170                 175

Thr Tyr Arg Cys Tyr Ser Phe Ser Ser Arg Asp Pro Tyr Leu Trp Ser
                180                 185                 190

Ala Pro Ser Asp Pro Leu Glu Leu Val Val Thr Gly Thr Ser Val Thr
                195                 200                 205

Pro Ser Arg Leu Pro Thr Glu Pro Pro Ser Ser Val Ala Glu Phe Ser
                210                 215                 220

Glu Ala Thr Ala Glu Leu Thr Val Ser Phe Thr Asn Lys Val Phe Thr
225                 230                 235                 240

Thr Glu Thr Ser Arg Ser Ile Thr Thr Ser Pro Lys Glu Ser Asp Ser
                245                 250                 255

Pro Ala Gly Pro Ala Arg Gln Tyr Tyr Thr Lys Gly Asn Leu Val Arg
                260                 265                 270

Ile Cys Leu Gly Ala Val Ile Leu Ile Ile Leu Ala Gly Phe Leu Ala
                275                 280                 285

Glu Asp Trp His Ser Arg Arg Lys Arg Leu Arg His Arg Gly Arg Ala
                290                 295                 300

Val Gln Arg Pro Leu Pro Pro Leu Pro Pro Leu Pro Gln Thr Arg Lys
305                 310                 315                 320

Ser His Gly Gly Gln Asp Gly Arg Gln Asp Val His Ser Arg Gly
                325                 330                 335

Leu Cys Ser

<210> SEQ ID NO 154
<211> LENGTH: 2263
<212> TYPE: DNA
<213> ORGANISM: Homo sapiens

<400> SEQUENCE: 154
acagagctca ggacagggct gaggaaccat gtctccatcc ccgaccgccc tcttctgtct      60
tgggctgtgt ctggggcgtg tgccagcgca gagtggaccg ctccccaagc cctccctcca     120
ggctctgccc agctccctgg tgcccctgga aagccagtga ccctccggt gccagggacc      180 tccgggcgtg gacctgtacc gcctggagaa gctgagttcc agcaggtacc aggatcaggc     240
agtcctcttc atcccggcca tgaagagaag tctggctgga cgctaccgct gctcctacca     300
gaacggaagc ctctggtccc tgcccagcga ccagctggag ctcgttgcca cgggagtttt     360
tgccaaaccc tcgctctcag cccagcccgg cccggcggtg tcgtcaggag gggacgtaac     420
```

```
cctacagtgt cagactcggt atggctttga ccaatttgct ctgtacaagg aaggggaccc      480
tgcgccctac aagaatcccg agagatggta ccgggctagt ttccccatca tcacggtgac      540
cgccgcccac agcggaacct accgatgcta cagcttctcc agcagggacc catacctgtg      600
gtcggccccc agcgaccccc tggagcttgt ggtcacagga acctctgtga cccccagccg      660
gttaccaaca gaaccacctt cctcggtagc agaattctca gaagccaccg ctgaactgac      720
cgtctcattc acaaacaaag tcttcacaac tgagacttct aggagtatca ccaccagtcc      780
aaaggagtca gactctccag ctggtcctgc ccgccagtac tacaccaagg caacctggt       840 ccggatatgc ctcggggctg tgatcctaat aatcctggcg gggtttctgg cagaggactg      900
gcacagccgg aggaagcgcc tgcggcacag gggcagggct gtgcagaggc cgcttccgcc      960
cctgccgccc ctcccgcaga cccggaaatc acacggggt caggatggag ccgacagga      1020 tgttcacagc cgcgggttat gttcatgacc gctgaacccc aggcacggtc gtatccaagg     1080
gagggatcat ggcatgggag cgactcaaa gactggcgtg tgtggagcgt ggaagcagga      1140
gggcagaggc tacagctgtg aaacgaggc catgctgcct cctcctggtg ttccatcagg      1200
gagccgttcg gccagtgtct gtctgtctgt ctgcctctct gtctgagggc accctccatt     1260
tgggatggaa ggaatctgtg agaccccat cctcctccct gcacactgtg gatgacatgg      1320
taccctggct ggaccacata ctggcctctt tcttcaacct ctctaatatg gctccagac      1380 ggatctctaa ggttcccagc tctcagggtt gactctgttc catcctctgt gcaaaatcct     1440
cctgtgcttc cctttggccc tctgtgctct tgtctggttt tccccagaaa ctctcaccct     1500
cactccatct cccactgcgg tctaacaaat ctcctttcgt ctctcagaac gggtcttgca     1560
ggcagtttgg gtatgtcatt cattttcctt agtgtaaaac tagcacgttg cccgcttccc     1620
ttcacattag aaaacaagat cagcctgtgc aacatggtga aacctcatct ctaccaacaa     1680 aacaaaaaa cacaaaaatt agccaggtgt ggtggtgcat ccctatactc ccagcaactc      1740 gggggggctga ggtgggagaa tggcttgagc ctggaggca gaggttgcag tgagctgaga     1800
tcacaccact gcactctagc tcgggtgacg aagcctgacc ttgtctcaaa aaatacaggg     1860
atgaatatgt caattacccct gatttgatca tagcacgttg tatacatgta ctgcaatatt    1920
gctgtccacc ccataaatat gtacaattat gtatacattt ttaaaatcat aaaaataaga    1980
taatgcaccg tctccacccc tctcatattt actttctgaa ggaaatgtta ggtcttctca     2040
aggtaaagtt ctatatttat tatagcgttt aggcatttct tgaccatcta atgagtgtaa     2100
aactgtacca ctgggccaag tgcagtggat catgtctgta atcctagcac tgtgggaggc     2160
caaggcagga ggatcgcttg agcccaggag ttcaagacca gcctgggcaa catagtgaga     2220
ccccatctct acttaaaata aagaagtaaa aattgtttta aaa                       2263
```

<210> SEQ ID NO 155
<211> LENGTH: 37
<212> TYPE: DNA
<213> ORGANISM: Artificial
<220> FEATURE:
<223> OTHER INFORMATION: Primer

<400> SEQUENCE: 155
cgcggggcgg ccgcgagtcc aaatcttgtg acaaaac                              37

<210> SEQ ID NO 156
<211> LENGTH: 33
<212> TYPE: DNA
<213> ORGANISM: Artificial
<220> FEATURE:

```
<223> OTHER INFORMATION: Primer

<400> SEQUENCE: 156
gcgggaagct tcatttacc cggagacagg gag                                33

<210> SEQ ID NO 157
<211> LENGTH: 36
<212> TYPE: DNA
<213> ORGANISM: Artificial
<220> FEATURE:
<223> OTHER INFORMATION: Primer

<400> SEQUENCE: 157
gcggggagat ctaccaccat gtctccatcc ccgacc                            36

<210> SEQ ID NO 158
<211> LENGTH: 34
<212> TYPE: DNA
<213> ORGANISM: Artificial
<220> FEATURE:
<223> OTHER INFORMATION: Primer

<400> SEQUENCE: 158
cgcggggcgg ccgccgttgc ccttggtgta gtac                              34

<210> SEQ ID NO 159
<211> LENGTH: 35
<212> TYPE: DNA
<213> ORGANISM: Artificial
<220> FEATURE:
<223> OTHER INFORMATION: Primer

<400> SEQUENCE: 159 gcggggcta gcaccaccat gtctccatcc ccgac                              35

<210> SEQ ID NO 160
<211> LENGTH: 34
<212> TYPE: DNA
<213> ORGANISM: Artificial
<220> FEATURE:
<223> OTHER INFORMATION: Primer

<400> SEQUENCE: 160 cgcggggat cctcatttac ccggagacag ggag                               34

<210> SEQ ID NO 161
<211> LENGTH: 25
<212> TYPE: PRT
<213> ORGANISM: Homo sapiens

<400> SEQUENCE: 161

Leu Gly Arg Val Pro Ala Gln Ser Gly Pro Leu Pro Lys Pro Ser Leu
1               5                   10                  15

Gln Ala Leu Pro Ser Ser Leu Val Pro
            20                  25

<210> SEQ ID NO 162
<211> LENGTH: 15
<212> TYPE: PRT
<213> ORGANISM: Homo sapiens

<400> SEQUENCE: 162

Leu Phe Ile Pro Ala Met Lys Arg Ser Leu Ala Gly Arg Tyr Arg
1               5                   10                  15
```

<210> SEQ ID NO 163
<211> LENGTH: 15
<212> TYPE: PRT
<213> ORGANISM: Homo sapiens

<400> SEQUENCE: 163

Ala Thr Gly Val Phe Ala Lys Pro Ser Leu Ser Ala Gln Pro Gly
1               5                   10                  15

<210> SEQ ID NO 164
<211> LENGTH: 7
<212> TYPE: PRT
<213> ORGANISM: Homo sapiens

<400> SEQUENCE: 164

Gln Ser Gly Pro Leu Pro Lys
1               5

<210> SEQ ID NO 165
<211> LENGTH: 9
<212> TYPE: PRT
<213> ORGANISM: Homo sapiens

<400> SEQUENCE: 165

Gln Ser Gly Pro Leu Pro Lys Pro Ser
1               5

<210> SEQ ID NO 166
<211> LENGTH: 11
<212> TYPE: PRT
<213> ORGANISM: Homo sapiens

<400> SEQUENCE: 166

Gln Ser Gly Pro Leu Pro Lys Pro Ser Leu Gln
1               5                   10

<210> SEQ ID NO 167
<211> LENGTH: 15
<212> TYPE: PRT
<213> ORGANISM: Homo sapiens

<400> SEQUENCE: 167

Gln Ser Gly Pro Leu Pro Lys Pro Ser Leu Gln Ala Leu Pro Ser
1               5                   10                  15

<210> SEQ ID NO 168
<211> LENGTH: 17
<212> TYPE: PRT
<213> ORGANISM: Homo sapiens

<400> SEQUENCE: 168

Gln Ser Gly Pro Leu Pro Lys Pro Ser Leu Gln Ala Leu Pro Ser Ser
1               5                   10                  15

Leu

<210> SEQ ID NO 169
<211> LENGTH: 19
<212> TYPE: PRT
<213> ORGANISM: Homo sapiens

<400> SEQUENCE: 169

Gln Ser Gly Pro Leu Pro Lys Pro Ser Leu Gln Ala Leu Pro Ser Ser
1               5                   10                  15

Leu Val Pro

```
<210> SEQ ID NO 170
<211> LENGTH: 11
<212> TYPE: PRT
<213> ORGANISM: Homo sapiens

<400> SEQUENCE: 170

Ile Pro Ala Met Lys Arg Ser Leu Ala Gly Arg
1               5                   10

<210> SEQ ID NO 171
<211> LENGTH: 9
<212> TYPE: PRT
<213> ORGANISM: Homo sapiens

<400> SEQUENCE: 171

Phe Ala Lys Pro Ser Leu Ser Ala Gln
1               5
```

ANTIBODIES WHICH BIND TO EPITOPES OF GLYCOPROTEIN VI

PRIORITY CLAIM

This application is a continuation of U.S. patent application Ser. No. 11/446,537, filed on Jun. 2, 2006, which is a continuation-in-part of U.S. application Ser. No. 11/009,106, filed Dec. 10, 2004 now U.S. Pat. No. 7,531,178, which is a continuation-in-part of U.S. application Ser. No. 10/489,053, filed Sep. 24, 2004 now U.S. Pat. No. 7,512,543, which is the national stage under 35 U.S.C. §371 of International Application No. PCT/EP2003/05929, filed Jun. 5, 2003, which was published in English under PCT Article 2(2), and which claims the benefit of European Patent Application No. EP 02 012 742.9, filed Jun. 7, 2002. This application is also a continuation-in-part of International Application No. PCT/EP2004/013779, which was published in English under PCT Article 2(2), and which claims the benefit of European Patent Application No. 03 027 772.7, filed Dec. 3, 2003. This application also claims the benefit under 35 U.S.C. §119 of Great Britain Application No. 0511590.2, filed Jun. 7, 2005. All of the prior applications are incorporated herein by reference in their entirety.

FIELD OF THE INVENTION

This disclosure relates in aspects to agents which bind to epitopes of glycoprotein VI, and uses thereof. The disclosure also concerns peptides comprising such epitopes and methods of using them.

The present invention relates also to an immunoadhesin comprising a specific glycoprotein VI domain. The immunoadhesin of the invention is obtainable by a specific process providing the immunoadhesin in the form of a dimer. The present invention also relates to the use of the immunoadhesin of glycoprotein VI for the preparation of a medicament for the prevention of intraarterial thrombosis in a specific group of patients. Moreover, the present invention relates to the use of the immunoadhesin of glycoprotein VI for the preparation of a medicament for the prevention and treatment of atheroprogression. The present invention also relates to the use of the immunoadhesin of glycoprotein VI for the preparation of a medicament for the prevention and treatment of chronic progression of atherosclerosis in diabetic patients. The present invention also relates to in vitro screening methods for an inhibitor of GPVI mediated adhesion of platelets to active intravascular lesions.

The present invention also relates to a specific inhibitor of human platelet glycoprotein VI (GPVI). The inhibitor may be an optionally humanized antibody or function-conservative fragments or variants thereof, a specific fusion protein or conjugate. The inhibitor may comprise a specific amino acid sequence or a function conservative variant or fragment thereof. Moreover, the present invention relates to pharmaceutical compositions containing the specific inhibitor of the invention. The present invention also relates to hybridomas expressing the antibody of the present invention. Furthermore, the present invention relates to the use of the specific inhibitor of glycoprotein VI for the preparation of a medicament for the prevention of acute and chronic vascular diseases associated with intraarterial and/or intravenous thrombosis, such as acute coronary syndrome, acute carotid artery syndrome, acute myocardial infarction, acute cerebral stroke and chronic coronary or peripheral vessel disease. The present invention also relates to a process for preparing the antibody of the invention and to a process for preparing a specific fragment of the antibody of the present invention.

The present disclosure further relates to agents which bind to glycoprotein VI (GPVI) protein or sequences thereof. More particularly, though without limitation, the invention concerns agents which bind one or more epitopes of human GPVI. The invention also relates to certain epitopes of human GPVI, methods of identifying or screening agents which bind to the epitopes. The invention also relates to the use of agents for treatment or prevention of diseases arising from processes of blood platelet aggregation, as well as other subject matter.

BACKGROUND OF THE INVENTION

Acute coronary or carotid syndromes are a major cause of death in Western societies. Even in case of an initial survival of such a cardiovascular event, many patients suffer from life-threatening complications such as intravascular thrombosis leading to further myocardial infarction or stroke.

The interaction between collagen and platelets is one of the first events of the normal haemostatic response to injury. Collagen is the major extracellular matrix protein present in the subendothelium of blood vessels. Collagen binds directly to platelets via specific platelet receptors such as integrin, collagen receptor, glycoprotein IV and GPVI.

The disruption of the atherosclerotic plaque initiates a cascade of events culminating in arterial thrombosis and ischemia of the downstream tissue, precipitating diseases such as myocardial infarction or ischemic stroke. The first response to vascular injury is adhesion of circulating platelets to exposed subendothelial matrix proteins, which triggers subsequent platelet aggregation. Among the macromolecular components of the subendothelial layer, fibrillar collagen is considered the most thrombogenic constituent, as it acts as a strong activator of platelets and supports platelet adhesion both in vitro and in vivo (Baumgartner, H. R. (1977) Platelet interaction with collagen fibrils in flowing blood. I. Reaction of human platelets with alpha chymotrypsin-digested subendothelium. *Thromb Haemost* 37, 1-16; Clemetson, K. J., Clemetson, J. M. (2001) Platelet collagen receptors. *Thromb. Haemost.* 86, 189-197; Massberg, S., Gawaz, M., Grüner, S., Schulte, V., Konrad, I., Zohlnhöfer, D., Heinzmann, U., Nieswandt, B. (2003) A crucial role of glycoprotein VI for platelet recruitment to the injured arterial wall in vivo. *J. Exp. Med.* 197, 41-49).

Intravascular thrombosis is the result of aggregation of platelets in a vessel whereby the blood flow in the vessel may be seriously reduced or even completely inhibited. Specifically, the disruption of an atherosclerotic plaque initiates a cascade of events culminating in arterial thrombosis and ischemia of the downstream tissue, precipitating diseases such as myocardial infarction or ischemic stroke. The first response to vascular injury is adhesion of circulating platelets to exposed subendothelial matrix proteins, which triggers subsequent platelet aggregation. Among the macromolecular components of the subendothelial layer fibrillar collagen is considered the most thrombogenic constituent, as it acts as a strong activator of platelets and supports platelet adhesion both in vitro and in vivo (1-3).

The platelet membrane proteins, which have been reported to be putative collagen receptors, may be divided into those which interact indirectly with collagen through collagen-bound von Willebrand factor (vWf), including GPIbα and the integrin $\alpha_{IIb}\beta_3$, and those which interact directly with collagen including GPVI, the integrin $\alpha_2\beta_1$ and CD36 (reviewed in (2)). Only recently, the platelet glycoprotein VI (GPVI) has been identified as the major platelet collagen receptor (4).

GPVI is a 60-65 kDa type I transmembrane glycoprotein, which belongs to the immunoglobulin superfamily (5; 6). In human and mouse platelets GPVI forms a complex with the FcR γ-chain at the cell surface (7; 8). Ligand binding to GPVI triggers tyrosine phosphorylation of the ITAM motif of the Fc receptor γ chain initiating downstream signaling via Syk kinases, LAT, SLP-76, and phospholipase C (9-13). Platelets deficient in GPVI show loss of collagen-induced adhesion and aggregation in vitro (4; 14). Likewise, function blocking anti-GPVI monoclonal antibodies attenuate ex vivo platelet aggregation in response to collagen and collagen-related peptide CRP, which mimics collagen triple helix (15; 16).

It is known that the problem of complications due to the aggregation of platelets can be addressed by administering inhibitors of platelet aggregation. For the treatment of acute coronary syndromes, GP IIb/IIIa inhibitors such as ReoPro significantly improve the outcome of patients. However, a recent meta-analysis of clinical trials revealed a significant remaining risk for death or myocardial infarction despite optimal antithrombotic intervention (Boersma E, Harrington R A, Moliterno D J, White H, Theroux P, Van de Werf F, de Torbal A, Armstrong P W, Wallentin L C, Wilcox R G, Simes J, Califf R M, Topol E J, Simoons M L. Platelet glycoprotein IIb/IIIa inhibitors in acute coronary syndromes: a meta-analysis of all major randomised clinical trials. Lancet 2002; 359:189-98). Specific severe side effects of this therapeutic regimen are bleeding complications. These occurred in 2.4% of the patients with the most severe form of intracranial bleeding occurring in almost 0.1% of the treated patients. Several mechanistic shortcomings of the GP IIb/IIIa receptor blockade have been revealed which account for suboptimal effectivity and side effects. (Dickfeld T, Ruf A, Pogatsa-Murray G, Muller I, Engelmann B, Taubitz W, Fischer J, Meier O, Gawaz M. Differential anti-platelet effects of various glycoprotein IIb-IIIa antagonists. Thromb Res. 2001; 101:53-64. Gawaz M, Neumann F J, Schomig A. Evaluation of platelet membrane glycoproteins in coronary artery disease: consequences for diagnosis and therapy. Circulation. 1999; 99:E1-E11). Besides their ability to aggregate, platelets play a crucial role for the induction of atherosclerosis (Ruggeri Z M. Platelets in atherothrombosis. Nature Medicine 2002; 8: 1227-1234). The interaction of platelets with the endothelium via secretion of a wide variety of different vaso-active and pro-inflammatory substances from intracellular storage vesicles is of prominent importance (Massberg S, Brand K, Grüner S, Page S, Müller E, Müller I, Bergmeier W, Richter T, Lorenz M, Konrad I, Nieswandt B, Gawaz M. A Critical Role of Platelet Adhesion in the Initiation of Atherosclerotic Lesion Formation. J. Exp. Med. 2002, 196, Number 7: 887-896). Moreover GPIIb/IIIa antagonists have no influence on the release mechanism of platelet or even enhance pro-inflammatory responses such CD 40L or P-Selectin expression (for review see Bhatt D L and Topol E J. Scientific and therapeutic advances in antiplatelet therapy. Nature Reviews Drug Discovery 2003; 2: 15-28).

The inhibition of platelet aggregation leads to a general impairment of the platelets with regard to their ability to aggregate. Accordingly, not only the undesired thrombosis formation is influenced, but also the general ability of the platelets to terminate bleeding. Therefore, the administration of inhibitors of platelet aggregation inherently leads to severe side effects such as bleedings which may cause further life-threatening complications. These side effects are of course still more problematic in patients suffering from diabetes.

Diabetes is one of the main risk factors for atherosclerosis. Additionally diabetes constitutes an increased risk of life threatening complications and excess morbidity in patients presenting with acute vascular and especially coronary syndromes. Diabetic patients with unstable angina present with a higher incidence of plaque ulceration and intracoronary thrombosis compared to non-diabetic patients. (Biondo-Zoccai G G L; Abbate A; Liuzzo G, Biasucci L: Atherothrombosis, inflammation, and diabetes. J Am Coll Cardiol 41; 1071-1077; 2003).

It is increasingly recognized that platelets are a major trigger for the progression of atherosclerosis. The link between increased atheroprogression, and increased platelet responsiveness and diabetes is so far an unresolved problem. Diabetic patients suffer from acute vascular complications independent of the degree of atherosclerosis indicative of different presently unknown mechanisms for platelet activation in the development of diabetic acute vascular complications and atherosclerotic acute vascular complications.

Antibodies directed against GPVI have been previously reported to induce platelet activation (Schulte, V., Snell, D., Bergmeier, W., Zirngibl, H., Watson, S. P., Nieswandt, B. (2001) Evidence for two distinct epitopes within collagen for activation of murine platelets. J. Biol. Chem. 276, 364-368) and immuno-thrombocytopenia, hampering their use in the clinical setting.

WO 01/16321 and WO 01/00810 and WO 00/68377 disclose a DNA and protein sequence of the human GPVI receptor. WO 03/05020 discloses specific binding members directed against the human glycoprotein VI (GPVI) and specific inhibitors of collagen-induced platelet aggregation. Antibodies of the single chain format and in particular single chain antibodies with a particular sequence are also disclosed. EP 1224942 and EP 1228768 disclose a monoclonal anti-GPVI antibody JAQ1, which specifically binds to mouse GPVI, for the treatment of thrombotic disease. JAQ1 antibody induces irreversible internalization of the GPVI receptor on mouse platelets. This mechanism has only been observed in mice and cannot be used in a patient. EP 1224942 does not disclose the humanized form of JAQ1 and does not provide data in man or human platelets. WO 03/008454 and WO 01/00810 disclose polypeptides, proteins and fusion proteins of GPVI as a pharmaceutical composition. Moreover, antibodies and single chains against GPVI are suggested.

Therefore, the present disclosure aims to provide a medicament which is useful for avoiding life-threatening complications subsequent to an acute coronary or carotid syndrome while maintaining the potency of the blood for hemostasis.

Moreover, the present disclosure aims to provide an active agent useful for preventing or treating chronic atherosclerotic disease. Moreover, the present disclosure aims to provide an inhibitor of glycoprotein VI, notably human glycoprotein VI, which does not activate the GPVI receptor by intrinsic antibody activity and which does not induce immuno-thrombocytopenia. Moreover, the present disclosure aims to provide an inhibitor for the release mechanism of platelets and the expression of pro-inflammatory responses.

The present disclosure aims to provide a medicament for the treatment or prevention of atheroprogression.

The present disclosure aims to provide a medicament for the treatment of diabetes, notably complications associated with diabetes.

The present disclosure aims to provide an in vitro screening method for inhibitors of adhesion of platelets to intravascular lesions.

The present invention is directed to a purely inhibitory anti-GPVI antibody or function-conservative fragments or variants thereof for the treatment of acute vascular diseases. Moreover, the invention addresses the problem of providing a pharmaceutical composition for the treatment of acute vascular complications such as intra-vascular thrombosis especially in patients with atherosclerosis and/or acute endothelial lesions. Moreover, the present invention addresses the problem of providing a pharmaceutical composition for the treatment of chronic coronary artery and peripheral vessel disease. The present invention provides a pharmaceutical composition for the treatment of acute coronary, carotid artery and peripheral vessel diseases as well as chronic atherosclerosis, wherein the medicament contains a specific optionally humanized antibody hGP 5C4, or a fragment thereof, notably an Fab fragment, a function-conservative variant thereof, a fusion protein or conjugate thereof.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE DISCLOSURE

The present disclosure provides the first direct in vivo evidence indicating that GPVI is in fact strictly required in the process of platelet recruitment under physiological shear stress following vascular injury. In different mouse models of endothelial denudation both inhibition or absence of GPVI virtually abolished platelet-vessel wall interactions and platelet aggregation, identifying GPVI as the major determinant of arterial thrombus formation. This indicates that inhibition of GPVI-ligand interactions prevents arterial thrombosis in the setting of atherosclerosis. The present invention uses the antithrombotic potential of a specific soluble form of GPVI. Specifically, a fusion protein is provided, which contains the extracellular domain of GPVI and a human N-terminal Fc tag. The soluble form of human GPVI specifically binds to collagen with high affinity and attenuated platelet adhesion to immobilized collagen in vitro and to sites of vascular injury in vivo. Accordingly, the present invention is based on the recognition that the precondition for intraarterial thrombosis as an acute clinical complication is the initial adhesion of platelets to active lesions in the vessel walls. The present inventors have recognised that platelet adhesion to subendothelial matrix collagen at a lesion of the vessel wall by the glycoprotein VI (GPVI) receptor represents the key event for the formation of thrombosis. The inhibition of the adhesion of platelets to subendothelial matrix collagen of the fusion protein of the invention is therefore capable of not only preventing adhesion of platelets to an active lesion, but also to prevent aggregation of platelets at the active lesion. Thereby, the formation of intravascular thrombosis can be efficiently avoided without impairing the general ability of the platelets for aggregation.

It is surprising that the complex process of the formation of thrombosis may be inhibited by the inhibition of a single platelet receptor in view of the fact that different components of the subendothelial layers are ligands and activators of platelets such as laminin, fibronectin, von Willebrand factor (vWf) and collagen. Moreover, a wide variety of receptors on the platelets had been proposed by in vitro examinations, but the relevant receptor or receptor combinations which influence adhesion of platelets to lesions in vivo had not been known before.

The present invention is also based on the recognition that GP VI is a major meditor of platelet activity for the progression of atherosclerosis. It is demonstrated that inhibition of the collagen-medited GPVI activation attenuates atheroprogression in atherosclerosis prone Apo e−/− mice (see FIG. 16). Moreover, it is demonstrated that the platelets from diabetic patients, who are also prone for advanced atherosclerosis and increased thrombotic complications show an increased expression of the GPVI-coreceptor Fc-receptor. Therefore platelets from diabetics might show increased responsiveness to collagen stimulation leading to the clinically observed increased thrombotic complications in unstable angina, where collagen is uncovered from subendothelial vascular layers by plaque rupture or endothelial denudation.

The present invention provides therefore a treatment of atheroprogression in patients, notably in patients suffering from diabetes. Moreover, the invention provides a medicament for the treatment of acute vascular complications such as intravascular thrombosis especially in patients with diabetes. Included in the invention is an immunoadhesin Fc-GPVI-nt which is a potent therapeutic tool to attenuate atheroprogression and increased responsiveness of platelets to collagen via the GPVI receptor. Therefore, Fc-GPVI-nt is a medicament for treatment of atherosclerosis and particularly for the treatment of atherosclerotic complications in diabetes.

In a first aspect of the present invention, there is provided a fusion protein comprising:
  a) a GPVI portion selected from an extracellular domain of glycoprotein VI (GPVI) and a variant thereof that is functional for binding to collagen; and
  b) an Fc portion selected from an Fc domain of an immunoglobulin and a functional conservative variant thereof, the extracellular domain or variant thereof and the Fc domain or variant thereof being fused via a linker characterised by the amino acid sequence Gly-Gly-Arg.

In one embodiment, the fusion protein is characterised by an amino acid sequence as shown in FIG. 7. The fusion protein according to the invention is obtained or obtainable by
(a) collecting 2 days after infection the culture supernatant of Hela cells infected with an adenovirus for the fusion protein of the invention coding for an amino acid sequence as shown in FIG. 7;
(b) centrifuging (3800 g, 30 min, 4° C.) the supernatant of step (a);
(c) filtrating (0.45 µm) the supernatant of step (b);
(d) precipitating the immunoadhesin by addition of 1 vol. ammonium sulfate (761 g/l) and stirring overnight at 4° C.;
(e) pelletizing the proteins by centrifugation (3000 g, 30 min, 4° C.)
(f) dissolving the pelletized proteins of step (e) in 0.1 Vol PBS and dialysed in PBS overnight at 4° C.;
(g) clarifying the protein solution by centrifugation (3000 g, 30 min, 4° C.);
(h) loading the solution of step (g) on a protein A column (HiTrap™ protein A HP, Amersham Pharmacia Biotech AB, Uppsala, Sweden);
(i) washing the column with binding buffer (20 mM sodium phosphate buffer pH 7.0, 0.02% $NaN_3$) until $OD_{280}<0.01$;
(k) eluting fractions with elution buffer (100 mM glycine pH 2.7)
(l) neutralizing the eluted fractions with neutralisation buffer (1 M Tris/HCl pH 9.0, 0.02% $NaN_3$);
(m) pooling the fractions;
(n) dialysing the pooled fractions in PBS overnight at 4° C.,
(o) aliquoting the dialysed product and freezing at −20° C.

Under the above conditions, the fusion protein is obtained as a covalently linked dimer of a molecular mass of 160 kDa as measured under non-reducing conditions by SDS-PAGE. Dimerisation of the fusion protein presumably occurs by inter-chain disulfide bonds of cysteins in a specific domain adjacent to the GPVI fragment of the amino acid sequence as shown in FIG. 7. The dimeric nature of the fusion protein depends at least from the presence of a specific region between the Fc portion and the GPVI portion as contained in FIG. 7, and the preparation process. A monomeric fusion protein is not useful as a therapeutic agent in practice since the inferior binding properties of a monomeric fusion protein as compared to the dimeric fusion protein would require administration of protein in an amount which is in the order of one magnitude larger than the amount of the dimeric fusion protein for obtaining a similar effect, cf. FIG. 9(e). The administration of large amounts of protein is, however, problematic from a therapeutic and economic point of view, in particular in the treatment of chronic disease.

The fusion protein of the invention is an immunoadhesin. It has a segment (a) that has the function of the extracellular domain of platelet GP VI. Said GPVI may be a mammalian GPVI, preferably it is human GPVI. Said function is preferably binding to the GP VI ligand collagen. The whole extracellular domain of GPVI may be used for said fusion protein or any fragments thereof provided said fragments are capable of binding to collagen. A variant of the fusion protein may have a modification at one or several amino acids of said fusion protein (e.g. glycosylation, phosphorylation, acetylation, disulfide bond formation, biotinylation, chromogenic labelling like fluorescein labelling etc.). Preferably, a variant is a homolog of said fusion protein. An engineered variant may be tested easily for its capability of binding to collagen using the methods disclosed herein. Most preferably, the polypeptide of residues 1 to 269 of SEQ ID NO: 147 (FIG. 7) is used as segment (a). However, said polypeptide may also be modified by exchanging selected amino acids or by truncating said sequence without abolishing said function.

Segment (b) of said fusion protein serves at least one of the following purposes: secretion of the fusion protein from cells that produce said fusion protein, providing segment (a) in a form (e.g. folding or aggregation state) functional for binding collagen, affinity purification of said fusion protein, recognition of the fusion protein by an antibody, providing favourable properties to the fusion protein when used as a medicament. Surprisingly and most importantly, segment (b) allows production of said fusion protein in mammalian, preferably human, cells and secretion to the cell supernatant in active form, i.e. in a form functional for binding to collagen. Segment (b) is most preferably an Fc domain of an immunoglobulin. Suitable immunoglobulins are IgG, IgM, IgA, IgD, and IgE. IgG and IgA are preferred. IgGs are most preferred. Said Fc domain may be a complete Fc domain or a function-conservative variant thereof. A variant of Fc is function-conservative if it retains at least one of the functions of segment (b) listed above. Most preferred is the polypeptide of residues 273 to 504 of SEQ ID NO: 147. It is, however, general knowledge that such a polypeptide may be modified or truncated without abolishing its function.

Segments (a) and (b) of the fusion protein of the invention may be linked by a linker. The linker may consist of about 1 to 100, preferably 1 to 10 amino acid residues. The linker of the amino acid sequence in FIG. 7 (SEQ ID NO: 147) is Gly-Gly-Arg.

Most preferably, said fusion protein has the amino acid sequence of SEQ ID NO: 147 (termed Fc-GPVI-nt herein).

FURTHER DISCLOSURE OF THE INVENTION

GPVI is a membrane bound protein expressed at the surface of platelets. Platelets bind to collagen via the extracellular domain of membrane bound GPVI. The present invention provides a fusion protein. The invention includes amongst other things fusion proteins which directly or indirectly inhibit collagen-induced platelet activation and have a longer plasma half-life than the extracellular domain of GPVI as an isolated protein. Included are fusion proteins containing an antibody-derived sequence, as in the case of proteins containing at least part of a heavy chain constant region (e.g. at least the hinge) linked to an active sequence (e.g. one having the inhibitory function described in the previous sentence) through a linker. The active sequence may to the N-terminal side of the linker and the antibody derived sequence to the C-terminal side.

Embodiments of the present invention reside in a protein which binds to collagen at the site at which the membrane bound GPVI binds to collagen.

Amongst the fusion proteins of the invention are those having an active part which binds to collagen competitively with platelet-bound GPVI linked, e.g. at its C-terminus, to a part which prolongs plasma half-life, e.g. an antibody derived sequence. Suitably, the two parts are linked through a linker; in embodiments the linker contains a hydrophilic amino acid and in other embodiments it contains a glycine, e.g. a polyglycine sequence. The part which prolongs plasma half life may contain at least one cysteine residue, e.g. two cysteine residues, whereby disulphide cross-links may form so that the protein may form a dimer.

In one class of proteins the linker comprises the amino acid sequence Gly-X-Z, where Z is a hydrophilic amino acid and X is any amino acid. In some embodiments, X is selected from Gly and Ala. In some embodiments, X may be Gly. In a class of proteins, Z may be selected from Arg, H is, Lys, Ser, Thr, Asp, Glu, Tyr, Asn and Gln. In some embodiments, Z may be selected from Arg, Ser, Lys and His: particularly Z is Arg.

The 20 common amino acids may be classified as hydrophobic, polar, positively charged and negatively charged as follows:

Hydrophobic Amino Acids
A=Ala=alanine
V=Val=valine
I=Ile=isoleucine
L=Leu=leucine
M=Met=methionine
F=Phe=phenylalanine
P=Pro=proline
W=Trp=tryptophan
Polar (Neutral or Uncharged) Amino Acids
N=Asn=asparagine
C=Cys=cysteine
Q=Gln=glutamine
G=Gly=glycine
S=Ser=serine
T=Thr=threonine
Y=Tyr=tyrosine
Positively Charged (Basic) Amino Acids
R=Arg=arginine
H=His=histidine
K=Lys=lysine
Negatively Charged Amino Acids
D=Asp=aspartic acid
E=Glu=glutamic acid.

Polar and charged amino acids may be considered hydrophilic, e.g. serine, arginine and lysine. One class of disclosed proteins comprises a linker having a hydrophilic amino acid selected from positively charged amino acids, e.g. arginine or lysine. A further class comprises a linker having a hydrophilic amino acid selected from negatively charged amino acids. A third class comprises a linker having a hydrophilic amino acid selected from polar uncharged charged amino acids.

The linker may contain additional amino acids to the N-terminal or C-terminal sides of Gly-X-Z, or both sides. Gly is one possible such amino acid. The linker may include the amino acid sequence Gly-Gly-Arg-Gly. Also to be mentioned are linkers comprising a polyglycine amino acid sequence e.g. containing 2, 3, 4, 5 or more contiguous glycine residues. In one embodiment, the linker comprises the amino acid sequence Gly-Arg-Gly.

In one class of proteins, the linker may comprise the amino acid sequence $X_1$-Gly-Z, where $X_1$ is not cysteine. $X_1$ may be Gly or Ala or another amino acid with a hydrophobic side chain, e.g. Val, Ile, Leu, Met, Phe, Pro or Trp. In other embodiments, $X_1$ is Asp, Gln, Ser, Thr or Tyr. The linker may contain additional amino acids to the N-terminal or C-terminal sides of $X_1$-Gly-Z, or both sides. Gly is one possible such amino acid.

In one class of proteins, the linker comprises the sequence Gly-Gly-Arg. Gly-Gly-Lys is another linker sequence.

In another class of proteins, the active sequence is at the N-terminal side of the linker and the antibody-derived sequence is at the C-terminal side of the linker. In a sub-class, the linker comprises at least one hydrophilic amino acid. In embodiments, the hydrophilic amino acid may be a residue Z as described above. Some linkers are of the amino acid sequence Gly-X-Z as previously described. Included are linkers containing at least one of the following sequences as well as 0, 1, 2, 3, 4, 5 or more additional amino acids:

```
Gly-Gly-Arg;

Gly-Gly-Ser;

Gly-Gly-His;

Gly-Gly-Lys;

Gly-Lys-Gly;

Ser-Gly-Arg;

Arg-Gly-Ser;

Gly-Arg-Arg;

Arg-Gly-Gly;

Gly-Ala-Arg;

Arg-Gly-Arg;
and

Arg-Gly-Gly-Ser.
```

Included are fusion proteins which comprise an antibody-derived polypeptide. In one class of protein, the antibody-derived polypeptide includes an Ig heavy chain constant part; in a sub-class of protein, the antibody-derived polypeptide includes a hinge region of an immunoglobulin and is functional to prolong the plasma half-life of the protein beyond that of a fusion protein which does not contain the antibody-derived polypeptide. In another embodiment, the antibody-derived polypeptide includes a hinge region and a CH2 region of an immunoglobulin. In one embodiment, the antibody-derived polypeptide includes a hinge region, a CH2 and CH3 region of an immunoglobulin. The antibody-derived polypeptide may be an Fc domain of an immunoglobulin, for example. Particular proteins comprise an antibody-derived polypeptide which is an Fc domain of an IgG molecule.

The IgG may be an IgG1.

In an alternative embodiment, the antibody-derived polypeptide is a polypeptide which has the properties of an Fc domain of an IgG molecule or a polypeptide which can confer such properties to a fusion protein. Such properties may include, for example, a prolonged serum half-life and thus the incorporation of such a sequence into a fusion protein confers a prolonged serum half-life on the fusion protein as compared to a protein which does not include the antibody-derived polypeptide.

The protein may be a dimer, for example a dimer containing disulfide bonds between Cys residues of two polypeptides. Typically, the dimer is a homodimer but heterodimers are not excluded. The dimer may be of a polypeptide containing at least part of an Fc hinge region, for example of a polypeptide as described above containing at least a CH2 region and a hinge region, such as CH2, CH3 and hinge regions, for example.

Thus polypeptides comprising conservative substitutions, insertions, or deletions, but which still retain the biological activity of the fusion protein of FIG. 7 (or SEQ ID NO: 147), are clearly to be understood to be within the scope of the invention.

The term "an extracellular domain of GPVI" includes fragments or analogues thereof which have the biological activity of the extracellular domain of GPVI as herein described. The biological activity of the extracellular domain of GPVI is considered to include, amongst others, collagen binding activity. It will be appreciated that fragments or analogues of GPVI may have greater or less binding affinity to collagen than the extracellular domain of GPVI, but nonetheless, will in practice have sufficient binding activity for the protein to be therapeutically useful.

The term "an Fc domain of an immunoglobulin" includes fragments or analogues thereof which have the properties of an Fc domain of an immunoglobulin as herein described.

Polynucleotides of the invention such as those described above, fragments of those polynucleotides, and variants of those polynucleotides with sufficient similarity to the non-coding strand of those polynucleotides to hybridise thereto e.g. under stringent conditions, are all aspects of the invention. Also included are nucleic acid sequences which differ from those described in the previous sentence by virtue of the degeneracy of the genetic code. Exemplary stringent hybridisation conditions are as follows: hybridisation at 42 DEG C in 5×SSC, 20 mM NaPO$_4$, pH 6.8, 50% formamide; and washing at 42 DEG C in 0.2×SSC. Those skilled in the art understand that it is desirable to vary these conditions empirically based on the length and the GC nucleotide base content of the sequences to be hybridised, and that formulae for determining such variation exist. See for example Sambrook et al, "Molecular Cloning: A Laboratory Manual", Second Edition, Cold Spring Harbor, N.Y.: Cold Spring Harbor Laboratory (1989). A common formula for calculating the stringency conditions required to achieve hybridisation between nucleic acid molecules of a specified homology is:

$$T_m = 81.5° C. + 16.6 \text{ Log } [Na^+] + 0.41 [\% G+C] - 0.63$$
(% formamide)

One aspect of the invention pertains to isolated nucleic acid molecules (e.g., cDNAs) comprising a nucleotide sequence encoding a fusion protein comprising an extracellular domain of GPVI and an Fc domain of an immunoglobulin. In particularly preferred embodiments, the isolated nucleic acid molecule comprises one of the nucleotide sequences set forth in Sequence SEQ ID NO: 148 (FIG. 8) or the coding region or a complement thereof. In other embodiments, the isolated nucleic acid molecule comprises a nucleotide sequence which hybridizes to or is at least about 50%, preferably at least about 60%, more preferably at least about 70%, 80% or 90%, and even more preferably at least about 95%, 96%, 97%, 98%, 99% or more homologous to a nucleotide sequence as in SEQ ID NO: 148 (FIG. 8), or a portion thereof. In other preferred embodiments, the isolated nucleic acid molecule encodes one of the amino acid sequences set forth in SEQ ID NO: 147 (FIG. 7).

In an embodiment, the fusion protein is expressed in CHO (Chinese hamster ovary) cells.

The disclosure further includes the subject matter of the following paragraphs:

1. A fusion protein comprising:
   a) a first polypeptide which is capable of inhibiting adhesion of platelets to collagen;
   b) a second, antibody-derived polypeptide; and
   c) a linker comprising an amino acid sequence Gly-X-Z or Z-P-Q, wherein X is an amino acid, P and Q are each independently amino acids provided that at least one of P and Q is Gly, and Z is a hydrophilic amino acid.
2. The fusion protein of Paragraph 1, wherein the first polypeptide is capable of binding to collagen.
3. The fusion protein of Paragraph 1 or Paragraph 2, wherein the first polypeptide comprises an extracellular domain of GPVI or a variant thereof that is functional for binding to collagen.
4. The fusion protein of any preceding Paragraph, wherein the first polypeptide binds to collagen competitively with platelet-bound GPVI.
5. The fusion protein of any preceding Paragraph, wherein the first polypeptide is functional for binding to collagen at the platelet-bound GPVI binding site of collagen.
6. The fusion protein of any preceding Paragraph, wherein the second polypeptide comprises an amino acid sequence of an Ig heavy chain constant part.
7. The fusion protein of any preceding Paragraph, wherein the second polypeptide comprises a hinge region of an immunoglobulin and is functional to prolong the plasma half-life beyond that of a protein consisting of the first polypeptide and the linker.
8. The fusion protein of any preceding Paragraph, wherein the second polypeptide comprises a hinge region and a CH2 region of an immunoglobulin.
9. The fusion protein of any preceding Paragraph, wherein the second polypeptide comprises a hinge region, a CH2 region and a CH3 region of an immunoglobulin.
10. The fusion protein of any preceding Paragraph, wherein the first polypeptide comprises an extracellular domain of GPVI or a variant thereof that is functional for binding to collagen; and the second polypeptide comprises an Fc domain of an immunoglobulin or a functional conservative part thereof.
11. The fusion protein of any preceding Paragraph wherein Z is selected from the group consisting of Arg, Ser, Thr, Asp, Glu, Tyr, Asn and Gln.
12. The fusion protein of any preceding Paragraph, wherein Z is Ser.
13. The fusion protein of any preceding Paragraph, wherein Z is Arg.
14. The fusion protein of any preceding Paragraph, wherein the linker comprises the amino acid sequence Gly-X-Z and X is Gly.
15. The fusion protein of any preceding Paragraph, wherein P is Gly.
16. The fusion protein of any preceding Paragraph, wherein the linker comprises a diglycine sequence.
17. The fusion protein of any preceding Paragraph, which is expressed in a mammalian cell.
18. A fusion protein comprising:
    a) an amino acid sequence which, when the protein is administered, results in inhibition of adhesion of platelets to collagen; and
    b) an antibody-derived amino acid sequence, wherein sequence (a) is linked at its C-terminus to the N-terminus of sequence (b) through a linker comprising a hydrophilic amino acid.
19. The fusion protein of Paragraph 18, wherein the antibody-derived amino acid sequence is an Fc domain of an immunoglobulin.
20. The fusion protein of Paragraph 18 or Paragraph 19, wherein the amino acid sequence which results in the inhibition of adhesion of platelets to collagen is an extracellular domain of GPVI.
21. The fusion protein of any of Paragraphs 18 to 20, wherein the hydrophilic amino acid is selected from Arg, Ser, Thr, Lys, His, Glu, Asp and Asn.
22. The fusion protein of any of Paragraphs 18 to 21, wherein the hydrophilic amino acid is Arg.
23. A fusion protein comprising:
    a) an amino acid sequence comprising an extracellular domain of GPVI or a variant thereof that is functional for binding to collagen;
    b) a linker comprising an amino acid sequence Gly-Gly-Z, wherein Z is a hydrophilic amino acid; and
    c) an amino acid sequence comprising an Fc domain of an immunoglobulin or a functional conservative part thereof.
24. The fusion protein of Paragraph 23, wherein the amino acid sequence (a) is encoded by:
    (i) a nucleic acid sequence of bases 1 to 807 of SEQ ID NO: 148 (FIG. 8);
    (ii) a nucleic acid sequence which hybridises to bases 1 to 807 of SEQ ID NO: 148 (FIG. 8); or
    (iii) a nucleic acid sequence which differs from bases 1 to 807 of SEQ ID NO: 148 (FIG. 8) by virtue of the degeneracy of the genetic code.
25. The fusion protein of Paragraph 23 or Paragraph 24, wherein amino acid sequence (b) is encoded by:
    (i) a nucleic acid sequence of bases 808 to 816 of SEQ ID NO: 148 (FIG. 8);
    (ii) a nucleic acid sequence which hybridises to bases 808 to 816 of SEQ ID NO: 148 (FIG. 8);
    (iii) a nucleic acid sequence which differs from bases 808 to 816 of SEQ ID NO: 148 (FIG. 8) by virtue of the degeneracy of the genetic code
26. The fusion protein of any of Paragraphs 23 to 25, wherein the hydrophilic amino acid is selected from Arg, His and Lys.
27. The fusion protein of any of Paragraphs 23 to 26, wherein amino acid sequence (c) is encoded by:
    (i) a nucleic acid sequence of bases 817 to 1515 of SEQ ID NO: 148 (FIG. 8);
    (ii) a nucleic acid sequence which hybridises to bases 817 to 1515 of SEQ ID NO: 148 (FIG. 8); or
    (iii) a nucleic acid sequence which differs from bases 817 to 1515 of SEQ ID NO: 148 (FIG. 8) by virtue of the degeneracy of the genetic code.
28. A protein having the characteristics of a protein obtained by expressing in a mammalian cell under non-reducing conditions a DNA sequence comprising in a 5' to 3' direction:
    (i) a DNA sequence comprising bases 1 to 807 of SEQ ID NO: 148 (FIG. 8) or a variant thereof in which said sequence encoded by bases 1 to 807 of SEQ ID NO: 148 (FIG. 8) is replaced by a variant having collagen binding activity;
  (ii) a DNA sequence comprising bases 808 to 816 of SEQ ID NO: 148 (FIG. 8); and
  (iii) a DNA sequence comprising bases 817 to 1515 of SEQ ID NO: 148 (FIG. 8) or a variant thereof in which said sequence encoded by bases 817 to 1515 of SEQ ID NO: 148 (FIG. 8) is replaced by a variant having the properties of an Fc region.

29. A dimer of a polypeptide, the polypeptide comprising
  a) an extracellular domain of GPVI or a variant thereof that is functional for binding to collagen; and
  b) a linker comprising an amino acid sequence Gly-Gly-Z, wherein Z is a hydrophilic amino acid; and
  c) an Fc domain of an immunoglobulin or a functional conservative part thereof.

30. A method of treating or preventing thrombosis in a subject, comprising administering to the subject a therapeutically effective amount of a fusion protein comprising:
  a) an amino acid sequence which, when the protein is administered, results in inhibition of collagen-induced platelet activation; and
  b) a antibody-derived amino acid sequence, wherein sequence (a) is linked at its C-terminus to the N-terminus of sequence (b) through a linker comprising a hydrophilic amino acid.

31. The method of Paragraph 30, wherein amino acid sequence (a) comprises an extracellular domain of GPVI or a variant thereof that is functional for binding to collagen; and the antibody-derived amino acid sequence comprises an Fc domain of an immunoglobulin or a functional conservative part thereof.

32. The method of Paragraph 30 or Paragraph 31, wherein the fusion protein comprises sequentially in an N-terminus to C-terminus direction, a first amino acid sequence, a second amino acid sequence and a third amino acid sequence wherein said first amino acid sequence comprises:
  A) i) an amino acid sequence encoded by a nucleic acid sequence of bases 1 to 807 of SEQ ID NO: 148 (FIG. 8);
    ii) an amino acid sequence encoded by a nucleic acid sequence which hybridises to bases 1 to 807 of SEQ ID NO: 148 (FIG. 8) and which codes for a polypeptide which binds to collagen; or
    iii) an amino acid sequence encoded by a nucleic acid sequence which differs from bases 1 to 807 of SEQ ID NO: 148 (FIG. 8) by virtue of the degeneracy of the genetic code and which binds to collagen; and wherein the second amino acid comprises
  B) i) an amino acid sequence encoded by a nucleic acid sequence of bases 808 to 816 of SEQ ID NO: 148 (FIG. 8);
    ii) a 3-mer amino acid sequence containing a hydrophilic amino acid or
    iii) an amino acid sequence encoded by a nucleic acid sequence which differs from bases 808 to 816 of SEQ ID NO: 148 (FIG. 8) by virtue of the degeneracy of the genetic code;
wherein the third amino acid sequence comprises:
  C) i) an amino acid sequence encoded by a nucleic acid sequence of bases 817 to 1515 of SEQ ID NO: 148 (FIG. 8);
    ii) an amino acid sequence encoded by a nucleic acid sequence which hybridises to bases 817 to 1515 of SEQ ID NO: 148 (FIG. 8) and which codes for a polypeptide which is functional as an Fc domain of an immunoglobulin; or
    iii) an amino acid sequence encoded by a nucleic acid sequence which differs from bases 817 to 1515 of SEQ ID NO: 148 (FIG. 8) by virtue of the degeneracy of the genetic code and which is functional as an Fc domain of an immunoglobulin.

33. A dimer of a polypeptide, the polypeptide comprising:
  a) a first polypeptide which is capable of inhibiting adhesion of platelets to collagen;
  b) a second, antibody-derived polypeptide; and
  c) a linker comprising an amino acid sequence Gly-X-Z or Z-P-Q, wherein X is an amino acid, P and Q are each independently amino acids provided that at least one of P and Q is Gly, and Z is a hydrophilic amino acid.

34. A dimer of a polypeptide, the polypeptide comprising:
  a) a first polypeptide which is capable of inhibiting adhesion of platelets to collagen;
  b) a second, antibody-derived polypeptide; and
  c) a linker comprising an amino acid sequence Gly-X-Z or Z-P-Q, wherein X is an amino acid, P and Q are each independently amino acids provided that at least one of P and Q is Gly, and Z is a hydrophilic amino acid,
wherein the first polypeptide binds to collagen competitively with platelet-bound GPVI, the second polypeptide comprises a hinge region of an immunoglobulin and is functional to prolong the plasma half-life beyond that of a protein consisting of the first polypeptide and the linker and wherein the linker comprises the amino acid sequence Gly-X-Z, wherein Z is selected from the group consisting of Arg, Ser, Thr, Asp, Glu, Tyr, Asn and Gln.

35. A dimer of a polypeptide, the polypeptide comprising:
  a) a first polypeptide which is capable of inhibiting adhesion of platelets to collagen;
  b) a second, antibody-derived polypeptide; and
  c) a linker comprising an amino acid sequence Gly-X-Z, wherein X is Gly and Z is selected from the group consisting of Lys and Arg,
wherein the first polypeptide binds to collagen competitively with platelet-bound GPVI and wherein the second polypeptide comprises a hinge region of an immunoglobulin and is functional to prolong the plasma half-life beyond that of a protein consisting of the first polypeptide and the linker.

In a second aspect of the present invention, there is provided a nucleic acid sequence comprising a sequence selected from the following group:
  a) the nucleic acid of FIG. 8 or a variant thereof that codes for the same polypeptide according to the degeneracy of the genetic code;
  b) a nucleic acid sequence coding for a polypeptide that has at least 70% sequence homology to the polypeptide encoded by FIG. 8, wherein the nucleic acid sequence encodes a polypeptide comprising, form its N-terminus to its C-terminus, an extracellular domain of GPVI or a variant thereof function for binding to collagen, a linker having the amino acid sequence Gly-Gly-Arg and an immunoglobulin Fc domain or a functional conservative variant thereof functional for enabling a protein encoded by the nucleic acid to be secreted from a cell in a form functional for binding to collagen;
  c) a nucleic acid coding for a polypeptide of at least 300 amino acids and having, in the 5' to 3' direction, a first segment encoding at least 100 amino acids comprising an extracellular domain of GPVI or a variant thereof that is functional for binding to collagen, a second segment which encodes the amino acid sequence Gly-Gly-Arg and a third segment encoding at least 200 amino acids functional as an immunoglobulin Fc domain for enabling a protein encoded by the nucleic acid to be secreted from a cell in a form functional for binding to collagen.

Thus, the invention further provides a nucleic acid sequence coding for the fusion protein of the invention. Said nucleic acid sequence comprises a sequence selected from the following group:
(i) the nucleic acid sequence of SEQ ID NO: 148 or a variant thereof that codes for the same polypeptide according to the degeneracy of the genetic code;
(ii) a nucleic acid sequence coding for a polypeptide that has at least 70% sequence homology to the polypeptide encoded by SEQ ID NO: 148;
(iii) a nucleic acid coding for a polypeptide of at least 300 amino acids, whereby a segment of at least 100 amino acids is functional for binding to collagen and a segment of at least 200 amino acids is functional as an Fc domain; and
(iv) a nucleic acid sequence coding for the fusion protein of the invention.

In a third aspect of the invention, the present invention provides monoclonal antibody hGP 5C4 or function-conservative fragments, notably hGP 5C4 Fab, or variants thereof which specifically bind to glycoprotein VI, in particular to human glycoprotein VI. The monoclonal antibody may be purified from an antibody producing cell designated hGP 5C4 deposited with DSMZ-Deutsche Sammlung von Mikroorganismen und Zellkulturen under Accession No. 2631, or progeny thereof. The monoclonal antibody or function-conservative fragments or variants thereof preferably inhibit collagen-binding of human glycoprotein VI. The fragment is preferably a Fab fragment obtainable by papain digestion of hGP 5C4 antibody. The present invention also provides humanized antibodies specifically binding to glycoprotein VI. Moreover, the present invention provides fusion proteins specifically binding to glycoprotein VI, which comprise an amino acid sequence of hGP 5C4 or function-conservative fragments thereof, notably hGP 5C4 Fab, or variants thereof. Moreover, the present invention also provides conjugates containing an effector moiety and the monoclonal antibody hGP 5C4 or function-conservative fragments, notably hGP 5C4 Fab, or variants thereof. The inhibitor of the present invention preferably does not activate platelets or does not induce immuno-thrombocytopenia. Moreover, the inhibitor of the present invention preferably inhibits the release mechanism of platelets and the expression of pro-inflammatory responses.

A fourth aspect of the present invention relates to a hybridoma cell line deposited as hGP 5C4 with DSMZ-Deutsche Sammlung von Mikroorganismen und Zellkulturen on Nov. 25, 2003 under accession number 2631, or progeny thereof.

A fifth aspect of the present invention relates to a nucleic acid coding for monoclonal antibody hGP 5C4 or a function-conservative fragment, notably hGP 5C4 Fab, or variants thereof, notably due to the degeneracy of the genetic code, wherein said nucleic acid is obtainable from the hybridoma cell line of the present invention, or progeny thereof. The amino acid sequence of the variable domains of the heavy chain and light chain of hGP 5C4 are shown by FIG. 11 (a) (SEQ ID NO: 149) and FIG. 12 (a) (SEQ ID NO: 151), respectively. The present invention also relates to a nucleic acid coding for a polypeptide comprising at least 5 consecutive amino acids of the monoclonal antibody hGP 5C4 and binding specifically to human glycoprotein VI. Moreover, the present invention relates to an amino acid sequence comprising the variable domains defined by the amino acid sequence of SEQ ID NO: 149 and SEQ ID NO: 151 or a function conservative fragment or variant thereof. In particular, the amino acid sequence may further comprise the constant regions of immunoglobulins such as an $IgG_1$, $IgG_2$, $IgG_{2a}$, $IgG_3$, $IgG_4$, IgD, IgM, IgA, and IgE.

In a sixth aspect of the invention, there is provided a pharmaceutical composition comprising an immunoadhesin, being a homodimeric fusion protein, comprising an extracellular domain of GPVI or a variant thereof that is functional for binding to collagen; and an Fc domain of an immunoglobulin or a functional conservative part thereof, the extracellular domain or variant thereof and the Fc domain or functional conservative part thereof being fused via a linker, said linker has the amino acid sequence Gly-Gly-Arg.

A seventh aspect of the present invention relates to a pharmaceutical composition comprising a pharmaceutically acceptable excipient and the inhibitor of the present invention.

An eighth aspect of the present invention relates to the use of the inhibitor of the present invention for the preparation of a medicament for the prevention or treatment of acute or chronic vascular diseases associated with intraarterial or intravenous thrombosis. Preferably, the medicament is administered parenterally.

The invention further provides a medicament for the prevention or treatment of intraarterial thrombosis, containing a protein that comprises the extracellular domain of glycoprotein VI or a variant thereof that is functional for binding to collagen. Preferably, said protein is said fusion protein of the invention. If said medicament contains said fusion protein, said medicament preferentially further comprises a suitable carrier. Said medicament is preferably administered parenterally, more preferably it is administered intravenously.

A ninth aspect of the invention relates to a process for producing monoclonal antibody hGP 5C4 or function-conservative fragments thereof, said process comprising
(i) culturing hybridomAn hGP 5C4, or progeny thereof in medium under conditions conducive to expression of antibody therefrom,
(ii) obtaining antibody hGP 5C4 from the culture medium; and
(iii) optionally preparing a Fab fragment of antibody hGP 5C4 by enzymatic digestion.

The present invention also relates to a process for preparing hGP 5C4 Fab, said process comprising the step of digesting hGP 5C4 antibodies and isolating the Fab fragments. Preferably, hGP 5C4 is digested by using papain or a derivative thereof.

As has been found by the present inventors, GP VI-collagen interactions are the major factor of platelet adhesion to an injured vessel wall. The fusion protein of the invention can prevent binding of platelets to blood-exposed collagen in the vascular system by blocking said blood-exposed collagen without inhibiting other platelet functions.

Included in the present disclosure is a medicament which contains nucleic acid that codes for said fusion protein of the invention for gene therapy. The nucleic acid of the invention preferably contains the nucleic acid sequence defined above. The nucleic acid is preferably contained in a vector, preferentially a viral vector. Vectors encoding the fusion protein may be introduced into the vascular system of a patient such that e.g. endothelial cells are transduced therewith. Suitable vectors for gene therapy are known in the art. They may be based e.g. on adenoviruses, on adeno-associated viruses, on retro viruses, or on herpes simplex viruses. Vectors may be adopted for long-term or for short-term expression of the fusion protein by transduced cells, as the patient requires. The Fc domain of the fusion protein enables secretion of the fusion protein in active form by transduced cells.

The invention further provides a method of in vitro screening for inhibitors of binding of glycoprotein VI to collagen, comprising
(i) providing a surface that exposes collagen;
(ii) contacting a portion of the surface with the fusion protein of the invention under predetermined conditions that allow binding of the fusion protein to said surface;
(iii) contacting another portion of said surface with the fusion protein in the presence of a test compound under conditions as in step (ii);
(iv) determining the amount of said fusion protein bound to the surface in the absence and in the presence of the test compound;
(v) identifying a test compound as inhibitor if binding of the fusion protein to the surface is less in the presence of the test compound as compared to the absence of the test compound; and
(vi) optionally determining the functional effect of the inhibitor on platelet aggregation and/or platelet activation.

The surface of step (i) may be a glass or plastic surface coated with collagen. The portions of said surface may be the wells of a titer plate or a multi-well plate. A surface that exposes collagen may be easily prepared by coating a glass or plastic surface with collagen as described in the examples. Collagen-coated plates or multi-well plates are also commercially available. In step (ii), a predetermined amount of the fusion protein is contacted with a first portion of the surface under conditions (notably pH, buffer, temperature) that allow binding of the fusion protein to the surface.

Preferably, conditions are chosen that allow optimal binding to the surface. In step (iii), another surface portion is contacted with the same amount of fusion protein and under the same conditions as in step (ii) in the presence of a predetermined amount or concentration of a test compound. More than one amount or concentration of a test compound may be used. Said determining of step (iv) preferably comprises washing of the surface portions contacted according to steps (ii) and (iiii) one or more times in order to remove unbound fusion protein. The amount of bound fusion protein may then be determined e.g. by measuring the fluorescence of a fluorescent label (e.g. fluorescein, rhodamine etc.) attached to the fusion protein. Alternatively, bound fusion protein may be detected using an antibody against the fusion protein, whereby the antibody may be fluorescently labelled. Alternatively, the antibody may be labelled with an enzyme (e.g. alkaline phosphatase, a peroxidase, luciferase) capable of producing a coloured or luminescent reaction product. Most conveniently, the fusion protein may be labelled with a chromogenic label such that the label changes its light absorption or light emission characteristics upon binding to collagen. In this embodiment, washing off of unbound fusion protein is not needed.

In step (v), inhibitors may be identified. Identified inhibitors or selected moieties thereof may be used as lead structures for improvement of the inhibitor. Such lead structures may be modified using chemical methods and the modified structures may again be tested with this screening method. Modified structures or test compounds with improved inhibition properties may be selected and optionally further varied by chemical methods. In this way, iterative improvement of an inhibitor may be achieved. The inhibitors identified using the screening methods of the invention are valuable as potential drugs against thrombosis and arteriosclerosis.

In step (vi), the functional effect of said inhibitor on platelet aggregation and/or platelet activation may be determined according to methods described below, e.g. by intravital fluorescence microscopy. Said screening method may be carried out on small, medium, or large scale depending on the number of test compounds to be tested. If many test compounds are to be tested (e.g. libraries of chemical compounds), the screening method preferably takes the form of a high-throughput screening (HTS). For HTS, the amount of bound fusion protein is preferably detected using fluorescently labelled fusion protein.

The above screening method may also be adopted for screening for antibodies that inhibit binding of GP VI to collagen, notably antibodies against the extracellular domain of GP VI. Such an antibody screening may be combined with e.g. hybridoma technology of generating monoclonal antibodies or any other antibody generating technique, whereby the fusion protein of the invention is preferably used as antigen. Antibodies in hybridoma cell supernatants may be used as said test compounds.

Method of in vivo screening for an inhibitor of GPVI mediated adhesion of platelets to active intravascular lesions, said method comprising the steps of
(i) providing an in vivo model for active intravascular lesions;
(ii) measuring the adhesion of platelets to an active intravascular lesion in the presence of a test compound, and
(iii) identifying the test compound as an inhibitor of GPVI when the adhesion of platelets to the active intravascular lesion is less in the presence of the test compound as compared to the absence of the test compound.

Said in vivo model may be a suitable mammal like a mouse, a rat, a rabbit etc. Preferably, it is a mouse. Platelets that are preferably fluorescently labelled are introduced into the model prior to measuring the adhesion of platelets to an active intravascular lesion in the presence and in the absence of a test compound. Said test compound has preferably been identified as an inhibitor in one of the above in vitro screening methods. Adhesion of platelets to an active intravascular lesion may be carried out by using in vivo fluorescence microscopy as described in example 8.

The present invention also provides a use of a fusion protein comprising
(a) the extracellular domain of glycoprotein VI or a variant thereof that is functional for binding to collagen and
(b) the Flexible coupling domain of an immunoglobulin or a function-conservative part thereof, for the manufacture of a medicament for the treatment of diabetes.

The invention further provides antibodies produced by using the fusion protein of the invention as an immunogen. Moreover, use of an antibody against GPVI may be used for the preparation of a medicament for the prevention of platelet adhesion at exposed subendothelial matrix collagens in active atherosclerotic lesions as the initial trigger for acute coronary or carotid syndrome. Such indications may be diagnosed as described below. Preferably, the patient is further characterized by suffering from unstable atherosclerotic plaque. Said medicament is preferably administered parenterally. Preferably, said antibodies are monoclonal antibodies. Such antibodies may e.g. be prepared using the fusion protein of the invention as immunogen.

Thus, the present invention provides a method of producing a monoclonal antibody from a non-human mammal comprising using homodimeric fusion protein according to the invention as an immunogen.

Furthermore, the invention provides a method of in vitro screening for an inhibitor of GPVI mediated adhesion of platelets to active intravascular lesions, said method comprising the steps of (i) providing a surface exposing collagen;
(ii) contacting the surface with platelets under predetermined conditions allowing for an adhesion of the platelets to the collagen;
(iii) measuring the adhesion of platelets in the presence of a test compound; and
(iv) identifying the test compound as an inhibitor of GPVI when the adhesion of platelets to collagen is less in the presence of the test compound as compared to the absence of the test compound; and
(v) optionally determining the functional effect of said inhibitor on platelet aggregation and/or platelet activation.

Platelets to be used in this method may be isolated according to known procedures (cf. example 7). They may be isolated from blood of mammals like mice, rats, rabbits, pigs etc. Preferably, they are isolated from humans. Said platelets may be labelled e.g. with a fluorescent dye like fluorescein. The adhesion of platelets to said surface may be measured as described in the examples. The test compounds for this method may be small organic molecules. Preferably, the test compounds for this methods are inhibitors identified in the above method of screening for inhibitors of binding of GP VI to collagen. In this way, the number of compounds to be screened using platelets can be significantly reduced and the likelihood of finding inhibitors functional with platelets can be increased.

The fusion protein of the invention used for the manufacture of a medicament for the treatment of diabetic patients as described later in this paragraph is preferably a dimeric fusion protein. In order to provide for the possibility of dimerisation, a hinge region must be present between domains (a) and (b) of the fusion protein. The hinge region is required for allowing suitable orientation of the polypeptide chains and formation of inter-chain disulfide bonds. Accordingly, the hinge region must have a sufficient length and contain cystein residues, preferably at least two cystein residues. Preferably, the fusion protein comprises residues 1 to 267 of SEQ ID NO: 147. The fusion protein is used for the treatment of acute complications of diabetes or for the treatment of chronic progression of atherosclerosis in diabetic patients. Preferably, the fusion protein is Fc-GPVI-nt.

The present invention also provides a method for the preparation of a fusion protein of the invention, which comprises the following steps:
(a) collecting 2 days after infection the culture supernatant of Hela cells infected with an adenovirus for the nucleic acid coding for an amino acid sequence as shown in FIG. 7;
(b) centrifuging (3800 g, 30 min, 4° C.) the supernatant of step (a);
(c) filtrating (0.45 μm) the supernatant of step (b);
(d) precipitating the immunoadhesin by addition of 1 vol. ammonium sulfate (761 g/l) and stirring overnight at 4° C.;
(e) pelletizing the proteins by centrifugation (3000 g, 30 min, 4° C.),
(f) dissolving the pelletized proteins of step (e) in 0.1 Vol PBS and dialysed in PBS overnight at 4° C.;
(g) clarifying the protein solution by centrifugation (3000 g, 30 min, 4° C.);
(h) loading the solution of step (g) on a protein A column (HiTrap™ protein A HP, Amersham Pharmacia Biotech AB, Uppsala, Sweden);
(i) washing the column with binding buffer (20 mM sodium phosphate buffer pH 7.0, 0.02% $NaN_3$) until $OD_{280}$<0.01;
(k) eluting fractions with elution buffer (100 mM glycine pH 2.7);
(l) neutralizing the eluted fractions with neutralisation buffer (1 M Tris/HCl pH 9.0, 0.02% $NaN_3$);
(m) pooling the fractions;
(n) dialysing the pooled fractions in PBS overnight at 4° C.,
(o) aliquoting the dialysed product and freezing at −20° C.

In a tenth aspect the present invention provides an agent that binds to GPVI or a sequence thereof. In an embodiment, it provides an agent which binds immunoglobulin like C2 domain 1 (D1) of GPVI. One class of agents binds specifically to GPVI. In one embodiment, the agent specifically binds to D1 of GPVI. In that the agent specifically binds to domain 1 of GPVI it does not bind significantly to immunoglobulin domain 2 of GPVI.

According to Smethurst et al (2004) Blood 103, 903-911, the junction between D1 and D2 (i.e. domain 1 and domain 2) appears to be located in the region of amino acid residues 113/114 as shown in FIG. 35. In some embodiments, whilst there might be the possibility of binding of agents of the present invention to linear epitopes of D2, these are generally insignificant compared to the binding to D1. Whilst not wishing to be bound by theory, the inventors believe that the binding of agents to D1 and not to D2 may avoid any cross-linking of D2 and the FcR-γ chain.

In an eleventh aspect, the invention provides an agent that binds to a ligand, the ligand consisting of one or a combination of:
(a) a peptide moiety of 5, 6, 7, 8, 9, 10, 11, 12, 13, 14 or 15 amino acid residues including a sequence of contiguous amino acid residues selected from the sequence of contiguous amino acids from position 15 to position 39 of human GP VI protein as shown in FIG. 35;
(b) a peptide moiety of 5, 6, 7, 8, 9, 10, 11, 12, 13, 14 or 15 amino acid residues including a sequence of contiguous amino acid residues selected from the sequence of contiguous amino acids from position 73 to position 87 of human GP VI protein as shown in FIG. 35;
(c) a peptide moiety of 5, 6, 7, 8, 9, 10, 11, 12, 13, 14 or 15 amino acid residues including a sequence of contiguous amino acid residues selected from the sequence of contiguous amino acids from position 107 to position 121 of human GP VI protein as shown in FIG. 35.

The eleventh aspect includes one class of agents whose members includes monoclonal antibody hGP 5C4. It includes another class of agents which class does not include monoclonal antibody hGP 5C4 or a fragment thereof, or at least a fragment thereof other than a Fab', a (Fab')$_2$, Fv or dsFv fragment. Further included is a class of agent wherein the members of the class have at least one CDR of antibody hGP 5C4. Also included is a class of agent wherein the members of the class do not have a CDR of antibody hGP 5C4.

In one embodiment, the agent binds to ligand (a) only and not ligand (b) or ligand (c).

In an alternative embodiment, the agent binds to ligand (a) and ligand (b) but does not bind to ligand (c).

In a further alternative embodiment, the agent binds to ligand (a) and ligand (c) and does not bind to ligand (b).

In an alternative embodiment, the agent binds to ligand (b) and ligand (c) and does not bind to ligand (a).

In an alternative embodiment, the agent binds to ligand (a), ligand (b) and ligand (c).

The binding of the agent is optionally binding with an affinity of greater than $10^{-7}$ M, $10^{-8}$ M, $10^{-9}$ M, $10^{-10}$ M, $10^{-11}$ M or $10^{-12}$ M. The binding may be specific for the ligand or non-specific, although in some instances there is a degree of lower affinity non-specific binding to certain other ligands unrelated to GP VI.

Peptide moieties (a), (b) and (c) independently of one another may have 5, 6, 7, 8, 9, 10, 11, 12, 13, 14 or 15 amino acid residues. They may have 5 to 13, 5 to 11 or 5 to 9 residues e.g. 13 amino acid residues, 11 amino acid residues or 9 residues. Also, within the scope of the invention are peptide moieties (a), (b) and (c) having (independently of one another) 5, 6, 7, 8, 10, 12, 14 or 15 amino acid residues. Larger numbers of amino acid residues for peptide moieties of (a), (b) and (c) are possible including 17, 18, 19, 20, 25 or 30 residues. The peptide moiety (a) may be a sequence starting at position 15, 16, 17, 18, 19, 20, 21, 22, 23, 24, 25, 26 or 27 of the sequence of FIG. 18.

In certain embodiments the peptide moiety (a) may be selected from one of the following sequences of contiguous amino acids of a human GPVI as shown in FIG. 35:
 (i) position 15 to position 27
 (ii) position 17 to position 29
 (iii) position 19 to position 31
 (iv) position 17 to position 29
 (v) position 21 to position 33
 (vi) position 23 to position 35
 (vii) position 25 to position 37
 (viii) position 27 to position 39
 (ix) position 21 to position 29.

As will be appreciated the referenced positions are for a GPVI sequence which includes the leader sequence.

In yet other embodiments, the peptide moiety (a) may be selected from one of the following sequences of contiguous amino acids of human GP VI as shown in FIG. 35:
 (i) position 21 to position 27
 (ii) position 21 to position 29
 (iii) position 21 to position 31
 (iv) position 21 to position 29
 (v) position 21 to position 33
 (vi) position 21 to position 35
 (vii) position 21 to position 37
 (viii) position 21 to position 39.

As will be appreciated from this, the aforementioned portions of the GPVI sequence do not include the leader sequence (though the numbering given starts at residue M of the leader). It is believed that the signal sequence is cleaved from the native GPVI protein before expression on the platelet cell surface.

In certain specific embodiments the peptide moiety (a) may be selected from one of the following amino acid sequences (see Table 2 for peptide SEQ ID NOs):
 SEQ ID NO: 8
 SEQ ID NO: 9
 SEQ ID NO: 10
 SEQ ID NO: 11
 SEQ ID NO: 12
 SEQ ID NO: 13
 SEQ ID NO: 14

In certain preferred embodiments the ligand includes a peptide moiety (a) which has amino acid residue 27 as part of the contiguous sequence of said peptide moiety. Specifically, the agent may bind at amino acid residue 27 comprised in the ligand. Whilst this will usually be lysine, conservative substitution of this residue is possible meaning, for example, that amino acid residue 27 may be a basic amino acid other than lysine e.g. arginine.

The invention includes agents which bind to a sequence of contiguous amino acids, e.g. 5, 6, 7, 8, 9, 10, 11, 12, 13, 14, or 15 amino acids, such as 5 to 13 amino acids, of the sequence of FIG. 35, which sequence of contiguous amino acids includes lysine 27.

Peptide moiety (b) may be selected from the contiguous sequence of amino acids from position 75 to position 85 of human GPVI as shown in FIG. 35. The number of contiguous amino acids forming peptide moiety (b) may be 5, 6, 7, 8, 9 or 10 and the starting position for selecting the contiguous sequences of less than 10 residues may be selected so that all possible contiguous length variants are made available.

In specific embodiments peptide moiety (b) may be selected from one of the following amino acid sequences:
 SEQ ID NO: 37
 SEQ ID NO: 38

In other embodiments the peptide moiety (c) may be selected from the contiguous sequence of amino acids from position 111 to position 119 of human GPVI as shown in FIG. 35. As described in connection with peptide moiety (b) above, and as also applicable in a similar way to (a) above, the number of contiguous amino acids may be 5, 6, 7, 8 or 9 and the starting position of the GP VI sequence for selecting sequences less than maximum number of residues may be performed so that all possible contiguous length segments are made available.

Peptide moiety (c) may be selected from one of the following amino acid sequences:
 SEQ ID NO: 54
 SEQ ID NO: 55

In another aspect, the ligand to which the agent of the invention binds consists of one or a combination of (a), (b) and (c) below:
 (a) a polypeptide comprising a peptide motif selected from:

```
SEQ ID NO: 132: LPKPS
SEQ ID NO: 133: PLPKP
SEQ ID NO: 134: GPLPK
SEQ ID NO: 135: PKPSL
SEQ ID NO: 136: KPSLQ;
```

(b) a polypeptide comprising a peptide motif selected from:

```
SEQ ID NO: 137: AMKRS
SEQ ID NO: 138: PAMKR
SEQ ID NO: 139: MKRSL
SEQ ID NO: 140: KRSLA
SEQ ID NO: 141: RSLAG
```

(c) a polypeptide comprising a peptide motif selected from:

```
SEQ ID NO: 142: KPSLS
SEQ ID NO: 143: AKPSL
SEQ ID NO: 144: FAKPS
SEQ ID NO: 145: PSLSA
SEQ ID NO: 146: SLSAQ.
```

In embodiments, the polypeptide (a), (b) and (c) comprising the peptide motifs as described above do not include the entirety of D2.

In the all of the embodiments of the invention described herein, the amino acid sequence of the ligand to which the agent binds may be modified by one or more changes in sequence which do not eliminate the underlying biological function and utility of the agents as described herein. Modifications may include substitution of individual amino acids with other naturally occurring or non-naturally occurring amino acids, as described in more detail later on.

The agents of the invention may be, for example, an antibody or fragment thereof, e.g. a Fab. fragment. However, also possible are aptamers, compounds, fusion proteins, proteins, peptides or combinations thereof as defined above. Preferred antibodies and fragments are Fab fragments or scFv. Naturally within the scope of the agents of the invention are antibodies or fragments which are monoclonal, polyclonal, chimeric, human, or humanized. Other agents which bind the ligand as defined herein are encompassed within the present invention.

As defined in more detail later, a "humanized" immunoglobulin is an immunoglobulin including a human framework region and one or more CDRs from a non-human (such as a mouse, rat, or synthetic) immunoglobulin. The non-human immunoglobulin providing the CDRs is termed a "donor" and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical, e.g. at least 96%, 97%, 98% or 99%. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs.

In embodiments of the invention, the described products, methods and uses do not include the subject matter of the monoclonal antibody described in PCT Application No. PCT/EP2004/013779 filed on 3 Dec. 2004 or EP patent application No. 0302777.2 filed on 3 Dec. 2003. In one embodiment therefore a monoclonal antibody hGP 5C4 and fragments thereof e.g. Fab fragment, as well as humanised hGP 5C4 and fragments are excluded from the invention. However, the invention does provide agents which are a Fab', a (Fab')$_2$, Fv or dsFv fragment of hGP 5C4.

Included in the invention are agents as described herein which bind to platelet-bound GPVI. Included are agents which do not significantly activate platelets.

In another aspect the invention provides an isolated nucleic acid comprising a nucleic acid sequence, which sequence encodes an agent described herein which is an antibody, a fusion protein, a peptide or a protein.

The agents of the present invention, if comprising a peptide sequence, for example an antibody, a fusion protein, a peptide or a protein, may be encoded by a nucleic acid sequence. The present invention includes any nucleic acid sequence which encodes an agent as defined herein. The present invention also includes a nucleic acid sequence which encodes the agent of the invention but which differs from the wild-type nucleic acid as a result of the degeneracy of the genetic code.

The present invention also includes nucleic acids that share at least 90% homology with a nucleic acid sequence which encodes an agent of the present invention. In particular, the nucleic acid may have 90%, 91%, 92%, 93%, 94%, 95%, 96% 97%, 98% or 99% homology to a nucleic acid which encodes an antibody or fragment thereof of the present invention.

In one aspect of the invention, there is provided a nucleic acid molecule which hybridises under stringent conditions to a nucleic acid molecule which encodes an agent of the present invention, when said agent is an antibody or fragment thereof or a fusion protein.

Hybridization of a nucleic acid molecule occurs when two complementary nucleic acid molecules undergo an amount of hydrogen bonding to each other. The stringency of hybridization can vary according to the environmental conditions surrounding the nucleic acids, the nature of the hybridization method, and the composition and length of the nucleic acid molecules used. Calculations regarding hybridization conditions required for attaining particular degrees of stringency are discussed in Sambrook et al., Molecular Cloning: A Laboratory Manual (Cold Spring Harbor Laboratory Press, Cold Spring Harbor, N.Y., 2001); and Tijssen, Laboratory Techniques in Biochemistry and Molecular Biology—Hybridization with Nucleic Acid Probes Part I, Chapter 2 (Elsevier, N.Y., 1993). The $T_m$ is the temperature at which 50% of a given strand of a nucleic acid molecule is hybridized to its complementary strand. The following have been found as exemplary for hybridization conditions but without limitation:

Very High Stringency (Allows Sequences that Share at Least 90% Identity to Hybridize)
    Hybridization: 5×SSC at 65° C. for 16 hours
    Wash twice: 2×SSC at room temperature (RT) for 15 minutes each
    Wash twice: 0.5×SSC at 65° C. for 20 minutes each
High Stringency (Allows Sequences that Share at Least 80% Identity to Hybridize)
    Hybridization: 5×-6×SSC at 65° C.-70° C. for 16-20 hours
    Wash twice: 2×SSC at RT for 5-20 minutes each
    Wash twice: 1×SSC at 55° C.-70° C. for 30 minutes each
Low Stringency (Allows Sequences that Share at Least 50% Identity to Hybridize)
    Hybridization: 6×SSC at RT to 55° C. for 16-20 hours
    Wash at least twice: 2×-3×SSC at RT to 55° C. for 20-30 minutes each.

In further aspect the invention provides an expression vector comprising a nucleic acid as described above and associated regulatory sequences necessary for expression of a protein or polypeptide in a host cell. Such regulatory sequences include promoters, termination sequences and enhancers, for example.

In another related aspect, the invention provides a host cell comprising a nucleic acid or a vector as described above. Such host cells are transfected or transformed so that they contain the nucleic acid or vector in such a way that they are effective in expressing the desired polypeptide/protein when cultured in appropriate media under the necessary growth conditions. In one embodiment the host cell is selected from a HeLa cell and a CHO (Chinese Hamster Ovary) cell. The host cells to be used are not particularly circumscribed so as long as they can be transfected by a vector to be used and can express the DNA of the present invention. For example, bacteria such as *Escherichia coli*, yeast such as *Saccharomyces cerevisiae*, and an animal cell such as a COS cell, a CHO cell, etc. can be used. Examples of prokaryotic host cells appropriate for use with this invention include *E. coli*. Examples of eukaryotic host cells include avian, insect, plant, and animal cells such as COS7, HeLa, and CHO cells.

By cultivating a transformant or transfected cell, an agent of the invention for example a fusion protein, antibody or antibody fragment having hGP 5C4 Fab activity or function can be produced in a cell or a culture medium. Then, by collecting the produced antibody (or antibody fragment), the antibody of the first aspect of the present invention can be obtained. The obtained antibody or protein can be isolated and purified by appropriately combining methods, for example, centrifugation, ammonium sulfate fractionation, salting out, ultrafiltration, affinity chromatography, ion-exchange chromatography, or gel-filtration chromatography.

For example, the cells can be cultured in a suitable medium, and spent medium can be used as an antibody source. Optionally, matrix-coated channels or beads and cell cocultures may be included to enhance growth of antibody-producing cells. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal is optionally primed for ascites production by prior administration of a suitable composition, for example, Pristane. Antibodies of the invention may also be obtained by employing routine recombinant methods such as described in Sambrook et al. (1989) supra. For instance, nucleic acid sequences of the invention can be cloned into a suitable expression vector (which contains control sequences for transcription, such as a promoter). The expression vector is in turn introduced into a host cell. The host cell is grown under suitable conditions such that the polynucleotide is transcribed and translated into a protein. Heavy and light chains of antibodies of the invention may be produced separately, and then combined by disulfide bond rearrangement. Alternatively, vectors with separate polynucleotides encoding each chain of an antibody of the invention, or a vector with a single polynucleotide encoding both chains as separate transcripts, may be transfected into a single host cell which may then produce and assemble the entire molecule. Preferably, the host cell is a higher eukaryotic cell that can provide the normal carbohydrate complement of the molecule. The fusion protein or antibody is thus produced in the host cell can be purified using standard techniques in the art.

Methods of antibody isolation are well known in the art. See, for example, Harlow and Lane (1988) Antibodies: A Laboratory Manual, Cold Spring Harbor Laboratory, New York. The method of isolation may depend on the immunoglobulin isotype. Purification methods may include salt precipitation (for example, with ammonium sulfate), ion exchange chromatography (for example, on a cationic or anionic exchange column run at neutral pH and eluted with step gradients of increasing ionic strength), gel filtration chromatography (including gel filtration HPLC), and chromatography on affinity resins such as protein A, protein G, hydroxyapatite, and anti-immunoglobulin. Particularly, the agent of the invention is purified by using Protein G-Sepharose columns.

The agents of this invention can be made by any suitable procedure, including by recombinant methods or by chemical synthesis. Peptides which are produced may then be separated from each other by techniques known in the art, including but not limited to gel filtration chromatography, gel electrophoresis, and reverse-phase HPLC.

For most applications, it is generally preferable that the polypeptide is at least partially purified from other cellular constituents. Preferably, the polypeptide is at least about 50% pure. as a weight percent of total protein. More preferably, the protein is at least about 50-75% pure. For clinical use, the polypeptide is preferably at least about 80% pure.

The invention also provides a ligand or peptide consisting of one or more of:
(a) a peptide moiety of 5, 6, 7, 8, 9, 10, 11, 12, 13, 14 or 15 amino acid residues including a sequence of contiguous amino acid residues selected from the sequence of contiguous amino acids from position 15 to position 39 of human GP VI protein as shown in FIG. 35 (epitope (a));
(b) a peptide moiety of 5, 6, 7, 8, 9, 10, 11, 12, 13, 14 or 15 amino acid residues including a sequence of contiguous amino acid residues selected from the sequence of contiguous amino acids from position 73 to position 87 of human GP VI protein as shown in FIG. 35 (epitope (b));
(c) a peptide moiety of 5, 6, 7, 8, 9, 10, 11, 12, 13, 14 or 15 amino acid residues including a sequence of contiguous amino acid residues selected from the sequence of contiguous amino acids from position 107 to position 121 of human GP VI protein as shown in FIG. 35 (epitope (c)).

In particular, the ligand or peptide has a peptide sequence selected from the following peptide sequences:

```
a) LGRVPAQSGPLPK     (SEQ ID NO: 8)
b) RVPAQSGPLPKPS     (SEQ ID NO: 9)
c) PAQSGPLPKPSLQ     (SEQ ID NO: 10)
d) QSGPLPKPSLQAL     (SEQ ID NO: 11)
e) GPLPKPSLQALPS     (SEQ ID NO: 12)
f) LPKPSLQALPSSL     (SEQ ID NO: 13)
g) KPSLQALPSSLVP     (SEQ ID NO: 14)
h) LFIPAMKRSLAGR     (SEQ ID NO: 37)
i) IPAMKRSLAGRYR     (SEQ ID NO: 38)
j) ATGVFAKPSLSAQ     (SEQ ID NO: 54)
k) GVFAKPSLSAQPG     (SEQ ID NO: 55)
l) FAKPSLSAQPGPA     (SEQ ID NO: 56)
```

An artificial homolog of the GP VI protein may be produced by synthetic or recombinant means. Such a homolog would comprise one or more of (a), (b) or (c) described above. In other words, the epitopes (a), (b) or (c) above could be combined in pairs, or all three together, plus a suitable framework in order to provide a GP VI homolog which could be used a ligand for binding studies, screening of binding agents, e.g. antibodies, or for generating antibodies by immunising an animal. Such homologs comprising the three epitopes (a), (b) and (c) would not include the native full length GP VI protein.

Other ligands or peptides in accordance with another aspect of the invention include:
(a) a polypeptide comprising a peptide motif selected from:

```
SEQ ID NO: 132: LPKPS
SEQ ID NO: 133: PLPKP
SEQ ID NO: 134: GPLPK
SEQ ID NO: 135: PKPSL
SEQ ID NO: 136: KPSLQ;
```

(b) a polypeptide comprising a peptide motif selected from:

```
SEQ ID NO: 137: AMKRS
SEQ ID NO: 138: PAMKR
SEQ ID NO: 139: MKRSL
```

```
SEQ ID NO: 140: KRSLA

SEQ ID NO: 141: RSLAG
```

(c) a polypeptide comprising a peptide motif selected from:

```
SEQ ID NO: 142: KPSLS

SEQ ID NO: 143: AKPSL

SEQ ID NO: 144: FAKPS

SEQ ID NO: 145: PSLSA

SEQ ID NO: 146: SLSAQ
``` but for (a), (b) and (c) above the polypeptide is not full-length GPVI. Where epitopes (a), (b) or (c) are referred to herein then, unless the context otherwise requires, it is contemplated that polypeptides (a), (b) or (c) or peptide moieties (a), (b) or (c) may be used in place of the corresponding epitope.

The polypeptide (a), (b) and (c) comprising the peptide motifs as described above preferably do not include the entirety of D2.

The ligands of the invention may include any of the further features as hereinbefore described.

Alternatively, agents of the invention can be chemically synthesized using information provided in this disclosure, in conjunction with standard methods of protein synthesis. A suitable method is the solid-phase Merrifield technique. Automated peptide synthesizers are commercially available, such as those manufactured by Applied Biosystems, Inc. (Foster City, Calif.).

In a preferred embodiment the ligand is a peptide and may be a fusion protein. A preferred fusion protein partner for the ligand is PR-15, as shown in FIG. 7.

In another aspect the invention provides an array of ligands as hereinbefore described. The array is provided on a solid substrate which in preferred arrangements is a flat substrate in the form of a membrane or sheet, e.g. a chip.

Also included is a population of ligands which differ from one another in the peptide moieties (a), (b) and/or (c) which they contain. Such a population of ligands may be used to screen for additional binding agents of the invention. In such screening procedures the ligands are preferably tagged with labels which may represent which of moieties (a), (b) or (c) (or combination thereof) are provided in the individual ligand.

In a further aspect the invention provides a humanized antibody comprising complementarity determining regions that bind, e.g. specifically binds, a ligand as described herein, and a human framework region, or a conservative substitution thereof of 1, 2, 3, 4, or 5 residues of the complementarity determining regions or the framework regions, wherein the antibody retains the binding affinity to the ligand as described herein.

In certain embodiments, the humanized antibody may comprise the complementarity determining regions of hGP 5C4 antibody or a conservative substitution thereof of 1, 2, 3, 4, or 5 residues of the complementarity determining regions or the framework regions hGP 5C4. In other embodiments, the humanized antibody does not include the CDRs of hGP 5C4.

In other embodiments there is provided a fragment of the humanized antibody of the invention described herein that specifically binds the ligand as hereinbefore described. In a particular embodiment, there is provided a humanized Fab fragment.

The humanized antibody preferably has a binding affinity which is greater for D1 than D2 of human GPVI. The binding affinity of the antibody for D1 may be greater than $10^{-6}$M, preferably greater than $10^{-7}$M, $10^{-8}$M, $10^{-9}$M, $10^{-10}$ M, $10^{-11}$ M, $10^{-12}$ M.

In other aspects the invention provides an agent, a ligand or a humanised antibody as hereinbefore described for use as a pharmaceutical.

In further aspects, there is provided a pharmaceutical formulation comprising an agent, a ligand or a humanised antibody as hereinbefore described. The formulation may contain at least one additional pharmaceutically acceptable component, e.g. an excipient, diluent or carrier. Preferably, the formulation is intended for parenteral administration.

The ligands disclosed herein to which the described agents, e.g. antibodies, bind have potential application as antidotes or reversal agents for the described agents, for example, for hGP 5C4, hGP 5C4 Fab fragments and humanized versions thereof.

Included therefore is the use of a ligand described herein for the manufacture of a medicament for therapeutically neutralising (i.e. reducing or substantially destroying the activity of) an anti-GPVI agent, i.e. an agent which binds to GPVI. The agent may be one described herein, e.g. hGP 5C4, humanised hGP 5C4 or fragments (e.g. a Fab fragment) thereof. Also included is the use of a ligand described herein for the manufacture of a medicament for treating bleeding resulting from the administration of an anti-GPVI agent.

Further included is a pharmaceutical formulation comprising a ligand described herein; in embodiments the formulation is a composition comprising the ligand and a pharmaceutically acceptable diluent, carrier or excipient. In another aspect there are provided the described ligands for use as a pharmaceutical. The formulation may be an intravenous formulation.

The invention also provides a method of neutralising (i.e. reducing or substantially destroying the activity of) an anti-GPVI agent comprising contacting said agent with a ligand of the disclosure. In embodiments said agent which has been administered to a patient and the method comprises administering an effective amount of the ligand to the patient. Further included is a method for treating bleeding resulting from the administration of an anti-GPVI agent to a subject, comprising administering an effective amount of a ligand of the disclosure to the subject. Suitably the ligand is administered intravenously.

The invention also includes a method of making an antibody comprising immunising an animal with a ligand as hereinbefore described.

In a yet further aspect of the invention there is provided a method for the production of the humanised or chimeric antibody comprising:
 (i) providing a cell transformed or transfected with a vector which comprises a nucleic acid molecule encoding the humanised or chimeric antibody according to the invention;
 (ii) growing said cell in conditions conducive to the manufacture of said antibody; and
 (iii) purifying said antibody from said cell, or its growth environment.

In yet another aspect, the invention provides a method of humanising antibodies comprising:
 (i) producing a monoclonal antibody;
 (ii) replacing constant regions of the antibody with a human immunoglobulin constant region;
 (iii) identifying the CDRs of the monoclonal antibody;

(iv) identifying suitable human framework regions and replacing the antibody framework regions with said human framework regions.

In another aspect, the invention provides a method of identifying an agent for binding to GPVI comprising contacting a candidate agent with any of the ligands of the invention as hereinbefore described. The binding assay can be carried out in a variety of formats, whether solid or liquid phase. A labelled ligand may be employed. The method can be used to screen libraries of potential GPVI binding agents. The screening can take advantage of protein array technology or it can rely on traditional binding assays where bound and free labelled ligand are separated and measured across a range of test agents and concentrations of test agents and/or ligand.

In a further aspect, the invention provides for the use of ligands as hereinbefore described in a binding assay for identifying an agent capable of binding GPVI, preferably an agent capable of inhibiting platelet aggregation, more preferably an agent capable of inhibiting platelet aggregation by collagen or collagen related peptides (CRP). Once a candidate agent has been identified which binds to GPVI then further assays can be carried out to check for the preferred activities described herein.

The ligands identified in the present invention may be used to further identify and characterise agents which bind to GPVI. In embodiments, ligands (b) and (c) mentioned above are used to further identify and characterise agents which bind to GPVI in such a way that GPVI interaction with collagen is reduced or inhibited. In embodiments of the present invention, GPVI peptide epitopes disclosed herein can be used in an assay to screen for inhibitors of a GPVI function. In one embodiment, said inhibitors bind to epitope (b) or (c) of GPVI and block, reduce or inhibit collagen interaction with GPVI. Agents which block or reduce the GPVI interaction with collagen may have utility in the treatment or prevention of cardiovascular disorders for example thrombotic disorders, stroke, atherosclerosis and other disorders mentioned herein.

Agents which bind to the epitopes may likewise be used as described in the previous paragraph. Examples of such agents are antibodies and aptamers, as well as small molecules. In embodiments, therefore, agents which bind to epitope (b) or epitope (c) are used to screen for inhibitors of collagen interaction with GPVI, i.e. are used to screen for products which block, reduce or inhibit collagen interaction with GPVI.

Thus, GPVI epitopes (i.e. ligands) disclosed herein may be used in a variety of assays to identify further inhibitors of the GPVI-collagen interaction. Such assays are well known in the art and can include in vivo, ex vivo and in vitro assays, as described herein. See, also, e.g., Loscalzo and Schaefer (eds), 1998, Thrombosis and Hemorrhage 2nd Edition, Chapter 16, Williams and Wilkins: Baltimore, Md.; Horton (ed), 1995, Adhesion Receptors as Therapeutic Targets, Chapter 15, CRC Press, Inc.: London, United Kingdom, and U.S. Pat. No. 5,976,532.

In view of the fact that GPVI is a cell surface receptor, in particular, a platelet receptor, standard quantitative binding studies can be utilized to measure modulator binding to platelets. Horton (ed), 1995, Adhesion Receptors as Therapeutic Targets, Chapter 15, CRC Press, Inc.: London, United Kingdom. Such binding assays can also be utilized to perform receptor blockade studies to measure the number of cellular sites available for binding modulator by comparing the number of molecules of labeled modulator molecules (e.g., labeled anti-GPVI antibodies) bound per platelet at a series of concentrations with the number of modulator molecules bound at saturation. See, e.g., Coller et al., 1985, J. Clin. Invest. 76: 101 or U.S. Pat. No. 5,854,005. The reversibility of an agent of the invention (e.g., anti-GPVI antibodies) binding on platelets can also be tested, using, e.g., techniques such as those described in Coller et al., 1985, J. Clin. Invest. 76: 101, and U.S. Pat. No. 5,976,532. In addition, under noncompetitive conditions, the rate of modulator dissociation can be assessed by, e.g., flow cytometry analysis of platelets when fluorescently labeled agent (e.g., anti-GPVI antibody)-coated platelets are mixed with an equal number of untreated platelets and incubated at physiological temperature. In instances wherein appreciable reversibility indicates that inhibitory effects of single in vivo injection can be relatively short-lived, suggesting that an administration regimen involving an initial bolus followed by continuous infusion may be most effective.

In vitro and ex vivo assays for inhibition of platelet aggregation can also be utilized. Such assays are well known to those of skill in the art and include, but are not limited to the turbidometric method, in which aggregation is measured as an increase in transmission of visible light through a stirred or agitated platelet suspension. See, e.g., Chanarin, L., 1989, Laboratory Haematology, Chapter 30, Churchill, Livingstone, London; and Schmidt, R. M. (ed), 1979, CRC Handbook Series in Clinical Laboratory Science, CRC Press, Inc.: Boca Raton, Fla. Platelet aggregation can also be assayed via methods such as those described in U.S. Pat. No. 5,976,532. For example, in a non-limiting example of such a method, the platelet concentration in platelet-rich plasma obtained (PRP) obtained from normal or patient blood samples is adjusted to 200,000 to 300,000/mm3. In an in vitro assay, the PRP is aliquoted and incubated in the presence or absence of a GPVI modulator (e.g., an anti-GPVI antibody) for a period of time (e.g., 15 minutes at 37 C) prior to the addition of a platelet inducing agonist (e.g., ADP, thrombin, collagen, epinephrine, and ristocetin). In an ex vivo assay, the PRP obtained from individuals treated with GPVI or a placebo is aliquoted and incubated in the presence of a platelet inducing agonist (e.g., ADP, thrombin, collagen, epinephrine, and ristocetin). Platelet aggregation is measured by assessing an increase in the transmission of visible light through a platelet suspension using a spectrophotometer. In certain embodiments, it is preferred that the agent of the invention does not effect platelet attributes or functions other than platelet aggregation. Such other platelet attributes or functions, include, for example, agonist-induced platelet shape change (e.g., GPIb-vWF-mediated platelet agglutination induced by ristocetin), release of internal platelet granule components, activation of signal transduction pathways or induction of calcium mobilization upon platelet activation.

Assays for these platelet attributes and functions are well known to those of skill in the art and can be utilized to routinely test, develop and identify anti-GPVI agents exhibiting a specificity for modulation of platelet aggregation, in particular, the modulation e.g. inhibition of GPVI-collagen interaction. The shape of a platelet can be analyzed in any in vitro assay known to those of skill in the art. Briefly, platelets are contacted in the presence or absence of an anti-GPVI agent with a platelet inducing agonist (e.g., ADP, thrombin, collagen, epinephrine, and ristocetin) and the shape of the platelets are assessed by microscopy or by flow cytometry. Platelet degranulation can be analyzed, for example, by measuring the presence of ATP in vitro following stimulation with a platelet inducing agonist in the presence or absence of an anti-GPVI agent (see, e.g., Loscalzo and Schaefer (eds), 1998, Thrombosis and Hemorrhage 2"d Edition, Chapter 16, Williams and Wilkins: Baltimore, Md.). The activation of platelet signal transduction pathways can be analyzed in in vitro and ex vivo assays using assays known to those of skill in the art. For example, the activation of signal transduction pathways in vitro can be analyzed by contacting platelet-rich plasma samples with platelet agonists (e.g., collagen and convulxin) in the presence or absence of an anti GPVI agent and measuring the effect of such treatment on the level of tyrosine phosphorylation of signaling molecules, such as FcRy, Syk, and PLCy 2 (e.g., tyrosine phosphorylation can be detected by immunoprecipitation followed by SDS-PAGE, kinase assays, etc.).

Other assays for platelets include in vivo assays such as assessment of prolongation of bleeding time. For example, the bleeding time resulting from an injury (e.g., a small tail vein incision) in an animal model treated with a GPVI modulator can be compared to an animal model treated with a placebo. In humans, the number of bleeding episodes and the length of the bleeding time during a bleeding episode for a human treated with a an anti-GPVI agent can be compared to a human treated with a placebo.

The efficacy of anti-GPVI agents can be assessed in a variety of animal models of arterial thrombosis, including, but not limited to, the Folts model, the electrolytic injury model, the thrombin-induced arterial thrombosis model, and a model of acute thrombosis resulting from injury induced by coronary balloon angioplasty (see, e.g., Loscalzo and Schaefer (eds), 1998, Thrombosis and Hemorrhage 2nd Edition, Chapter 16, Williams and Wilkins: Baltimore, Md.). The Folts model, which is the most widely used animal model of coronary and carotid artery thrombosis, is produced by mechanical concentric vessel narrowing using a cylinder placed around the artery. The electrolytic model, which is used for deep arterial injury, is produced by introducing an electric current via an electrode to the intimal layer of a stenosed vessel. By applying species specificity data that can readily be obtained using, e.g., the platelet aggregation assays described herein, animal models particularly well suited to study of any given anti-GPVI agent can be chosen.

In particular, the GPVI epitopes disclosed herein and agents (e.g. antibodies, aptamers or small molecules) which bind to these epitopes can be utilized in assays, such as those described above, to identify inhibitors which bind to GPVI. In embodiments, there are identified inhibitors which specifically bind to GPVI; in other embodiments, binding is non-specific. To be mentioned are epitopes (b) and (c) as well agents which bind to them, and their utilization in assays to identify inhibitors which bind to GPVI and prevent GPVI binding to collagen.

In instances wherein an anti-GPVI antibody or other anti-GPVI agent as described herein is to be utilized as a therapeutic, characterization of the antibody or agent can routinely be assayed and ascertained via the methods presented herein. For example, the fact that platelets are readily available, coupled with the availability of multiple assays for platelet function provide for routine testing and analysis (e.g., for in vitro testing and analysis) of such antibodies. For example, the in vivo pharmacodynamic characterization of anti-GPVI antibodies can be facilitated via the availability of various platelet assays (e.g., prolongation of bleeding time, quantitative measurement of GPVI receptor blockade, inhibition of ex vivo platelet aggregation) such as those described herein and those known in the art that can be correlated with each other to permit more effective assessment of a modulator's functional consequences. The correlation available for such assays, therefore, allows for the in vitro characterization of an anti-GPVI antibody to more directly apply to the measurement of the antibody's therapeutic effect. In addition to utilizing the availability of platelets and platelet assays for assessing the therapeutic efficacy, including clinical efficacy, of an anti-GPVI antibody, this availability can also be utilized for preclinical drug development aspects such as determining antibody dosage response, toxicology, magnitude of effect (e.g., magnitude of initial effect and magnitude of effect's duration), function, specificity (e.g., specificity with respect to particular platelet functions), receptor specificity, and species specificity (which, in turn, can identify appropriate animal models for pharmacology studies). The techniques described in this paragraph are of course applicable to other anti-GPVI agents and not only to antibodies against GPVI (e.g. against an epitope disclosed herein).

Thus, the present disclosure provides a method (also referred to herein as a "screening assay") for identifying modulators, i.e., candidate or test compounds or agents (e.g., peptides, peptidomimetics, small molecules or other drugs) which bind to GPVI and which inhibit binding of GPVI to collagen.

In one embodiment, the invention provides assays for screening candidate or test compounds which bind to or modulate the activity of the membrane-bound form of GPVI or biologically active portion thereof. In particular, the epitopes of GPVI mentioned herein as being useful in collagen binding assays may be used in the screening assays.

The test compounds and agents of the present disclosure can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) Anticancer Drug Des. 12: 145).

Examples of methods for the synthesis of molecular libraries can be found in the art, for example in DeWitt et al. (1993) Proc. Natl. Acad. Sci. USA 90: 6909; Erb et al. (1994) Proc. Natl. Acad. Sci. USA 91: 11422; Zuckermann et al. (1994). J Med. Chem. 37: 2678; Cho et al. (1993) Science 261: 1303; Carrell et al. (1994) Angew. Chem. Int. Ed. Engl. 33: 2059; Carell et al. (1994) Angew. Chem. Int. Ed. Engl. 33: 2061; and Gallop et al. (1994) J. Med. Chem. 37: 1233. Libraries of compounds may be presented in solution (e.g., Houghten (1992) Bio/Techniques 13:412-421), or on beads (Lam (1991) Nature 354: 82-84), chips (Fodor (1993) Nature 364: 555-556), bacteria (U.S. Pat. No. 5,223,409), spores (U.S. Pat. Nos. 5,571,698; 5,403,484; and 5,223,409), plasmids (Cull et al. (1992) Proc. Natl. Acad. Sci. USA 89: 1865-1869) or phage (Scott and Smith (1990) Science 249: 386-390; Devlin (1990) Science 249: 404-406; Cwirla et al. (1990) Proc. Natl. Acad. Sci. USA 87: 6378-6382; and Felici (1991) J Mol. Biol. 222:301-310).

In one embodiment, an assay is a cell-based assay in which a cell which expresses a membrane-bound form of GPVI, or a biologically active portion therefore, for example peptide comprising epitope (b) or (c), on the cell surface is contacted with a test compound and the ability of the test compound to bind to GPVI determined. The cell, for example, can be a yeast cell or a cell of mammalian origin. Determining the ability of the test compound to bind to GPVI can be accomplished, for example, by coupling the test compound with a radioisotope or enzymatic label such that binding of the test compound to GPVI or biologically active portion thereof can be determined by detecting the labeled compound in a complex. For example, test compounds can be labeled with 125I, 35S, 14C, or 3H, either directly or indirectly, and the radioisotope detected by direct counting of radioemmission or by scintillation counting.

Alternatively, test compounds can be enzymatically labeled with, for example, horseradish peroxidase, alkaline phosphatase, or luciferase, and the enzymatic label detected by determination of conversion of an appropriate substrate to product. In a preferred embodiment, the assay comprises contacting a cell which expresses a membrane-bound form of GPVI, or a biologically active portion thereof, on the cell surface with a known compound which binds GPVI to form an assay mixture, contacting the assay mixture with a test compound, and determining the ability of the test compound to interact with GPVI, wherein determining the ability of the test compound to interact with the polypeptide comprises determining the ability of the test compound to preferentially bind to GPVI or a biologically active portion thereof as compared to the known compound.

In another embodiment, an assay is a cell-based assay comprising contacting a cell expressing on the cell surface a membrane-bound form of GPVI, or a biologically active portion thereof, for example a peptide comprising epitope (b) or (c), with a test compound and determining the ability of the test compound to modulate (e.g., stimulate or inhibit) the activity of the polypeptide or biologically active portion thereof. Determining the ability of the test compound to modulate the activity of the polypeptide or a biologically active portion thereof can be accomplished, for example, by determining the ability of the polypeptide protein to bind to or interact with a target molecule.

Reference to peptide GPVI epitopes herein includes the linear peptide epitopes of GPVI identified using hGP 5C4 as described in the examples included herein. Preferably, the epitopes used in assays to screen for new anti-GPVI compounds include those identified as having higher than background binding to hGP 5C4 antibody, as described herein.

In yet another embodiment, an assay of the present invention is a cell-free assay comprising contacting GPVI or a portion thereof, for example one or more of the peptide GPVI epitopes identified herein (i.e the ligands disclosed herein), with a test agent and determining the ability of the test agent to bind to the polypeptide or biologically active portion thereof. Binding of the test agent to the polypeptide or peptides of the invention can be determined either directly or indirectly as described above. In a preferred embodiment, the assay includes contacting one or more linear GPVI peptides disclosed herein, with a known compound which binds the peptide to form an assay mixture, contacting the assay mixture with a test agent, and determining the ability of the test agent to interact with the peptide or plurality of peptides, wherein determining the ability of the test agent to interact with the peptide(s) comprises determining the ability of the test agent to preferentially bind to the peptide or peptides as compared to the known compound. In embodiments, the assay uses epitope (b) or (c) disclosed herein.

In another embodiment, an assay is a cell-free assay comprising contacting a peptide or plurality of GPVI peptides as described herein as comprising at least one epitope for hGP 5C4 with a test agents and determining the ability of the test agents to modulate (e.g., stimulate or inhibit) the activity of GPVI, for example the interaction between GPVI and collagen. Determining the ability of the test agent to modulate the activity of GPVI, e.g. GPVI-collagen interaction can be accomplished, for example, by determining the ability of GPVI to bind to collagen by one of the methods described above for determining direct binding.

In yet another embodiment, the cell-free assay comprises contacting GPVI or one or more of the GPVI peptide epitopes identified herein with a known compound which binds the peptide to form an assay mixture, contacting the assay mixture with a test agent, and determining the ability of the test agent to interact with the peptide, wherein determining the ability of the test agent to interact with the peptide(s) comprises determining the ability of the peptide(s) to preferentially bind to or modulate the activity of a target molecule.

In more than one embodiment of the above assay methods of the present invention, it may be desirable to immobilize either GPVI or one or more of the GPVI peptides of the present disclose or its target molecule to facilitate separation of complexed from uncomplexed forms of one or both of the proteins/peptides, as well as to accommodate automation of the assay. Binding of a test agent to the peptide(s), or interaction of the peptide(s) with a target molecule, for example collagen, in the presence and absence of a candidate agent, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase fusion proteins or glutathione-S-transferase fusion proteins can be adsorbed onto glutathione sepharose beads (Sigma Chemical; St. Louis, Mo.) or glutathione derivatized microtitre plates, which are then combined with the test agent or the test agent and the GPVI epitope peptides of the invention, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of binding or activity of the peptides of the invention can be determined using standard techniques.

Other techniques for immobilizing proteins on matrices can also be used in the screening assays of the invention. For example, either the GPVI peptide of the invention or its target molecule can be immobilized utilizing conjugation of biotin and streptavidin.

Biotinylated GPVI peptides of the invention or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with GPVI or target molecules but which do not interfere with binding of GPVI to its target molecule can be derivatized to the wells of the plate, and unbound target or polypeptide of the invention trapped in the wells by antibody conjugation. Methods for detecting such complexes, in addition to those described above for the GST-immobilized complexes, include immunodetection of complexes using antibodies reactive with the polypeptide of the invention or target molecule, as well as enzyme-linked assays which rely on detecting an enzymatic activity associated with GPVI or target molecule.

In another aspect the invention provides a method for inhibiting platelet aggregation in a subject, comprising administering to a subject a therapeutically effective amount of an agent as hereinbefore described, thereby inhibiting platelet aggregation. In one embodiment, the agent is an antibody or fragment thereof.

In another aspect the invention provides a method for inhibiting platelet aggregation, comprising contacting platelets with an effective amount of the agent or an antibody as hereinbefore described, thereby inhibiting platelet aggregation. The platelets may be in vitro or they may be in vivo.

In yet another aspect, the invention provides a method for treating a disease or disorder selected from therapeutic or prophylactic cardiovascular conditions, thrombosis, heart attack, stroke, intermittent coagulation, conditions with disseminated intravascular coagulation, thrombocytopenic purpura, haemolytic uraemic syndrome, damage to blood vessel wall resulting from surgery or therapy, collagen-induced inflammation, homozygous sickle disease, kidney damage by platelet and fibrin disposition on the glomerular member and micro-angiopathic vasculitides comprising administering an agent of the invention, to a subject with the disease or disorder or at risk of developing the disease or disorder. The treatment may be therapeutic and/or prophylactic.

Consequently, the invention provides for the use of an agent of the invention for the manufacture of a medicament to treat or prevent of a disease or disorder selected from cardiovascular conditions, thrombosis, heart attack, stroke, intermittent coagulation, conditions with disseminated intravascular coagulation, thrombocytopenic purpura, haemolytic uraemic syndrome, damage to blood vessel wall resulting from surgery or therapy, collagen-induced inflammation, homozygous sickle disease, kidney damage by platelet and fibrin disposition on the glomerular member and micro-angiopathic vasculitides.

Advantageously, the agents of the invention may have a reduced tendency to cause unwanted bleeding in patients and medical uses of the agents described herein are useful in the treatment of certain patient groups such as those suffering from identifiable bleeding disorders for example thrombocytopenia purpura.

There are provided agents which bind to a GPVI receptor on platelets and not activate the platelets. Also provided are agents which have little or no effects on ADP-mediated activation of PAC-1 and CD 62P. Additionally, agents are provided which have little or no effect on TRAP- and ADP-mediated platelet aggregation and ATP release of human platelets ex vivo. As a consequence, the agents should be a highly selective inhibitor of arterial thrombosis with reduced or no effects on venous thrombosis and hemostasis. Further provided are inhibitors which do not activate platelets and should have reduced or no effect in the induction of immunothrombocytopenia. The inhibitor of the present invention may also inhibit the release of pro-inflammatory substances by platelets and therefore inhibit pro-inflammatory responses.

In one class of embodiments the agent is not a full length antibody; it may be an antibody fragment or humanized antibody fragment for example a Fab or a single chain variable fragment e.g. humanized in either case.

Thus, the present invention includes agents which advantageously circumvent an almost inherent problem of antiplatelet drugs (Quinn M J et al (2002): *Circulation* 106: 379-385; Bhatt D L & Topol E J; (2003): *Nat Rev Drug Discov* 22: 15-28) i.e. agents which are used to block platelet interactions can also trigger pro-inflammatory platelet responses which can potentially lead to fatality. The agents of the invention at least in some embodiments are advantageously highly potent and selective inhibitors of platelet activation and show little prolongation of bleeding time. The invention includes agents which can advantageously also be drugs for use in the treatment of acute vascular syndromes like acute coronary syndromes or ischemic stroke because they avoid or reduce unwanted and potentially fatal side effects like intra cranial hemorrhage or other bleeding complications. The agents of the invention advantageously are also potent and highly selective inhibitors of release of transmitter substances such as ATP from intracellular storage vesicles of human platelets. Without being bound by any particular theory, this may be important for platelet-endothelium interactions which promote atherosclerosis. Agents of the invention are advantageously used as drugs for the treatment and prevention of atherosclerosis. The agents also solve the problem of treatment of atherosclerosis by inhibition of platelet secretion.

It will be appreciated from the above that the invention provides GPVI inhibitors, which in embodiments are selective GPVI inhibitors.

The invention further includes medical devices which are coated or impregnated with an anti-GPVI agent described herein, for example implants and prostheses, particularly cardiovascular implants and prostheses, of which may be mentioned arterial prostheses, venous prostheses, vascular grafts, vascular stents, vascular catheters, prosthetic valves, ventricular assist devices, anuloplasty rings, prostheses for aortic aneurysms and vena cava filters; haemodialysis and other apheresis machines and parts and fittings therefor; extracorporeal blood circuit equipment, for example cardiopulmonary bypass machines and parts and fittings therefor.

Further aspects and embodiments of the disclosure are set forth in the following description and claims.

The extent of protection includes counterfeit or fraudulent products which contain or purport to contain a compound of the invention irrespective of whether they do in fact contain such a compound and irrespective of whether any such compound is contained in a therapeutically effective amount. Included in the scope of protection therefore are packages which include a description or instructions which indicate that the package contains a species or pharmaceutical formulation of the invention and a product which is or comprises, or purports to be or comprise, such a formulation or species.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

Throughout the description and claims of this specification, the words "comprise" and "contain" and variations of the words, for example "comprising" and "comprises", mean "including but not limited to", and are not intended to (and do not) exclude other moieties, additives, components, integers or steps.

Figure 1A:
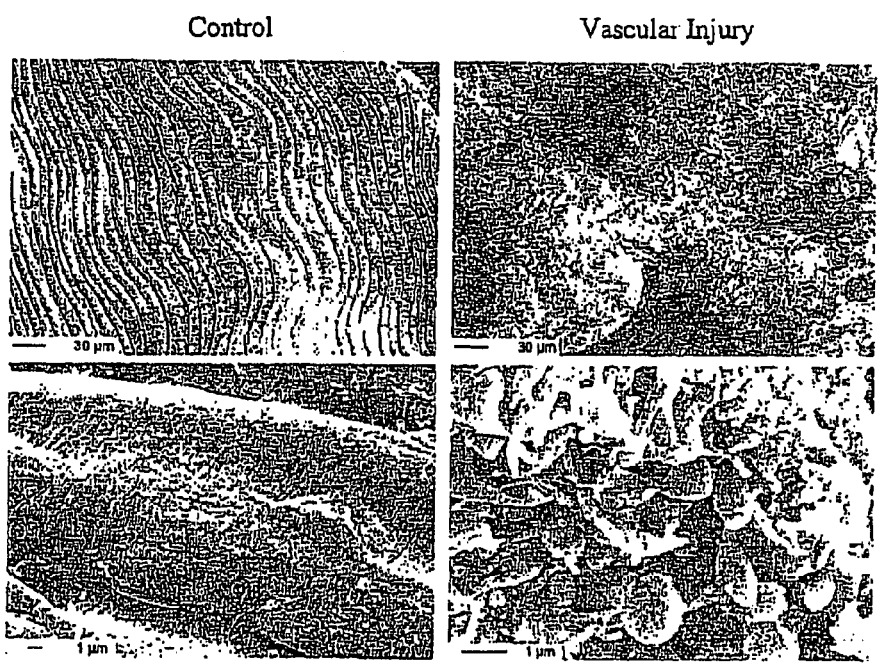
FIG. 1 Platelet adhesion and aggregation following vascular injury of the common carotid artery in C57BL6/J mice in vivo.
(a) Scanning electron micrographs of carotid arteries prior to (left panels) and 2 hrs after (right panels) vascular injury. Endothelial denudation induces platelet adhesion and aggregation, resulting in the formation of a platelet-rich (lower left) thrombus.
(b) Platelet-endothelial cell interactions 5 min after vascular injury were investigated by in vivo fluorescence microscopy of the common carotid artery in situ (black columns). Animals without vascular injury served as controls (open columns). The left and right panels summarize transient and firm platelet adhesion, respectively, of eight experiments per group. Platelets were classified according to their interaction with the endothelial cell lining as described[24] and are given per mm$^2$ of vessel surface. Mean±s.e.m., asterisk indicates significant difference compared to control, P<0.05.

(c) Platelet aggregation following vascular injury was determined by fluorescence microscopy in vivo (black columns). Animals without vascular injury served as controls (open columns). Mean±s.e.m., n=8 each group, asterisk indicates significant difference compared to wild type mice, P<0.05. The microphotographs (right) show representative in vivo fluorescence microscopy images in control animals (upper panel) or following vascular injury (lower panel). White arrows indicate adherent platelets.

FIG. 2 Inhibition of GPVI abrogates platelet adhesion and aggregation after vascular injury. (a) Platelet adhesion following vascular injury was determined by intravital videofluorescence microscopy. Fluorescent platelets were preincubated with 50 µg/ml anti-GPVI (JAQ1) Fab fragments or control rat IgG. Platelets without mAb preincubation served as control. The left and right panels summarize transient and firm platelet adhesion, respectively. Mean±s.e.m., n=8 each group, asterisk indicates significant difference compared to control, P<0.05. (b) illustrates the percentage of platelets establishing irreversible adhesion after initial tethering/slow surface translocation is. (c) Platelet aggregation following vascular injury in vivo. Aggregation of platelets preincubated with tyrodes, irrelevant rat IgG, or anti-GPVI Fab (JAQ1) was assessed by fluorescence microscopy as described. Mean±s.e.m., n=8 each group, asterisk indicates significant difference compared to control, P<0.05. (d) The photomicrographs show representative in vivo fluorescence microscopy images illustrating platelet adhesion in the absence or presence of anti-GPVI Fab (JAQ1) or control IgG.

FIG. 3 Platelet adhesion following endothelial denudation in GPVI-deficient mice. (a) JAQ1-treated mice lack GPVI. Upper panels: Platelets from mice pretreated with irrelevant control IgG (left) or anti-GPVI (JAQ1) (right) were incubated with FITC-labeled JAQ1 and PE-labeled anti-mouse CD41 for 10 min at room temperature and directly analyzed on a FACScan™. A representative dot blot of 3 mice per group is presented. Lower panel: Whole platelet lysates from three control IgG or JAQ1-treated mice were separated by SDS-PAGE under non-reducing conditions and immunoblotted with FITC-labeled JAQ1, followed by incubation with HRP-labeled rabbit-anti-FITC mAb. (b) Scanning electron micrographs of carotid arteries 2 hrs after vascular injury in control animals (upper panels) or GPVI-depleted mice (lower panels). Endothelial denudation induced platelet adhesion and platelet aggregation in control animals. In contrast, only very few platelets attached along the damaged vessel wall in GPVI-depleted mice. Subendothelial collagen fibers are visible along the denuded area. (c) Platelet tethering and firm platelet adhesion, (d) transition from initial tethering to stable arrest (percentage of tethered platelets), and (e) platelet aggregation following vascular injury of the carotid artery was determined in GPVI-deficient (JAQ1-pretreated mice) or control IgG-pretreated mice (for details see Materials and Methods). The panels summarize platelet adhesion (transient and firm) and platelet aggregation in eight experiments per group. Mean±s.e.m., asterisk indicates significant difference compared to control IgG, P<0.05. (f) The photomicrographs show representative in vivo fluorescence microscopy images illustrating platelet adhesion in GPVI-deficient (JAQ1) and control IgG-treated mice.

Figure 4:
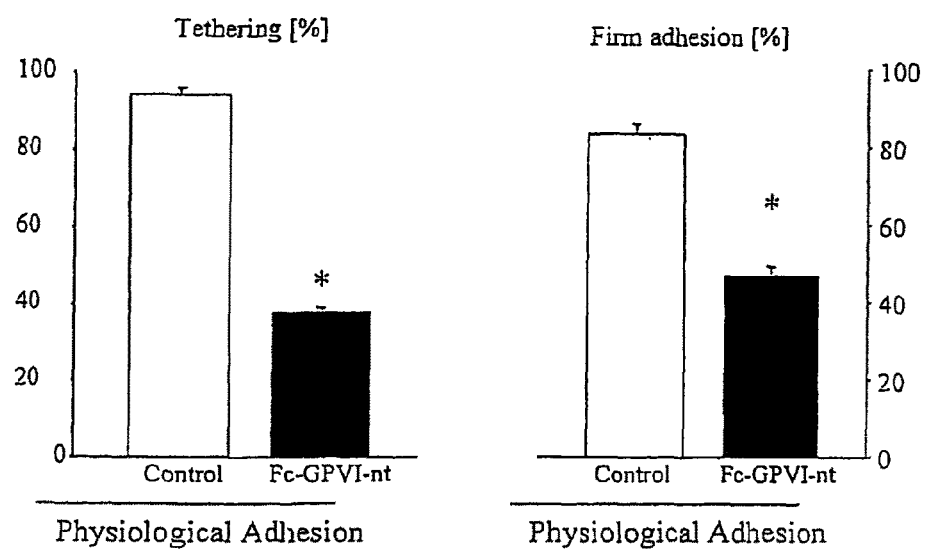

FIG. 4 Platelet adhesion to the surface of collagen coated glass coverslips under physiological flow conditions was assessed ex vivo. Left panel: Platelets from mice pretreated with irrelevant control IgG immunoadhesin (control) (left) or anti-GPVI immunoadhesin (Fc-GPVI-nt) (right) were investigated for adhesion under physiological flow conditions. The number of platelets was assessed by FACS counting of the washed coverslips at the end of each experiment. Platelet tethering as the first step of platelet adhesion was assessed after 30 seconds and firm platelet adhesion after 5 min under flow conditions. (for details see Example 6). The panels summarize transient and firm platelet adhesion in eight experiments per group. Mean±s.e.m., asterisk indicates significant difference compared to control IgG, P<0.05.

Figure 5:
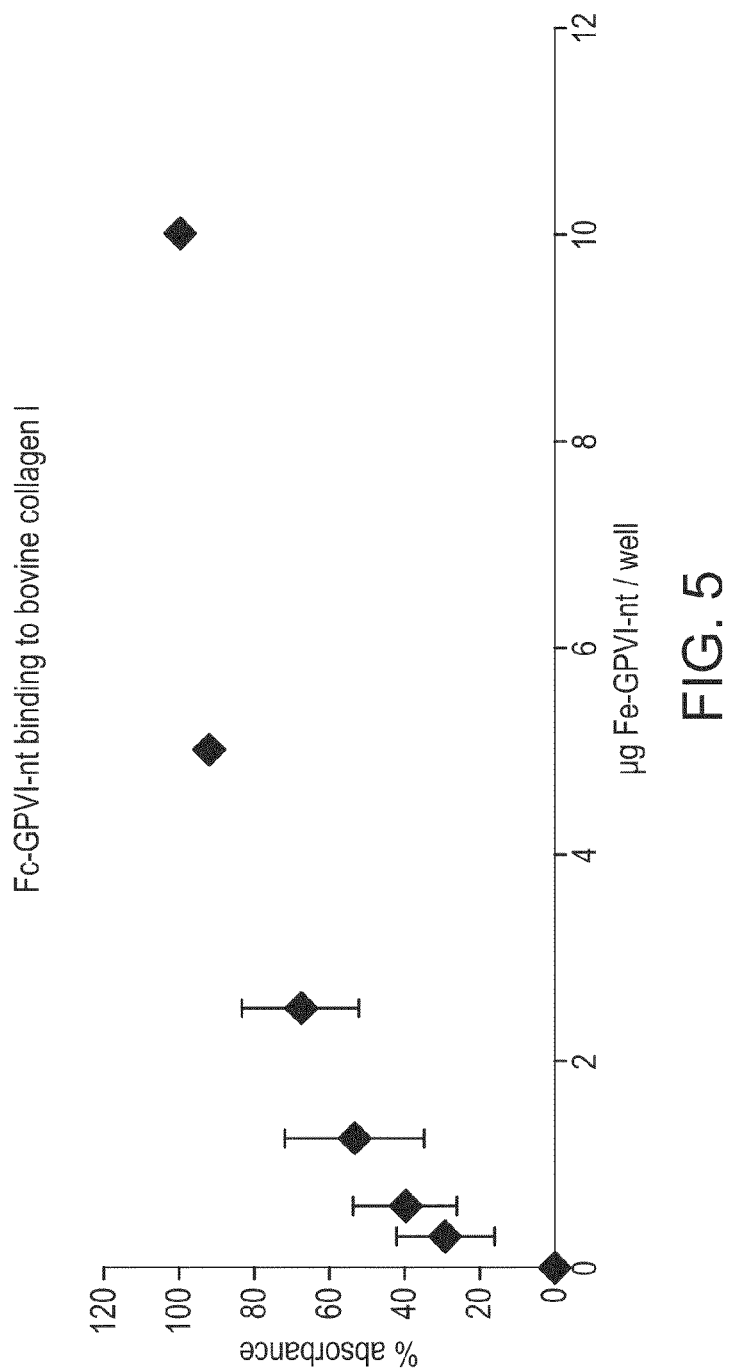

FIG. 5 Interaction of Fc-GPVI-nt with collagen was monitored in an ELISA based assay. Adhesion of the immunoadhesin Fc-GPVI-nt consisting of the extracellular domain of GPVI and the FC part of an IgG to collagen coated plates with increasing concentrations of Fc-GP VI-nt (0.5 µg to 10 µg) was investigated. The binding is visualised with a secondary antibody labelled with peroxidase directed to the Fc part of Fc-GPVI-nt. Peroxidase is finally detected by ELISA. In this representative experiment binding of Fc-GPVI-nt to collagen was monitored with sufficient affinity, which reached saturation at µg concentrations.

FIG. 6 Interaction of the Fc-GPVI-nt with collagen and the possibility to screen for GP VI inhibitors was demonstrated with the inhibitory anti mouse GP VI antibody JAQ 1. Adhesion of the immunoadhesin Fc-GP VI-nt (2 µg/well) to collagen coated ELISA plates is shown to be specific: the empty immunoadhesin Fc-nt did not show any binding. Thus, this provides an ELISA based assay for the screening against GP VI inhibitors with the upscale potential to high-throughput capacities.

FIG. 7 Amino acid sequence of Fc-GPVI-nt: SEQ ID NO: 147. A peptide having the amino acid sequence of Fc-GPVI-nt is used in dimeric form as an antigen for the preparation of the antibody of the present invention.

FIG. 8 DNA-Sequence of immunoadhesin Fc-GPVI-nt: SEQ ID NO: 148. Bases 1 to 807 encode the extracellular domain of GP VI. Bases 817 to 1515 encode the Fc part of the IgG.

Figure 9:
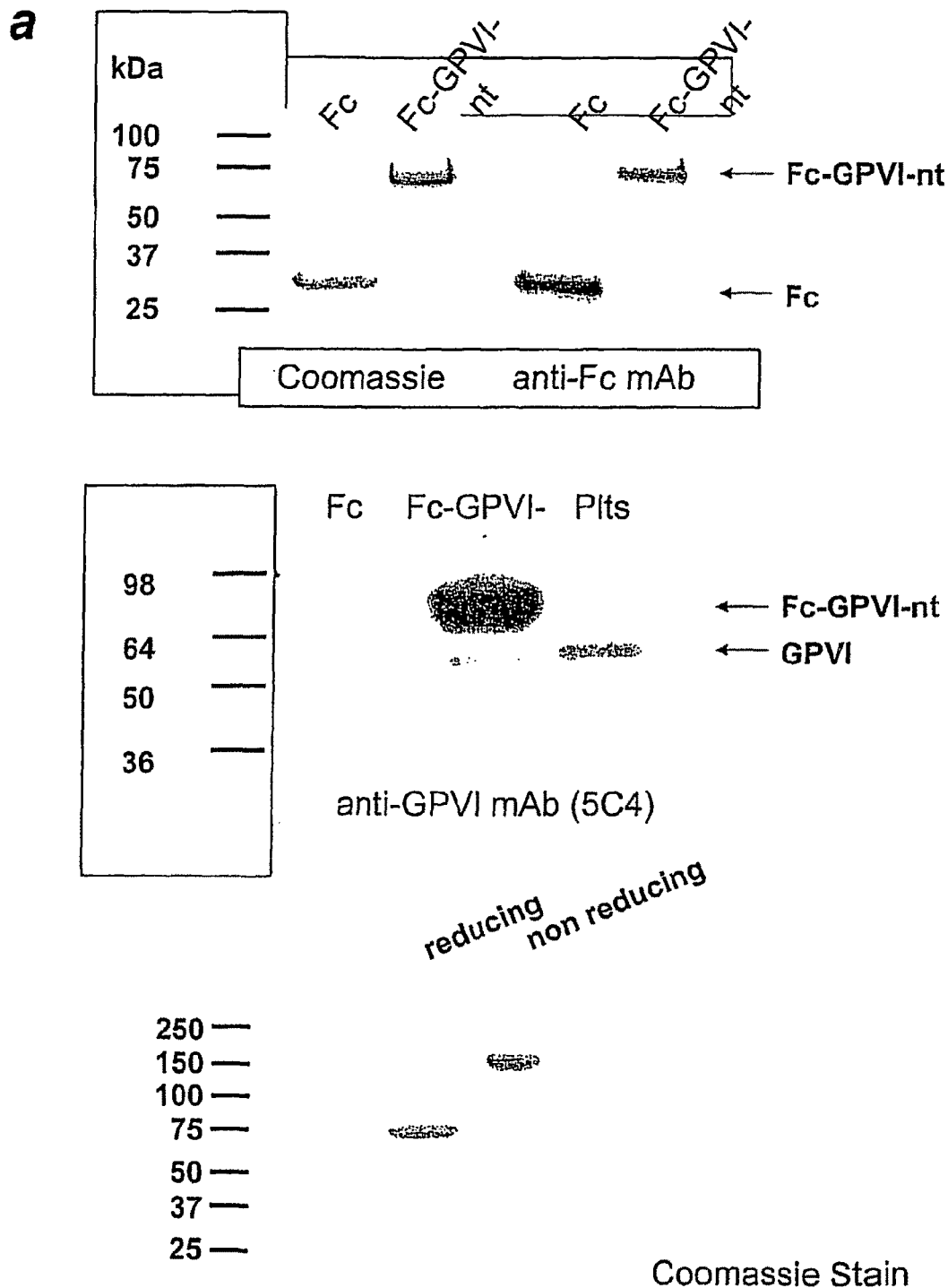
Figure 9:
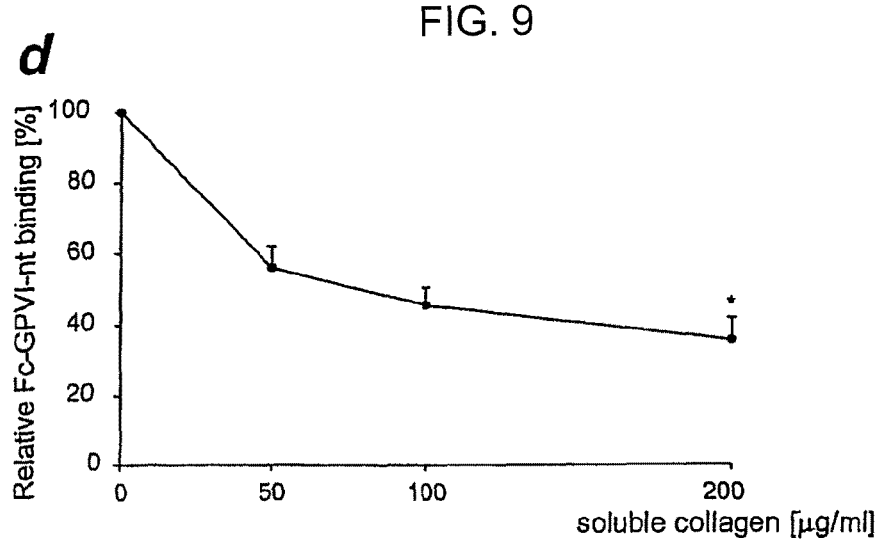
Figure 9E:
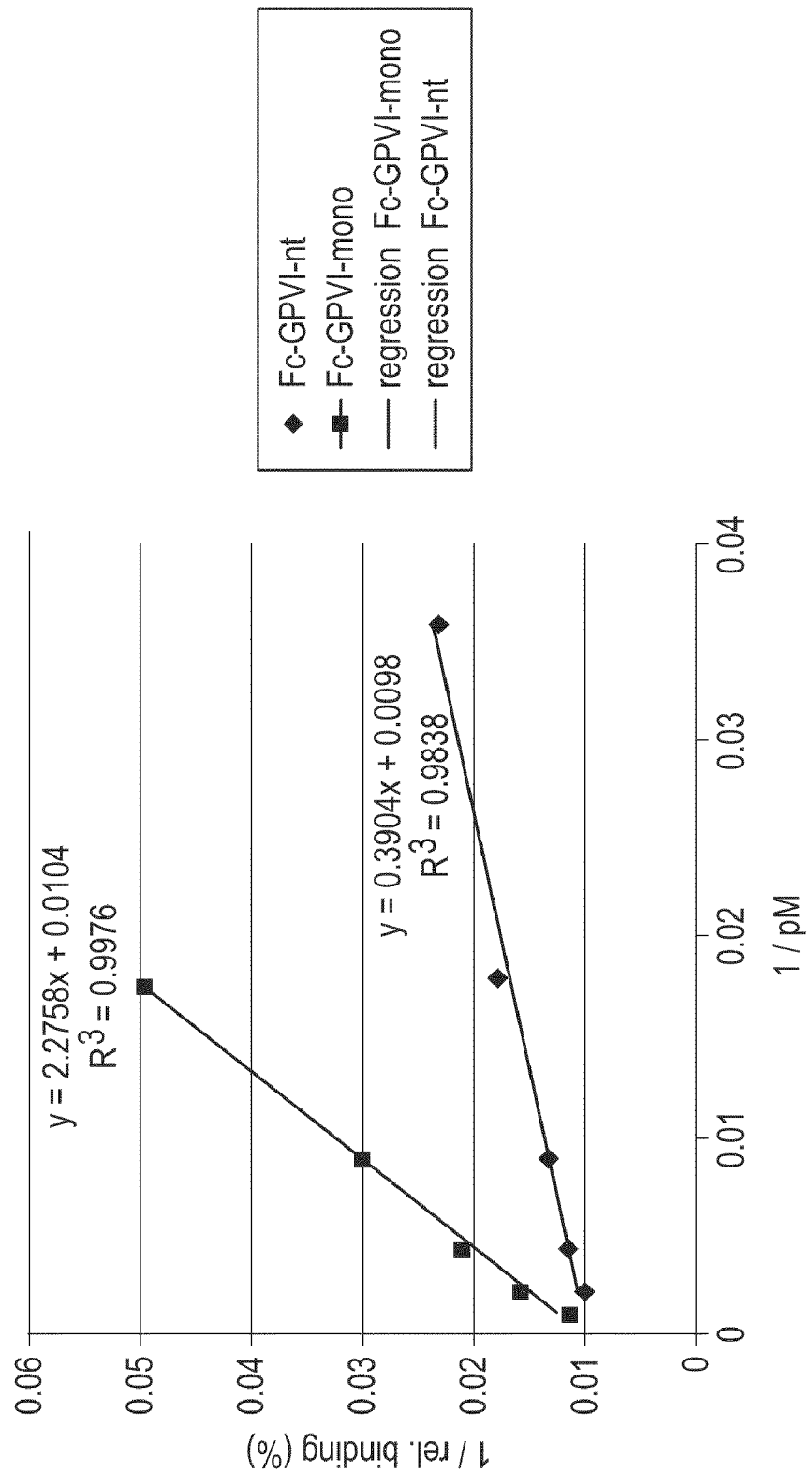

FIG. 9 Characterization of GPVI-Fc. (a) upper panel: Fc-GPVI-nt and control Fc lacking the extracellular GPVI domain were used for SDS-PAGE under reducing conditions. Coomassie blue stain (left) and immunoblotting with peroxidase-conjugated goat anti-human Fc antibody (right) identified Fc-GPVI-nt with a molecular mass of ~80 kDa. Middle panel: Immunoblotting of Fc, Fc-GPVI-nt, or human platelets using the anti-GPVI monoclonal antibody 5C4. 5C4 detected both adenovirally expressed Fc-GPVI-nt fusion protein and platelet GPVI, but not the control Fc. Lower panel: Molecular mass under reducing (right) and non-reducing (left) conditions. While the molecular mass of Fc-GPVI-nt was approximately 80 kDa under reducing conditions, the complete nt with ~160 kDa protein was identified under non-reducing conditions. (b-d) Characterization of Fc-GPVI-nt collagen interactions. (b) Binding assays using different concentrations of soluble Fc-GPVI-nt and immobilized collagen (10 µg/ml) were performed to define Fc-GPVI-nt-collagen interactions. Bound Fc-GPVI-nt was detected by anti-Fc mAb antibody (dilution 1:10.000) and is given relative to the binding observed at 10 µg/ml Fc-GPVI-nt. Fc-GPVI-nt binds to collagen in a saturable manner. Mean±s.e.m., n=6 each Fc-GPVI-nt concentration, asterisk indicates significant difference compared to 0 µg/ml Fc-GPVI-nt, P<0.05. (c, left panel) shows binding of Fc-GPVI-nt (20 µg/ml) to various substrates. Binding of Fc-GPVI-nt to BSA (10 µg/ml) or vWF (10 µg/ml) is given as percentage of GPVI-dimer-binding to immobilized collagen. Binding of Fc-GPVI-nt did not occur to BSA or vWF, supporting the specificity of Fc-GPVI-nt binding. Mean±s.e.m., asterisk indicates significant difference compared to collagen, P<0.05. (c, right panel) illustrates binding of Fc-GPVI-nt (20 µg/ml) or Fc (20 µg/ml) to immobilized collagen (10 µg/ml). Bound Fc-GPVI-nt or Fc was detected by anti-Fc mAb antibody (dilution 1:10.000) and is given relative to the binding observed with Fc-GPVI-nt. Only Fc-GPVI-nt, but not Fc or anti-Fc mAb binds to immobilized collagen. Mean±s.e.m., n=8 each group, asterisk indicates significant difference compared to Fc-GPVI-nt binding, P<0.05. (d) Fc-GPVI-nt (20 µg/ml) was preincubated for 10 min with different concentrations of soluble collagen. After incubation the plates were washed and Fc-GPVI-nt binding was detected by peroxidase-conjugated goat anti-human IgG antibody (dilution 1:10.000). Fc-GPVI-nt binding is given relative to the binding observed in the absence of soluble collagen. Soluble collagen inhibits GPVI-Fc-dimer-dimer binding to immobilized collagen in a dose-dependent manner. Mean±s.e.m., n=3 each collagen concentration, asterisk indicates significant difference compared to 0 µg/ml collagen, P<0.05. (e) The difference of the binding affinity between the monomeric form of the GPVI-Fc fusion protein and Fc-GPVI-nt was assessed in direct comparison. The binding of the monomer and dimer was assessed on collagen type 1 coated ELISA plates. Increasing concentrations of the GPVI fusion proteins bond to collagen in a sturable manner. Here a Linewaver Burke plot is demonstrated for affinity assessment (e). The affinity of the monomeric GPVI fusion protein was about 10 times lower compared to equimolar concentrations of the dimeric form Fc-GPVI-nt.

Figure 10:
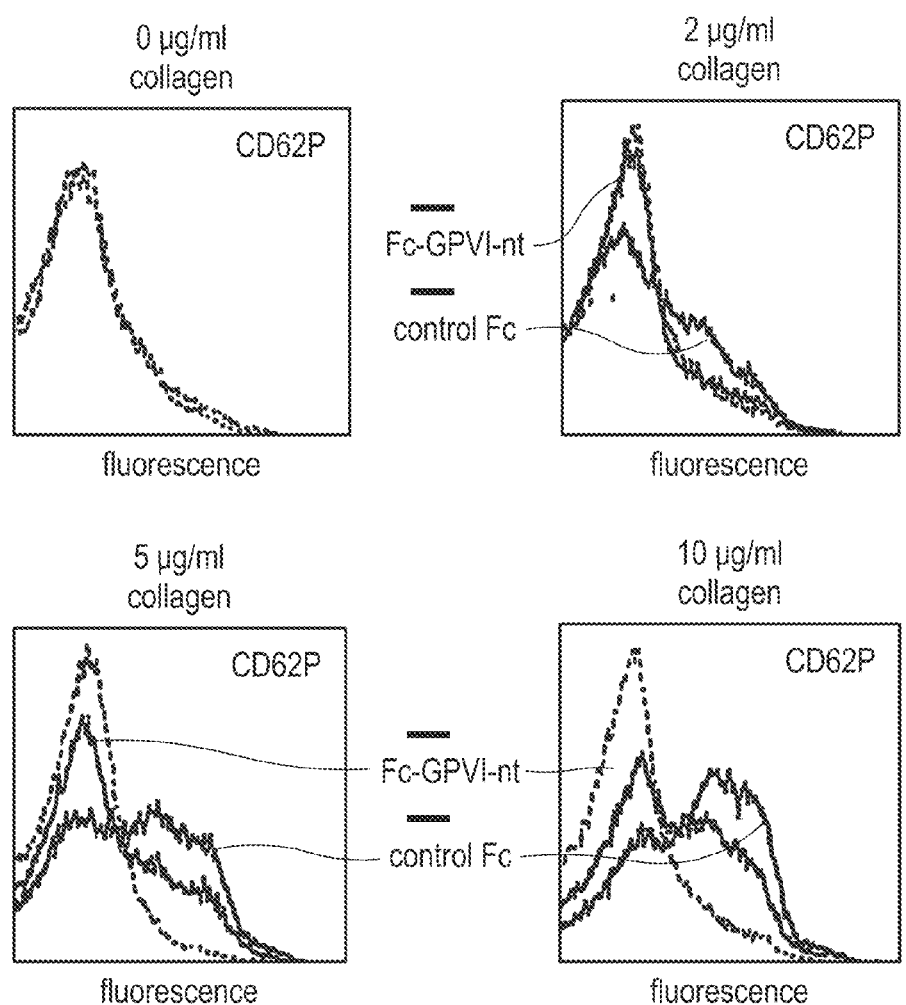

FIG. 10 Fc-GPVI-nt inhibits CD 62 P activation on human platelets as a parameter of release of intracellular transmitter substances from alpha granules by increasing doses of collagen. Human platelets were isolated from whole blood and incubated with anti-CD 62 antibodies labelled with PE (for details see Material and Methods). Fluorescence was determined in a Becton Dickenson FACS device. Representative histograms are shown. Increasing concentrations of collagen from 0 to 10 µg/ml induced a shift of fluorescence in the presence of the control Fc protein (100 µg/ml; blue line). In the presence of Fc-GPVI-nt (100 µg/ml; red line), the shift of fluorescence and hence CD 62 P activation was markedly inhibited.

Figure 11:
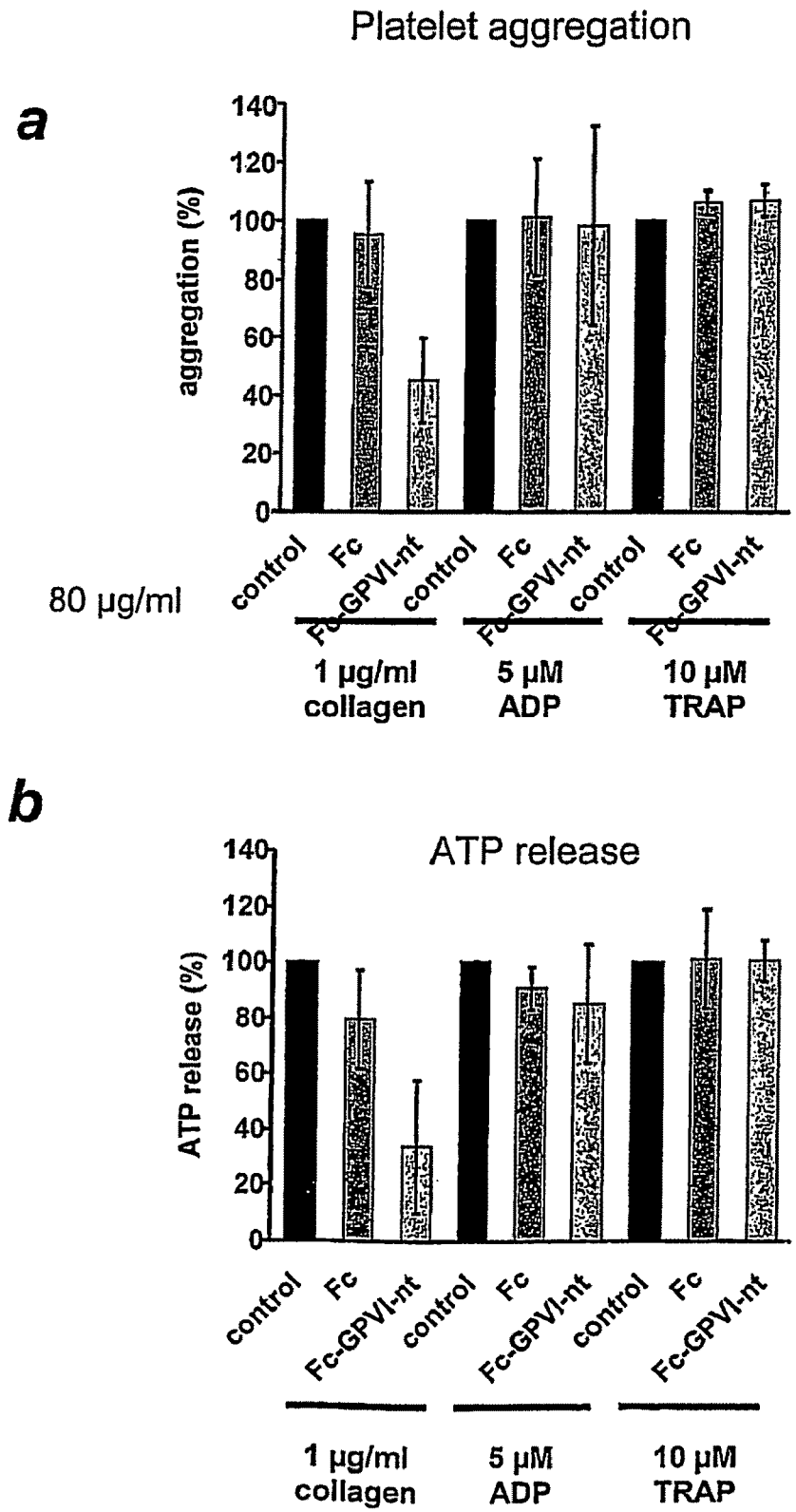
Figure 11:
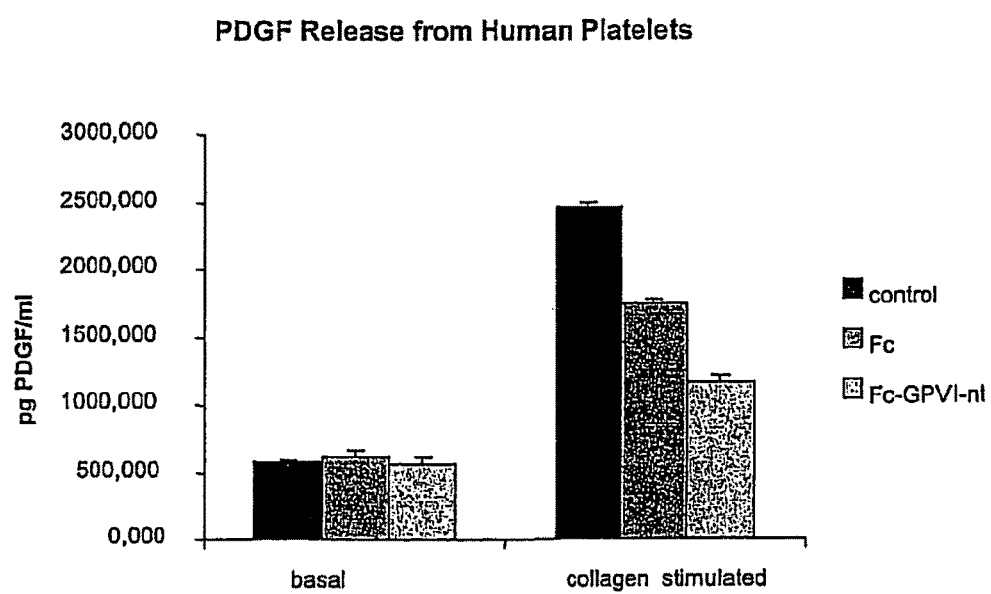

FIG. 11 Specific inhibition of collagen-mediated platelet aggregation and release of endogenous transmitters from dense and alpha granules by Fc-GPVI-nt. (a) Human platelets were incubated with control Fc (80 µg/ml) or Fc-GPVI-nt (80 µg/ml). Aggregation of platelets was induced with collagen (1 µg/ml) or ADP (5 µM) or TRAP (10 µM) and aggregation was determined in an aggregometer under stirring conditions (for details see Material and Methods). Triplet measurements from n=5 different blood donors were carried out. The means±s.e.m are given in % aggregation of the control aggregation without fusion proteins. (b) ATP release was measured simultaneously in the same probes after incubation with control Fc (80 µg/ml) or Fc-GPVI-nt (80 µg/ml). The amount of ATP release is given in % of controls without fusion protein. (c) PDGF release was determined in human platelets with an ELISA system specific for human PDGF under basal conditions and after collagen (20 µg/ml) stimulation (for details see Material and Methods). Preincubation with control Fc had no significant effect on PDGF release from collagen-stimulated platelets, whereas Fc-GPVI-nt (100 µg/ml) reduced the PDGF release significantly. Inhibition of PDGF release did not occur in unstimulated platelets.

Figure 12:
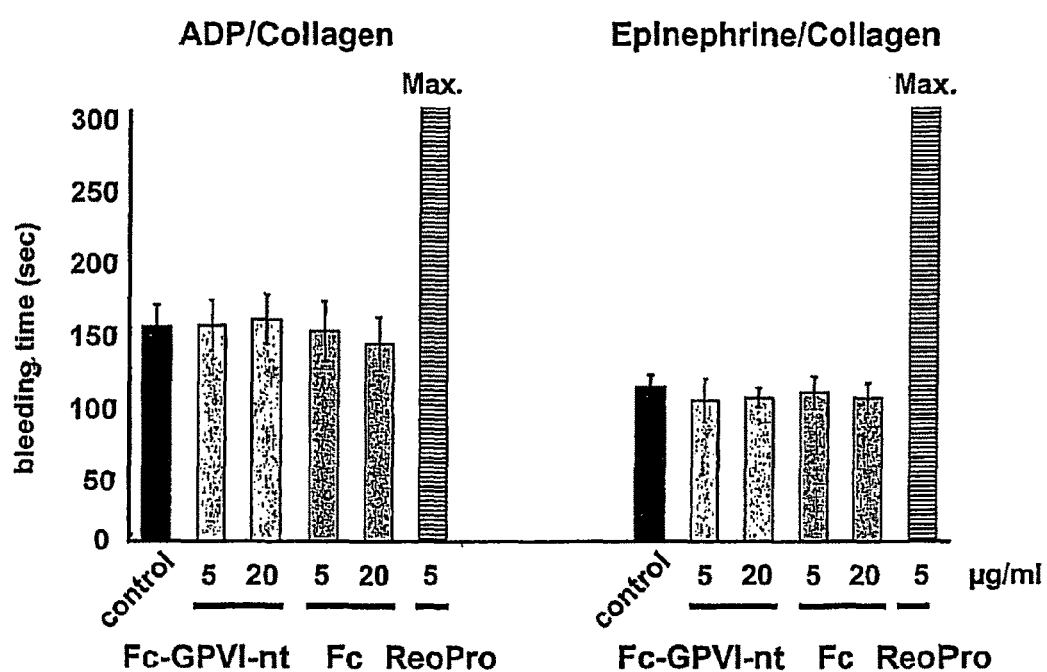

FIG. 12 Fc-GPVI-nt has no significant effect on bleeding time in human blood ex vivo. Bleeding time in human blood was measured ex vivo after ADP/collagen stimulation and epinephrine/collagen stimulation in a PFA-100 device. Fc-GPVI-nt (5 and 20 µg/ml) and Fc (5 and 20 µg/ml) did not prolong bleeding time whereas ReoPro$^R$ in a therapeutically relevant concentration (5 µg/ml) maximally prolonged bleeding time under both conditions. The means±s.e.m. from n=4 blood donors with triplet measurements are summarized.

FIG. 13 Fc-GPVI-nt inhibits platelet adhesion to immobilized collagen under flow conditions. Human platelets ($2\times10^8$ cells/ml) were isolated from whole blood (for details see "materials and methods"). Plates were coated with immobilized collagen (10 µg/ml) or vWF (10 µg/ml). Platelet adhesion to the coated plates was determined in a parallel plate flow chamber in the presence of Fc-GPVI-nt or Fc lacking the extracellular GPVI domain (200 µg/ml). Inhibition of platelet adhesion by Fc-GPVI-nt is given in % of control (Fc control). Fc-GPVI-nt significantly attenuated platelet adhesion on immobilized collagen at shear rates of 500 sec$^{-1}$ and 1000 sec$^{-1}$, respectively. In contrast, Fc-GPVI-nt did not affect platelet adhesion on immobilized vWF. Mean±s.e.m., n=4 each group, asterisk indicates significant difference compared to control Fc, P<0.05. The lower panels show representative microscopic images.

Figure 14:
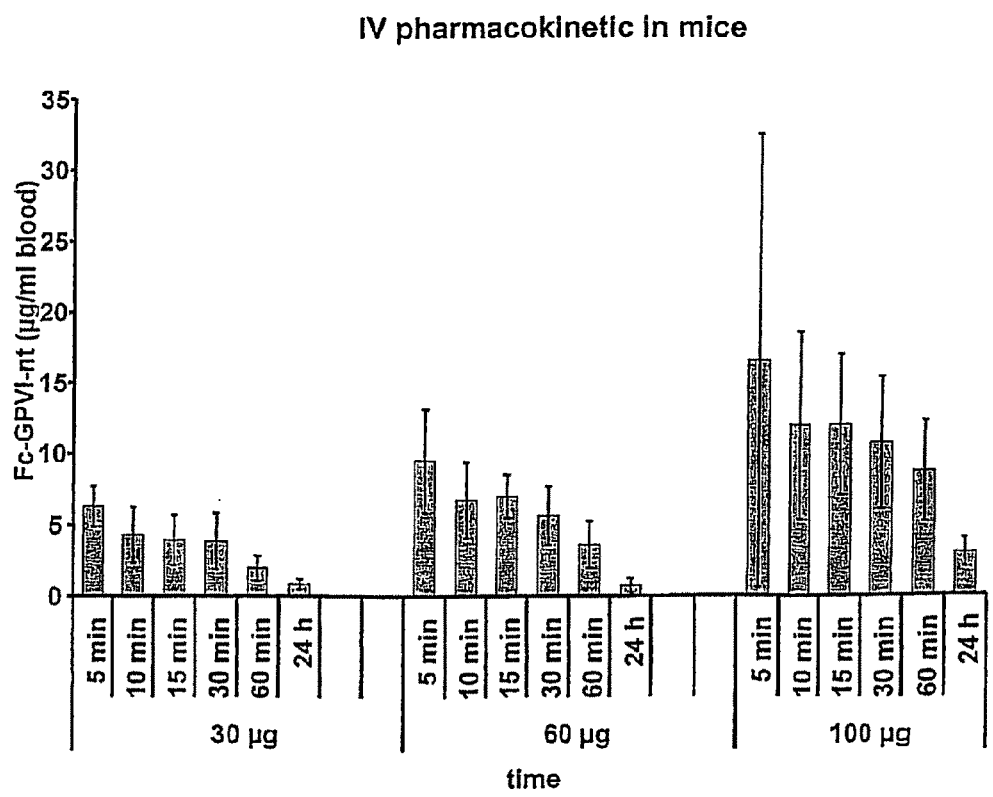

FIG. 14 Fc-GPVI-nt has favourable pharmacokinetics with a prolonged plasma half life after intraperitoneal injection in mice in vivo. Blood concentrations of Fc-GPVI-nt were determined with specific anti-Fc antibodies and ELISA (for details please see "material and methods"). (a) Single intraperitoneal injection of Fc-GPVI-nt (4 µg/g) led to rapid peak blood concentrations of Fc-GPVI-nt after ~24 h with slow decline of Fc-GPVI-nt blood concentrations. The means±s.e.m. from 10 animals are demonstrated. (b) Repeated intraperitoneal applications (10 µg/g; twice weekly) leads to continuos accumulation of Fc-GPVI-nt in mice in vivo over 28 days. The means±s.e.m. from 6 animals are demonstrated. (c) Intravenous single dose injection of 30 µg Fc-GPVI-nt (1 µg/g body weight); 60 µg (2 µg/g body weight) and 100 µg Fc-GPVI-nt (3 µg/g body weight) per mouse led to a dose-dependent increase of immunoadhesin plasma concentration. The plasma concentration in the two higher doses in these mice in vivo reached prolonged elevated levels from 5 to 60 minutes and after 24 hours, sufficient for effective collagen scavenging and therefore effective inhibition of GPVI receptor activation on platelets. The means±s.e.m. from 5 animals are demonstrated.

Figure 15:
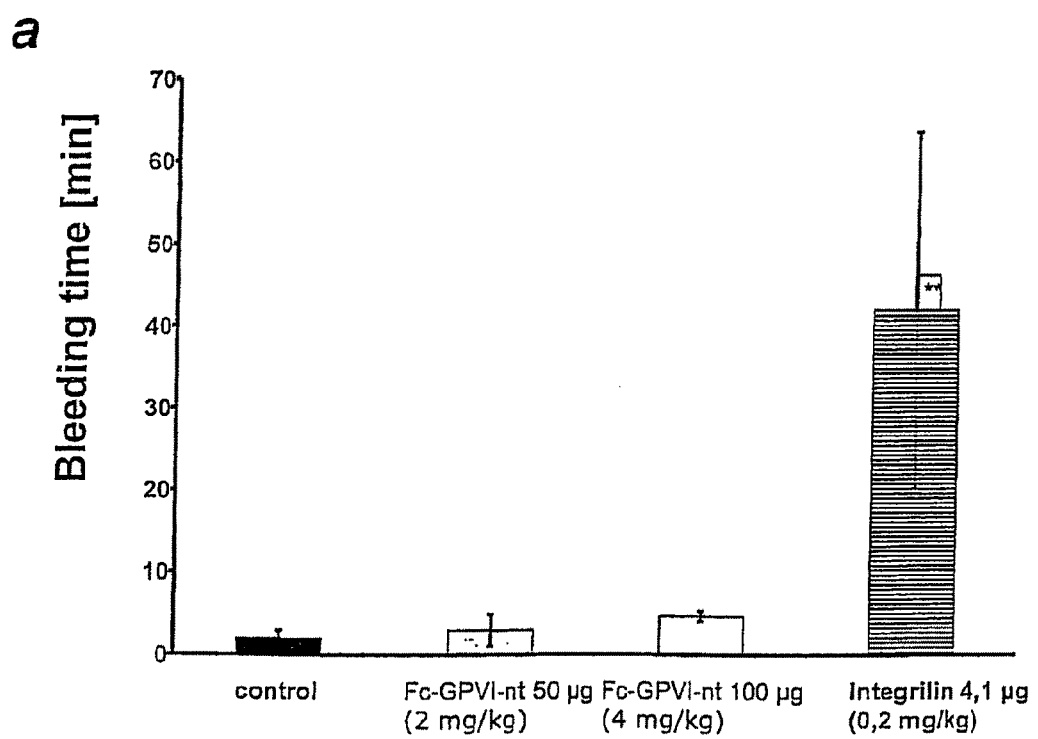

FIG. 15 Effects of Fc-GPVI-nt on platelet adhesion and aggregation in vivo. (a) Mice (n=6 per group) were treated with 2 mg/kg or 4 mg/kg Fc-GPVI-nt iv. Integrilin (0.2 mg/kg)-treated mice served as positive controls (n=8). Bleeding times were determined as described (see "materials and methods"). The Fc-GPVI-nt fusion protein did not increase tail bleeding times compared to control animals. In Integrilin-treated mice tail bleeding time was massively prolonged. **P<0.05 vs. control. (b) Inhibition of GPVI abrogates platelet adhesion and aggregation after vascular injury. Platelet adhesion following vascular injury was determined by intravital video fluorescence microscopy. Mice were pretreated with 1 or 2 mg/kg Fc-GPVI-nt or equimolar amounts of control Fc. The left and right panels summarize platelet tethering and firm platelet adhesion, respectively. Mean±s.e.m., n=5 each group, asterisk indicates significant difference compared to Fc, P<0.05. (c) Effects of Fc-GPVI-nt on thrombus formation following vascular injury in vivo. The number of platelet thrombi (right) and the total thrombus area (left) were assessed by fluorescence microscopy as described. Mean±s.e.m., n=5 each group, asterisk indicates significant difference compared to Fc, P<0.05. (d) The photomicrographs show representative in vivo fluorescence microscopy images illustrating platelet adhesion in the absence or presence of 1 or 2 mg/kg Fc-GPVI-nt or control Fc. Bars represent 50 µm. (e) Scanning electron micrographs of carotid arteries 1 hr after vascular injury in Fc- or Fc-GPVI-nt treated animals. Endothelial denudation induced platelet adhesion and platelet aggregation in Fc-treated mice. In contrast, only very few platelets attached along the damaged vessel wall in Fc-GPVI-nt-treated mice. Subendothelial collagen fibers are visible along the denuded area. Bars represent 10 µm (f) Fc-GPVI-nt specifically binds to the subendothelium of carotid arteries. The binding of Fc-GPVI-nt to the subendothelium was determined on carotid sections, stained with peroxidase-conjugated goat anti-human IgG antibody. Carotid arteries obtained from Fc-treated mice served as controls. Fc-GPVI-nt but not Fc control protein was detected at the subendothelium, as indicated by the brown staining. Original magnification: 100-fold.

Figure 16:
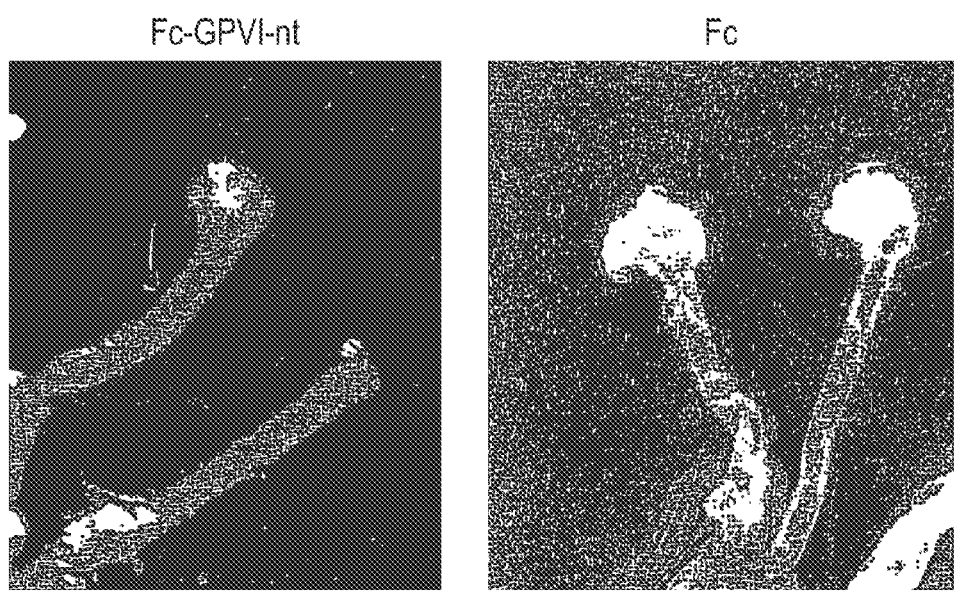

FIG. 16 Fc-GPVI-nt significantly attenuates atheroprogression in apo e−/− knockout mice in vivo. Apo e−/− mice were treated with Fc-GPVI-nt (4 µg/g) or control Fc (4 µg/g) intraperitoneally for 4 weeks twice weekly. Atheroprogression was investigated post mortem after sudan red staining of the large vessels to visualise atheroma and plaque formation. In control animals extensive plaque formation of carotid artery preparations was indicated by the red colour in particular in the branching region. In Fc-GPVI-nt treated animals atherosclerosis was almost completely abolished in carotid arteries of apo e−/− mice. Representative macroscopic whole vascular preparations of the carotid arteries of an apo e−/− mouse after 4 weeks treatment with Fc-GPVI-nt (left side) and of an apo e−/− mouse after 4 weeks treatment with the control Fc protein (right side) are shown.

FIG. 17 Freshly isolated platelets from patients suffering from diabetes mellitus show reduced expression of the fibrinogen receptor (CD61, top) and increased expression of the Fc receptor (CD32, middle) and therefore increased expression of GPVI. The correlation between CD32 expression and GPVI expression (detected by the specific monoclonal antibody 4C9) is shown on human platelets (bottom). Human platelets were isolated from whole blood from patients suffering from diabetes and incubated with fluorescent anti-CD61 and anti CD32 antibodies or FITC labelled 4C9 antibodies. Fluorescence was determined in a Becton Dickenson FACScalibur device. The means+/−s.e.m. from n=111 diabetic patients and from n=363 patients without diabetes are summarized. Correlation of CD32 fluorescence and 4C9 fluorescence was calculated with the correlation coefficient r=0.516.

FIG. 18 Amino acid sequence of a monomeric fusion protein based on Fc-GPVI-nt.

Figure 19A:
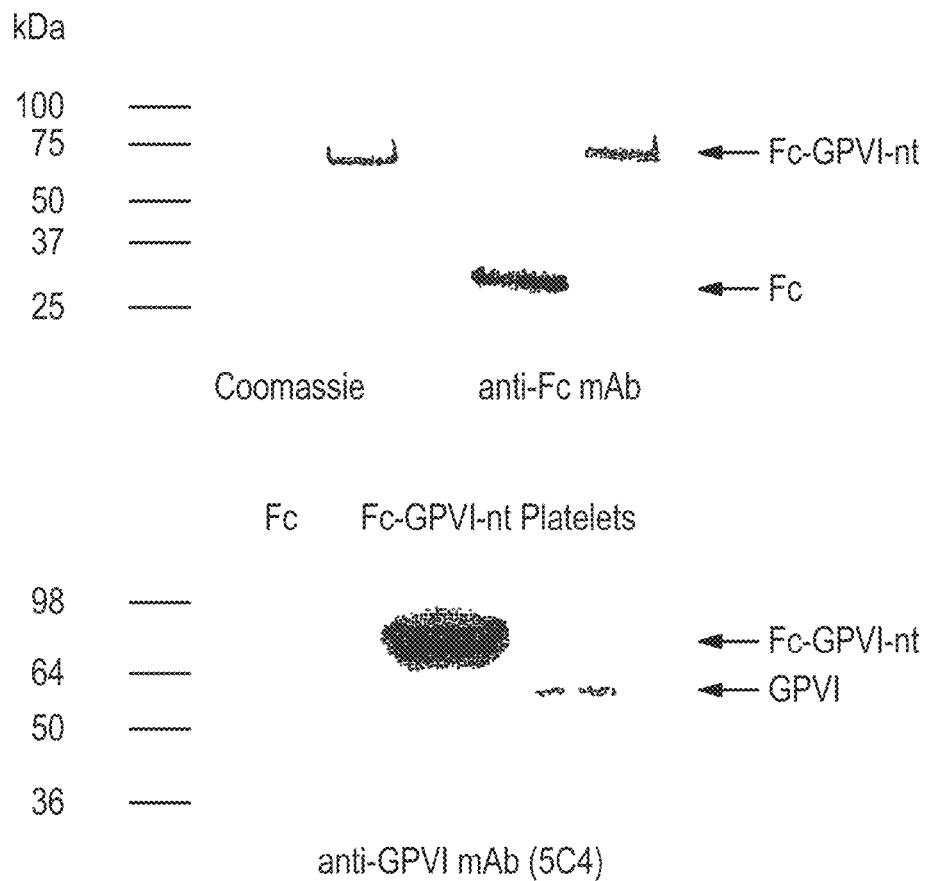
Figure 19B:
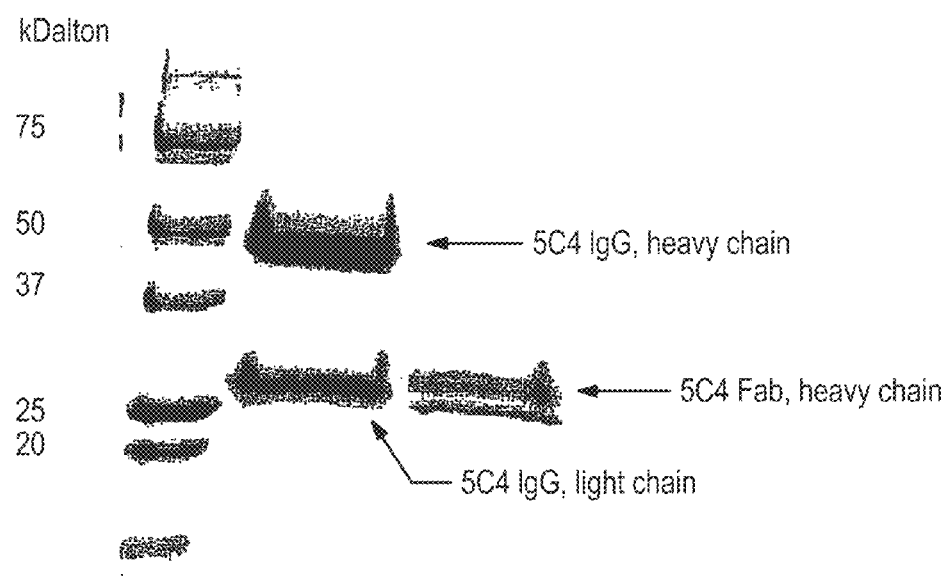

FIG. 19 Characterization of antigen binding of hGP 5C4. (a) upper panel: Fc-GPVI-nt and control Fc lacking the extracellular GPVI domain were applied for SDS-PAGE under reducing conditions. Coomassie blue stain (left) and immunoblotting with peroxidase-conjugated goat anti-human Fc antibody (right) identified Fc-GPVI-nt with a molecular mass of ~80 kDa. Lower panel: Immunoblotting of Fc, Fc-GPVI-nt, or human platelets using the anti-GPVI monoclonal antibody hGP 5C4. hGP 5C4 specifically detected purified Fc-GPVI-nt fusion protein and GPVI receptor on platelets, but not the control Fc protein. (b) The generation of Fab fragments of the IgG hGP 5C4 was verified in a SDS gel with Coomassie staining after digestion with an ImmunoPure Fab Kit (Pierce Biotechnology, Inc., Rockford, Ill., USA).

FIG. 20 The ability of hGP 5C4 Fab to inhibit GPVI binding to collagen was monitored in an ELISA-based assay. Adhesion of the Fc-GPVI-nt—consisting of the extracellular domain of GPVI and the Fc part of an IgG—to immobilised collagen was investigated in the presence of different anti-GPVI antibody Fab fragments (20 µg/ml). Binding of the Fc part without the GPVI receptor domain served as control. The binding is visualised with a secondary antibody directed to the Fc part of Fc-GPVI-nt labelled with peroxidase. Peroxidase (PE) is finally detected by an ELISA system measuring the absorption photometrically at 450 nm. hGP 5C4 prevents Fc-GPVI-nt binding to collagen, whereas 4C9 could not prevent collagen interaction with GPVI. The means±SEM are shown.

Figure 21:
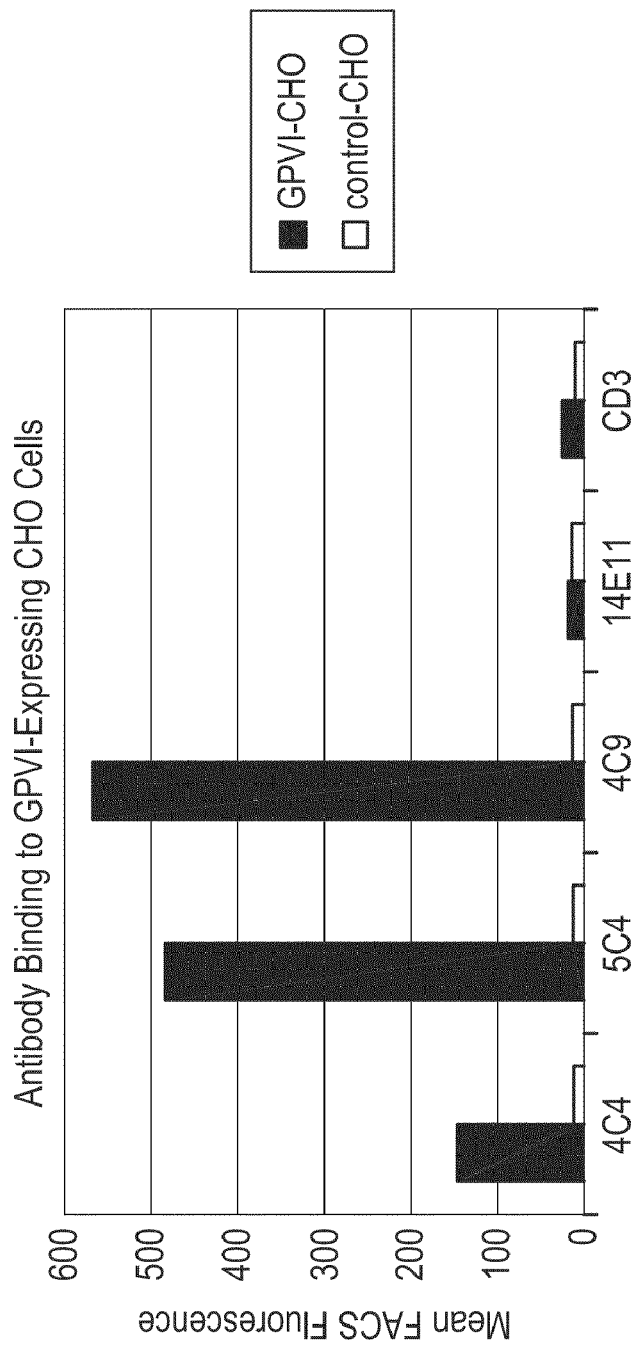

FIG. 21 The binding of different antibodies to stable GPVI-expressing CHO cells was measured by FACS. The binding of the specific antibodies to control CHO cells served as control. After incubation with the primary antibodies CHO cells were incubated with anti-IgG rat antibodies labelled with PE. Specific PE fluorescence was determined in a Becton Dickenson FACScalibur device.

Figure 22:
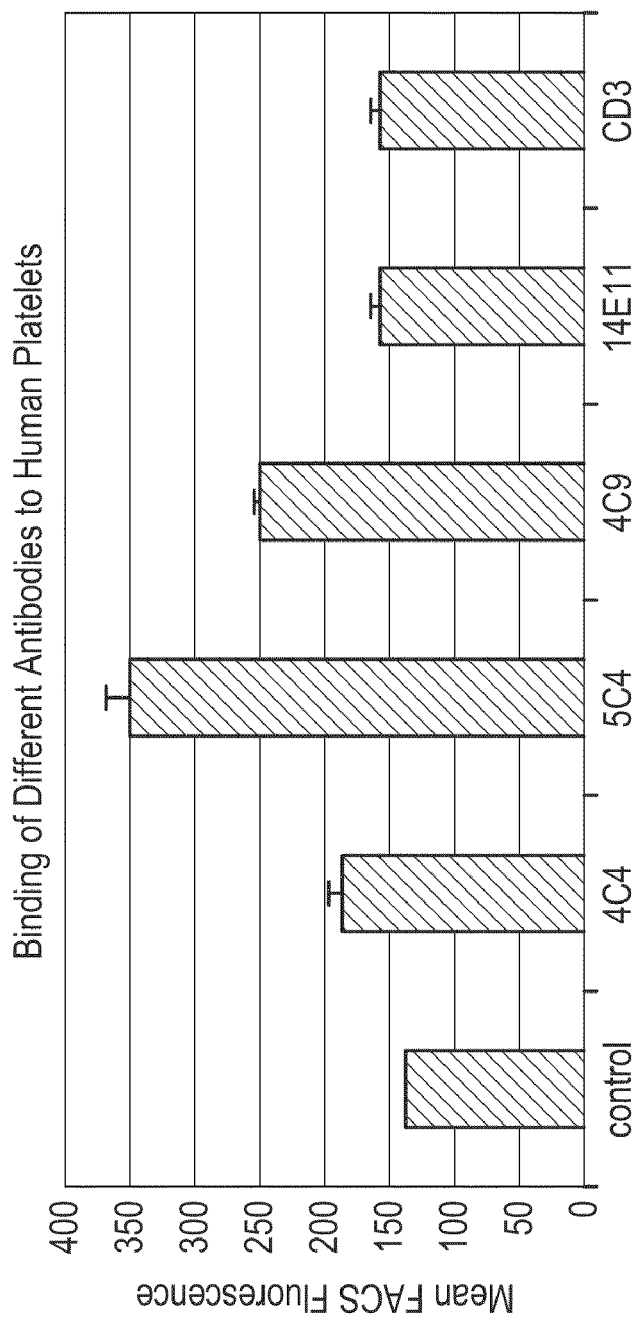

FIG. 22 The binding of different antibodies to human platelets was determined by FACS. Platelets were washed and platelet rich plasma was prepared as described in Material and Methods. After incubation with the primary antibodies, human platelets were incubated with anti-IgG rat antibodies labeled with peroxidase (PE). Specific PE fluorescence was determined in a Becton Dickenson FACScalibur device. The means±SEM are shown.

Figure 23A:
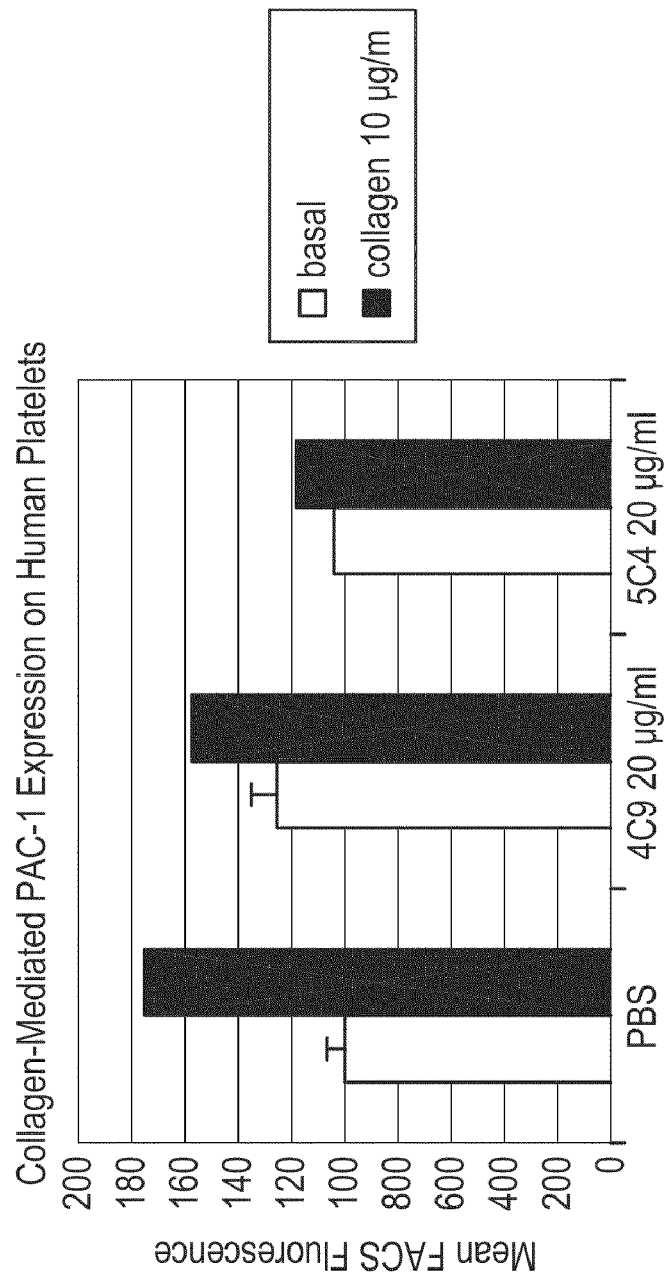
Figure 23B:
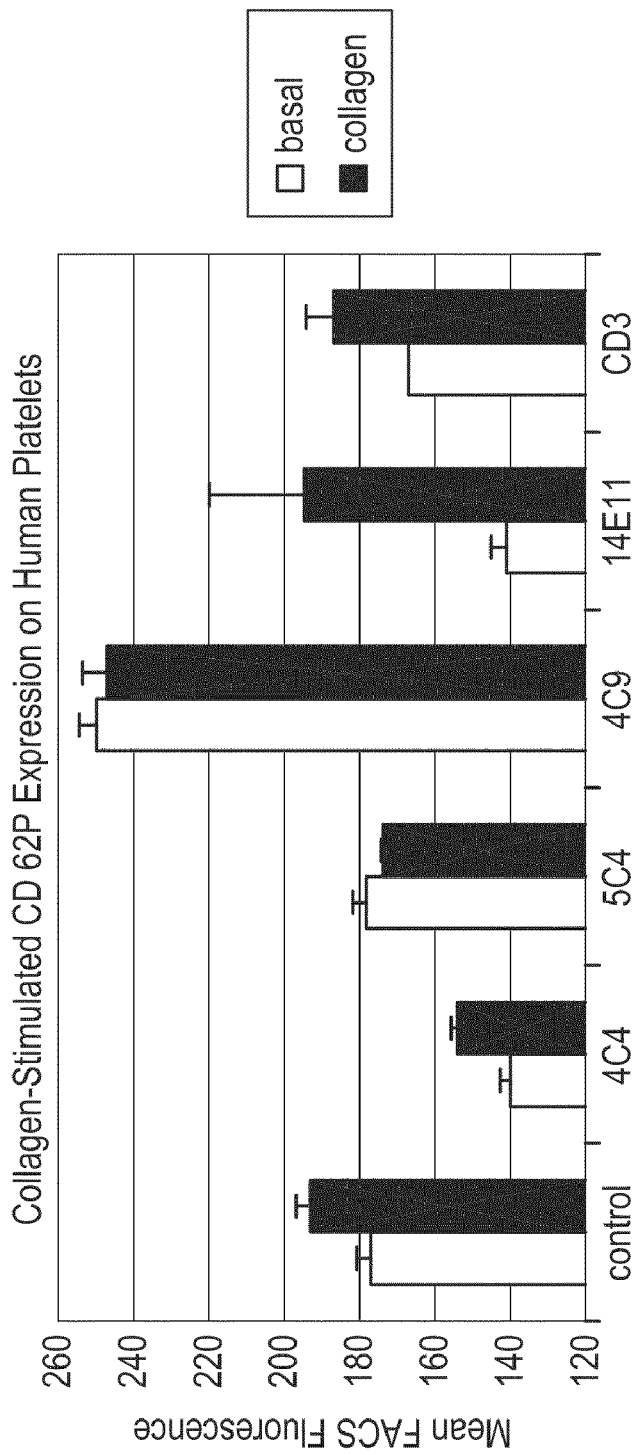

FIG. 23 The ability of different anti-GPVI antibodies to inhibit collagen-mediated platelet activation was measured for different activation markers by FACS. (a) Incubation with bovine collagen type I (10 µg/ml) activated PAC-1 on human platelets. Preincubation with the anti-GPVI antibody hGP 5C4 Fab (20 µg/ml) prevented PAC-1 activation, whereas 4C9 Fab (20 µg/ml) led to additional stimulation of platelets and could not prevent collagen-mediated PAC-1 activation. Specific PAC-1 fluorescence was determined in a Becton Dickenson FACScalibur device. The means±SEM are shown. (b) Pre-incubation of human platelets with hGP 5C4 Fab (20 µg/ml) inhibited CD 62 P activation by collagen type I (10 µg/ml), whereas other antibodies could not prevent collagen-mediated CD 62P activation. 4C9 (20 mg/ml) or 14E11 (20 µg/ml) had even stimulating effects on human platelets. The means±SEM are shown.

Figure 24A:
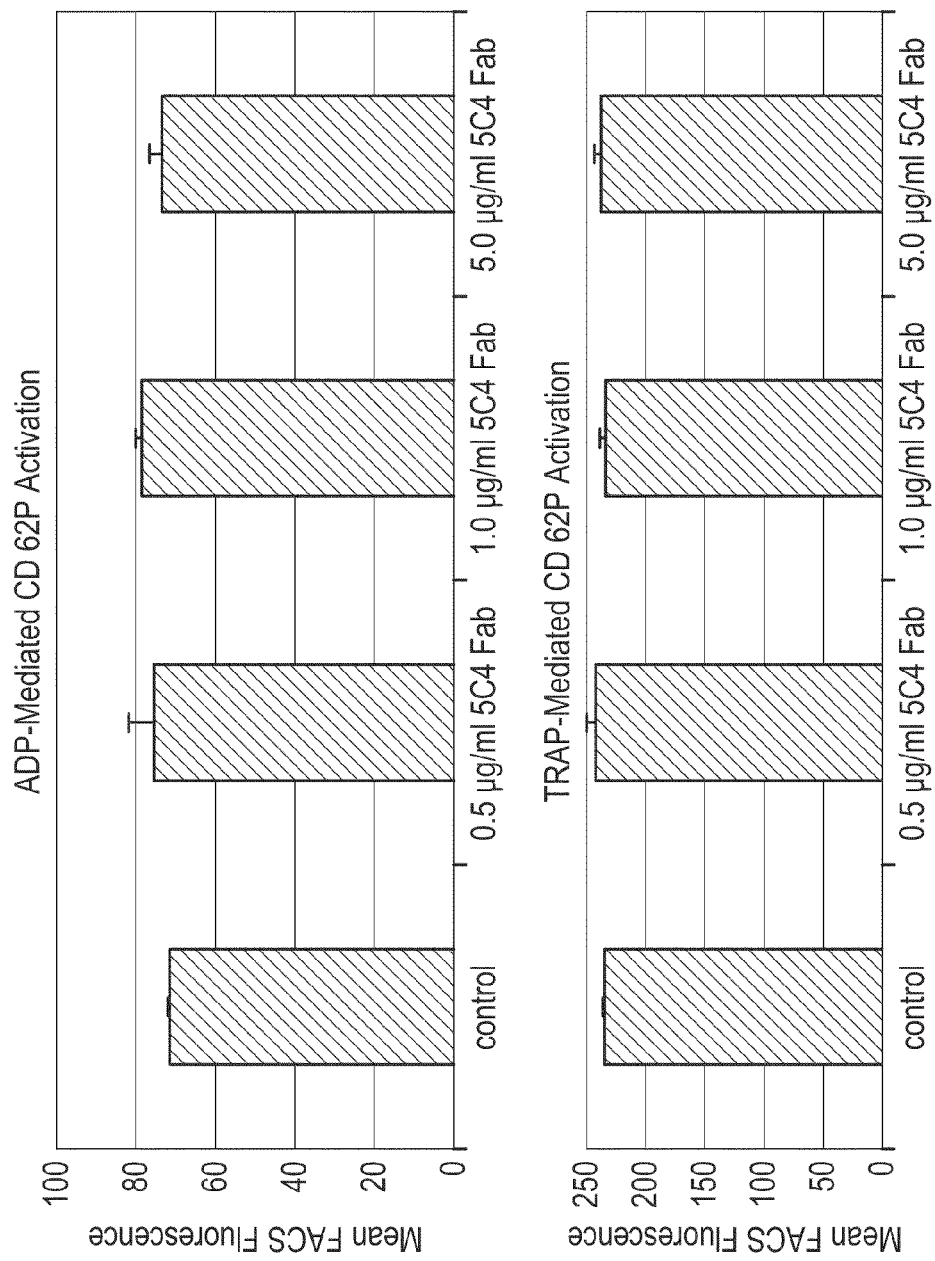
Figure 24B:
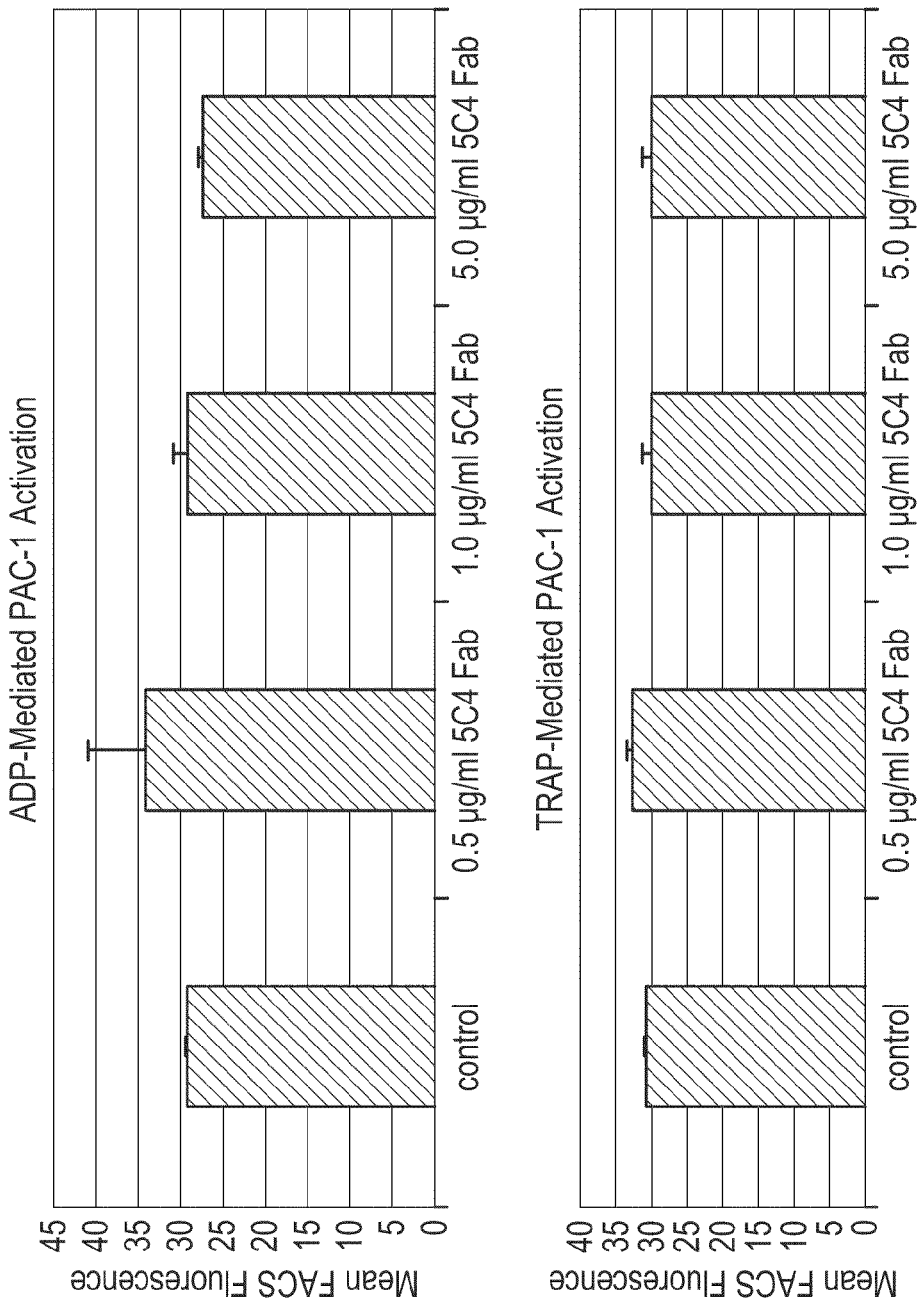
Figure 24C:
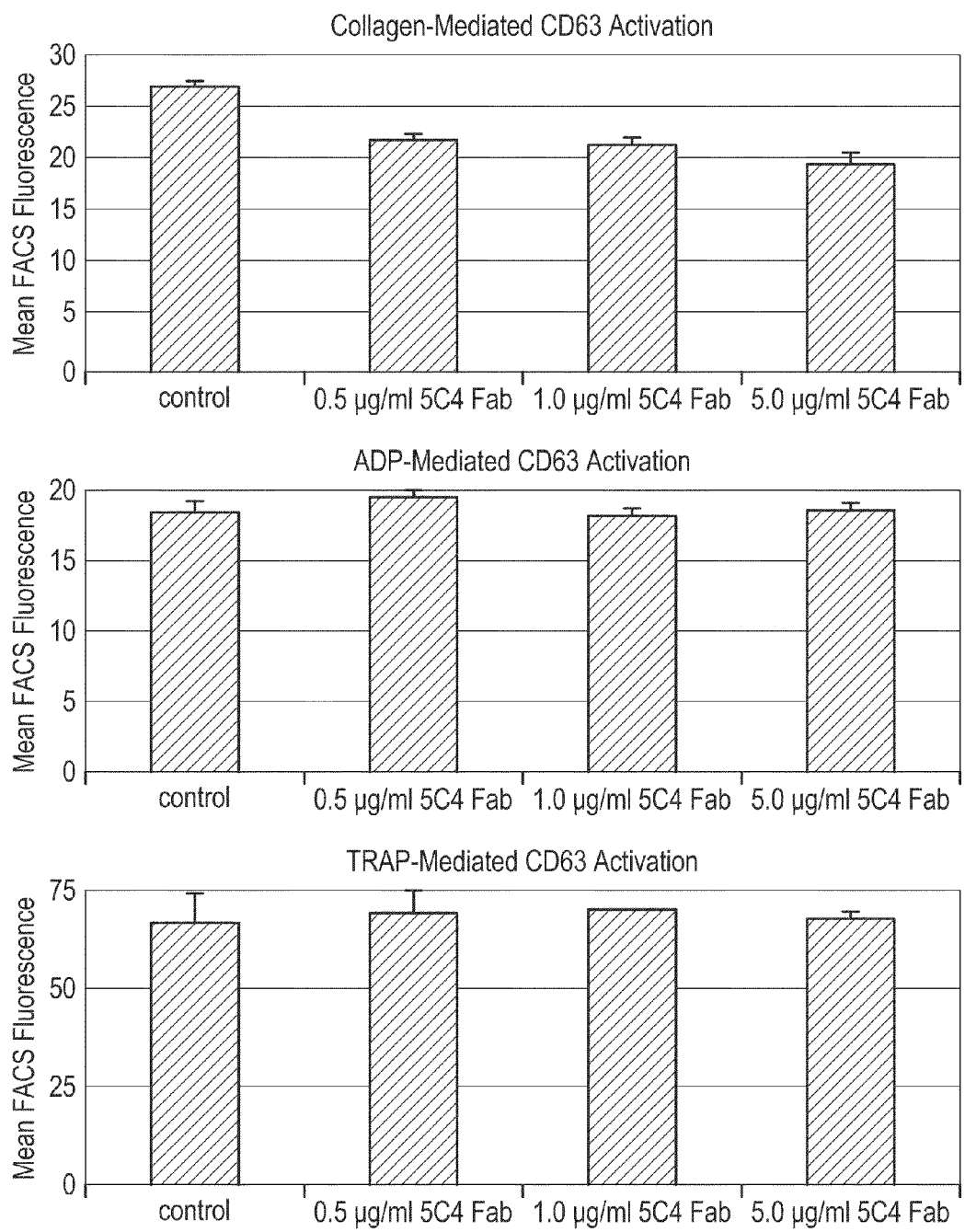

FIG. 24 The specificity of hGP 5C4 for collagen-mediated processes was investigated by ADP- and thrombin induced human platelet activation in FACS. (a) Preincubation with 0.5 µg/ml to 5 µg/ml hGP 5C4 Fab with human platelets was followed by ADP (20 µM) stimulation (top). The CD 62 P expression was determined in a Becton Dickenson FACScalibur device with specific antibodies as described in Material and Methods. hGP 5C4 had no influence on ADP-mediated CD 62 P activation in human platelets. The TRAP-mediated activation of CD62P was also tested (bottom). hGP 5C4 had no effect on TRAP (25 µM)-mediated CD62P activation in human platelets. The means±SEM are summarized. (b) Human platelets were incubated with 0.5 µg/ml to 5 µg/ml hGP 5C4 Fab and stimulated with ADP (20 µM; top) or TRAP (25 µM; bottom). PAC-1 fluorescence was measured in a Becton Dickenson FACScalibur. hGP 5C4 had no influence on ADP-mediated or TRAP-mediated PAC-1 activation. The means±SEM are shown. (c) Collagen (10 µg/ml), ADP (20 µM) and TRAP-mediated (25 µM) platelet activation and the effect of hGP 5C4 Fab on CD63 activation was investigated.

hGP 5C4 inhibited collagen-mediated CD63 activation, whereas ADP- and TRAP-mediated CD63 activation was unaffected. The means±SEM are summarized.

Figure 25A:
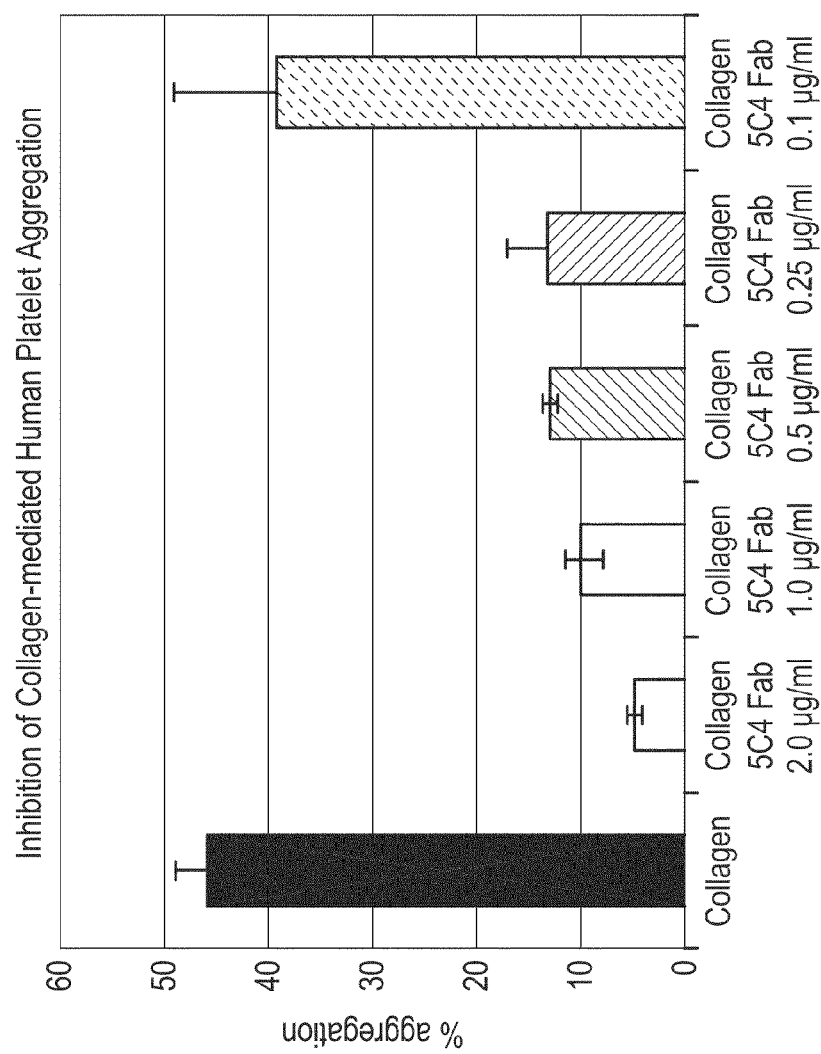
Figure 25B:
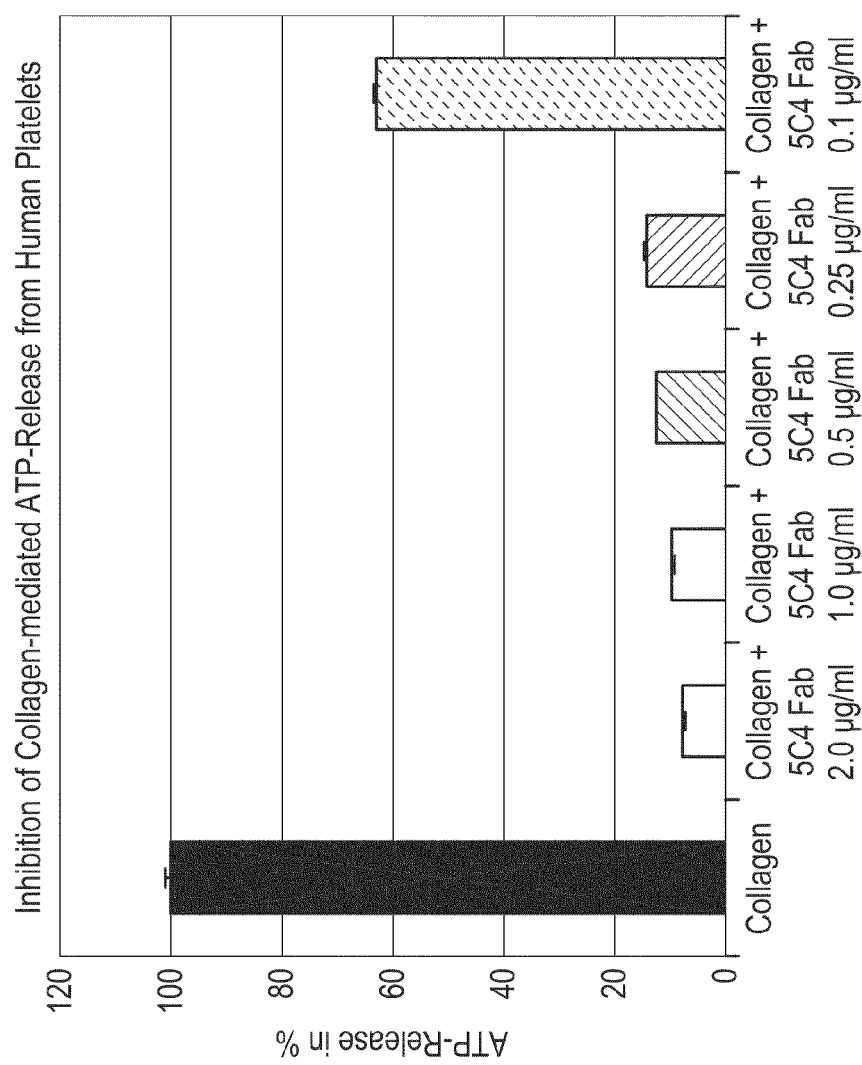

FIG. 25 The inhibition of collagen-mediated aggregation and ATP release by hGP 5C4 was tested in human platelets. Increasing concentrations of hGP 5C4 Fab (0.1 µg/ml to 2 µg/ml) were incubated with human platelets and collagen-induced (3 µg/ml) aggregation and ATP release was measured simultaneously ex vivo in an aggregometer. (a) The aggregation is expressed relative to an internal standard [in %] (see Material and Methods for description). From 0.25 µg/ml hGP 5C4 Fab concentration the collagen-mediated aggregation of human platelets was almost completely abolished. (b) In simultaneous experiments, ATP release was measured form these platelets. Collagen induced marked release of ATP from intracellular stores. hGP 5C4 potently inhibited this collagen-induced ATP release. The ATP release is given in % of control release. The means±SEM are shown.

Figure 26A:
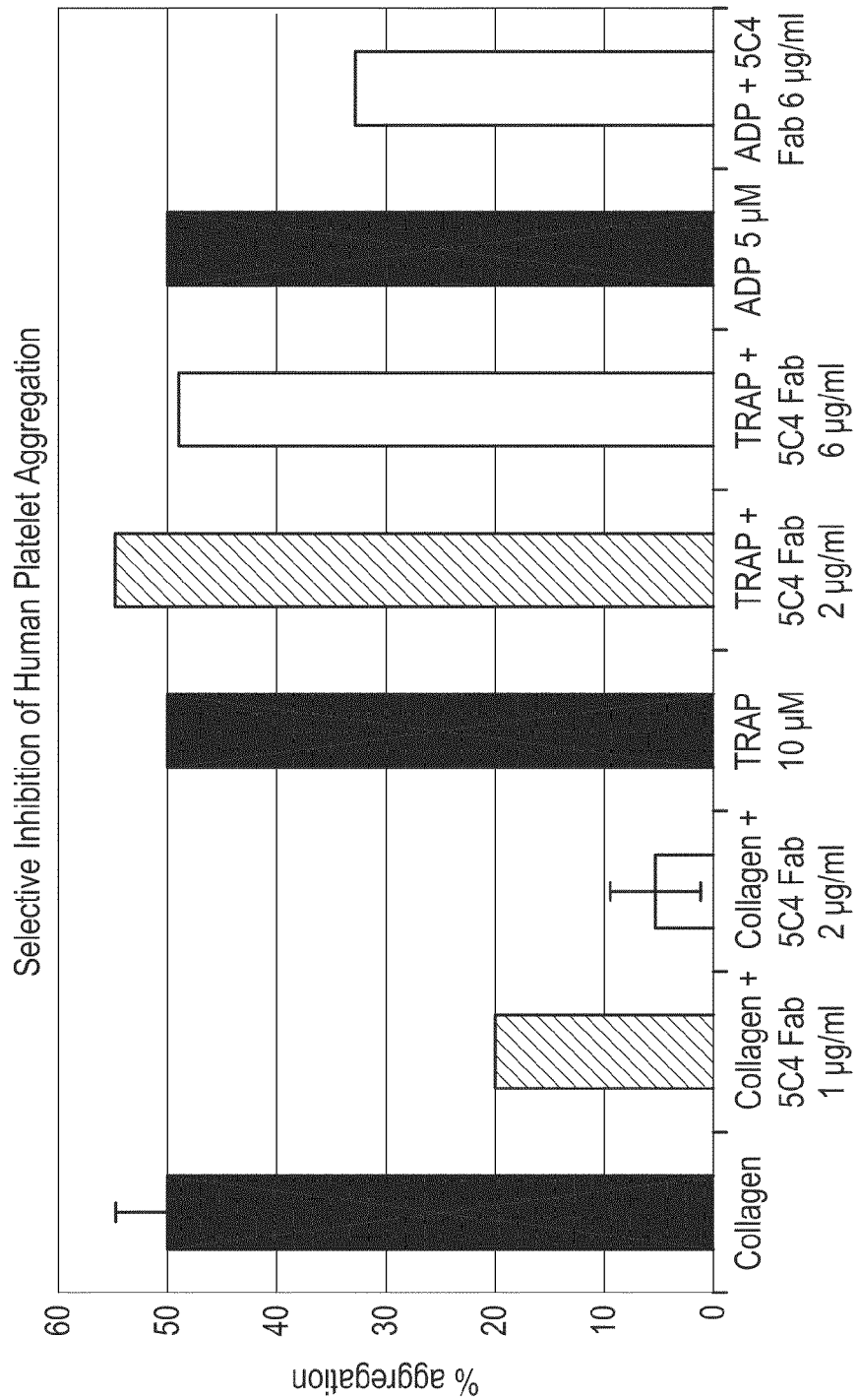
Figure 26B:
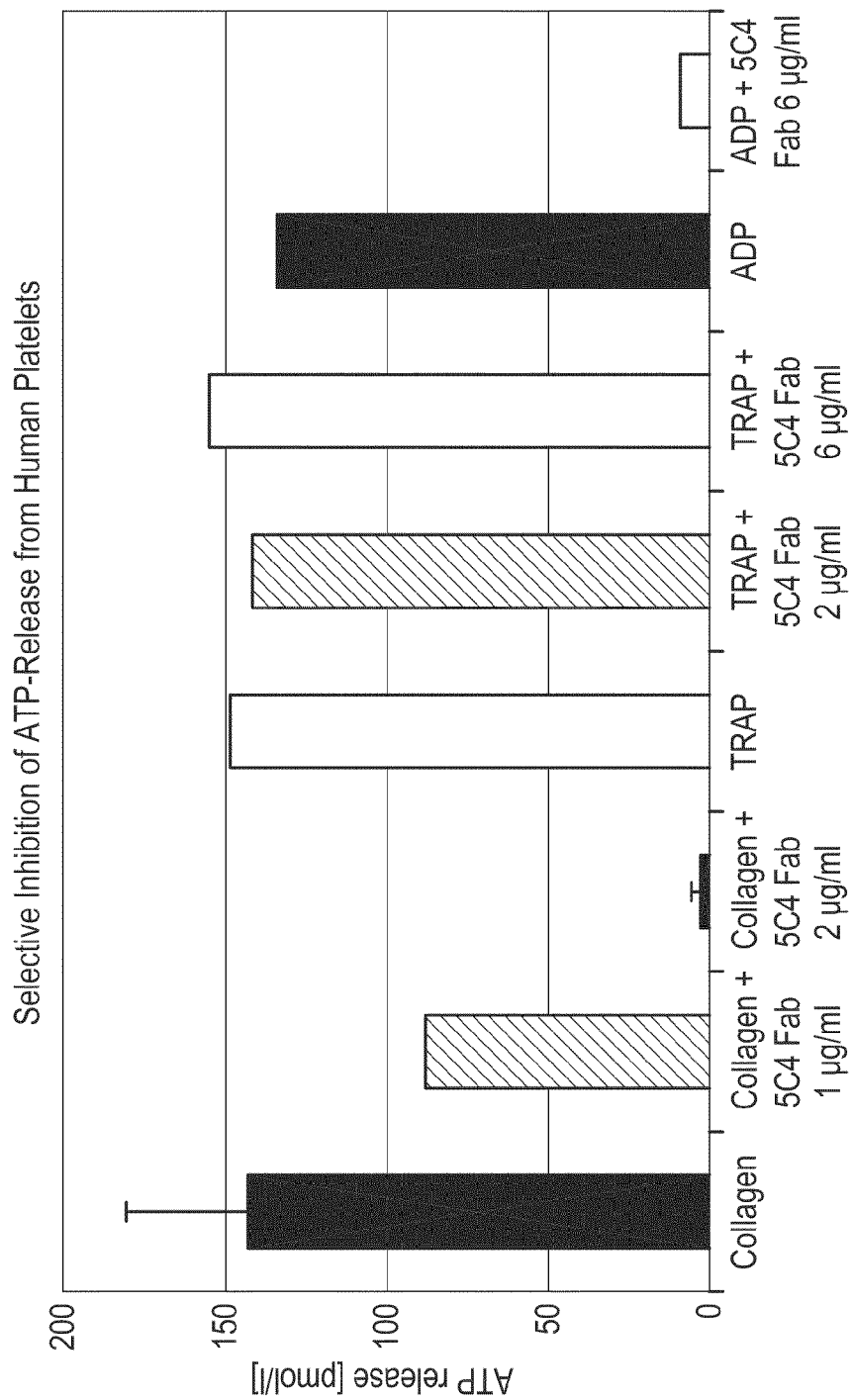

FIG. 26 The specificity of hGP 5C4Fab for collagen-mediated inhibition of human platelet aggregation and ATP release was tested. (a) Different agonists (collagen 2 µg/ml, TRAP 10 mmol/l, and ADP 5 µmol/l) were used to induce aggregation ex vivo in an aggregometer [in % of internal standard](see Methods for description). hGP 5C4 Fab (1 µg/ml and 2 µg/ml) almost completely abolished the collagen-mediated aggregation of human platelets. TRAP- and ADP-mediated aggregation was largely unaffected by substantially higher doses of hGP 5C4 Fab (2 µg/ml and 6 µg/ml). (b) ATP release was measured simultaneously given in µmol ATP/l. hGP 5C4 (1 µg/ml and 2 µg/ml) inhibited collagen-mediated ATP release. Substantially higher concentrations of hGP 5C4 Fab (2 µg/ml and 6 µg/ml) had no effect on thrombin/TRAP-mediated ATP release. The highest dose of hGP 5C4 Fab (6 µg/ml) also inhibited ADP-mediated ATP release. The means±SEM are shown.

Figure 27A:
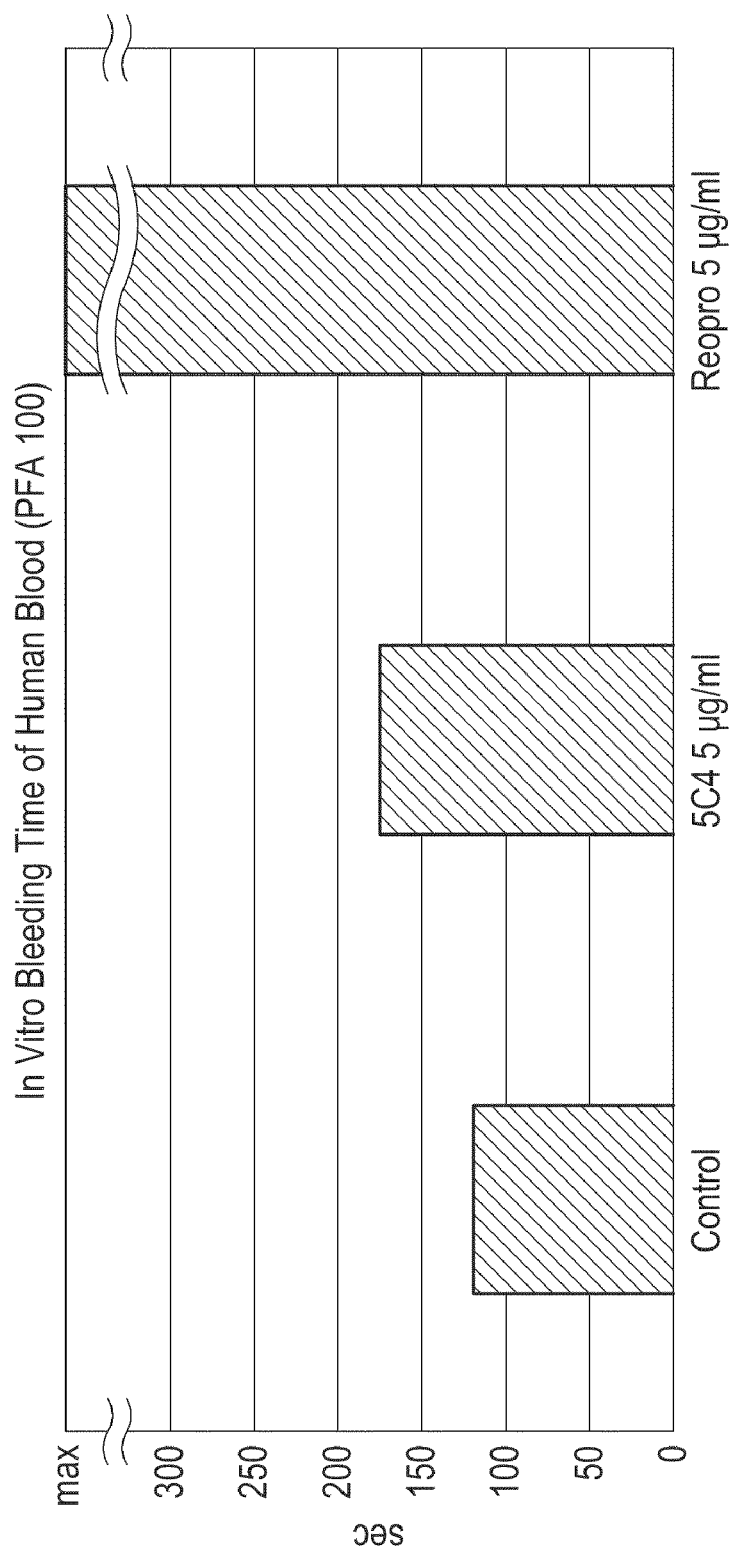
Figure 27B:
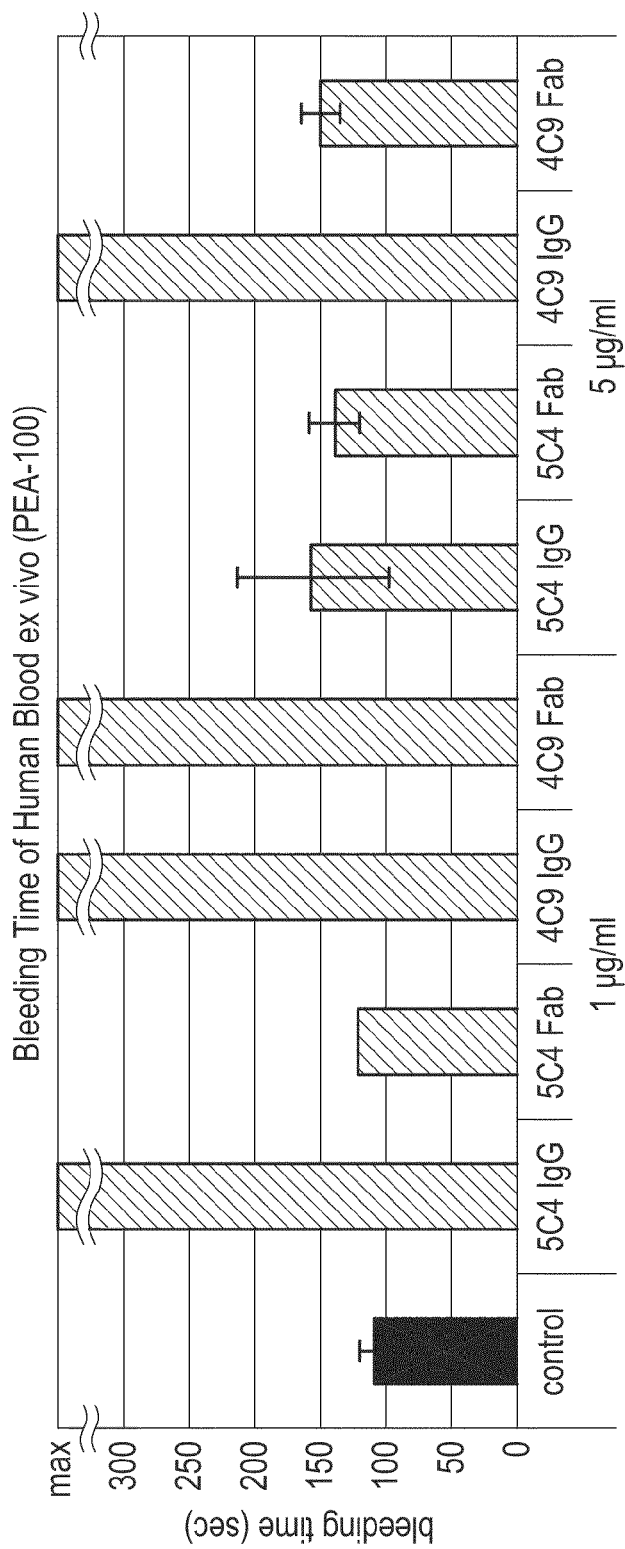

FIG. 27 The influence of hGP SC4 on bleeding time was tested in human blood ex vivo. (a) Human blood was incubated with hGP 5C4 Fab in 10 to 20 fold therapeutic concentrations (5 µg/ml) and bleeding time was determined with a PFA-100 device (see Methods for description). Bleeding time was compared to ReoPro$^R$ in equivalent concentrations. There was no significant prolongation of the bleeding time with hGP 5C4 Fab compared to control blood, whereas Reopro led to a maximal prolongation of bleeding time. (b) hGP 5C4 and 4C9 in different antibody formats were tested for bleeding time of human blood. hGP 5C4 Fab (1 µg/ml and 5 µg/ml) did not show any prolongation of bleeding time. In contrast, 4C9 markedly prolonged bleeding time both as Fab and as IgG antibody. The means±SEM are shown.

FIG. 28(a) Amino acid sequence of hGP 5C4 heavy chain variable domain (γ2a) (SEQ ID NO: 149)

FIG. 28(b) Nucleic acid sequence of 5C4 heavy chain variable domain (γ2a) (SEQ ID NO: 150)

FIG. 29(a) Amino acid sequence of 5C4 light chain variable domain (κ) (SEQ ID NO: 151)

FIG. 29(b) Nucleotide acid sequence of 5C4 light chain variable domain (κ) (SEQ ID NO: 152)

Figure 30:
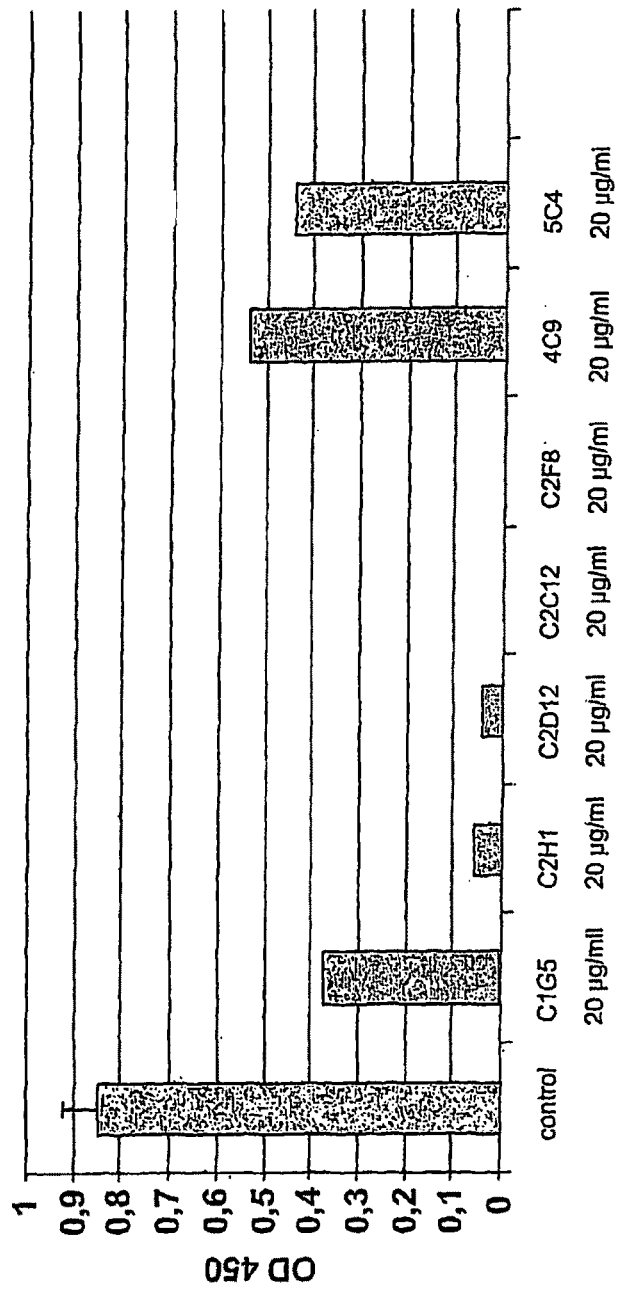

FIG. 30 Ability of anti-GPVI antibodies to inhibit binding of GPVI to collagen

Figure 31:
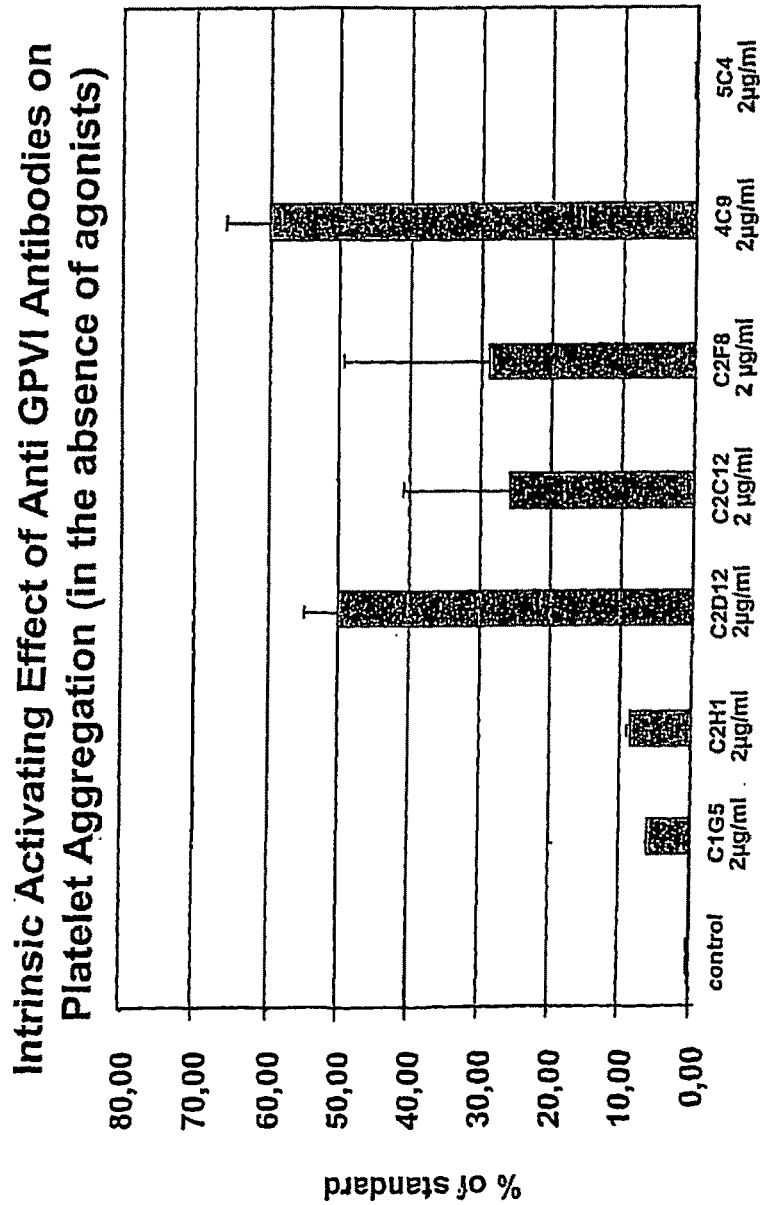

FIG. 31 Intrinsic activating effect of anti-GPVI antibodies on platelet aggregation (in the absence of an agonist)

Figure 32:
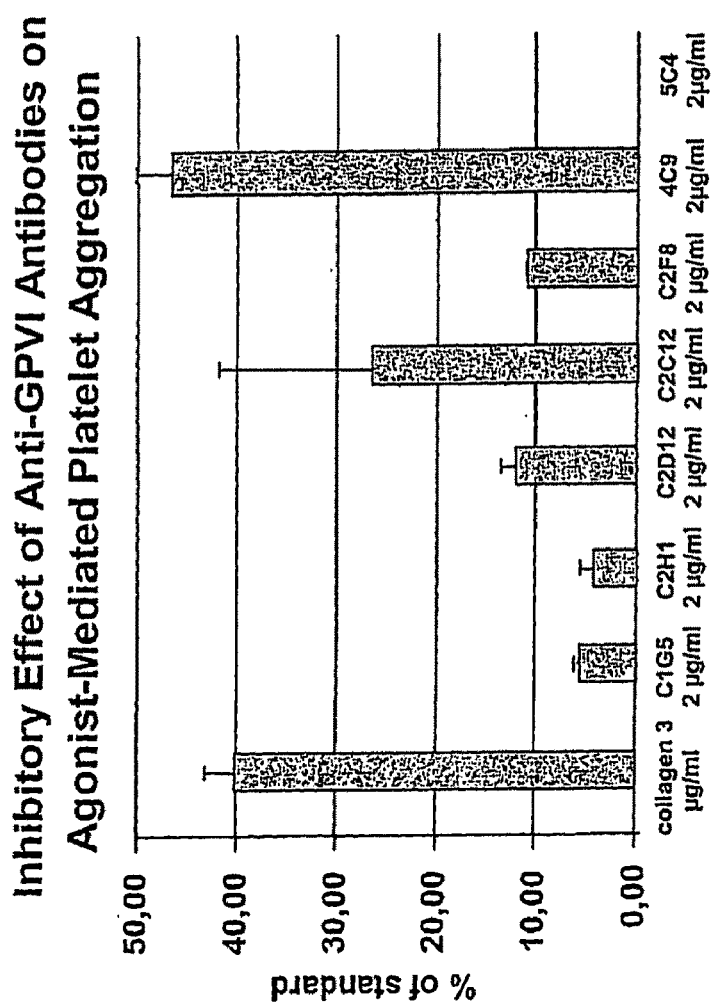

FIG. 32 Inhibitory effect of anti-GPVI antibodies on agonist-mediated platelet aggregation FIG. 33 Epitope mapping studies using monoclonal antibody hGP 5C4 to screen a human Glycoprotein VI peptide library.

FIG. 34 Epitope mapping studies using a control monoclonal antibody anti-rat HRP to screen a human Glycoprotein VI peptide library.

FIG. 35 Amino acid sequence of a human Glycoprotein VI.

FIG. 36A-36B Nucleic acid sequence encoding a human Glycoprotein VI.

DETAILED DESCRIPTION OF SEVERAL EXAMPLES

The following terms and abbreviations are used in this specification:

DEFINITIONS

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). Definitions and additional information known to one of skill in the art in immunology can be found, for example, in Fundamental Immunology, W. E. Paul, ed., fourth edition, Lippincott-Raven Publishers, 1999.

"hGP 5C4" is a specific antibody raised against human glycoprotein VI. The generation and characterization of hGP 5C4 is described in the Examples. A hybridoma expressing hGP 5C4 has been deposited with deposited with DSMZ-Deutsche Sammlung von Mikroorganismen und Zellkulturen under Accession No. 2631. "hGP 5C4 Fab" is the Fab fragment of hGP 5C4. The generation and characterization of hGP 5C4 Fab is described in the examples. The nucleic acid sequence of the variable domain of the heavy chain and the light chain are as given in SEQ ID NO: 150 and SEQ ID No 152. "Immunological activity" of hGP 5C4 and hGP 5C4 Fab refers to any of the following activities: ability to specifically bind human glycoprotein VI; ability to inhibit the binding of human glycoprotein VI to collagen in a specific manner; lack of activation of platelets or induction of immuno-thrombocytopenia; inhibition of the release mechanism of platelets and the expression of pro-inflammatory responses.

hGP 5C4 or hGP 5C4 Fab "activity" or "function" refers to any of the immunological activities of hGP 5C4 or hGP 5C4 Fab, or to any other biological activity ascribed to hGP 5C4 or hGP 5C4 Fab in this disclosure, including the role of hGP 5C4 or hGP 5C4 Fab in the prevention or treatment of acute or chronic cardiovascular disease associated with intraarterial and/or intravenous thrombosis. A specific aspect of hGP 5C4 or hGP 5C4 Fab "activity" or "function" relates to the binding of human glycoprotein VI exposed on the surface of platelets thereby functionally neutralizing the glycoprotein VI mediated activation of the platelets. This activity or function is essentially different from the activity or function of an antibody capable of binding to human glycoprotein VI thereby activating the platelet.

The antibody fragment hGP 5C4 Fab has inhibitory effects on the main physiological functions of platelets induced by collagen stimulation. The stimulation of collagen-mediated physiological activation parameters PAC-1 and CD 62P-Selectin is prevented by hGP 5C4 Fab. Anti-GPVI antibodies other than hGP 5C4 present with a well known problem for inhibitors: despite specific binding to GPVI some antibodies activate PAC-1 and CD 62P even in the absence of agonists which can lead to platelet activation. Additionally, hGP 5C4 Fab inhibits human platelet aggregation ex vivo without any intrinsic activity.

The inhibitory antibody had no effects on ADP-mediated activation of PAC-1 and CD 62P. Additionally, hGP 5C4 Fab had no effect on TRAP- and ADP-mediated aggregation and ATP release of human platelets ex vivo. As a consequence, hGP 5C4 Fab may be a highly selective inhibitor of arterial thrombosis with no effects on venous thrombosis and hemostasis. Experiments have shown that bleeding time of human blood was not prolonged in the PFA-100 device. In this way, hGP 5C4 Fab circumvents an almost inherent problem of anti-platelet drugs (Quinn M J; Plow E F; Topol E J. 2002: Platelet Glycoprotein IIb/IIIa inhibitors—Recognition of a two-edged sword. Circulation 106: 379-385; Bhatt D L & Topol E J; 2003: Scientific and therapeutic advances in antiplatelet therapy. Nat Rev Drug Discov 2: 15-28). hGP 5C4 Fab shows inhibition of platelet activation with no prolongation of bleeding time. Thus, hGP 5C4 has some properties of an ideal drug for the treatment of acute vascular syndromes like acute coronary syndromes or ischemic stroke without unwanted and potentially fatal side effects like intra cranial hemorrhage or other bleeding complications. Moreover, hGP 5C4 Fab shows inhibition of release of transmitter substances such as ATP from intracellular storage vesicles of human platelets. As this is a crucial parameter for the platelet-endothelium interaction promoting atherosclerosis, the hGP 5C4 Fab has a property of an ideal drug for the treatment and prevention of atherosclerosis.

The antibody hGP 5C4 is a GPVI inhibitor inhibiting the activated branch of GPVI mediated effects without significant bleeding complications. The antibody fragment hGP 5C4 Fab has one or more properties of a drug which can be used for the treatment of atherosclerotic complications caused by unstable atherosclerotic plaques with plaque rupture or endothelial lesion. Therefore, the antibody fragment hGP 5C4 Fab has at least one property of therapeutic inhibitors for collagen-mediated GPVI activation without affecting the intrinsic activity of the GPVI receptor with the relevant signalling system. Moreover, these inhibitors can be used for the prevention and treatment of atherosclerosis.

It will be understood that reference to An hGP 5C4 Fab fragment in the specification further includes other hGP 5C4 fragments for example scFv or F(ab)$^2$ fragments.

Antibody fragment (fragment with specific antigen binding): Various fragments of antibodies have been defined, including Fab, (Fab')$_2$, Fv, dsFV and single-chain Fv (scFv). These antibody fragments are defined as follows: (1) Fab, the fragment that contains a monovalent antigen-binding fragment of an antibody molecule produced by digestion of whole antibody with the enzyme papain to yield an intact light chain and a portion of one heavy chain or equivalently by genetic engineering; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction or equivalently by genetic engineering; (4) F(Ab')$_2$, a dimer of two FAb' fragments held together by disulfide bonds; (5) Fv, a genetically engineered fragment containing the variable region of the light chain and the variable region of the heavy chain expressed as two chains; dsFV, which is the variable region of the light chain and the variable region of the heavy chain linked by disulfide bonds and (6) single chain antibody ("SCA"), a genetically engineered molecule containing the variable region of the light chain, the variable region of the heavy chain, linked by a suitable polypeptide linker as a genetically fused single chain molecule. Single chain antibodies may also be referred to as single chain variable fragments (scFv). Methods of making these fragments are routine in the art.

Cell line/Cell culture A "cell line" or "cell culture" denotes higher eukaryotic cells gown or maintained in vitro. It is understood that the progeny of a cell may not be completely identical (either morphologically, genotypically, or phenotypically) to the parent cell. "Heterologous" means derived from a genotypically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence with which it is not naturally found linked is a heterologous promoter. An "isolated" polynucleotide or polypeptide is one that is substantially free of the materials with which it is associated in nature. By substantially free is meant at least 50%, preferably at least 70%, more preferably at least 80%, and even more preferably at least 90% free of the materials with which it is associated in nature.

Complementarity-determining region (CDR): The CDRs are three hypervariable regions within each of the variable light (VL) and variable heavy (VH) regions of an antibody molecule that form the antigen-binding surface that is complementary to the three-dimensional structure of the bound antigen. Proceeding from the N-terminus of a heavy or light chain, these complementarity-determining regions are denoted as "CDR1", "CDR2," and "CDR3," respectively. CDRs are involved in antigen-antibody binding, and the CDR3 comprises a unique region specific for antigen-antibody binding. An antigen-binding site, therefore, may include six CDRs, comprising the CDR regions from each of a heavy and a light chain V region. Alteration of a single amino acid within a CDR region can alter the affinity of an antibody for a specific antigen (see Abbas et al., *Cellular and Molecular Immunology*, 4th ed. 143-5, 2000). The locations of the CDRs have been precisely defined, e.g., by Kabat et al., *Sequences of Proteins of Immunologic Interest*, U.S. Department of Health and Human Services, 1983. The light and heavy chains of an Ig each have three CDRs, designated L-CDR1, L-CDR2, L-CDR3 and H-CDR1, H-CDR2, H-CDR3, respectively. By definition, the CDRs of the light chain are bounded by the residues at positions 24 and 34 (L-CDR1), 50 and 56 (L-CDR2), 89 and 97 (L-CDR3); the CDRs of the heavy chain are bounded by the residues at positions 31 and 35b (H-CDR1), 50 and 65 (H-CDR2), 95 and 102 (H-CDR3), using the numbering convention delineated by Kabat et al., (1991) *Sequences of Proteins of Immunological Interest*, 5$^{th}$ Edition, Department of Health and Human Services, Public Health Service, National Institutes of Health, Bethesda (NIH Publication No. 91-3242).

Reference is made to the numbering scheme from Kabat, E. A., et al., Sequences of Proteins of Immunological Interest (National Institutes of Health, Bethesda, Md. (1987) and (1991). In these compendiums, Kabat lists many amino acid sequences for antibodies for each subclass, and lists the most commonly occurring amino acid for each residue position in that subclass. Kabat uses a method for assigning a residue number to each amino acid in a listed sequence, and this method for assigning residue numbers has become standard in the field. For purposes of this invention, to assign residue numbers to a candidate antibody amino acid sequence which is not included in the Kabat compendium, one follows the following steps. Generally, the candidate sequence is aligned with any immunoglobulin sequence or any consensus sequence in Kabat. Alignment may be done by hand, or by computer using commonly accepted computer programs; an example of such a program is the Align 2 program discussed in this description. Alignment may be facilitated by using some amino acid residues which are common to most Fab sequences. For example, the light and heavy chains each typically have two cysteines which have the same residue numbers; in VL domain the two cysteines are typically at residue numbers 23 and 88, and in the VH domain the two cysteine residues are typically numbered 22 and 92. Framework residues generally, but not always, have approximately the same number of residues, however the CDRs will vary in size. For example, in the case of a CDR from a candidate sequence which is longer than the CDR in the sequence in Kabat to which it is aligned, typically suffixes are added to the residue number to indicate the insertion of additional residues (see, e.g. residues 100 abcde in FIG. 5). For candidate sequences which, for example, align with a Kabat sequence for residues 34 and 36 but have no residue between them to align with residue 35, the number 35 is simply not assigned to a residue.

CDR and FR residues are also determined according to a structural definition (as in Chothia and Lesk, J. Mol. Biol. 196:901-917 (1987). Where these two methods result in slightly different identifications of a CDR, the structural definition is preferred, but the residues identified by the sequence definition method are considered important FR residues for determination of which framework residues to import into a consensus sequence.

Constant Region The portion of the antibody molecule which confers effector functions. In the present disclosure, the variant antibodies of use can include constant regions derived from human immunoglobulins. The heavy chain constant region can be selected from any of five isotypes: alpha, delta, epsilon, gamma or mu. Heavy chains of various subclasses (such as the IgG subclass of heavy chains) are responsible for different effector functions. Thus, by choosing the desired heavy chain constant region, humanized antibodies with the desired effector function can be produced. The light chain constant region can be of the kappa or lambda type.

Epitope: The site on an antigen recognized by an agent as determined by the specificity of the amino acid sequence. Two agents are said to bind to the same epitope if each competitively inhibits (blocks) binding of the other to the antigen as measured in a competitive binding assay (see, e.g., Junghans et al., *Cancer Res.* 50:1495-1502, 1990). Alternatively, two antibodies have the same epitope if most amino acid mutations in the antigen that reduce or eliminate binding of one antibody reduce or eliminate binding of the other. Two antibodies are said to have overlapping epitopes if each partially inhibits binding of the other to the antigen, and/or if some amino acid mutations that reduce or eliminate binding of one antibody reduce or eliminate binding of the other.

Framework region (FR): Relatively conserved sequences flanking the three highly divergent complementarity-determining regions (CDRs) within the variable regions of the heavy and light chains of an antibody. Hence, the variable region of an antibody heavy or light chain consists of a FR and three CDRs. Some FR residues may contact bound antigen; however, FRs are primarily responsible for folding the variable region into the antigen-binding site, particularly the FR residues directly adjacent to the CDRs. Without being bound by theory, the framework regions serve to hold the CDRs in an appropriate orientation for antigen binding. The numbering of the residues in the light chain and heavy chain framework regions follows the numbering convention delineated by Kabat et al., (1991, supra). The sequences of the framework regions of different light or heavy chains are relatively conserved within a species. A "human" framework region is a framework region that is substantially identical (about 85% or more, usually 90-95% or more) to the framework region of a naturally occurring human immunoglobulin.

Immunogenicity: A measure of the ability of a targeting protein, a therapeutic moiety or an agent to elicit an immune response (humoral or cellular) when administered to a subject.

Immunoglobulin: Immunoglobulin (Ig) molecules and immunologically active portions of Ig molecules, for instance, molecules that contain an antigen binding site which specifically binds (immunoreacts with) an antigen.

A naturally occurring antibody (for example, IgG) includes four polypeptide chains, two heavy (H) chains and two light (L) chains interconnected by disulfide bonds. The two heavy chains are linked to each other by disulfide bonds and each heavy chain is linked to a light chain by a disulfide bond. There are two types of light chain, lambda ($\square$) and kappa (k). There are five main heavy chain classes (or isotypes) which determine the functional activity of an antibody molecule: IgM, IgD, IgG, IgA and IgE. Full-length immunoglobulin light chains are generally about 25 Kd or 214 amino acids in length. Full-length immunoglobulin heavy chains are generally about 50 Kd or 446 amino acid in length. Light chains are encoded by a variable region gene at the NH2-terminus (about 110 amino acids in length) and a kappa or lambda constant region gene at the COOH-terminus. Heavy chains are similarly encoded by a variable region gene (about 116 amino acids in length) and one of the other constant region genes.

The basic structural unit of an antibody is generally a tetramer that consists of two identical pairs of immunoglobulin chains, each pair having one light and one heavy chain. In each pair, the light and heavy chain variable regions bind to an antigen, and the constant regions mediate effector functions. Immunoglobulins also exist in a variety of other forms including, for example, Fv, Fab, and (Fab')$_2$, as well as bifunctional hybrid antibodies and single chains (e.g., Lanzavecchia et al., *Eur. J. Immunol.* 17:105, 1987; Huston et al., *Proc. Natl. Acad. Sci. U.S.A.,* 85:5879-5883, 1988; Bird et al., *Science* 242:423-426, 1988; Hood et al., *Immunology*, Benjamin, N.Y., 2nd ed., 1984; Hunkapiller and Hood, *Nature* 323:15-16, 1986).

Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors. An immunoglobulin light or heavy chain variable region includes a framework region interrupted by three hypervariable regions, also called complementarity determining regions (CDR's) (see, *Sequences of proteins of Immunological Interest*, E. Kabat et al., U.S. Department of Health and Human Services, 1983). As noted above, the CDRs are primarily responsible for binding to an epitope of an antigen. The specificity of the antibody resides in the structural complementarity between the antibody combining site and the antigenic determinant.

Chimeric antibodies are antibodies whose light and heavy chain genes have been constructed, typically by genetic engineering, from immunoglobulin variable and constant region genes belonging to different species. For example, the variable segments of the genes from a mouse monoclonal antibody can be joined to human constant segments, such as kappa and gamma 1 or gamma 3. In one example, a therapeutic chimeric antibody is thus a hybrid protein composed of the variable or antigen-binding domain from a mouse antibody and the constant or effector domain from a human antibody, although other mammalian species can be used, or the variable region can be produced by molecular techniques. Methods of making chimeric antibodies are well known in the art, e.g., see U.S. Pat. No. 5,807,715, which is herein incorporated by reference.

A "humanized" immunoglobulin is an immunoglobulin including a human framework region and one or more CDRs from a non-human (such as a mouse, rat, or synthetic) immunoglobulin. The non-human immunoglobulin providing the CDRs is termed a "donor" and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Exemplary conservative substitutions are those such as gly, ala; val, ile, leu; asp, glu; asn, gin; ser, thr; lys, arg; and phe, tyr (see U.S. Pat. No. 5,585,089, which is incorporated herein by reference). Humanized immunoglobulins can be constructed by means of genetic engineering, e.g., see U.S. Pat. No. 5,225,539 and U.S. Pat. No. 5,585,089, which are herein incorporated by reference.

A human antibody is an antibody wherein the light and heavy chain genes are of human origin. Human antibodies can be generated using methods known in the art. Human antibodies can be produced by immortalizing a human B cell secreting the antibody of interest. Immortalization can be accomplished, for example, by EBV infection or by fusing a human B cell with a myeloma or hybridoma cell to produce a trioma cell. Human antibodies can also be produced by phage display methods (see, e.g., Dower et al., PCT Publication No. WO91/17271; McCafferty et al., PCT Publication No. WO92/001047; and Winter, PCT Publication No. WO92/20791, which are herein incorporated by reference), or selected from a human combinatorial monoclonal antibody library (see the Morphosys website). Human antibodies can also be prepared by using transgenic animals carrying a human immunoglobulin gene (e.g., see Lonberg et al., PCT Publication No. WO93/12227; and Kucherlapati, PCT Publication No. WO91/10741, which are herein incorporated by reference).

Antibodies may also be obtained using phage display technology. Phase display technology is known in the art for example Marks et al J. Mol. Biol. 222: 581-597 and Ckackson et al, Nature 352: 624-628, both incorporated herein by reference. Phage display technology can also be used to increase the affinity of an antibody. To increase antibody affinity, the antibody sequence is diversified, a phage antibody library is constructed, and a higher affinity binders are selected on antigen (see for example Marks et al Bio/Technology 10:779-783, Barbas et al Proc. Natl. Acad. Sci. USA 91:3809-3813 and Schier et al J. Mol. Biol. 263: 551-567, all incorporated herein by reference).

Aptamer: The agent of the present invention may also be an aptamer. Aptamers have been defined as artificial nucleic acid ligands that can be generated against amino acids, drugs, proteins and other molecules. They are isolated from complex libraries of synthetic nucleic acids by an iterative process of adsorption, recovery and re-amplification.

RNA aptamers are nucleic acid molecules with affinities for specific target molecules. They have been likened to antibodies because of their ligand binding properties. They may be considered as useful agents for a variety of reasons. Specifically, they are soluble in a wide variety of solution conditions and concentrations, and their binding specificities are largely undisturbed by reagents such as detergents and other mild denaturants. Moreover, they are relatively cheap to isolate and produce. They may also readily be modified to generate species with improved properties. Extensive studies show that nucleic acids are largely non-toxic and non-immunogenic and aptamers have already found clinical application. Furthermore, it is known how to modulate the activities of aptamers in biological samples by the production of inactive dsRNA molecules in the presence of complementary RNA single strands (Rusconi et al., 2002).

It is known from the prior art how to isolate aptamers from degenerate sequence pools by repeated cycles of binding, sieving and amplification. Such methods are described in U.S. Pat. No. 5,475,096, U.S. Pat. No. 5,270,163 and EP0533 38 and typically are referred to as SELEX (Systematic Evolution of Ligands by EX-ponential Enrichment). The basic SELEX system has been modified for example by using Photo-SELEX where aptamers contain photo-reactive groups capable of binding and/or photo cross-linking to and/or photo-activating or inactivating a target molecule. Other modifications include Chimeric-SELEX, Blended-SELEX, Counter-SELEX, Solution-SELEX, Chemi-SELEX, Tissue-SELEX and Transcription-free SELEX which describes a method for ligating random fragments of RNA bound to a DNA template to form the oligonucleotide library. However, these methods even though producing enriched ligand-binding nucleic acid molecules, still produce unstable products. In order to overcome the problem of stability it is known to create enantiomeric "spiegelmers" (WO 01/92566). The process involves initially creating a chemical mirror image of the target, then selecting aptamers to this mirror image and finally creating a chemical mirror image of the SELEX selected aptamer. By selecting natural RNAs, based on D-ribose sugar units, against the non-natural enantiomer of the eventual target molecule, for example a peptide made of D-amino acids, a spiegelmer directed against the natural L-amino acid target can be created. Once tight binding aptamers to the non-natural enantiomer target are isolated and sequenced, the Laws of Molecular Symmetry mean that RNAs synthesised chemically based on L-ribose sugars will bind the natural target, that is to say the mirror image of the selection target. This process is conveniently referred to as reflection-selection or mirror selection and the L-ribose species produced are significantly more stable in biological environments because they are less susceptible to normal enzymatic cleavage, i.e. they are nuclease resistant.

Immunoreactivity: A measure of the ability of an agent, sometimes an antibody, to recognize and bind to a specific antigen. "Specifically binds" refers to the ability of individual agents or antibodies to specifically immunoreact with an antigen. This binding is a non-random binding reaction between an agent, for example but not limited to a antibody molecule, and the antigen. In one embodiment, the antigen is glycoprotein VI (GPVI). Binding specificity is typically determined from the reference point of the ability of the agent to differentially bind the antigen of interest and an unrelated antigen, and therefore distinguish between two different antigens, particularly where the two antigens have unique epitopes. An antibody that specifically binds to a particular epitope is referred to as a "specific antibody."

Typically, specificity may be determined by means of a binding assay such as ELISA employing a panel of antigens, e.g. as disclosed herein with reference to Table 2. An agent according to the present invention may recognise GPVI on cells of the platelet/megakaryocyte lineage, and not other human blood cells, in particular granulocytes, lymphocytes and erythrocytes. Reactivity of a specific binding member according to the invention with human platelets may be abolished by competition with recombinant GPVI.

Specificity may also be confirmed by means of comparison between the effective inhibitory dose in a collagen-binding assay such as platelet aggregometry conducted in plasma or whole blood perfusion and saturable binding of washed platelets in flow cytometry or substance having an antibody antigen-binding domain with the required specificity.

Monoclonal antibody: An antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Generally, a monoclonal antibody is produced by a specific hybridoma cell, or a progeny of the hybridoma cell propagated in culture. A hybridoma or other cell producing an antibody may be subject to genetic mutation or other changes, which may or may not alter the binding specificity of antibodies produced.

Nucleic Acid A "nucleic acid" is a polymeric form of nucleotides of any length, which contain deoxyribonucleotides, ribonucleotides, and analogs in any combination. Nucleic acids may have any three-dimensional structure, and may perform any function, known or unknown. The term "nucleic acid" includes double-, single-stranded, and triple-helical molecules. Unless otherwise specified or required, any embodiment of the invention described herein that is a nucleic acid encompasses both the double-stranded form and each of two complementary single-stranded forms known or predicted to make up the double stranded form. Specific examples of nucleic acid sequences of the variable domains that characterize the invention are the nucleic acid sequences given in SEQ ID NO: 150 and SEQ ID NO: 152 of the heavy chain and light chain of hGP 5C4, respectively.

Polypeptide The terms "polypeptide", "peptide" and "protein" are used interchangeably herein to refer to polymers of amino acids of any length. The polymer may be linear or branched, it may comprise modified amino acids or amino acid analogs, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labelling component.

Amino acid substitutions can range from changing or modifying one or more amino acids to complete redesign of a region, such as the variable region. Amino acid substitutions are preferably conservative substitutions that do not deleteriously affect folding or functional properties of the peptide. Groups of functionally related amino acids within which conservative substitutions may be made are glycine/alanine; valine/isoleucine/leucine; asparagine/glutamine; aspartic acid/glutamic acid; serine/threonine/methionine; lysine/arginine; and phenylalanine/tryosine/tryptophan. Polypeptides of this invention may be in glycosylated or unglycosylated form, may be modified post-translationally (e.g., acetylation, and phosphorylation) or may be modified synthetically (e.g., the attachment of a labeling group).

Treatment As used herein, "treatment" refers to clinical intervention in an attempt to alter the natural course of the individual or cell being treated, and may be performed either for prophylaxis or during the course of clinical pathology. Desirable effects include preventing occurrence or recurrence of disease, alleviation of symptoms, diminishment of any direct or indirect pathological consequences of the disease, lowering the rate of disease progression, amelioration or palliation of the disease state, and remission or improved prognosis. Following rupture of the atherosclerotic plaque, exposure of subendothelial collagen is the major trigger that initiates platelet adhesion and aggregation at the site of injury, followed by arterial thrombosis (van Zanten, G. H., de Graaf, S., Slootweg, P. J., Heijnen, H. F., Connolly, T. M., de Groot, P. G., Sixma, J. J. (1994) Increased platelet deposition on atherosclerotic coronary arteries. *J Clin. Invest* 93, 615-632; Baumgartner, H. R., Muggli, R., Tschopp, T. B., Turitto, V. T. (1976) Platelet adhesion, release and aggregation in flowing blood: effects of surface properties and platelet function. *Thromb. Haemost.* 35, 124-138). The platelet glycoprotein GPVI, which has been cloned recently (Clemetson, J. M., Polgar, J., Magnenat, E., Wells, T. N., Clemetson, K. J. (1999) The platelet collagen receptor glycoprotein VI is a member of the immunoglobulin superfamily closely related to FcalphaR and the natural killer receptors. *J Biol. Chem.* 274, 29019-29024; Jandrot-Perrus, M., Busfield, S., Lagrue, A. H., Xiong, X., Debili, N., Chickering, T., Le Couedic, J. P., Goodearl, A., Dussault, B., Fraser, C., Vainchenker, W., Villeval, J. L. (2000) Cloning, characterization, and functional studies of human and mouse glycoprotein VI: a platelet-specific collagen receptor from the immunoglobulin superfamily. *Blood* 96, 1798-1807), has been identified to be the major platelet collagen receptor, mediating platelet adhesion both in vitro (Chen, H., Locke, D., Liu, Y., Liu, C., Kahn, M. L. (2002) The platelet receptor GPVI mediates both adhesion and signaling responses to collagen in a receptor density-dependent fashion. *J Biol. Chem.* 277, 3011-3019) and under (patho-)physiological conditions in vivo (Massberg, S., Gawaz, M., Grüner, S., Schulte, V., Konrad, I., Zohlnhöfer, D., Heinzmann, U., Nieswandt, B. (2003) A crucial role of glycoprotein VI for platelet recruitment to the injured arterial wall in vivo. *J. Exp. Med.* 197, 41-49). This identifies the inhibition of GPVI as a promising strategy to prevent platelet recruitment and arterial thrombosis in patients with advanced atherosclerosis.

Variable region (also variable domain or V domain): The regions of both the light chain and the heavy chain of an Ig that contain antigen-binding sites. The regions are composed of polypeptide chains containing four relatively invariant "framework regions" (FRs) and three highly variant "hypervariable regions" (HVs). Because the HVs constitute the binding site for antigen(s) and determine specificity by forming a surface complementarity to the antigen, they are more commonly termed the "complementarity-determining regions," or CDRs, and are denoted CDR1, CDR2, and CDR3. Because both of the CDRs from the heavy and light chain domains contribute to the antigen-binding site, it is the three-dimensional configuration of the heavy and the light chains that determines the final antigen specificity.

Within the heavy and light chain, the framework regions surround the CDRs. Proceeding from the N-terminus of a heavy or light chain, the order of regions is: FR1-CDR1-FR2-CDR2-FR3-CDR3-FR4. As used herein, the term "variable region" is intended to encompass a complete set of four framework regions and three complementarity-determining regions. Thus, a sequence encoding a "variable region" would provide the sequence of a complete set of four framework regions and three complementarity-determining regions.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated. CDR regions; (vi) F(ab')$_2$ fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (viii) bispecific single chain Fv dimers (PCT/US92/09965) and (ix) "diabodies", multivalent or multispecific fragments constructed by gene fusion (WO94/13804; P. Holliger et al, Proc. Natl. Acad. Sci. USA 90 6444-6448, 1993). Fv, scFv or diabody molecules may be stabilised by the incorporation of disulphide bridges linking the VH and VL domains (Y. Reiter et al, Nature Biotech, 14, 1239-1245, 1996). Minibodies comprising ascFv joined to a CH3 domain may also be made (S. Hu et al, Cancer Res., 56, 3055-3061, 1996).

Where bispecific antibodies are to be used, these may be conventional bispecific antibodies, which can be manufactured in a variety of ways (Holliger, P. and Winter G. Current Opinion Biotechnol. 4, 446-449 (1993)), e.g. prepared chemically or from hybrid hybridomas, or may be any of the bispecific antibody fragments mentioned above. Diabodies and scFv can be constructed without an Fc region, using only variable domains, potentially reducing the effects of anti-idiotypic reaction.

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against GPVI, then a library can be made where the other arm is varied and an antibody of appropriate specificity selected. Bispecific whole antibodies may be made by knobs-into-holes engineering (J. B. B. Ridgeway et al, Protein Eng., 9,616-621, 1996). or substance having an antibody antigen-binding domain with the required specificity. Thus, this term covers antibody fragments and derivatives, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

The term "amino-group protecting moiety" refers to any group used to derivatise an amino group, especially an N-terminal amino group of a peptide or amino acid. Such groups include, without limitation, alkyl, acyl, alkoxycarbonyl, aminocarbonyl, and sulfonyl moieties. However, the term "amino-group protecting moiety" is not intended to be limited to those particular protecting groups that are commonly employed in organic synthesis, nor is it intended to be limited to groups that are readily cleavable.

The phrase "pharmaceutically acceptable" is employed herein to refer to those compounds, materials, compositions, and/or dosage forms which are, within the scope of sound medical judgment, suitable for use in contact with the tissues of human beings or animals without excessive toxicity, irritation, allergic response, or other problem or complication, commensurate with a reasonable benefit/risk ratio.

The expression "GPVI inhibitor" refers to a product which, within the scope of sound pharmacological judgement, is potentially or actually pharmaceutically useful as an inhibitor of GPVI, and includes reference to substance which comprises a pharmaceutically active species and is described, promoted or authorised as a GPVI inhibitor. Such GPVI inhibitors may be selective, that is they are regarded, within the scope of sound pharmacological judgement, as selective towards GPVI in contrast to other receptors or targets; the term "selective GPVI inhibitor" includes reference to substance which comprises a pharmaceutically active species and is described, promoted or authorised as a selective GPVI inhibitor. A "low molecular weight GPVI inhibitor" may have a molecular weight of less than 2,000, e.g. of less than 1,000; aptamers are examples of such inhibitors. Also to be mentioned as potential competitive inhibitors of GPVI-collagen binding are ligands and (poly)peptides mentioned herein as being useful in GPVI-collagen binding assays.

The "variable region" of hGP 5C4 refers to the variable region of the hGP 5C4 light chain or the variable region of the hGP 5C4 heavy chain. Specific variable regions are shown by SEQ ID NO: 149 and SEQ ID NO: 151. A "nucleic acid" is a polymeric form of nucleotides of any length, which contain deoxyribonucleotides, ribonucleotides, and analogs in any combination. Nucleic acids may have any three-dimensional structure, and may perform any function, known or unknown. The term "nucleic acid" includes double-, single-stranded, and triple-helical molecules. Unless otherwise specified or required, any embodiment of the invention described herein that is a nucleic acid encompasses both the double-stranded form and each of two complementary single-stranded forms known or predicted to make up the double stranded form. Specific examples of nucleic acid sequences of the variable domains that characterize the invention are the nucleic acid sequences given in SEQ ID NO: 150 and SEQ ID NO: 152 of the heavy chain and light chain of hGP 5C4, respectively.

The term "recombinant" polynucleotide as used here intends a polynucleotide of genomic, cDNA, semisynthetic, or synthetic origin which either does not occur in nature or is linked to another polynucleotide in an arrangement not found in nature.

The term "function conservative fragments or variants of hGP 5C4" or "function conservative fragments or variants of the amino acid sequence of SEQ ID NO: 149 or SEQ ID NO: 151" includes any peptide, polypeptide or protein monomer or polymer with hGP 5C4 Fab activity, derived from hGP 5C4 IgG antibody, and smaller and larger functionally equivalent polypeptides, as described herein. A "function conservative fragment or variant" of An hGP 5C4 polypeptide or polynucleotide varies from the native sequence by any combination of additions deletions, or substitutions while preserving at least the affinity to human glycoprotein VI. A function-conservative fragment may be obtained by digesting hGP 5C4 with a suitable enzyme or by chemical synthesis of a portion of hGP 5C4. A typical fragment is hGP 5C4 Fab. A function-conservative fragment of An hGP 5C4 polynucleotide either encodes a polypeptide that is functionally equivalent to hGP 5C4 Fab when used in an expression system, or has similar hybridization specificity as An hGP 5C4 Fab polynucleotide when used in a hybridization assay.

A previous hypothesis suggested that platelet glycoprotein (GP) Ib binding to von vWf recruits flowing platelets to the injured vessel wall (Ruggeri, Z. M: Mechanisms initiating platelet thrombus formation. *Thromb. Haemost* 1997, 78, 611-616), whereas subendothelial fibrillar collagens support firm adhesion and activation of platelets (van Zanten, G. H. et al. Increased platelet deposition on atherosclerotic coronary arteries. *J Clin. Invest* 1994; 93, 615-632; Clemetson, K. J. & Clemetson, J. M. Platelet collagen receptors. *Thromb. Haemost.* 2001, 86, 189-197). However, the present invention demonstrates by in vivo fluorescence microscopy of the mouse carotid artery that inhibition or absence of the major platelet collagen receptor, GPVI, instead, abolishes platelet-vessel wall interactions following an endothelial erosion. Unexpectedly, inhibition of GPVI reduces platelet tethering and adhesion to the subendothelium by approximately 89%. Furthermore, stable arrest and aggregation of platelets is virtually abolished under these conditions. The strict requirement for GPVI in these processes was confirmed in GPVI-deficient mice, where platelets also fail to adhere and aggregate on the damaged vessel wall. These findings reveal an unexpected role of GPVI in the initiation of platelet attachment at sites of vascular injury and unequivocally identify platelet-collagen interactions as the major determinant of arterial platelet-induced atherosclerotic complications.

The fact that GP VI generally functions as a receptor for the subendothelial matrix collagen has been described (Moroi M, Jung S M, Okuma M, Shinmyozu K. A patient with platelets deficient in glycoprotein VI that lack both collagen-induced aggregation and adhesion. J Clin Invest 1989; 84: 1440-1445). These authors characterized platelets in vitro originating from patients with a GP VI receptor deficiency. However, the physiological significance of the interaction of collagen and GP VI receptor in the in vivo context and the relative contribution of the GP VI receptor for adhesion following vascular injury was unknown. In particular, it was not known that inhibition of this receptor inhibits the key step in the formation of intravascular thrombosis that is platelet tethering.

The present invention reveals the GP VI receptor as an essential receptor for platelet adhesion to the subendothelium via the attachment to subendothelial matrix collagen in vivo. Amongst the variety of other platelet surface proteins such as GP Ib (von Willebrand receptor), the $\alpha IIb\beta 3$ integrin receptor, the $\alpha 2\beta 1$ integrin or the GP V receptors, we have surprisingly identified the GP VI receptor to be an essential receptor to mediate platelet adhesion to the vascular wall. Since platelet adhesion is the first and most important step for platelet aggregation and intraarterial thrombus formation under physiologic shear stress conditions, the following deleterious effects leading to intraarterial occlusion are the functional basis for the clinical syndromes of myocardial infarction or cerebral stroke. In a chronic setting, the interaction of platelets with the endothelium propagates early steps of arteriosclerosis. Our invention also showed for the first time that the GP VI receptor plays a crucial role amongst the complex variety of several platelet surface proteins for initial platelet adhesion and for chronical platelet-endothelium interaction in the propagation of arteriosclerosis.

WO 01/16321 and WO 01/00810 disclose a DNA and protein sequence of the human GPVI receptor. However, the significance on platelet adhesion and activation by endothelial lesions has not been demonstrated in an in vivo background.

U.S. Pat. No. 6,383,779 discloses fusion proteins of GPVI. However, this reference does not disclose a dimeric fusion protein or any therapeutic effect of GPVI.

Recently, the different phases of platelet-collagen interaction to artificial collagen in vitro during perfusion conditions were investigated (Moroi M, Jung S M, Shinmyozu K, Tzomiyama Y, Ordinas A and Diaz-Ricart M. Analysis of platelet adhesion to collagen-coated surface under flow conditions: the involvement of glycoprotein VI in the platelet adhesion. Blood 1997; 88: 2081-2092). The authors of that study already pointed out the importance of collagen-GP VI interaction during shear stress conditions. However, the relevance of subendothelial matrix collagen for the adhesion could not be studied in this artificial in vitro situation. As a consequence of limited relevance of their in vitro model, the authors of the above mentioned study came to the conclusion that GP VI receptors are rather involved in platelet activation than in platelet adhesion to the endothelium. In contrast, the von Willebrand GP Ib receptor is significantly involved in platelet-subendothelial interaction. These authors also focussed all available information about platelet-collagen interaction in a review of the current literature. Previously, Moroi M and Jung, S M (Platelet receptors for collagen. Thromb. Haemost. 1997; 78: 439-444) have discussed collagen fibril interaction with different collagen receptors on platelets for the adhesion and thrombus formation of platelets. However, the authors did not expect a relevant role of the GP VI receptor for the adhesion in a clinically relevant in vivo situation as they could not validate the significance of the different collagen receptors to the adhesion process.

Following rupture of the atherosclerotic plaque, exposure of subendothelial collagen is the major trigger that initiates platelet adhesion and aggregation at the site of injury, followed by arterial thrombosis (van Zanten, G. H., de Graaf, S., Slootweg, P. J., Heijnen, H. F., Connolly, T. M., de Groot, P. G., Sixma, J. J. (1994) Increased platelet deposition on atherosclerotic coronary arteries. *J. Clin. Invest* 93, 615-632; Baumgartner, H. R., Muggli, R., Tschopp, T. B., Turitto, V. T. (1976) Platelet adhesion, release and aggregation in flowing blood: effects of surface properties and platelet function. *Thromb. Haemost.* 35, 124-138). The platelet glycoprotein GPVI, which has been cloned recently (Clemetson, J. M., Polgar, J., Magnenat, E., Wells, T. N., Clemetson, K. J. (1999) The platelet collagen receptor glycoprotein VI is a member of the immunoglobulin superfamily closely related to FcalphaR and the natural killer receptors. *J. Biol. Chem.* 274, 29019-29024; Jandrot-Perrus, M., Busfield, S., Lagrue, A. H., Xiong, X., Debili, N., Chickering, T., Le Couedic, J. P., Goodearl, A., Dussault, B., Fraser, C., Vainchenker, W., Villeval, J. L. (2000) Cloning, characterization, and functional studies of human and mouse glycoprotein VI: a platelet-specific collagen receptor from the immunoglobulin superfamily. *Blood* 96, 1798-1807), has been identified to be the major platelet collagen receptor, mediating platelet adhesion both in vitro (Chen, H., Locke, D., Liu, Y., Liu, C., Kahn, M. L. (2002) The platelet receptor GPVI mediates both adhesion and signaling responses to collagen in a receptor density-dependent fashion. *J. Biol. Chem.* 277, 3011-3019) and under (patho-)physiological conditions in vivo (Massberg, S., Gawaz, M., Grüner, S., Schulte, V., Konrad, I., Zohlnhöfer, D., Heinzmann, U., Nieswandt, B. (2003) A crucial role of glycoprotein VI for platelet recruitment to the injured arterial wall in vivo. J. Exp. Med. 197, 41-49). This identifies the inhibition of GPVI as a promising strategy to prevent platelet recruitment and arterial thrombosis in patients with advanced atherosclerosis.

Therefore, the present invention provides a solution to the problem of inhibiting the relevant target for the platelet-subendothelial interaction and for platelet adhesion without provoking undesired side effects of bleeding complications. Besides the well known of collagen-platelet interaction via the GP VI receptor, we could provide data for the interaction of the native subendothelial matrix and platelets measured by in vivo platelet adhesion. Consecutively, we could validate the significance of the GP VI-endothelium interaction for platelet adhesion as initial step of intravascular thrombosis. Thus, our invention solves the problem of an effective antiplatelet drug treatment for the important step of platelet adhesion without undesired side effects.

Therefore, the immunoadhesin consists of the extracellular domain of the GP VI receptor together with the Fc part of an IgG immunoglobulin (Fc-GPVI-nt) fused via a linker having the amino acid sequence Gly-Gly-Arg. This novel fusion protein is based approximately 50% on the original DNA sequence of GPVI as published previously. The protein structure of the immunoadhesin is novel as the recombinant fusion protein does not form a membrane protein like the GP VI receptor but is a soluble, immunoglobulin-like immunoadhesin released by the respective host cell. This immunoadhesin can block the ligand-receptor interaction of collagen and GP VI. Our results demonstrate that the immunoadhesin has marked effects on the main physiological functions of platelets induced by collagen stimulation. Collagen-induced aggregation, adhesion and the release function can be inhibited by the immunoadhesin to the same extent as by a specific, monoclonal antibody. The mechanism, however, is different: whereas the antibody inhibits GP VI activation by directly binding to the ligand binding site of the GP VI receptor, the immunoadhesin scavenges the GP VI ligand collagen and therefore prevents ligand-mediated GP VI activation.

The immunoadhesin of the invention is a novel GP VI inhibitor. It has the advantage of selective inhibition of the activated branch of GP VI mediated effects by ligand scavenging. Secondary effects of using an anti-GPVI antibody, like antibody mediated effects on GP VI receptor internalisation are prevented when a fusion protein of the invention is used in place of an antibody. The fusion protein of the invention can be used for the treatment of atherosclerotic complications caused by unstable atheroslerotic plaques with plaque rupture or endothelial lesion. Therefore, the immunoadhesin Fc-GPVI-nt serves as a therapeutic inhibitor for collagen-mediated GP VI activation without affecting the intrinsic activity of the GP VI receptor with the relevant signalling system. Moreover, the GP VI immunoadhesin serves as an ideal epitope for antibody selection. The Fc part allows the convenient purification of the protein and simple fixation to surfaces to perform large scale antibody selection against antibody libraries i.e. by phage display. The selection allows selective antibody screening to the relevant epitope that resembles the intact protein with a similar structure as the native protein.

Finally, the Fc-GPVI-nt is an important tool for the screening for inhibitors of GP VI receptor activation. We have established an ELISA-based in vitro assay simulating the collagen GP VI interaction by collagen precoated plates as the ligand. This assay can alternatively be run with fluorescence-labelled Fc-GPVI-nt and thus be upscaled to high-throughput formats. This assay allows for the screening of both, inhibitory antibodies or small molecules for their potency to inhibit GP VI function by fluorescence measurement. With this cell free screening assay, a prototype method for a high-throughput-scaleable fluorescence screening assays for drug testing has been established.

Based on the recent improvements in imaging techniques by intravascular ultrasound or nuclear magnetic resonance imaging, it is possible to identify patients with atherosclerosis being at risk of acute clinical complications such as acute coronary or carotid syndrome, whereby the patients have active lesions as possible causes for intravascular thrombosis.

Active lesions are characterized by the unmasking of subendothelial matrix collagens and platelet activation. The occurrence of such lesions can be investigated e.g. by intravascular ultrasound or thermography (e.g., Fayed and Fuster, Clinical imaging of the high-risk or vulnerable atherosclerotic plaque. Circulation 2001; 89:305-316) or nuclear resonance imaging (Helft et al., Progression and Regression of Atherosclerotic Lesions. Circulation 2002; 105:993-998). Such lesions are highly probable in patients with acute coronary or carotid syndromes, and the risk of the reoccurrence of acute clinical complications such as myocardial infarction or stroke is very high, decreasing progressively with increasing time distance from the primary event.

Accordingly, based on the present invention, it is possible to treat patients being at risk of atherosclerosis. In order to prevent atheroprogression, a patient is treated with the fusion protein of the invention in order to prevent interaction between platelets and exposed subendothelial collagen. The fusion protein of the invention blocks the ligand for the GPVI platelet receptor in the vascular wall (e.g. subendothelium) so that an interaction between the platelets and exposed collagen is inhibited.

The fusion protein of the invention may be in the form of a lyophilised powder which is dispersed in a suitable pharmaceutically acceptable liquid carrier prior to administration to a patient. The fusion protein of the invention can also be incorporated into pharmaceutical compositions suitable for parenteral, in case of the treatment of acute complications preferably intraarterial or intravenous administration. Such compositions usually comprise the fusion protein and a pharmaceutically acceptable carrier. A pharmaceutically acceptable carrier includes solvents, dispersion media, antibacterial and antifungal agents and isotonic agents, which are compatible with pharmaceutical administration. The present invention includes methods for manufacturing pharmaceutical compositions for the treatment of chronic or acute cardiovascular disease. Such methods comprise formulating a pharmaceutically acceptable carrier with the fusion protein of the invention. In case of the treatment of acute cardiovascular disease, the composition is preferably administered intravenously or intraarterially. In case of the treatment of chronic cardiovascular disease, the composition may also be administered subcutaneously and intraperitoneally. Such compositions can further include additional active compounds, such as further polypeptides (such as insulin) or therapeutically active small molecules. Thus, the invention further includes methods for preparing a pharmaceutical composition by formulating a pharmaceutically acceptable carrier with the fusion protein of the invention and one or more additional active compounds such as insulin. In case of the coformulation of the fusion protein and insulin for the treatment of diabetic patients, it is preferred that the dosage form allows separate storage of the different proteins whereby mixing of the proteins is carried out just prior or during the administration of the composition. Accordingly, application by a multi-chamber syringe is considered. A pharmaceutical composition of the invention is formulated to be compatible with its intended parenteral route of administration.

Examples of routes of parenteral administration include, e.g., intraarterial and intravenous administration. Solutions or suspensions used for parenteral may include a sterile diluent such as water for injection, saline solution, polyethylene glycols, fixed oils, glycerine, propylene glycol, TWEEN or other synthetic solvents; antibacterial agents such as benzyl alcohol or methyl parabens; chelating agents such as ethylenediaminetetraacetic acid; antioxidants such as ascorbic acid or sodium bisulfite; buffers such as acetates, citrates or phosphates and agents for the adjustment of tonicity such as sodium chloride, dextrose, saccarose or mannitose. The pH can be adjusted with acids or bases, such as hydrochloric acid or sodium hydroxide. The parenteral preparation can be enclosed in ampoules, disposable syringes or multiple dose vials made of glass or plastic. Pharmaceutical compositions suitable for injectable use include sterile aqueous solutions or dispersions and sterile powders for the extemporaneous preparation of sterile injectable solutions or dispersions. For intravenous administration, suitable carriers include physiological saline, bacteriostatic water, or phosphate buffered saline (PBS). The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants.

Prevention of the action of micoorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin. Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. It is especially advantageous to formulate oral or parenteral compositions in dosage unit form. A dosage unit form is a discrete unit suited as a unitary dosage for a patient. Each unit contains a predetermined quantity of active compound to produce the desired therapeutic effect in association with the required pharmaceutical carrier. A therapeutically effective amount of fusion protein (i.e., an effective dosage) for the treatment of acute complications ranges from 0.05 to 5 mg/kg body weight, preferably 0.1 to 2 mg/kg body weight, more preferably 0.1 to 1 mg/kg body weight. A therapeutically effective amount of fusion protein (i.e., an effective dosage) for the treatment of chronic atheroprogression ranges from 0.5 to 6 mg/kg body weight, preferably 1 to 5 mg/kg body weight, more preferably 2 to 5 mg/kg body weight. The treatment of a subject with a therapeutically effective amount of the fusion protein can include a single treatment or, preferably, can include a series of treatments. In a preferred example, a subject is treated with the fusion protein of the invention against chronic atheroprogression in the range of between 0.5 to 6 mg/kg body weight, preferably 1 to 5 mg/kg body weight, more preferably 2 to 5 mg/kg body weight, at least twice per week.

Therefore, the GPVI-endothelium interaction for platelet adhesion is the initial step of intravascular thrombosis. Thus, an effective anti-platelet drug for the prevention of collagen GPVI interactions is an ideal treatment for this initial step of platelet adhesion without undesired side effects. Therefore, the invention provides an inhibitor such as a specific antibody or a fragment thereof or a function conservative variant thereof against GPVI. The protein structure of the antibody is novel. This antibody specifically binds to GPVI as purified protein, GPVI expressed on the surface of GPVI expressing CHO cells and native GPVI on the surface of freshly isolated human platelets. Moreover, the hGP 5C4 Fab prevents collagen-GPVI interaction in vitro and hence can block the ligand-receptor interaction of collagen and GPVI.

The antibody fragment hGP 5C4 Fab has marked inhibitory effects on the main physiological functions of platelets induced by collagen stimulation. The stimulation of collagen-mediated physiological activation parameters PAC-1 and CD 62P-Selectin was completely prevented by hGP 5C4 Fab. Other putative anti-GPVI antibodies had no significant inhibitory effect on PAC-1 and CD 62 P. Moreover, other putative anti-GPVI antibodies presented with a well known problem for inhibitors: Despite specific binding to GPVI some antibodies like 14E11 and 4C9 activated PAC-1 and CD 62P even in the absence of agonists. This is a common problem for the development of inhibitory antibodies. The antibody fragment hGP 5C4 Fab did not show any intrinsic GPVI activity. Additionally, hGP 5C4 Fab potently inhibited human platelet aggregation ex vivo without any intrinsic activity.

The inhibitory antibody had no effects on ADP-mediated activation of PAC-1 and CD 62P. Additionally, hGP 5C4 Fab had no effect on TRAP- and ADP-mediated aggregation and ATP release of human platelets ex vivo. As a consequence, hGP 5C4 Fab has some properties of a highly selective inhibitor of arterial thrombosis with no effects on venous thrombosis and hemostasis. Our experiments clearly showed that bleeding time of human blood was not prolonged in the PFA-100 device. In this way, hGP 5C4 Fab circumvents an almost inherent problem of anti-platelet drugs (Quinn M J; Plow E F; Topol E J. 2002: Platelet Glycoprotein IIb/IIIa inhibitors—Recognition of a two-edged sword. Circulation 106: 379-385; Bhatt D L & Topol E J; 2003: Scientific and therapeutic advances in antiplatelet therapy. Nat Rev Drug Discov 2: 15-28). hGP 5C4 Fab shows inhibition of platelet activation with no prolongation of bleeding time. Thus, hGP 5C4 has some properties of an ideal drug for the treatment of acute vascular syndromes like acute coronary syndromes or ischemic stroke without unwanted and potentially fatal side effects like intra cranial hemorrhage or other bleeding complications. Moreover, hGP 5C4 Fab shows inhibition of release of transmitter substances such as ATP from intracellular storage vesicles of human platelets. As this is a crucial parameter for the platelet-endothelium interaction promoting atherosclerosis, the antibody hGP 5C4 has a property of a drug for the treatment and prevention of atherosclerosis. Accordingly, the invention provides antibody products having one or more properties of a drug for solving the problem of treatment of atherosclerosis by inhibition of platelet secretion.

The antibody hGP 5C4 of the invention is a novel GPVI inhibitor inhibiting the activated branch of GPVI mediated effects without significant bleeding complications. The antibody hGP 5C4 and the antibody fragment hGP 5C4 Fab have one or more properties of a drug to be used for the treatment of atherosclerotic complications caused by unstable atherosclerotic plaques with plaque rupture or endothelial lesion. Therefore, the antibody hGP 5C4 and the antibody fragment hGP 5C4 Fab as appear to have a property appropriate to therapeutic inhibitors for collagen-mediated GPVI activation without affecting the intrinsic activity of the GPVI receptor with the relevant signalling system. Moreover, these inhibitors can be used for the prevention and treatment of atherosclerosis.

Based on the recent improvements in imaging techniques by intravascular ultrasound or nuclear magnetic resonance imaging, it is possible to identify patients with atherosclerosis being at risk of acute clinical complications such as acute coronary or carotid syndrome, whereby the patients have active lesions as possible causes for intravascular thrombosis. It may then be possible by the present invention to prevent the formation of intravascular thrombosis by the administration of a medicament containing the antibody hGP 5C4 against platelet GPVI without undesired side effects discussed above.

Active lesions are characterized by the unmasking of subendothelial matrix collagens and platelet activation. The occurrence of such lesions can be investigated e.g. by intravascular ultrasound or thermography (e.g., Fayed and Fuster, Clinical imaging of the high-risk or vulnerable atherosclerotic plaque. Circulation 2001; 89:305-316) or nuclear resonance imaging (Helft et al., Progression and Regression of Atherosclerotic Lesions. Circulation 2002; 105:993-998). Moreover, the dimeric form of the Fc-GPVI-nt fusion protein serves as and ideal diagnostic tool for the identification of endothelial lesions in patients (EP 03/05929). Such lesions are highly probable in patients with acute coronary or carotid syndromes, and the risk of the reoccurrence of acute clinical complications such as myocardial infarction or stroke is very high, decreasing progressively with increasing time distance from the primary event.

Therefore, the present invention provides a method of treating a patient suffering from an acute coronary or carotid syndrome for avoiding intravascular thrombosis. Moreover, based on the present invention, it is possible to treat patients being at risk of intravascular thrombosis due to the rupture of complex arteriosclerotic plaques. The rupture also unmasks the subendothelial collagen matrix. As a consequence of intraarterial thrombus formation, the perfusion of vital organs is blocked with the above described important and life threatening clinical syndromes.

The present invention relates in embodiments to monoclonal antibody hGP 5C4 which binds to human glycoprotein VI. The present invention encompasses fragments or function-conservative variants of monoclonal antibody hGP 5C4 such as the hGP 5C4 Fab fragment or polypeptide fragments of hGP 5C4 Fab containing at least a portion of a variable region of hGP 5C4 Fab. Preferred fragments are those with immunological activity of hGP 5C4 Fab. Also preferred are fragments which comprise amino acid sequences substantially different from other immunoglobulins, and fragments comprising a complementarity defining region (CDR). In one embodiment, the invention includes a polypeptide fragment of the hGP 5C4 Fab light chain variable region, comprising at least 5 consecutive amino acids, more preferably 15 consecutive amino acids, still more preferably 30 consecutive amino acids. In other embodiments, the invention includes a polypeptide fragment of the hGP 5C4 Fab heavy chain variable region, comprising the 5 amino acids. The size of the hGP 5C4 polypeptide fragments may be only the minimum size required to provide a desired function. They may optionally comprise additional sequence, either native to hGP 5C4, or from a heterologous source. hGP 5C4 fragments may contain only 5 consecutive amino acids from An hGP 5C4 Fab variable region sequence. Polypeptides comprising 7 amino acids, more preferably about 10 amino acids, more preferably about 15 amino acids, more preferably about 25 amino acids, more preferably about 50 amino acids, more preferably about 75 amino acids from the hGP 5C4 Fab light or heavy chain variable region are also included. Even more preferred are polypeptides comprising the entire hGP 5C4 Fab light or heavy chain variable region. The invention includes modified hGP 5C4 Fab polypeptides which are functionally equivalent to hGP 5C4 Fab, or have altered but measurable hGP 5C4 Fab immunologic activity. Fragments with improved hGP 5C4 Fab immunologic activity are preferred. Examples of modified polypeptides include polypeptides with conservative substitutions of amino acid residues, and one or more deletions or additions of amino acids which do not significantly deleteriously change the functional activity. One example is An hGP 5C4 Fab polypeptide comprising one or more amino acid substitution in comparison with the prototype hGP 5C4 Fab sequence. Substitutions can range from changing or modifying one or more amino acids to complete redesign of a region, such as the variable region. Amino acid substitutions are preferably conservative substitutions that do not deleteriously affect folding or functional properties of the peptide. Groups of functionally related amino acids within which conservative substitutions may be made are glycine/alanine; valine/isoleucine/leucine; asparagine/glutamine; aspartic acid/glutamic acid; serine/threonine/methionine; lysine/arginine; and phenylalanine/tryosine/tryptophan. Polypeptides of this invention may be in glycosylated or unglycosylated form, may be modified post-translationally (e.g., acetylation, and phosphorylation) or may be modified synthetically (e.g., the attachment of a labeling group).

The present invention also relates to humanized hGP 5C4. Since hGP 5C4 is a rodent antibody obtained from a rat, repeated in vivo administration in a human patient will bring about an immune response against the rodent antibody. This response may limit the effectiveness of the pharmaceutical if repeated dosing is required. The immunogenicity of the antibody may be reduced by chemical modification of the antibody with a hydrophilic polymer such as polyethylene glycol or by using the methods of genetic engineering to make the antibody binding structure more human like. For example, these procedures are described in EP 0173494, EP 194276, EP 0120694, EP 0125023, EP 0171496, EP 023940, WO 86/01533, WO 90/07861, WO91/09967 or Mol. Immunol. 28, 489 (1991). The invention also encompasses fusion proteins comprising one or more hGP 5C4 Fab polypeptides. An hGP 5C4 Fab fusion polypeptide can be prepared, for example, by chemical synthesis, or by creating and translating a polynucleotide in which the peptide regions are encoded in the desired relationship. Alternatively, fusion proteins may be provided in expression systems constructed by co-transfection with plasmids comprising encoding regions for different functional regions of the protein.

The invention also encompasses a conjugate which comprises an effector moiety and an hGP 5C4 antibody or a function conservative fragment or variant thereof. An effector moiety may be any entity having the effect of providing an additional activity or function (e.g. a radioactivity or an enzymatic function or therapeutic activity) to the activity or function of hGP 5C4 antibody in forming the conjugate. Conjugation of the effector moiety and antibody or function-conservative fragment or variant thereof may be achieved by conventional methods such as chemical linkage via heterobifunctional linkers or recombinant gene fusion techniques.

The present invention also relates to a pharmaceutical composition for treatment and prevention of acute or chronic vascular diseases associated with intraarterial and/or intravenous thrombosis. The composition contains a pharmaceutically acceptable excipient and a pharmaceutically active amount of an inhibitor selected from
(a) the antibody, or function-conservative fragments or variants thereof, according to the invention,
(b) the humanized antibody according to the invention,
(c) the fusion protein according to the invention, and
(d) the conjugate according to the invention.

The excipient may be a pharmaceutically-acceptable diluent or carrier. Pharmaceutical compositions of the present invention may be formulated in a variety of dosage forms. Generally, the compositions of the present invention will be administered parenterally, preferably intravenously. A particular parenteral pharmaceutical composition is formulated in a unit dosage form suitable for administration by injection. A pharmaceutically acceptable carrier or diluent may be a solid or liquid filler, diluent or substance which may be safely used in parenteral administration. Depending on the particular route of administration, a variety of pharmaceutically acceptable carriers well known in the art include solid or liquid fillers, diluents, hydrotropes, surface active agents, and encapsulating substances. The amount of carrier employed in conjunction with the inhibitor of the invention is used to provide practical quantity of material per unit dose of composition. Pharmaceutically acceptable carriers for systemic administration that may be incorporated in the composition of the invention include sugar, starches, cellulose, vegetable oils, buffers, polyols and alginic acid. Specific carriers are disclosed in U.S. Pat. No. 4,401,663, EP-A 0 089 710, EP-A 0 068 592. Preferred carriers for parenteral administration include propylene glycol, pyrrolidone, ethyl oleate, aqueous ethanol, and combinations thereof. Particularly suitable compositions comprise a solution, emulsion or suspension of the inhibitor of the invention in association with a pharmaceutically acceptable parenteral carrier or diluent. Suitable carriers or diluents include aqueous vehicles, for example water or saline, and non-aqueous vehicles, for example fixed oils or liposomes. The compositions may include agents which enhance the stability of the inhibitor in the composition. For example, the composition may include a buffer such as phosphate buffered saline (PBS) containing sugars such as sucrose and mannitol. The concentration of the conjugate will vary, but in general, the conjugate will be formulated at concentrations of about 1 to 10 mg/ml. The compositions may be prepared prior to use based on a freeze-dried preparation of the inhibitor.

The dose and dosage regimen will depend upon the particular inhibitor employed, the platelet population and the patient's history. The dose of the inhibitor administered will typically be in the range 0.1 to 100 mg/patient/day.

The present invention also relates to an amino acid sequence, in particular to an amino acid sequence of the antibody hGP 5C4, fragments thereof such as hGP 5C4 Fab, or function-conservative variants of monoclonal antibody hGP 5C4 of the present invention. In particular, the present invention relates to a protein comprising an amino acid sequence of SEQ ID NO: 149 or SEQ ID NO: 151 or a function conservative fragment or variant of the heavy chain or the light chain of hGP 5C4, which has hGP 5C4 or hGP 5C4 Fab activity or function. The present invention relates to a DNA of a polypeptide having hGP 5C4 or hGP 5C4 Fab activity or function. In particular, the DNA includes DNAs encoding for the polypeptide of a human chimeric antibody and a human CDR-grafted antibody, which have the above-mentioned activity, and a DNA encoding for the polypeptide of an antibody fragment. The present invention also includes DNAs encoding the heavy chain or the light chain of these antibodies or antibody fragments. Furthermore, the present invention includes DNAs encoding the polypeptide of the heavy chain variable region or the light chain variable region of these antibodies or antibody fragments. A concrete example of the nucleic acid sequence of the heavy chain variable region includes a sequence shown in SEQ ID NO: 150. Furthermore, an example of the nucleic acid sequence of the specific light chain variable region includes a sequence shown in SEQ ID NO: 152.

Furthermore, the present invention includes a sequence of a gene encoding a variable region CDR of an antibody having hGP 5C4 or hGP 5C4 Fab activity or function. Moreover, the present invention relates to or the polypeptide containing a variable region CDR of an antibody having hGP 5C4 or hGP 5C4 Fab activity or function.

The nucleic acid, in particular DNA, of the present invention is incorporated into a vector, then by using this vector, a host cell can be transfected. Furthermore, in the DNAs of the present invention, a DNA encoding an antibody heavy chain (or a heavy chain variable region) is incorporated into one vector and a DNA encoding an antibody light chain (or a light chain variable region) is incorporated into another vector to form two expression vectors. Then, a host cell may be cotransfected with the two resultant expression vectors. Furthermore, in the DNAs of the present invention, the DNA encoding the antibody heavy chain (or the heavy chain variable region) and the DNA encoding the antibody light chain (or the light chain variable region) are incorporated into one same vector, and then by using this vector, a host cell may be transfected.

Kinds of vectors to be used are not particularly limited as long as the DNA of the present invention can be incorporated in a manner capable of expression, and can be in deed expressed in a host cell.

Kinds of host cells are not particularly limited as long as they can be transfected by a vector to be used and can express the DNA of the present invention. For example, bacteria such as *Escherichia coli*, yeast such as *Saccharomyces cerevisiae*, and an animal cell such as a COS cell, a CHO cell, etc. can be used.

By cultivating a transformant or transfected cell, an antibody or antibody fragment having hGP 5C4 or hGP 5C4 Fab activity or function can be produced in a cell or a culture medium. Then, by collecting the produced antibody (including antibody fragment), the antibody of the first aspect of the present invention can be obtained. The obtained antibody can be isolated and purified by appropriately combining methods, for example, centrifugation, ammonium sulfate fractionation, salting out, ultrafiltration, affinity chromatography, ion-exchange chromatography, or gel-filtration chromatography.

Whether or not the polypeptide of the present invention has an activity of recognizing glycoprotein VI can be confirmed by observing the binding property between a subject polypeptide and glycoprotein VI, when the subject antibody is brought into contact with glycoprotein VI.

The present invention further relates to the use of the inhibitor of the invention for the preparation of medicament for the treatment or prevention of acute or chronic vascular diseases associated with intraarterial and/or intravenous thrombosis.

General preparation process of hGP 5C4 antibody: hGP 5C4 antibody of this invention can be prepared in several ways. It is most conveniently obtained from the hybridoma deposited as hGP 5C4 with DSMZ-Deutsche Sammlung von Mikroorganismen und Zellkulturen under Accession No. 2631, or the progeny thereof. For example, the cells can be cultured in a suitable medium, and spent medium can be used as an antibody source. Optionally, matrix-coated channels or beads and cell cocultures may be included to enhance growth of antibody-producing cells. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal is optionally primed for ascites production by prior administration of a suitable composition, for example, Pristane. hGP 5C4 may also be obtained by employing routine recombinant methods such as described in Sambrook et al. (1989). For instance, using the sequences as shown by SEQ ID NO: 150 and/or SEQ ID NO: 152, or sequences obtainable from the hybridoma deposited with deposited with DSMZ-Deutsche Sammlung von Mikroorganismen und Zellkulturen under Accession No. 2631 or the progeny thereof, a polynucleotide encoding either the hGP 5C4 heavy or light chain can be cloned into a suitable expression vector (which contains control sequences for transcription, such as a promoter). The expression vector is in turn introduced into a host cell. The host cell is grown under suitable conditions such that the polynucleotide is transcribed and translated into a protein. Heavy and light chains of hGP 5C4 may be produced separately, and then combined by disulfide bond rearrangement. Alternatively, vectors with separate polynucleotides encoding each chain of hGP 5C4, or a vector with a single polynucleotide encoding both chains as separate transcripts, may be transfected into a single host cell which may then produce and assemble the entire molecule. Preferably, the host cell is a higher eukaryotic cell that can provide the normal carbohydrate complement of the molecule. The hGP 5C4 thus produced in the host cell can be purified using standard techniques in the art.

Alternatively, hGP 5C4 Fab can be chemically synthesized using information provided in this disclosure, in conjunction with standard methods of protein synthesis. A suitable method is the solid-phase Merrifield technique. Automated peptide synthesizers are commercially available, such as those manufactured by Applied Biosystems, Inc. (Foster City, Calif.).

Methods of antibody isolation are well known in the art. See, for example, Harlow and Lane (1988) Antibodies: A Laboratory Manual, Cold Spring Harbor Laboratory, New York. The hGP 5C4 antibody is a mouse immunoglobulin of the IgG class, and may be isolated by any technique suitable for immunoglobulins of this isotype. Purification methods may include salt precipitation (for example, with ammonium sulfate), ion exchange chromatography (for example, on a cationic or anionic exchange column run at neutral pH and eluted with step gradients of increasing ionic strength), gel filtration chromatography (including gel filtration HPLC), and chromatography on affinity resins such as protein A, protein G, hydroxyapatite, and anti-immunoglobulin. Most preferably, the antibody of the invention is purified by using Protein G-Sepharose columns.

The polypeptides of his invention can be made by any suitable procedure, including proteolysis of the hGP 5C4 antibody, by recombinant methods or by chemical synthesis. hGP 5C4 polypeptides, especially shorter polypeptides up to about 50 amino acids, are conveniently made by chemical synthesis, based on the information provided herein. Certain hGP 5C4 polypeptides which are fragments of the whole molecule may alternatively be prepared from enzymatic cleavage of intact hGP 5C4. Examples of proteolytic enzymes include, but are not limited to, trypsin, chymotrypsin, pepsin, papain, V8 protease, subtilisin, plasmin, and thrombin. Intact hGP 5C4 can be incubated with one or more proteinases simultaneously or sequentially. Preferably, hGP 5C4 is digested with papain for obtaining hGP 5C4 Fab. Alternatively, or in addition, intact hGP 5C4 can be treated with disulfide reducing agents. Peptides may then be separated from each other by techniques known in the art, including but not limited to gel filtration chromatography, gel electrophoresis, and reverse-phase HPLC. An hGP 5C4 polypeptide can also be made by obtaining a polynucleotide encoding it according to the information obtainable from the hGP 5C4 expressing hybridomas, and introducing it into a suitable expression system. Typically, polynucleotides encoding An hGP 5C4 Fab polypeptide are ligated into an expression vector under control of a suitable promoter and used to genetically alter the intended host cell. Both eukaryotic and prokaryotic host systems can be used. The polypeptide is then isolated from lysed cells or from the culture medium and purified to the extent needed for its intended use. Examples of prokaryotic host cells appropriate for use with this invention include *E. coli*. Examples of eukaryotic host cells include avian, insect, plant, and animal cells such as COS7, HeLa, and CHO cells.

For most applications, it is generally preferable that the polypeptide is at least partially purified from other cellular constituents. Preferably, the polypeptide is at least about 50% pure. as a weight percent of total protein. More preferably, the protein is at least about 50-75% pure. For clinical use, the polypeptide is preferably at least about 80% pure.

Antibody fragment hGP 5C4 Fab may be obtained by using antibody hGP 5C4 as a starting material. Specifically hGP 5C4 may be digested with a suitable proteolytic enzyme and the Fab fragments may be isolated. Preferably, hGP 5C4 is digested by using papain or a derivative thereof. Fab fragments may be purified by using affinity chromatography such as anti-immunoglobulin or ion exchange chromatography, or hydrophobic interaction chromatography.

The hGP 5C4 antibody or hGP 5C4 Fab polypeptides of this invention can be characterized in several ways. For instance, An hGP 5C4 antibody or hGP 5C4 Fab polypeptide may be tested for its ability to bind specifically to human glycoprotein VI, for its ability to specifically inhibit the binding between human glycoprotein VI and intact hGP 5C4 Fab, or for its ability to specifically inhibit the binding between human glycoprotein VI and subendothelial collagen. hGP 5C4 antibody or hGP 5C4 Fab polypeptides can also be tested for their ability to treat or prevent cardiovascular disease. hGP 5C4 antibody or hGP 5C4 Fab polypeptides can also be tested for their ability not to activate the GPVI receptor by intrinsic antibody activity or not to induce immuno-thrombocytopenia. Moreover, hGP 5C4 antibody or hGP 5C4 Fab polypeptides can also be tested for the inhibition of the release mechanism of platelets and the lack of expression of pro-inflammatory responses.

The ability of An hGP 5C4 Fab polypeptide to bind human glycoprotein VI may be tested by immunoassay. Any form of direct binding assay is suitable. In one such assay, the human glycoprotein VI or alternatively the hGP 5C4 Fab polypeptide is labeled. Suitable labels include radioisotopes such as $^{125}$I, enzymes such as peroxidase, fluorescent labels such as fluorescein, and chemiluminescent labels. Typically, the other binding partner is insolubilized (for example, by coating onto a microtiter plate) to facilitate washing. After combining the labeled component with the insolubilized component, the solid phase is washed and the amount of bound label is determined. To conduct the inhibition assays, the putative hGP 5C4 Fab polypeptide is titered for its ability to decrease the binding of hGP 5C4 Fab to human glycoprotein VI, or human glycoprotein VI to subendothelial collagen. Either of the binding pairs in the reaction to be inhibited is labeled, while the other is typically insolubilized in order to facilitate washing. Polypeptides with the characteristics of hGP 5C4 Fab will proportionately decrease the amount of label attached to the solid phase, compared with control polypeptides. Any other characterization may be carried out as specifically described in the examples.

If hGP 5C4 Fab is to be administered to an individual, it is preferably at least 80% pure, more preferably it is at least 90% pure, even more preferably it is at least 95% pure and free of pyrogens and other contaminants. In this context, the percent purity is calculated as a weight percent of the total protein content of the preparation, and does not include constituents which are deliberately added to the composition after the hGP 5C4 Fab is purified.

The present invention provides a method of treatment of a human or animal body in need of treatment or prevention of acute or chronic vascular diseases associated with intraarterial and/or intravenous thrombosis, which comprises administration to a human or animal of a pharmaceutically effective amount of an inhibitor of the invention. If hGP 5C4 antibody or hGP 5C4 Fab are used as a medicament, the dosage will usually be in the range of from 0.1 to 100 mg/patient/day. Preferably, hGP 5C4 antibody or hGP 5C4 Fab are used as lyophilised powders solubilised in PBS/sucrose/mannitol-buffer prior to parenteral administration. A human or animal body in need of treatment or prevention of acute or chronic vascular diseases associated with intraarterial and/or intravenous thrombosis is characterized by active lesions due to unmasking of subendothelial matrix collagens and platelet activation. The occurrence of such lesions can be investigated e.g. by intravascular ultrasound or thermography (e.g., Fayed and Fuster, Clinical imaging of the high-risk or vulnerable atherosclerotic plaque. Circulation 2001; 89:305-316) or nuclear resonance imaging (Helft et al., Progression and Regression of Atherosclerotic Lesions. Circulation 2002; 105:993-998). Such lesions are highly probable in patients with acute coronary or carotid syndromes, and the risk of the reoccurrence of acute clinical complications such as myocardial infarction or stroke is very high, decreasing progressively with increasing time distance from the primary event.

Further novel products of the disclosure are described in this section of the specification. As previously described, there are provided agents which bind to GPVI, and more specifically, to a ligand of the disclosure. In one aspect of the invention, the agent is hGP 5C4 Fab or has the same or similar immunological activity as hGP 5C4 Fab.

The invention includes all variant forms of the described GPVI binding agents which retain GPVI binding function, in particular clinically useful function, especially ability to inhibit GPVI-collagen binding and not to significantly activate platelets to promote aggregation. For example, proteins and other poly(amino acids) may be derivatised as by glycosylation, for example, to modify their properties. Other modifications included within the disclosure include without limitation attachment of natural or synthetic polymers (e.g. a polyethylene glycol or dextran) albumin affinity tags (see for example *Bioorg Med Chem. Lett.* 2002 Oct. 21; 12(20):2883-6). Also included are peptides containing one or more d-amino acids.

Table 2 shows peptides consisting of contiguous sequences of GPVI. The binding affinity of peptides 9 to 14 may be compared to a comparative peptide. The comparative peptide may contain between five and fifteen contiguous amino acid residues of human GPVI (FIG. 35), excluding amino acid residues 15 to 39 of FIG. 35. Thus, the comparative peptide may contain amino acid residues 1 to 14 or 40 onwards of FIG. 35.

In one embodiment, the agent of the present invention binds to one or more than one or a combination of peptide sequences selected from SEQ ID NOs: 9, 10 11, 12, 13 and 14 with greater affinity than any comparative peptide of human GPVI e.g. at least twice as strongly as any comparative peptide sequence of a human GPVI. The strength of the binding of an agent to a peptide sequence of GPVI may be analysed using chemiluminescence and quantified by measuring signal intensity. Thus, the strength of binding of an agent to a peptide may be indicated by a signal:noise ratio. In one embodiment, the agent of the present invention binds to one or more than one or a combination of peptide sequences selected from SEQ ID NOs: 11, 12 and 13 at least twice as strongly as any comparative peptide sequence of a human GPVI. In an alternative embodiment, the agent of the present invention binds to one or more than one or a combination of peptide sequences selected from SEQ ID NOs: 11 and 12 at least twice as strongly as any comparative peptide sequence of a human GPVI.

Included are embodiments in which the agent of the invention binds to peptide sequence SEQ ID NO: 9. with greater affinity than it does to a peptide having a sequence of any of SEQ ID NOs: 1-8 and 15-131.

Included also are embodiments in which the agent of the invention binds to peptide sequence SEQ ID NO: 10 with greater affinity than it does to a peptide having a sequence of any of SEQ ID NOs: 1-8 and 15-131.

Included further are embodiments in which the agent of the invention binds to peptide sequence SEQ ID NO: 11 with greater affinity than it does to a peptide having a sequence of any of SEQ ID NOs: 1-8 and 15-131.

Included additionally are embodiments in which the agent of the invention binds to peptide sequence SEQ ID NO: 12 with greater affinity than it does to a peptide having a sequence of any of SEQ ID NOs: 1-8 and 15-131.

The invention also includes embodiments in which the agent of the invention binds to peptide sequence SEQ ID NO: 13 with greater affinity than it does to a peptide having a sequence of any of SEQ ID NOs: 1-8 and 15-131.

The invention further includes embodiments in which the agent of the invention binds to peptide sequence SEQ ID NO: 14 with greater affinity than it does to a peptide having a sequence of any of SEQ ID NOs: 1-8 and 15-131.

Agents of the invention may bind with greater affinity to each of the peptides of sequences SEQ ID NOs: 9, 10 11, 12, 13 and 14 affinity than it does to any of the peptides having a sequence of SEQ ID NOs: 1-8 and 15-131.

Those agents which bind with greater affinity to a particular peptide or peptides than to other specified peptide(s) may have an affinity two, five, 10, fifteen or twenty times greater for the particular peptide(s) than for any of the specified peptide(s). The binding affinity of an agent to a peptide may be analysed using chemiluminescence and measured, at least relative to the binding affinity to other peptides, by measuring signal intensity.

In particular, analysis of agent binding to the peptides may be carried out by PepSpot™ analysis (see: *Molecular Basis for the Binding Promiscuity of an Anti-p24 (HIV-J) Monoclonal Antibody*, Kramer et al., Cell Vol. 91 (1997), p. 799-

809, *Antigen sequence and library-based mapping of linear and discontinuous protein-protein-interaction sites by spot synthesis*, Reineke et al., Curr. Top. Microbiol. Immunol. Vol. 243 (1999), p. 23-36; *Coherent Membrane Supports for Parallel Microsynthesis and Screening of Bioactive Peptides*, Wenschuh et al., Biopolymers Vol. 55 (2000), p. 188-206; *Applications of peptide arrays prepared by the SPOT-technology*, Reineke et al., Curr. Opin. Biotechnol. Vol. 12 (2001), p. 59-64; *Peptide arrays: from macro to micro*, Reimer et al., Curr. Opin. Biotechnol. Vol. 13 (2002), p. 315-320 and *Identification of distinct antibody epitopes and mimotopes from a peptide array of 5520 randomly generated sequences*, Reineke et al., J. Immun. Methods Vol. 267 (2002), p. 37-51, all incorporated herein by reference).

In an embodiment of the present invention, the agent binds to peptide sequence SEQ ID NO: 11 at least five times as strongly as any comparative peptide sequence of human GPVI. In an embodiment, the agent binds to peptide sequence SEQ ID NO: 11 at least ten times as strongly as any comparative peptide sequence of human GPVI. The strength of the binding of an agent to a peptide sequence of GPVI may be analysed using chemiluminescence and quantified by measuring signal intensity. Thus, the strength of binding of an agent to a peptide may be indicated by a signal:noise ratio.

In one embodiment, the agent binds to peptide sequence SEQ ID NO: 11 at least fifteen times as strongly as it binds to any comparative peptide sequence of human GPVI. In one embodiment, the agent binds to peptide sequence SEQ ID NO: 11 at least twenty times as strongly as it binds to any comparative peptide sequence of human GPVI. The strength of the binding of an agent to a peptide sequence of GPVI may be analysed using chemiluminescence and quantified by measuring signal intensity. Thus, the strength of binding of an agent to a peptide may be indicated by a signal:noise ratio and quantified by Light Units (LU).

In one embodiment of the present invention, the agent binds to one of or both of peptide sequence SEQ ID NO: 37 and 38 at least twice as strongly as any peptide sequence in Table 2 other than SEQ ID NOs: 9 to 14, 37, 38, 54, 55, and 56. In one embodiment, the agent binds to one of or both of peptide sequence SEQ ID NOs: 37 and 38 at least twice as strongly as any comparative peptide sequence of human GPVI, wherein the comparative peptide sequence contains between five and fifteen contiguous amino acid residues.

In one embodiment of the present invention, the agent binds to one or more than one or a combination of peptide sequence SEQ ID NOs: 54, 55, and 56 at least one and a half times as strongly as any comparative peptide sequence. In one embodiment, the agent binds to one of or a combination of peptide sequences SEQ ID NOs: 54, 55 and 56 at least one and a half times as strongly as any comparative peptide sequence of human GPVI, wherein the comparative peptide sequence contains between five and fifteen contiguous amino acid residues.

In one embodiment of the invention, the agent binds to one or more than one or a combination of peptide sequences selected from SEQ ID NOs: 9, 10 11, 12, 13 and 14 and also to peptides SEQ ID NOs: 37 and 38 at least twice as strongly as to any comparative peptide disclosed in Table 2 excluding SEQ ID NOs: 9, 10 11, 12, 13, 14, 37, 38, 54, 55 and 56.

In one embodiment, the agent binds to one or more than one or a combination of peptide sequences selected from SEQ ID NOs: 9, 10 11, 12, 13 and 14 and also to peptides SEQ ID NOs: 37 and 38 at least twice as strongly as to any comparative peptide disclosed in Table 2 and also to one of or a combination of peptide sequences SEQ ID NOs: 54, 55 and 56 at least twice as strongly as to any comparative peptide disclosed in Table 2, excluding SEQ ID NOs: 9, 10 11, 12, 13, 14, 37, 38, 54, 55 and 56.

In one embodiment, the agent binds to one or both of peptides sequences SEQ ID NOs: 37 and 38 at least twice as strongly as to any comparative peptide sequence disclosed in Table 2 and also to one of or a combination of peptide sequences SEQ ID NOs: 54, 55 and 56 at least twice as strongly as to any comparative peptide sequence disclosed in Table 2 excluding SEQ ID NOs: 9, 10 11, 12, 13, 14, 37, 38, 54, 55 and 56.

In one embodiment, the agent binds to one or more than one or a combination of peptide sequences SEQ ID NOs: 9, 10 11, 12, 13 and 14 at least twice as strongly as to any comparative peptide disclosed in Table 2 and also to one of or a combination of peptide sequences SEQ ID NOs: 54, 55 and 56 at least twice as strongly as to any comparative peptide sequence disclosed in Table 2 excluding SEQ ID NOs: 9, 10 11, 12, 13, 14, 37, 38, 54, 55 and 56.

In one embodiment, the agents of the invention bind with greater affinity to one or more of peptides 8, 9, 10 11, 12, 13 or 14 of Table 2 than to any comparative peptide sequence listed in Table 2. In one aspect of the invention there is provided agents which bind to peptides 8, 9, 10 11, 12, 13 and 14 with similar or greater affinity than monoclonal antibody 5C4. In one embodiment, the agent binds to peptides 9, 10 11, 12, 13 and 14 with a binding affinity of within 5% of the binding affinity of hGP 5C4 for each of peptides 9, 10 11, 12, 13 and 14. In one embodiment, the agent binds to peptides 9, 10 11, 12, 13 or 14 with a binding affinity of within 10% of the binding affinity of hGP 5C4 for each of peptides 9, 10 11, 12, 13 and 14. Particularly, these are provided agents which bind to peptide 11 with an affinity described previously in this paragraph.

Binding affinity of an agent for example an antibody or fusion protein may be measured using for example BIA-CORE systems.

In one aspect of the present invention, the agents bind to one or more than one or a combination of peptide sequences selected from SEQ ID NOs: 9, 10, 11, 12, 13 and 14 (shown in Table 2) such that the signal:noise ratio produced by chemiluminescence analysis is at least twice the signal produced as background. The binding affinity of the agent in this embodiment is quantified in Light Units (LU).

In one embodiment, the agent of the invention binds to one or more or a combination of peptides SEQ ID NOs: 9, 10, 11, 12, 13 or 14 such that the signal:noise ratio produced by chemiluminescence analysis is at least twice the signal produced as background.

In one aspect of the present invention, the agents bind to one or more than one or a combination of peptide sequences selected from SEQ ID NOs: 11, 12 and 13 (shown in Table 2) such that the signal:noise ratio produced by chemiluminescence analysis is at least three times the signal produced as background. The binding affinity of the agent in this embodiment is quantified in Light Units (LU).

In one aspect of the present invention, the agents bind to one or more than one or a combination of peptide sequences selected from SEQ ID NO: 11 (shown in Table 2) such that the signal:noise ratio produced by chemiluminescence analysis is at least five times the signal produced as background. The binding affinity of the agent in this embodiment is quantified in Light Units (LU).

In one embodiment, the agent of the present invention binds to at least one of or a combination of peptide sequences selected from SEQ ID NO: 37 and SEQ ID NO: 38 with an affinity such that the signal:noise ratio produced by chemiluminescence analysis is at least twice the signal produced as background. The binding affinity of the agent in this embodiment is quantified in Light Units (LU).

In one embodiment, the invention provides agents which bind to at least one of or a combination of peptide sequences selected from SEQ ID NOs: 8, 54, 55 and 56 with an affinity such that the signal:noise ratio produced by chemiluminescence analysis is at least one and a half times the signal produced as background. The binding affinity of the agent in this embodiment is quantified in Light Units (LU).

In one embodiment, the invention provides agents which bind to at least one of or a combination of peptide sequences selected from SEQ ID NOs: 9, 10, 11, 12, 13 and 14 and also with an affinity such that the signal:noise ratio produced by chemiluminescence analysis is at least twice the signal produced as background and wherein the agent also binds to SEQ ID NOs: 8, 54, 55 and 56 with an affinity such that the signal:noise ratio produced by chemiluminescence analysis is at least one and a half times the signal produced as background. The binding affinity of the agent in this embodiment is quantified in Light Units (LU).

In one embodiment, the invention provides agents which bind to at least one of or a combination of peptide sequences selected from SEQ ID NOs: 9, 10, 11, 12, 13 and 14 and also with an affinity such that the signal:noise ratio produced by chemiluminescence analysis is at least twice the signal produced as background and wherein the agent also binds to SEQ ID NOs: 37 and 38 with an affinity such that the signal:noise ratio produced by chemiluminescence analysis is at least twice the signal produced as background. The binding affinity of the agent in this embodiment is quantified in Light Units (LU).

In one embodiment, the invention provides agents which bind to at least one of or a combination of peptide sequences selected from SEQ ID NOs: 37 and 38 and also with an affinity such that the signal:noise ratio produced by chemiluminescence analysis is at least twice the signal produced as background and wherein the agent also binds to SEQ ID NOs: 54, 55 and 56 with an affinity such that the signal:noise ratio produced by chemiluminescence analysis is at least one and a half times the signal produced as background. The binding affinity of the agent in this embodiment is quantified in Light Units (LU).

In the above disclosure there are numerous references to peptides SEQ ID NOs: 9 to 14. In other embodiments there is provided an agent binds to peptide SEQ ID NO: 8 in a similar way to as described above.

The present invention also provides a pharmaceutical composition comprising a pharmaceutical acceptable carrier and an effective amount, e.g. a therapeutically effective amount, including a prophylactically effective amount, of one or more products of the invention.

Epitope mapping studies were carried out using monoclonal antibody hGP 5C4 against short peptide sequences of a human Glycoprotein VI. The antibody bound to the extracellular domain of GPVI at three distinct linear regions (see Table 2 and FIG. 33). It is considered that agents which bind to these epitopes will possess advantageous properties for example, the non-activation of human platelets. Particular agents are antibody fragments, aptamers or small molecules; the antibody fragments, e.g. Fab fragments may be humanized. The peptide sequences of GPVI of the present invention are as shown in Table 2.

In a further aspect of the invention there is provided a method for preparing a hybridoma cell-line producing monoclonal antibodies according to the invention comprising the steps of:

i) immunising an immunocompetent mammal with an immunogen comprising at least one peptide moiety (a) described herein, e.g. one which includes lysine 27 for example, polypeptide having the amino acid sequence as represented in SEQ ID NOs: 8 to 14, e.g. 11;

ii) fusing lymphocytes of the immunised immunocompetent mammal with myeloma cells to form hybridoma cells;

iii) screening monoclonal antibodies produced by the hybridoma cells of step (ii) for binding activity to the amino acid sequences of (i);

iv) culturing the hybridoma cells to proliferate and/or to secrete said monoclonal antibody; and v) recovering the monoclonal antibody from the culture supernatant.

Preferably, the said immunocompetent mammal is a mouse. Alternatively, said immunocompetent mammal is a rat.

Competition Assays

In one aspect of the invention there is provided a method of identifying agents which bind to the ligands as hereinbefore described, the method comprising using competition assays. In particular, competition between binding members or agents may be assayed easily in vitro, for example using ELISA and/or by tagging a specific reporter molecule to one agent which can be detected in the presence of other untagged agent (s), to enable identification of agents which bind the same epitope or linear peptide sequence or an overlapping epitope or linear peptide sequence.

Various methods are available in the art for obtaining agents against human GPVI and which may compete with antibody hGP 5C4 for binding to human GPVI.

In a further aspect, the present invention provides a method of obtaining one or more agents able to bind an epitope of GPVI, the method including bringing into contact a library of agents according to the invention and the GPVI epitope or linear peptide sequence, and selecting one or more agents of the library able to bind the epitope or linear peptide sequence. The GPVI epitope or linear peptide epitope is in particular a peptide moiety (a) as described herein e.g. one which binds to lysine 27 e.g. one represented by SEQ ID NOs: 8-14 e.g. SEQ ID NO: 11.

The library may be displayed on the surface of bacteriophage particles, each particle containing nucleic acid encoding the antibody VH variable domain displayed on its surface, and optionally also a displayed VL domain if present.

Following selection of agents able to bind the epitope or linear peptide sequence and displayed on bacteriophage particles, nucleic acid may be taken from a bacteriophage particle displaying a said selected agent. Such nucleic acid may be used in subsequent production of an agent or an antibody VH variable domain (optionally an antibody VL variable domain) by expression from nucleic acid with the sequence of nucleic acid taken from a bacteriophage particle displaying a said selected agent.

An antibody VH variable domain with the amino acid sequence of an antibody VH variable domain of a said selected specific binding member may be provided in isolated form, as may an agent comprising such a VH domain.

In one aspect of the invention, there is ability to bind human GPVI may be further tested, also ability to compete with hGP 5C4.

The ability of an agent to bind human glycoprotein VI may be tested by immunoassay. Any form of direct binding assay is suitable. In one such assay, the human glycoprotein VI or alternatively the agent is labeled. Suitable labels include radioisotopes such as $^{125}$I, enzymes such as peroxidase, fluorescent labels such as fluorescein, and chemiluminescent labels. Typically, the other binding partner is insolubilized (for example, by coating onto a microtiter plate) to facilitate washing. After combining the labeled component with the insolubilized component, the solid phase is washed and the amount of bound label is determined. To conduct the inhibition assays, the agent is titered for its ability to decrease the binding of for example hGP 5C4 Fab to human glycoprotein VI, or human glycoprotein VI to subendothelial collagen. Either of the binding pairs in the reaction to be inhibited is labeled, while the other is typically insolubilized in order to facilitate washing. Agents with the characteristics of hGP 5C4 Fab will proportionately decrease the amount of label attached to the solid phase, compared with control polypeptides. Any other characterization may be carried out as specifically described in the examples.

The present invention provides a method of inhibiting platelet-collagen interaction in a mammal, which method comprises acutely or chronically administering to a mammal in need of inhibition of platelet-collagen interaction a therapeutically effective amount, including a prophylactically effective amount, of one or more products of the invention.

Included in the invention is a method of screening a plurality of compounds by an assay which utilises at least one ligand, (poly)peptide or agent of the present disclosure to determine whether a compound binds to GPVI, in particular at an epitope identified herein, or to an epitope identified herein.

Also provided by the present invention is a process for preparing a pharmaceutical composition for treating thrombotic disorders, comprising:
(a) screening a plurality of compounds by an assay which utilises at least one target molecule selected from the ligands, (poly)peptides and agents of the present disclosure to measure the binding affinity of the compounds for the target (e.g. to an epitope disclosed herein);
(b) selecting a said compound having a binding affinity of at least a predetermined amount;
(c) synthesising the selected compound; and
(d) incorporating the synthesized compound into a pharmaceutical composition.

The binding affinity may be measured by measuring the IC50 values of the compounds. Thus, step (a) may comprise obtaining IC50 value for each compound. In embodiments, the selected compound has an IC50 of less than 500 nM, e.g. less than 100 nM, less than 10 nm, less than 1 nM or less than 0.1 nM. The predetermined binding affinity may be selected accordingly. In any event, the predetermined binding affinity is suitably one which, within the scope of sound pharmacological judgement, is potentially or actually useful for a therapeutic inhibitor of GPVI.

The screening methods described above may further include the step of providing the plurality of compounds, e.g. at least 100 compounds, at least 100 compounds or at least 10,000 compounds.

In one class of methods the at least one target is at least one ligand or (poly)peptide of the disclosure which binds to antibody hGP 5C4 or includes an amino acid sequence comprising at least a portion of an epitope to the antibody. In another class of embodiments, the at least one target is at least one agent of the disclosure which binds to a said ligand or (poly)peptide, e.g. which binds to antibody hGP 5C4.

The present invention also provides use of a compound as identified by the method described in a method to treat and/or prevent thrombotic disorders.

Further included are GPVI antagonists which bind to a ligand, epitope or (poly)peptide of the disclosure, for example with a binding affinity which, within the scope of sound pharmacological judgement, is potentially or actually useful for a therapeutic inhibitor of GPVI. Exemplary antagonists have an IC50 of less than 100 nM, more particularly of less than 500 nM, e.g. less than 100 nM, less than 10 nm, less than 1 nM or less than 0.1 nM. The antagonist may be an antibody (including an antibody fragment or a molecule comprising an antigen-binding region of an antibody) or an aptamer.

In Vivo Applications

The method of the present invention has particular usefulness in in vivo applications. For example, agents which bind to an epitope of, or linear peptide sequence comprised within, human Glycoprotein VI can be used in the treatment of any disease, state or condition involving the interaction of platelet bound GPVI and collagen and subsequent activation of the platelets. The disclosure therefore includes a method for treating such a disease, state or condition mentioned herein, the method comprising administering to a subject a therapeutically (including prophylactically) useful amount of a GPVI antagonist which binds to a ligand, epitope or (poly)peptide of the disclosure. Provided by the disclosure is a method for selectively inhibiting GPVI activity in a human, comprising administering to a human subject in need of such treatment a low molecular weight GPVI inhibitor which binds to, or was identified as binding to, a ligand, epitope or (poly)peptide of the disclosure. It is contemplated that potential competitive inhibitors of GPVI-collagen binding are ligands and (poly)peptides mentioned herein as being useful in GPVI-collagen binding assays Based on the recent improvements in imaging techniques by intravascular ultrasound or nuclear magnetic resonance imaging, it is possible to identify patients with atherosclerosis being at risk of acute clinical complications such as acute coronary or carotid syndrome, whereby the patients have active lesions as possible causes for intravascular thrombosis. It is then possible by the present invention to prevent the formation of intravascular thrombosis by the administration of a medicament containing the agents against platelet GPVI without undesired side effects.

Active lesions are characterized by the unmasking of subendothelial matrix collagens and platelet activation. The occurrence of such lesions can be investigated e.g. by intravascular ultrasound or thermography (e.g., Fayed and Fuster, Clinical imaging of the high-risk or vulnerable atherosclerotic plaque. Circulation 2001; 89:305-316) or nuclear resonance imaging (Helft et al., Progression and Regression of Atherosclerotic Lesions. Circulation 2002; 105:993-998). Moreover, the dimeric form of the Fc-GPVI-nt fusion protein serves as and ideal diagnostic tool for the identification of endothelial lesions in patients (EP 03/05929). Such lesions are highly probable in patients with acute coronary or carotid syndromes, and the risk of the reoccurrence of acute clinical complications such as myocardial infarction or stroke is very high, decreasing progressively with increasing time distance from the primary event.

Therefore, the present invention provides a method of treating a patient suffering from an acute coronary or carotid syndrome for avoiding intravascular thrombosis. Moreover, based on the present invention, it is possible to treat patients being at risk of intravascular thrombosis due to the rupture of complex arteriosclerotic plaques. The rupture also unmasks the subendothelial collagen matrix. As a consequence of intraarterial thrombus formation, the perfusion of vital organs is blocked with the above described important and life threatening clinical syndromes.

Accordingly, further aspects of the invention provide methods of treatment comprising, administration of an agent as provided, pharmaceutical compositions comprising such a agent, and use of such an agent in the manufacture of a medicament for administration, for example in a method of making a medicament or pharmaceutical composition comprising formulating the agent with a pharmaceutically acceptable excipient.

Clinical indications in which an agent which binds to an epitope of GPVI may be used to provide therapeutic benefit include any condition in which collagen recognition by GPVI has pathological consequences, for example in cardiovascular conditions such as thrombosis, including for example arterial thrombosis occurring in blood vessel wall disease (e.g. coronary artery thrombosis, which causes myocardial infarction). Similar thrombotic processes may occur in other serious conditions at diverse anatomical locations, for instance in the cerebral vasculature, leading to stroke, or in the peripheral extremities. In the latter case for instance, patients with intermittent claudication may be treated. Agent-mediated blockade of GPVI may be used and be beneficial during therapeutic procedures which induce damage to the blood vessel wall, for instance vascular surgery. Examples of vascular surgery may include, but are not limited to, coronary artery bypass grafting, balloon angioplasty and stenting. In other, unrelated disease processes, circulating platelets may be exposed to collagens where they may contribute to local thrombotic effects and to the inflammatory processes which ensue. An example of the latter occurs in hepatitis where the hepatic circulation is compromised by the disease. In addition diseases of generalised platelet activation such as thrombocytopenic purpura and haemolytic uraemic syndrome and other clinical conditions with disseminated intravascular coagulation may be ameliorated. Furthermore multi-organ damage because of arterial insufficiency in patients with homozygous sickle disease may be beneficially affected by inhibiting the activation of platelets via GPVI. Similarly kidney damage by platelet and fibrin disposition on the glomerular membrane and other conditions such as micro-angiopathic vasculitides may be treated by agent-mediated GPVI blockade.

Anti-GPVI treatment in accordance with the present invention may be used to provide clear benefit for patients with cardiovascular disease, especially those who have undergone corrective vessel surgery or angioplasties with or without stenting. Anti-GPVI treatment may be given by injection (e.g. intravenously) or by local delivery methods (e.g. pre-coating of stents or other indwelling devices). Anti-GPVI may be delivered by gene-mediated technologies. Alternative formulation strategies may provide preparations suitable for oral or suppository route. The route of administration may be determined by the physicochemical characteristics of the treatment, by special considerations for the disease, to optimise efficacy or to minimise side-effects. Thus, the agents of the inventions may be used to treat and/or protect against a variety of disorders, including, for example, seizures, transient ischemic shock, strokes, focal ischemia originating from thrombus or cerebral hemorrhage, global ischemia originating from cardiac arrest, trauma, neonatal palsy, hypovolemic shock, and hyperglycemia and associated neuropathies.

The present inventive method includes the administration to an animal, such as a mammal, particularly a human, in need of the inhibition of platelet activation of an effective amount, e.g., a therapeutical effective amount, of one or more of the aforementioned present inventive agents, alone or in combination with one or more other pharmaceutically active agents.

The agents of the invention will normally be administered orally, intravenously, subcutaneously, buccally, rectally, dermally, nasally, tracheally, bronchially, by any other parenteral route, as an oral or nasal spray or via inhalation. The agents may be administered in the form of pharmaceutical preparations in a pharmaceutical acceptable dosage form. Depending upon the disorder and patient to be treated and the route of administration, the compositions may be administered at varying doses.

If an agent of the invention is to be administered to an individual, it is particularly at least 80% pure, more preferably it is at least 90% pure, even more preferably it is at least 95% pure and free of pyrogens and other contaminants. In this context, the percent purity is calculated as a weight percent of the total protein content of the preparation, and does not include constituents which are deliberately added to the composition after the agent is purified. The present invention provides a method of treatment of a human or animal body in need of treatment or prevention of acute or chronic vascular diseases associated with intraarterial and/or intravenous thrombosis, which comprises administration to a human or animal of a pharmaceutically effective amount of an inhibitor or agent of the invention. If the agent is used as a medicament, the dosage will usually be in the range of from 0.1 to 100 mg/patient/day. In one embodiment the agents are used as lyophilised powders solubilised in PBS/sucrose/mannitol-buffer prior to parenteral administration. A human or animal body in need of treatment or prevention of acute or chronic vascular diseases associated with intraarterial and/or intravenous thrombosis is characterized by active lesions due to unmasking of subendothelial matrix collagens and platelet activation. The occurrence of such lesions can be investigated e.g. by intravascular ultrasound or thermography (e.g., Fayed and Fuster, Clinical imaging of the high-risk or vulnerable atherosclerotic plaque. Circulation 2001; 89:305-316) or nuclear resonance imaging (Helft et al., Progression and Regression of Atherosclerotic Lesions. Circulation 2002; 105:993-998). Such lesions are highly probable in patients with acute coronary or carotid syndromes, and the risk of the reoccurrence of acute clinical complications such as myocardial infarction or stroke is very high, decreasing progressively with increasing time distance from the primary event.

The most preferred routes of administration are injection and infusion, especially intravenous administration.

The compounds of the invention may be combined and/or co-administered with any antithrombotic agent, such as the antiplatelet agents acetylsalicylic acid, ticlopidine, clopidogrel, thromboxane receptor and/or synthetase inhibitors, fibrinogen receptor antagonists, prostacyclin mimetics and phosphodiesterase inhibitors and ADP-receptor (P2T) antagonists.

The agents of the invention may be combined and/or co-administered with thrombolytics such as tissue plasminogen activator (natural, recombinant or modified), streptokinase, urokinase, prourokinase, anisoylated plasminogen-streptokinase activator complex (APSAC), animal salivary gland plasminogen activators, and the like, in the treatment of thrombotic diseases, in particular myocardial infarction.

Typically, therefore, the pharmaceutical compounds of the invention may be administered orally or parenterally ("parenterally" as used herein, refers to modes of administration which include intravenous, intramuscular, intraperitoneal, intrasternal, subcutaneous and intraarticular injection and infusion of which intravenous is most preferred) to a host to obtain a desired effect, for example protection against thrombosis. In the case of larger animals, such as humans, the compounds may be administered alone or as compositions in combination with pharmaceutical acceptable diluents, excipients or carriers.

Actual dosage levels of active ingredients in the pharmaceutical compositions of this invention may be varied so as to obtain an amount of the active agent (s) that is effective to achieve the desired therapeutic response for a particular patient, compositions, and mode of administration. The selected dosage level will depend upon the activity of the particular agent, the route of administration, the severity of the condition being treated and the condition and prior medical history of the patient being treated. However, it is within the skill of the art to start doses of the agent at levels lower than required for to achieve the desired therapeutic effect and to gradually increase the dosage until the desired effect is achieved.

In one embodiment, the products of this invention are administered prophylactically.

Another aspect of this invention is directed to methods for treating cardiovascular diseases comprising administering to a mammal a therapeutically effective amount of a product of the invention.

Another aspect of this invention is directed to methods for treating arteriosclerosis comprising administering to a mammal a therapeutical effective amount of a product of the invention.

Another aspect of this invention is directed to methods for treating arrhythmia comprising administering to a mammal a therapeutical effective amount of a product of the invention.

Another aspect of this invention is directed to methods for treating angina pectoris comprising administering to a mammal a therapeutically effective amount of a product of the invention.

Another aspect of this invention is directed to methods for treating cardiac hypertrophy comprising administering to a mammal a therapeutically effective amount of a product of the invention.

Another aspect of this invention is directed to methods for treating renal diseases comprising administering to a mammal a therapeutical effective amount of a product of the invention.

Another aspect of this invention is directed to methods for treating diabetic complications comprising administering to a mammal a therapeutical effective amount of a product of the invention.

Another aspect of this invention is directed to methods for treating restenosis comprising administering to a mammal a therapeutically effective amount of a product of the invention.

Another aspect of this invention is directed to methods for treating organ hypertrophies or hyperplasias comprising administering to a mammal a therapeutically effective amount of a product of the invention.

Another aspect of this invention is directed to methods for treating septic shock and other inflammatory diseases (septicemia, endotoxemia) comprising administering to a mammal a therapeutically effective amount of a product of the invention.

Another aspect of this invention is directed to methods for treating cerebro ischemic disorders comprising administering to a mammal a therapeutically effective amount of a product of the invention.

The present invention further provides a method of modulating GPVI activity comprising administering an effective amount of an agent of the present invention.

A method for treating therapeutic or prophylactic a disease or disorder selected from therapeutic or prophylactic cardiovascular conditions, thrombosis, heart attack, stroke, intermittent coagulation, conditions with disseminated intravascular coagulation, thrombocytopenic purpura, haemolytic uraemic syndrome, damage to blood vessel wall resulting from surgery or therapy, collagen-induced inflammation, homozygous sickle disease, kidney damage by platelet and fibrin disposition on the glomerular member and micro-angiopathic vasculitides comprising administering an agent of the disclosure, to a subject with the disease or disorder or at risk of developing the disease or disorder.

The agents included in the invention may be used for the manufacture of a medicament to treat or prevent of a disease or disorder selected from cardiovascular conditions, thrombosis, heart attack, stroke, intermittent coagulation, conditions with disseminated intravascular coagulation, thrombocytopenic purpura, haemolytic uraemic syndrome, damage to blood vessel wall resulting from surgery or therapy, collagen-induced inflammation, homozygous sickle disease, kidney damage by platelet and fibrin disposition on the glomerular member and micro-angiopathic vasculitides.

The compounds of the invention will normally be administered orally, intravenously, subcutaneously, buccally, rectally, dermally, nasally, tracheally, bronchially, by any other parenteral route, as an oral or nasal spray or via inhalation, The compounds may be administered in the form of pharmaceutical preparations. Depending upon the disorder and patient to be treated and the route of administration, the compositions may be administered at varying doses.

The products of the invention may also be combined and/or co-administered with any antithrombotic agent with a different mechanism of action, such as the inhibitors of thrombin or other coagulation enzymes (e.g. Factor IXa or X), antiplatelet agents acetylsalicylic acid, ticlopidine, clopidogrel, thromboxane receptor and/or synthetase inhibitors, fibrinogen receptor antagonists, prostacyclin mimetics and phosphodiesterase inhibitors and ADP-receptor ($P_2$ T) antagonists.

The GPVI inhibitors of the invention may further be combined and/or co-administered with thrombolytics such as tissue plasminogen activator (natural, recombinant or modified), streptokinase, urokinase, prourokinase, anisoylated plasminogen-streptokinase activator complex (APSAC), animal salivary gland plasminogen activators, and the like, in the treatment of thrombotic diseases, in particular myocardial infarction.

The products of the disclosure may be combined and/or co-administered with any cardiovascular treatment agent. There are large numbers of cardiovascular treatment agents available in commercial use, in clinical evaluation and in pre-clinical development, which could be selected for use with a product of the disclosure for the prevention of cardiovascular disorders by combination drug therapy. Such agent can be one or more agents selected from, but not limited to several major categories, namely, a lipid-lowering drug, including an IBAT (ileal $Na^+$/bile acid cotransporter) inhibitor, a fibrate, niacin, a statin, a CETP (cholesteryl ester transfer protein) inhibitor, and a bile acid sequestrant, an antioxidant, including vitamin E and probucol, a IIb/IIIa antagonist (e.g. abciximab, eptifibatide, tirofiban), an aldosterone inhibitor (e.g. spirolactone and epoxymexrenone), an adenosine A2 receptor antagonist (e.g. losartan), an adenosine A3 receptor agonist, a beta-blocker, acetylsalicylic acid, a loop diuretic, an angiotensin receptor blocker and an ACE (angiotensin converting enzyme) inhibitor.

The products of the disclosure may be combined and/or co-administered with a cardioprotectant, for example an adenosine A1 or A3 receptor agonist.

There is also provided a method for treating a cardiovascular disease in a patient that comprises treating the patient with a product of the disclosure and an NSAID, e.g., a COX-2 inhibitor. Accordingly, the products of the disclosure may be combined and/or co-administered with an NSAID.

Actual dosage levels of active ingredients in the pharmaceutical compositions of this disclosure may be varied so as to obtain an amount of the active compound(s) that is effective to achieve the desired therapeutic response for a particular patient, composition, and mode of administration (referred to herein as a "therapeutically effective amount"). The selected dosage level will depend upon the activity of the particular compound, the severity of the condition being treated and the condition and prior medical history of the patient being treated. However, it is within the skill of the art to start doses of the compound at levels lower than required for to achieve the desired therapeutic effect and to gradually increase the dosage until the desired effect is achieved.

According to a further aspect there is provided a parenteral formulation including a product as described herein. The formulation may consist of the product alone or it may contain additional components, in particular the product may be in combination with a pharmaceutically acceptable diluent, excipient or carrier, for example a tonicity agent for the purpose of making the formulation substantially isotonic with the body of the subject to receive the formulation, e.g. with human plasma. The formulation may be in ready-to-use form or in a form requiring reconstitution prior to administration.

Parenteral preparations can be administered by one or more routes, such as intravenous, subcutaneous, intradermal and infusion; a particular example is intravenous. A formulation disclosed herein may be administered using a syringe, injector, plunger for solid formulations, pump, or any other device recognized in the art for parenteral administration.

Liquid dosage forms for parenteral administration may include solutions, suspensions, liposome formulations, or emulsions in oily or aqueous vehicles. In addition to the active compounds, the liquid dosage forms may contain other compounds. Tonicity agents (for the purpose of making the formulations substantially isotonic with the subject's body, e.g. with human plasma) such as, for instance, sodium chloride, sodium sulfate, dextrose, mannitol and/or glycerol may be optionally added to the parenteral formulation. A pharmaceutically acceptable buffer may be added to control pH. Thickening or viscosity agents, for instance well known cellulose derivatives (e.g. methylcellulose, carboxymethylcellulose, hydroxyethylcellulose and hydroxypropylmethylcellulose), gelatin and/or acacia, may optionally be added to the parenteral formulation.

Solid dosage forms for parenteral administration may encompass solid and semi-solid forms and may include pellets, powders, granules, patches, and gels. In such solid dosage forms, the active compound is typically mixed with at least one inert, pharmaceutically acceptable excipient or carrier.

The disclosed products may be presented as solids in finely divided solid form, for example they may be milled or micronised.

The formulations may also include antioxidants and/or preservatives. As antioxidants may be mentioned thiol derivatives (e.g. thioglycerol, cysteine, acetylcysteine, cystine, dithioerythreitol, dithiothreitol, glutathione), tocopherols, butylated hydroxyanisole, butylated hydroxytoluene, sulfurous acid salts (e.g. sodium sulfate, sodium bisulfite, acetone sodium bisulfite, sodium metabisulfite, sodium sulfite, sodium formaldehyde sulfoxylate, sodium thiosulfate) and nordihydroguaiareticacid. Suitable preservatives may for instance be phenol, chlorobutanol, benzylalcohol, methyl paraben, propyl paraben, benzalkonium chloride and cetylpyridinium chloride.

The parenteral formulations may be prepared as large volume parenterals (LVPs), e.g. larger than 100 ml, more particularly about 250 ml, of a liquid formulation of the active compound. Examples of LVPs are infusion bags. The parenteral formulations may alternatively be prepared as small volume parenterals (SVPs), e.g. about 100 ml or less of a liquid formulation of the active compound. Examples of SVPs are vials with solution, vials for reconstitution, prefilled syringes for injection and dual chamber syringe devices.

One class of formulations disclosed herein is intravenous formulations. For intravenously administered formulations, the active compound or compounds can be present at varying concentrations, with a carrier acceptable for parenteral preparations making up the remainder. Particularly, the carrier is water, particularly pyrogen free water, or is aqueous based. Particularly, the carrier for such parenteral preparations is an aqueous solution comprising a tonicity agent, for example a sodium chloride solution.

By "aqueous based" is meant that formulation comprises a solvent which consists of water or of water and water-miscible organic solvent or solvents; as well as containing a product of disclosure in dissolved form, the solvent may have dissolved therein one or more other substances, for example an antioxidant and/or an isotonicity agent. As organic cosolvents may be mentioned those water-miscible solvents commonly used in the art, for example propyleneglycol, polyethyleneglycol 300, polyethyleneglycol 400 and ethanol. Preferably, organic co-solvents are only used in cases where the active agent is not sufficiently soluble in water for a therapeutically effective amount to be provided in a single dosage form.

The solubility of the active compound in the present formulations may be such that the turbidity of the formulation is lower than 50 NTU, e.g. lower than 20 NTU such as lower than 10 NTU.

It is desirable that parenteral formulations are administered at or near physiological pH. It is believed that administration in a formulation at a high pH (i.e., greater than 8) or at a low pH (i.e., less than 5) is undesirable. In particular, it is contemplated that the formulations would most desirably be administered at a pH of between 6.0 and 7.0 such as a pH of 6.5. The pH values mentioned in this paragraph are not critical, however, and formulations may fall outside them.

The parenteral formulation may be purged of air when being packaged. The parenteral formulation may be packaged in a sterile container, e.g. vial, as a solution, suspension, gel, emulsion, solid or a powder. Such formulations may be stored either in ready-to-use form or in a form requiring reconstitution prior to administration.

Parenteral formulations according to the disclosure may be packaged in containers. Containers may be chosen which are made of material which is non-reactive or substantially non-reactive with the parenteral formulation. Glass containers or plastics containers, e.g. plastics infusion bags, may be used. A concern of container systems is the protection they afford a solution against UV degradation. If desired, amber glass employing iron oxide or an opaque cover fitted over the container may afford the appropriate UV protection.

Plastics containers such as plastics infusion bags are advantageous in that they are relatively light weight and non-breakable and thus more easily stored. This is particularly the case for Large Volume parenterals.

The intravenous preparations may be prepared by combining the active product or products with the carrier. After the formulation is mixed, it may be sterilized, for example using known methods. Once the formulation has been sterilized, it is ready to be administered or packaged, particularly in dark packaging (e.g. bottles or plastics packaging), for storage. It is envisaged, however, that the disclosed products might not be stored in solution but as dry solids, particularly a finely divided form such as, for example, a lyophilisate, in order to prolong shelf life; this would of course apply to other parenteral formulations, not only intravenous ones.

The intravenous preparations may take the form of large volume parenterals or of small volume parenterals, as described above.

In a specific embodiment, the present disclosure is directed to products, particularly kits, for producing a single-dose administration unit. The products (kits) may each contain both a first container having the active compound (optionally combined with additives, for example anti-oxidant, preservative and, in some instances, tonicity agent) and a second container having the carrier/diluent (for example water, optionally containing one or more additives, for example tonicity agent). As examples of such products may be mentioned single and multi-chambered (e.g. dual-chamber) pre-filled syringes; exemplary pre-filled syringes are available from Vetter GmbH, Ravensburg, Germany. Such dual chamber syringes or binary syringes will have in one chamber a dry preparation including or consisting of the active compound and in another chamber a suitable carrier or diluent such as described herein. The two chambers are joined in such a way that the solid and the liquid mix to form the final solution.

One class of formulations disclosed herein comprises subcutaneous or intradermal formulations (for example formulations for injection) in which the active product (or active agent combination) is formulated into a parenteral preparation that can be injected subcutaneously or intradermally. The formulation for administration will comprise the active product and a liquid carrier.

The carrier utilized in a parenteral preparation that will be injected subcutaneously or intradermally may be an aqueous carrier (for example water, typically containing an additive e.g. an antioxidant and/or an isotonicity agent) or a nonaqueous carrier (again one or more additives may be incorporated). As a non-aqueous carrier for such parenteral preparations may be mentioned highly purified olive oil.

The active compound and the carrier are typically combined, for example in a mixer. After the formulation is mixed, it is preferably sterilized, such as with U.V. radiation. Once the formulation has been sterilized, it is ready to be injected or packaged for storage. It is envisaged, however, that the disclosed products will not be stored in liquid formulation but as dry solids, in order to prolong shelf life.

For making subcutaneous implants, the active product may suitably be formulated together with one or more polymers that are gradually eroded or degraded when in use, e.g. silicone polymers, ethylene vinylacetate, polyethylene or polypropylene.

Transdermal formulations may be prepared in the form of matrices or membranes, or as fluid or viscous formulations in oil or hydrogels or as a compressed powder pellet. For transdermal patches, an adhesive which is compatible with the skin may be included, such as polyacrylate, a silicone adhesive or polyisobutylene, as well as a foil made of, e.g., polyethylene, polypropylene, ethylene vinylacetate, polyvinylchloride, polyvinylidene chloride or polyester, and a removable protective foil made from, e.g., polyester or paper coated with silicone or a fluoropolymer. For the preparation of transdermal solutions or gels, water or organic solvents or mixtures thereof may be used. Transdermal gels may furthermore contain one or more suitable gelling agents or thickeners such as silicone, tragacanth, starch or starch derivatives, cellulose or cellulose derivatives or polyacrylic acids or derivatives thereof. Transdermal formulations may also suitably contain one or more substances that enhance absorption though the skin, such as bile salts or derivatives thereof and/or phospholipids. Transdermal formulations may be prepared according to a method disclosed in, e.g., B W Barry, "Dermatological Formulations, Percutaneous Absorption", Marcel Dekker Inc., New York—Basel, 1983, or Y W Chien, "Transdermal Controlled Systemic Medications", Marcel Dekker Inc., New York—Basel, 1987.

Typically, therefore, the pharmaceutical products of the invention may be administered orally or parenterally ("parenterally" as used herein, refers to modes of administration which include intravenous, intramuscular, intraperitoneal, intrasternal, subcutaneous and intraarticular injection and infusion.) to a host to obtain an protease-inhibitory effect. In the case of larger animals, such as humans, the compounds may be administered alone or as compositions in combination with pharmaceutically acceptable diluents, excipients or carriers.

According to a further aspect of the invention there is thus provided a pharmaceutical composition including a described product, in admixture with a pharmaceutically acceptable adjuvant, diluent or carrier.

Pharmaceutical compositions of this invention for parenteral injection or infusion, e.g. intravenous injection or infusion, suitably comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants.

As solvents, co-solvents or additives for parenteral, e.g. intravenous, or other formulations may be mentioned:

Acids, e.g. with pH greater than 1.8
Bases, e.g. with pH less than 14
Cremophor EL, e.g. up to 25% in water
Dextrose, e.g. up to 5%, in water or NaCl
Ethanol, e.g. up to 15% in water
Glycerol
sorbitol
Phosphate buffer
Polyethylene glycol 300 or 400, neat or in water
Propylene glycol, neat or in water
Saline, 0.9% (or other aqueous salt solution)
poloxamer
Solutol, e.g. up to 30% in water
Tween surfactants, e.g. up to 2%
Water.

Also to be mentioned are microsphere-based delivery systems composed of the desired bioactive molecule incorporated into a matrix of poly-DL-lactide-co-glycolide (PLG).

As a further option may be mentioned lipophilic carbohydrate excipients, termed oligosaccharide ester derivatives (OEDs), which have been used to modify pharmacokinetic profiles of drugs (SoliDose™ technology, Elan Pharmaceuticals). This technology offers the ability to formulate drug molecules with modified-release characteristics and improved bioavailability. Another technology from the same company makes use of select carbohydrate excipients, such as trehalose and sucrose to stabilize molecules in the dry state, thereby preventing their physical and chemical degradation at ambient temperatures and above.

Intravenous and other parenteral compositions may be provided as ready-to-use solutions or as lyophilisates or dry powders for reconstitution prior to administration.

Parenteral and other compositions may also contain adjuvants such as preservative, wetting agents, emulsifying agents and dispersing agents. Prevention of the action of microorganisms may be ensured by the inclusion of various antibacterial and antifungal agents, for example, paraben, chlorobutanol or phenol sorbic acid. It may also be desirable to include isotonic agents such as sugars or sodium chloride, for example. Prolonged absorption of the injectable pharmaceutical form may be brought about by the inclusion of agents (for example aluminum monostearate and gelatin) which delay absorption.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are suitably made by forming microencapsule matrices of the drug in biodegradable polymers, for example polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations may also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use.

Solid dosage forms for oral administration include capsules, tablets, pills, powders and granules. In such solid dosage forms, the active compound is typically mixed with at least one inert, pharmaceutically acceptable excipient or carrier such as sodium citrate or dicalcium phosphate and/or one or more: a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycol, for example.

Suitably, oral formulations contain a dissolution aid. The dissolution aid is not limited as to its identity so long as it is pharmaceutically acceptable. Examples include nonionic surface active agents, such as sucrose fatty acid esters, glycerol fatty acid esters, sorbitan fatty acid esters (e.g., sorbitan trioleate), polyethylene glycol, polyoxyethylene hydrogenated castor oil, polyoxyethylene sorbitan fatty acid esters, polyoxyethylene alkyl ethers, methoxypolyoxyethylene alkyl ethers, polyoxyethylene alkylphenyl ethers, polyethylene glycol fatty acid esters, polyoxyethylene alkylamines, polyoxyethylene alkyl thioethers, polyoxyethylene polyoxypropylene copolymers, polyoxyethylene glycerol fatty acid esters, pentaerythritol fatty acid esters, propylene glycol monofatty acid esters, polyoxyethylene propylene glycol monofatty acid esters, polyoxyethylene sorbitol fatty acid esters, fatty acid alkylolamides, and alkylamine oxides; bile acid and salts thereof (e.g., chenodeoxycholic acid, cholic acid, deoxycholic acid, dehydrocholic acid and salts thereof, and glycine or taurine conjugate thereof); ionic surface active agents, such as sodium laurylsulfate, fatty acid soaps, alkylsulfonates, alkylphosphates, ether phosphates, fatty acid salts of basic amino acids; triethanolamine soap, and alkyl quaternary ammonium salts; and amphoteric surface active agents, such as betaines and aminocarboxylic acid salts.

The solid dosage forms of tablets, dragees, capsules, pills, and granules can be prepared with coatings and shells such as enteric coatings and other coatings well known in the pharmaceutical formulating art. They may optionally contain opacifying agents and may also be of a composition such that they release the active ingredient(s) only, or preferentially, in a certain part of the intestinal tract, and/or in delayed fashion. Examples of embedding compositions which can be used include polymeric substances and waxes.

The active compounds may also be in micro-encapsulated form, if appropriate, with one or more of the above-mentioned excipients.

The active compounds may be in finely divided form, for example it may be micronised.

Liquid dosage forms for oral administration include pharmaceutically acceptable emulsions, solutions, suspensions, syrups and elixirs. In addition to the active compounds, the liquid dosage forms may contain inert diluents commonly used in the art such as water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan and mixtures thereof. Besides inert diluents, the oral compositions may also include adjuvants such as wetting agents, emulsifying and suspending agents, sweetening, flavoring and perfuming agents. Suspensions, in addition to the active compounds, may contain suspending agents such as ethoxylated isostearyl alcohols, polyoxyethylene sorbitol and sorbitan esters, microcrystalline cellulose, aluminum metahydroxide, bentonite, agar-agar, and tragacanth and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolisable lipid capable of forming liposomes can be used. The present compositions in liposome form can contain, in addition to a compound of the present invention, stabilisers, preservatives, excipients and the like. The preferred lipids are the phospholipids and the phosphatidyl cholines (lecithins), both natural and synthetic. Methods to form liposomes are known in the art, for example, Prescott, Ed., Methods in Cell Biology, Volume XIV, Academic Press, New York, N.Y. (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants which may be required. Ophthalmic formulations, eye ointments, powders and solutions are also contemplated as being within the scope of this invention.

It will be appreciated from the aforegoing that the present invention provides inter alia antibody hGP 5C4 and its fragments, as well as humanised versions thereof such as humanised Fab fragments, for example, in a formulation as described above. Exemplary formulations are parenteral formulations as described above. To be mentioned, therefore, are the following formulations containing as active agent hGP 5C4, humanized hGP 5C4 or a Fab or other fragment, optionally in combination with one or more other active agents:

1. A liquid dosage form for parenteral administration, for example a solution, suspension, liposome formulation, or emulsion in oily or aqueous vehicles. In addition to the active compounds, the liquid dosage forms may contain e.g. tonicity agents (for the purpose of making the formulations substantially isotonic with the subject's body, e.g. with human plasma) such as, for instance, sodium chloride, sodium sulfate, dextrose, mannitol and/or glycerol may be optionally added to the parenteral formulation. A pharmaceutically acceptable buffer may be added to control pH. Thickening or viscosity agents, for instance well known cellulose derivatives (e.g. methylcellulose, carboxymethylcellulose, hydroxyethylcellulose and hydroxypropylmethylcellulose), gelatin and/or acacia, may optionally be added to the parenteral formulation.

2. A large volume parenteral (LVP), e.g. more than 100 ml of a liquid formulation, more particularly about 250 ml, of a liquid formulation of the active compound. Examples of LVPs are infusion bags.

3. A small volume parenteral (SVP), e.g. about 100 ml or less of a liquid formulation of the active compound. Examples of SVPs are vials with solution, vials for reconstitution, pre-filled syringes for injection and dual chamber syringe devices.

4. A formulation having a pH of from 5 to 8 of from 6.0 to 7.0 such as a pH of 6.5.

5. Parenteral formulations in glass containers. If desired, amber glass employing iron oxide or an opaque cover fitted over the container may afford the appropriate UV protection.

6. Parenteral formulations in plastics containers such as plastics infusion bags, for example.

7. Dry solid formulations for reconstitution, particularly a finely divided form such as, for example, a lyophilisate, for intravenous or other parenteral use. Solid dosage forms for parenteral administration may encompass solid and semi-solid forms and may include pellets, powders, granules, patches, and gels.

8. Subcutaneous or intradermal formulations (for example formulations for injection) in which the active product (or active agent combination) is formulated into a parenteral preparation that can be injected subcutaneously or intradermally. The formulation for administration will comprise the active product and a liquid carrier.

9. A parenteral preparation having an aqueous carrier (for example water, typically containing an additive e.g. an antioxidant and/or an isotonicity agent), for example solutions, dispersions, suspensions or emulsions.

10. A parenteral formulation having a nonaqueous carrier (again one or more additives may be incorporated), for example solutions, dispersions, suspensions or emulsions. Pharmaceutically acceptable non-aqueous carriers can be fully saturated, or partially or fully unsaturated. Examples of non-aqueous carriers include, but are not limited to:

(i) Vegetable oils (such as cottonseed oil, corn oil, sesame oil, soybean oil, olive oil, fractionated coconut oils, peanut oil, sunflower oil, safflower oil, almond oil, avocado oil, palm oil, palm kernel oil, babassu oil, beechnut oil, linseed oil, rape oil, and the like), mineral oils, synthetic oils, and combinations thereof.

(ii) Fully saturated non-aqueous carriers, examples of which include, but are not limited to, medium to large chain fatty acids (e.g. capric acid and/or caprylic acid) and particularly esters thereof (such as fatty acid triglycerides with a chain length of about 6 C to about 24C); mixtures of fatty acids are split from the natural oil (for example coconut oil palm kernel oil, babassu oil, or the like) and are refined. In some embodiments, about 8 C to about 12 C fatty acid medium chain triglycerides are useful. Other fully saturated non-aqueous carriers include, but are not limited to, saturated coconut oil (which typically includes a mixture of lauric, myristic, palmitic, capric and capric acids), including those sold under the Miglyo trademark from Huls and bearing trade designations 810, 812, 829, and 840). Also noted are the NeoBee products sold by Drew Chemicals. Isopropyl myristate is another example of a non-aqueous carrier.

(iii) Synthetic oils, examples of which include triglycerides, and propylene glycol diesters of saturated or unsaturated fatty acids having from 6 to 24 carbon atoms such as, for example hexanoic acid, octanoic (caprylic), nonanoic (pelargonic), decanoic (capric), undecanoic, lauric, tridecanoic, tetradecanoic (myristic), pentadecanoic, hexadecanoic (palmitic), heptadecanoic, octadecanoic (stearic), nonadecanoic, heptadecanoic, eicosanoic, heneicosanoic, docosanoic, and lignoceric acids, and the like.

(iv) Unsaturated carboxylic acids, examples of which include oleic, linoleic, and linolenic acids, and the like.

(v) A "non-oil", for example polyethylene glycol.

It will be understood that the non-aqueous carrier can comprise the mono-, di-, and triglyceryl esters of fatty acids or mixed glycerides and/or propylene glycol diesters wherein at least one molecule of glycerol has been esterified with fatty acids of varying carbon atom length 11. Sterile powders for reconstitution into sterile injectable or infusable solutions, dispersions, suspensions or emulsions just prior to use. The injectable formulation may be in an aqueous carrier or a non-aqueous carrier.

12. Formulations comprising as aqueous and nonaqueous carriers, diluents, solvents or vehicles water, ethanol, polyols (such as glycerol, propylene glycol, polyethylene glycol, for example), and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. The features of this paragraph may be applied to the formulations of any of preceding paragraphs 1, 2, 3, 4, 5, 6, 8, 9, 10 and 11.

13. Formulations comprising an acid, e.g. formulations with pH greater than 1.8, for example at least 2, e.g. at least 3, as in the case of formulations having a pH of at least 4. Often acidic formulations have a pH of at least 5.

14. Formulations comprising a base, e.g. formulations with pH of less than 14 for example less than 13, e.g. no more than 12, as in the case of formulations having a pH of no more than 11. Often acidic formulations have a pH of no more than 10, particularly no more than 9. In particular embodiments, the pH is no more than 8.

15. Formulations comprising Cremophor EL®, suitably in an aqueous carrier, e.g. up to 25% in water. Cremophor EL is also known aspolyoxyl 35 Castor Oil. Cremophor EL is a non-ionic solubilizer and emulsifier obtained by causing ethylene oxide to react with castor oil of German Pharmacopoeia (DAB 8) quality in a molar ratio of 35 moles to 1 mole. Cremophor EL forms clear solutions in water. It is also soluble in ethyl alcohol, n-propyl alcohol, isopropyl alcohol, ethyl acetate, chloroform, carbon tetrachloride, trichloroethylene, toluene and xylene.

15. Formulations comprising dextrose, e.g. up to 5%, in an aqueous solvent, for example water or saline.

16. Formulations comprising ethanol, e.g. up to 15% and optionally up to 5%, in an aqueous solvent, for example water or saline.

17. Formulations comprising glycerol, e.g. in an alcoholic or aqueous solvent, for example water or saline.

18. Formulations comprising sorbitol, e.g. in an alcoholic or aqueous solvent, for example water or saline.

19. Formulations comprising phosphate buffer.

20. Formulations comprising polyethylene glycol, e.g. PEG 300 or 400, neat or e.g. in an alcoholic or aqueous solvent, for example water or saline.

21. Formulations comprising propylene glycol or a propylene glycol derivative, for example propylene glycol alginate, neat or e.g. in an alcoholic or aqueous solvent, for example water or saline.

22. Formulations comprising a sugar, e.g. lactose, sucrose or glucose, whether as a solid or in solution, e.g. in an alcoholic or aqueous solvent, for example water or saline.

23. Formulations comprising an antioxidant, e.g. in an alcoholic or aqueous solvent, for example water or saline.

24. Formulations comprising an amino acid additive, e.g. in an alcoholic or aqueous solvent, for example water or saline.

25. Formulations comprising a lipid, e.g. a phospholipid.

26. Formulations comprising saline.

27. Formulations comprising a polyoxyethylenesorbitan ester surfactant, e.g. Tween 20 (polyoxyethylenesorbitan monolaurate), Tween 40 (polyoxyethylenesorbitan monopalmitate), Tween 60 (polyoxyethylenesorbitan monostearate), Tween 80 (polyoxyethylenesorbitan monooleate) or Tween 85 (polyoxyethylenesorbitan trioleate).

28. Formulations comprising a poloxamer (poly(oxyethylene)-poly(oxypropylene) block copolymer).

29. Formulations comprising a Solutol, for example Solutol HS 15 (Polyethylene glycol-15-hydroxystearate), e.g. up to 30% in water 30. Formulations comprising a microsphere-based delivery system, e.g. composed of the desired bioactive molecule incorporated into a matrix of poly-DL-lactide-co-glycolide (PLG).

31. Formulations comprising lipophilic carbohydrate excipients, termed oligosaccharide ester derivatives (OEDs), which have been used to modify pharmacokinetic profiles of drugs (SoliDose™ technology, Elan Pharmaceuticals).

32. Intravenous and other parenteral compositions provided as ready-to-use solutions, suspensions, liposome formulations, or emulsions in oily or aqueous vehicles 33. Intravenous and other parenteral compositions provided as lyophilisates or dry powders for reconstitution prior to administration.

34. A subcutaneous implant.

35. A transdermal formulation, for example in the form of matrices or membranes, or as fluid or viscous formulations in oil or hydrogels or as a compressed powder pellet. See above for further details.

36. Injectable depot forms, e.g. comprising microencapsule matrices of the drug in biodegradable polymers, for example a polylactide-polyglycolide, poly(orthoester) and poly(anhydride), or comprising the drug entrapped in liposomes or microemulsions which are compatible with body tissues.

37. Formulations comprising a biodegradable polymer, e.g. one mentioned previously.

Advantageously, the compounds of the invention are orally active, have rapid onset of activity and low toxicity.

The compounds of the invention have the advantage that they may be more efficacious, be less toxic, be longer acting, have a broader range of activity, be more potent, produce fewer side effects, be more easily absorbed than, or that they may have other useful pharmacological properties over, compounds known in the prior art.

The invention includes a method for the peri-interventional prevention of restenosis and/or thrombosis comprising administering to a subject an effective amount of an agent of the disclosure, e.g. hGP 5C4, humanised hGP 5C4 or a fragment of either. The invention also includes a method for the long term or chronic prevention of atherosclerosis and/or arterial thrombosis, comprising administering to a subject an effective amount of an agent of the disclosure, e.g. hGP 5C4, humanised hGP 5C4 or a fragment of either.

Materials and Methods
Methods to Investigate Platelet-Collagen Interaction and Modulation by Inhibitors
Platelet Aggregation and ATP Release Stimulation of mouse platelet-rich plasma with increasing concentrations of bovine type I collagen from 0.2 to 4 µg/ml elicits a dose-dependent aggregation from 2 to 95% and a dose-dependent ATP release from 0 to 1.66 nM ATP release. A half-maximal collagen concentration was chosen for further experiments. Incubation of the mouse platelet-rich plasma with the specific anti-mouse GP VI antibody JAQ 1 (50 µg/ml and 100 µg/ml) almost completely abolished platelet aggregation after stimulation with 2 µg collagen/ml (with 50 µg JAQ 1:2+/−0.7; with 100 µg JAQ 1:1.5+/−0.3%). Moreover, ATP release was inhibited in an antibody dose-dependent manner to 1.09 nM ATP (10 µg antibody/ml) or completely abolished (50 and 100 µg antibody/ml).

Similarly, incubation of mouse platelet-rich plasma with the immunoadhesin for GP VI (Fc-GPVI-nt) (50 µg/ml and 100 µg/ml) almost completely abolished platelet aggregation after stimulation with 2 µg collagen/ml (with 50 µg Fc-GPVI-nt: 2+/−0.7; with 100 µg Fc-GPVI-nt: 1.5+/−0.3%) and ATP release to 0 nM ATP.

Therefore, the immunoadhesin sufficiently inhibited GP VI activation by scavenging the natural GP VI ligand collagen. Both the crucial platelet function aggregation and the platelet release mechanism as determined by ATP release could be influenced by the Fc-GPVI-nt.

GP VI Mediated Adhesion Under Physiological Flow Conditions (Flow Chamber)

Adhesion of platelets under physiological shear conditions was tested in a flow chamber. Initial and firm adhesion of platelets was significantly inhibited by addition of the Fc-GPVI-nt immunoadhesin by 60% (see FIG. 4).

GP VI Binding Assay

Adhesion of Fc-GPVI-nt to collagen coated plates was determined in an ELISA based fluorescence assay. The binding of the immunoadhesin Fc-GPVI-nt dose dependently increased up to saturation levels in a concentration from 0.2 to 10 µg Fc-GPVI-nt (please see FIG. 5). The specificity was demonstrated by comparing binding of Fc-GPVI-nt with that of the empty immunoadhesin Fc-nt or the uncoated plastic surface (see FIG. 6).

Methods to Investigate Platelet Adhesion and Aggregation at Vascular Injury In Vivo as the Crucial Steps for Platelet Activation in Acute Vascular Events To test the biological significance of platelet-collagen interactions in the processes of adhesion to lesions in vivo, platelet-vessel wall interactions following vascular injury of the mouse carotid artery are assessed. Vascular injury to this important vascular bed may serve as a model for the first steps of arteriosclerosis such as the endothelial lesion in early stage arteriosclerosis or the plaque rupture in later stages of arteriosclerosis with the unmasking of collagen fibrils from the subendothelium. Moreover, this model allows the study of the subsequent complications of vascular injury. Small endothelial lesions lead to maximal activation of platelets with the following steps of platelet adhesion and aggregation. In further steps platelet aggregates can lead to embolism from the carotid artery with consecutive ischemic cerebral stroke. Thus, this experimental setup serves as a relevant in vivo model for a subgroup of patients with unstable atherosclerosis involving plaque rupture and endothelial lesions leading to acute coronary syndrome and stroke.

Figure 1B:
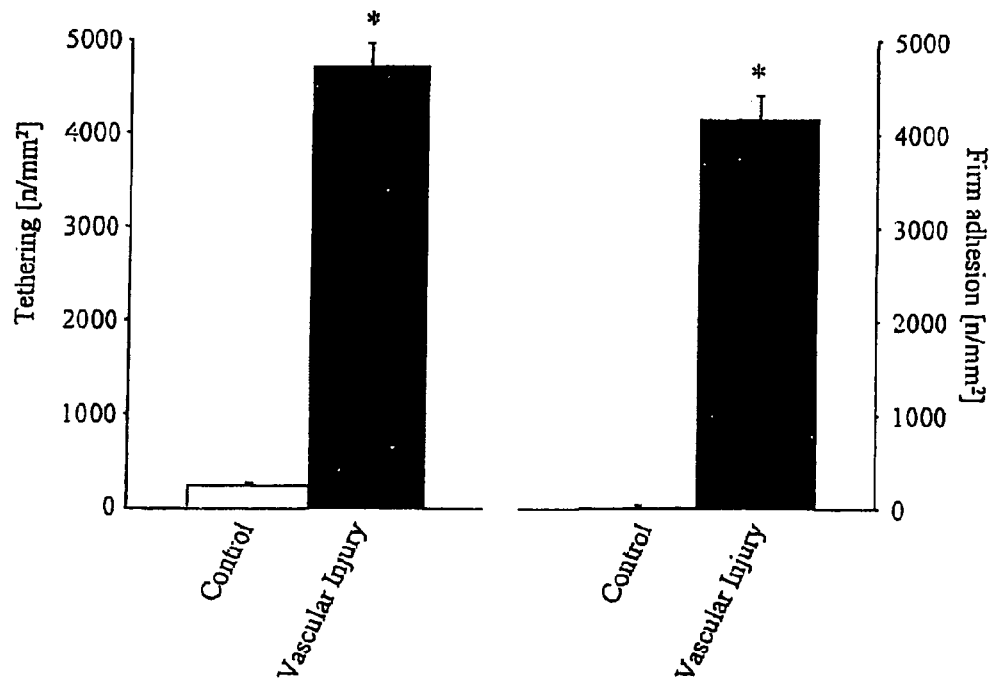

Vigorous ligation of the carotid artery for 5 min consistently causes complete loss of the endothelial cell layer and initiates platelet adhesion at the site of injury, as assessed by scanning electron microscopy (FIG. 1a). In vivo fluorescence microscopy may be used to directly visualize and quantify the dynamic process of platelet accumulation following vascular injury. Numerous platelets are tethered to the vascular wall within the first minutes after endothelial denudation ($4620 \pm 205$ platelets/mm$^2$). Virtually all platelets establishing contact with the subendothelium exhibit initially a slow surface translocation of the "stop-start" type (Savage, B., Saldivar, E. & Ruggeri, Z. M. Initiation of platelet adhesion by arrest onto fibrinogen or translocation on von Willebrand factor. Cell 1996; 84, 289-297). While we observed transition from initial slow surface translocation to irreversible platelet adhesion in 88% of all platelets ($4182 \pm 253$ platelets/mm$^2$) (FIG. 1b), platelet arrest remains transient in only 12% ($543 \pm 32$ platelets/mm$^2$). Once firm arrest is established, adherent platelets recruit additional platelets from the circulation, resulting in aggregate formation (FIG. 1c). Similar characteristics of platelet recruitment are obtained with immobilized collagen in vitro. In contrast, only few platelets are tethered to the intact vascular wall under physiological conditions (P<0.05 vs. vascular injury) and virtually 100% of these platelets are displaced from the vascular wall without firm arrest (P<0.05 vs. vascular injury, FIG. 1a-c).

Identification of GP VI as a Novel and Relevant Target Protein in Platelets for Vascular Injury In Vivo The high complexity of the platelet-vessel wall interaction which involves a variety of different receptors and signaling pathways makes the in vivo inhibition of this process very difficult. Besides GPIb-V-I-X and $\alpha_{IIb}\beta_3$ integrin which interact indirectly with collagen via von Willebrand factor (vWF), a large number of collagen receptors have been identified on platelets, including most importantly $\alpha_2\beta_1$ integrin (Santoro, S. A. Identification of a 160,000 dalton platelet membrane protein that mediates the initial divalent cation-dependent adhesion of platelets to collagen. Cell 1986; 46, 913-920), GPV (Moog, S. et al. Platelet glycoprotein V binds to collagen and participates in platelet adhesion and aggregation. Blood 2001; 98, 1038-1046), and GPVI (Moroi, M., Jung, S. M., Okuma, M. & Shinmyozu, K. A patient with platelets deficient in glycoprotein VI that lack both collagen-induced aggregation and adhesion. J. Clin. Invest 84, 1440-1445). Amidst several reports on different signaling systems which play a role in vitro, also GPVI has now been discussed (Gibbins, J. M., Okuma, M., Farndale, R., Barnes, M. & Watson, S. P. Glycoprotein VI is the collagen receptor in platelets which underlies tyrosine phosphorylation of the Fc receptor gamma-chain. FEBS Lett. 1997; 413, 255-259; Nieswandt, B. et al. Long-term antithrombotic protection by in vivo depletion of platelet glycoprotein VI in mice. J. Exp. Med. 2001; 193, 459-469, Nieswandt, B. et al. Glycoprotein VI but not □2□1 integrin is essential for platelet interaction with collagen. EMBO J 2001; 20, 2120-2130).

Figure 2A:
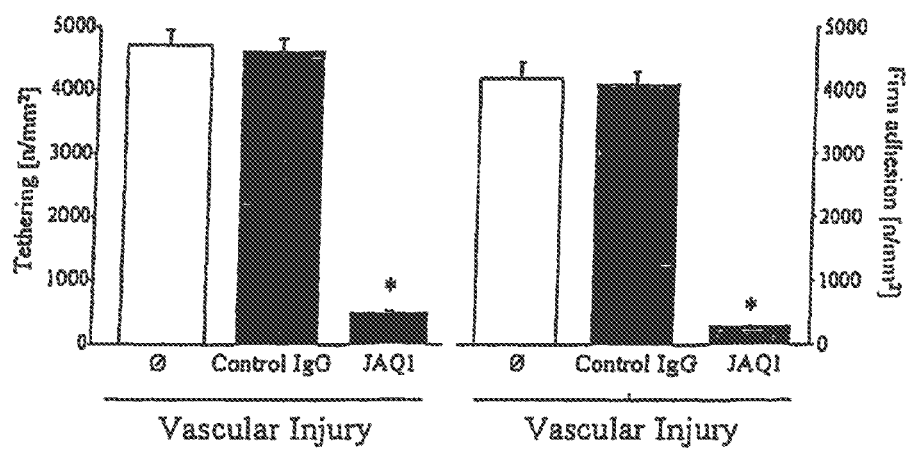
Figure 2B:
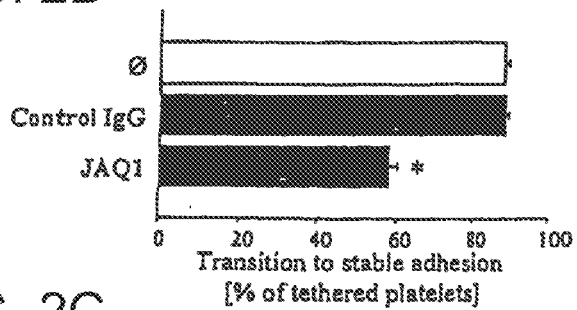
Figure 2C:
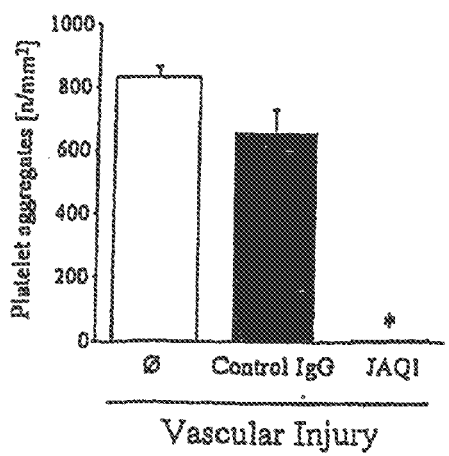
Figure 2D:
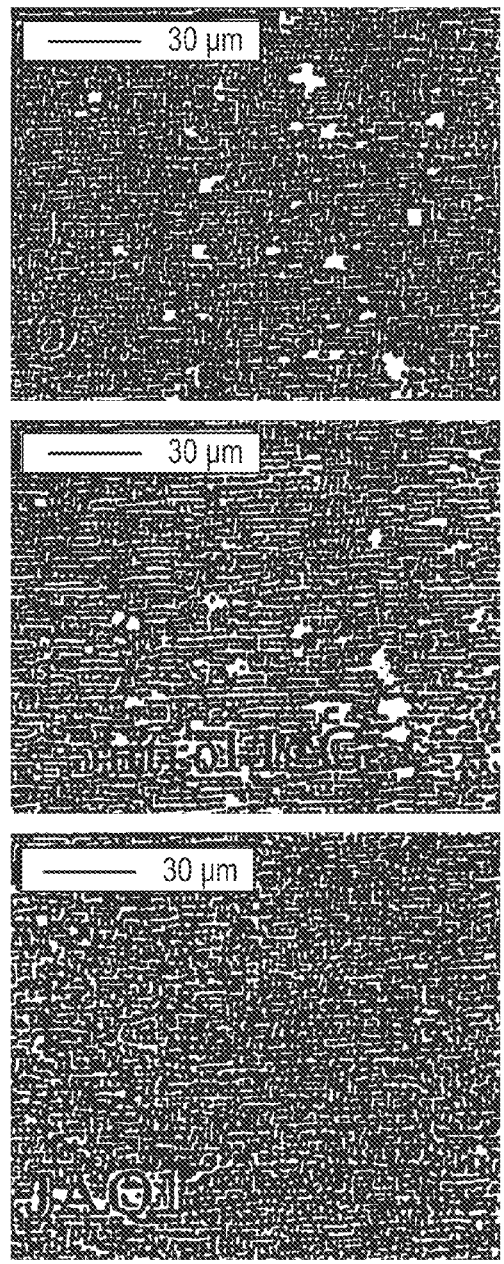

To directly test the in vivo relevance of platelet-collagen interactions in arterial thrombus formation, we inhibited or deleted GPVI in vivo. The monoclonal antibody (mAb) JAQ1 blocks the major collagen-binding site on mouse GPVI (Schulte, V. et al. Evidence for two distinct epitopes within collagen for activation of murine platelets. J. Biol. Chem. 2001; 276, 364-368) and almost completely inhibits firm platelet adhesion to immobilized fibrillar collagen under high shear flow conditions (Nieswandt, B. et al. Glycoprotein VI but not alpha2beta1 integrin is essential for platelet interaction with collagen. EMBO J. 2001; 20, 2120-2130). To study the significance of GPVI-collagen interactions in the dynamic process of platelet adhesion/aggregation in arterial thrombus formation, mice received syngeneic, fluorescence-tagged platelets pre-incubated with JAQ1 Fab fragments or isotype-matched control IgG and carotid injury was induced as described above. Very unexpectedly, we found that the inhibition of GPVI reduced initial platelet tethering following endothelial denudation in the common carotid artery by 89% (P<0.05 vs. control IgG, FIG. 2a), a process thought to be mediated mainly by GPIbα interaction with immobilized vWF (Goto, S., Ikeda, Y., Saldivar, E. & Ruggeri, Z. M. Distinct mechanisms of platelet aggregation as a consequence of different shearing flow conditions. J. Clin. Invest 1998; 101, 479-486; Sixma, J. J., van Zanten, G. H., Banga, J. D., Nieuwenhuls, H. K. & de Groot, P. G. Platelet adhesion. Semin. Hematol. 1995; 32, 89-98). Furthermore, stable platelet arrest was reduced by 93% by JAQ1 (FIG. 2a). We observed transition from initial tethering/slow surface translocation to irreversible platelet adhesion in only 58% of those platelets establishing initial contact with the subendothelial surface (compared to 89% with control IgG-pretreated platelets, P<0.05, FIG. 2b). Aggregation of adherent platelets was virtually absent following pretreatment of platelets with JAQ1 Fab fragments, but not in the controls (P<0.05 vs. control, FIGS. 2c and d). These data demonstrated that direct platelet-collagen interactions are crucial for initial platelet tethering and subsequent stable platelet adhesion and aggregation at sites of vascular injury. Furthermore, these findings show that GPVI is a key regulator in this process, while other surface receptors, most importantly GPIb-V-IX and $\alpha_2\alpha_1$ are not sufficient to initiate platelet adhesion and aggregation on the subendothelium in vivo.

Figure 3A:
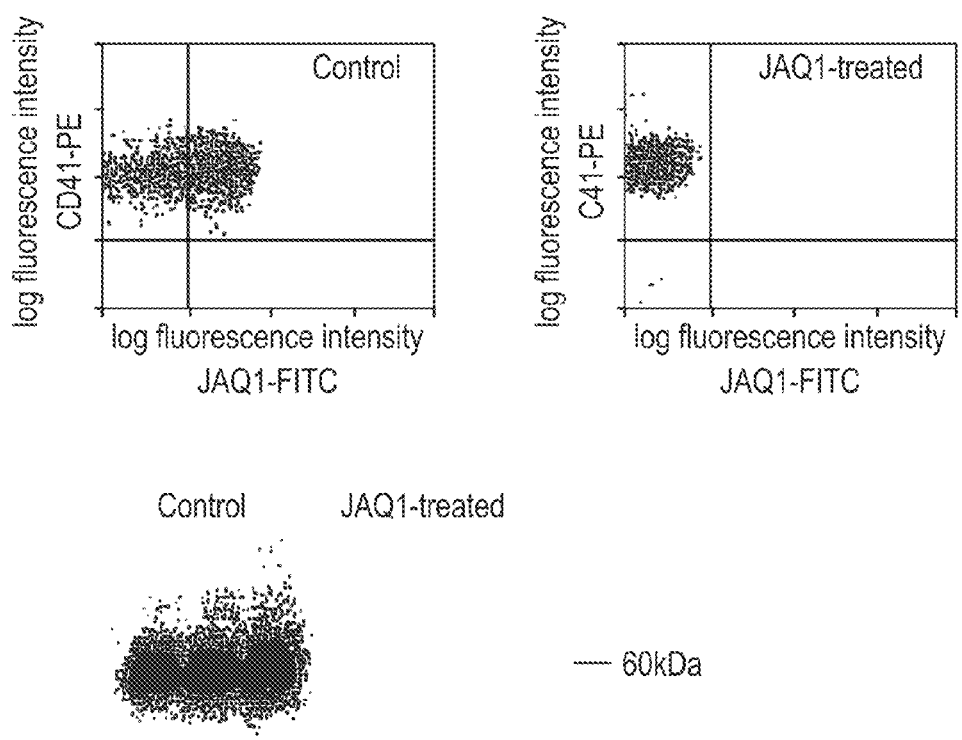

To exclude the possibility that this effect is based on steric impairment of other receptors, e.g. GPIb-V-IX, by surface-bound JAQ1, we generated GPVI-deficient mice by injection of JAQ1 five days prior to vascular injury. As reported previously, such treatment induces virtually complete loss of GP VI e.g. by internalization and proteolytic degradation of GPVI in circulating platelets, resulting in a "GPVI knock out"-like phenotype for at least two weeks (Nieswandt, B. et al. Long-term antithrombotic protection by in vivo depletion of platelet glycoprotein VI in mice. *J. Exp. Med.* 2001; 193, 459-469). As illustrated in FIG. 3a, GPVI was undetectable in platelets from JAQ1-treated mice on day 5 after injection of 100 μg/mouse JAQ1, but not control IgG, while surface expression and function of all other tested receptors, including GPIb-V-IX, $\alpha_{IIb}\beta_3$, and $\alpha_2\beta_1$ was unchanged in both groups of mice, confirming earlier results (data not shown and Nieswandt, B. et al. Long-term antithrombotic protection by in vivo depletion of platelet glycoprotein VI in mice. *J. Exp. Med.* 2001; 193, 459-469).

Figure 3B:
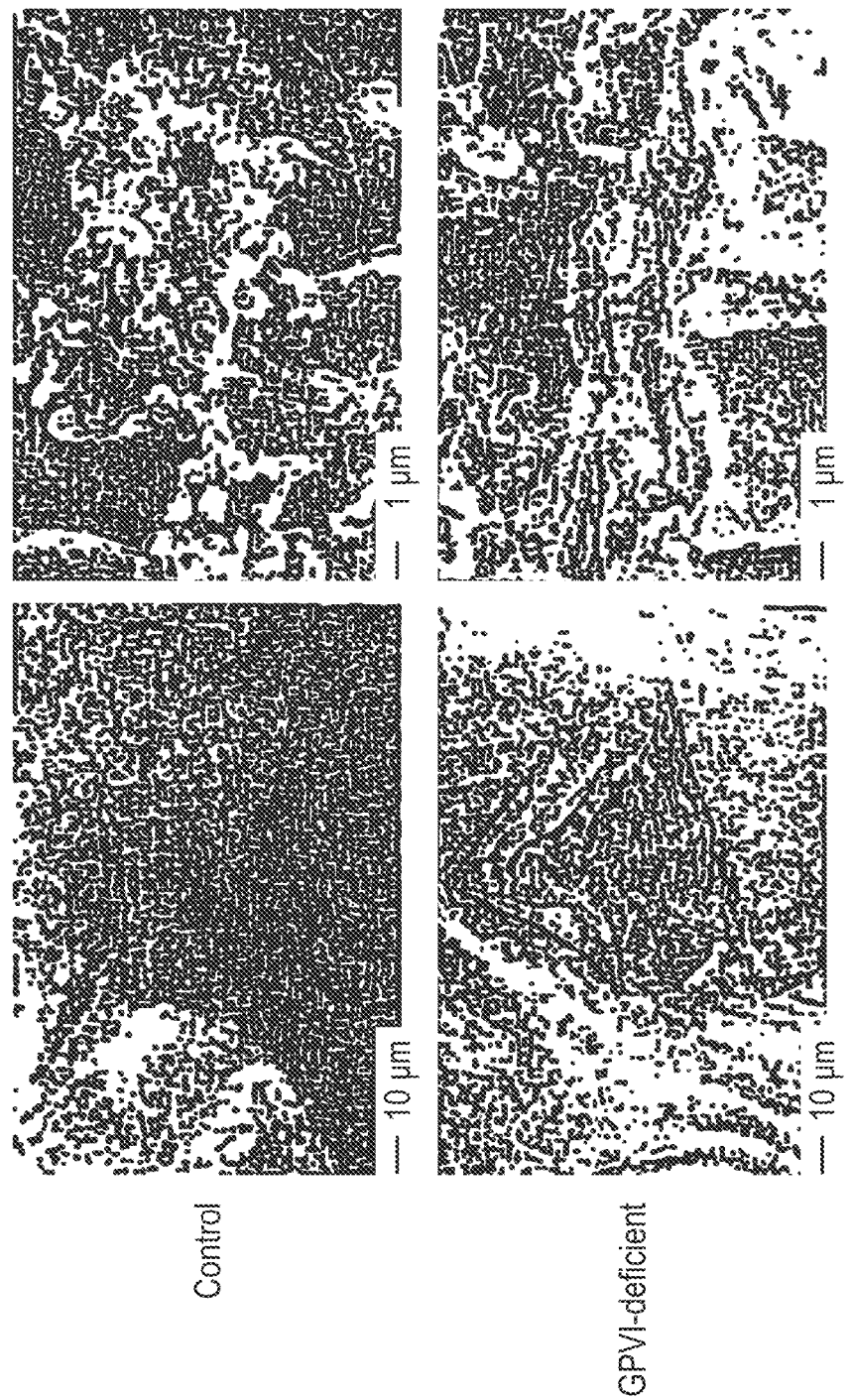
Figure 3C:
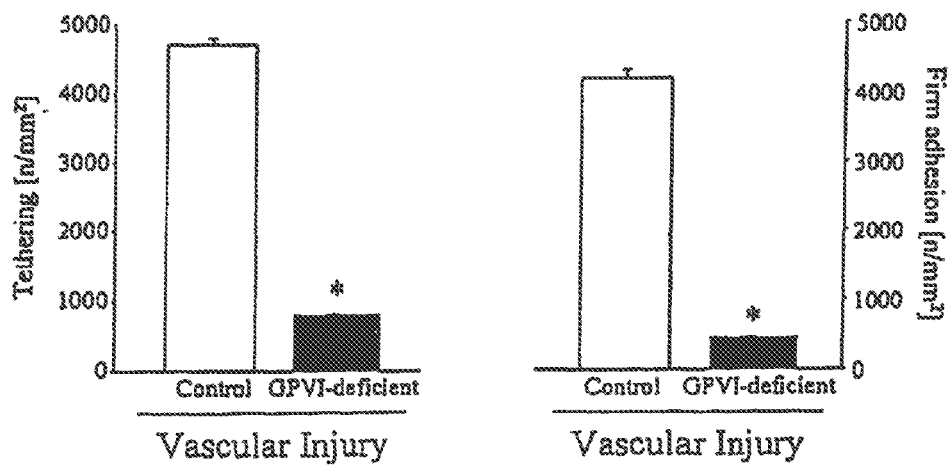
Figure 3D:
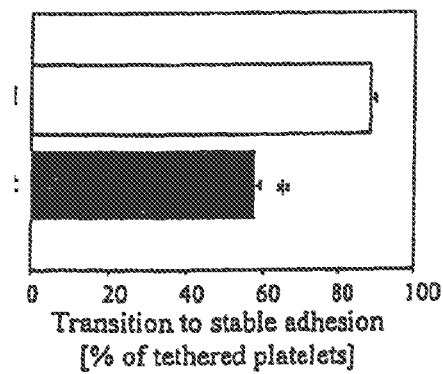
Figure 3E:
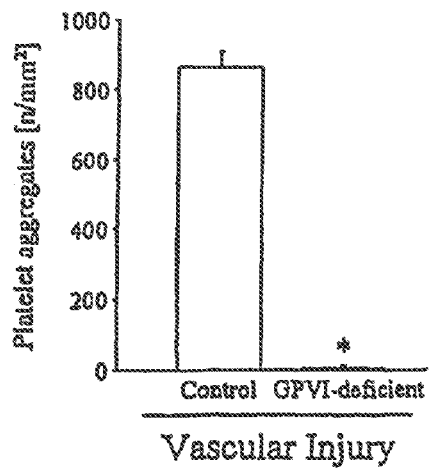

As shown by scanning electron microscopy, platelet adhesion and aggregation following endothelial denudation of the common carotid artery is virtually absent in GPVI-deficient, but not in IgG-pretreated mice (FIG. 3b). Next, in vivo video fluorescence microscopy was used to define platelet adhesion dynamics following vascular injury in GPVI-deficient mice (FIG. 3c-f). The loss of GPVI significantly reduces tethering/slow surface translocation of platelets at the site of vascular injury (by 83% compared to IgG-pretreated mice, P<0.05). This GPVI-independent slow surface translocation requires vWF-GPIb_-interaction, since it is abrogated by preincubation of the platelets with Fab fragments of a function blocking mAb against GPIbα (p0p/B) confirming the critical role of GPIbα in this process (not shown). In the absence of GPVI, stable platelet adhesion is reduced by approximately 90% compared to the (IgG-treated) control, while aggregation of adherent platelets is virtually absent (FIG. 3b-f). We saw transition from platelet tethering to stable platelet adhesion in only 58% of all platelets initially tethered to the site of injury (compared to 89% with control mAb-pretreated platelets, P<0.05, FIG. 3d), indicating that GPIb_-dependent surface translocation is not sufficient to promote stable platelet adhesion and subsequent aggregation.

The profound inhibition of platelet tethering by GPVI blockade was surprising and suggested a previously unrecognized function of this receptor in the very initial phase of firm platelet adhesion to vascular lesions. Fibrillar collagen is a major constituent of human atherosclerotic lesions (Rekhter, M. D. Collagen synthesis in atherosclerosis: too much and not enough. *Cardiovasc. Res.* 1999; 41, 376-384; Rekhter, M. D. et al. Type I collagen gene expression in human atherosclerosis. Localization to specific plaque regions. *Am. J. Pathol.* 1993; 143, 1634-1648); enhanced collagen synthesis (by intimal smooth muscle cells and fibroblasts) significantly contributes to luminal narrowing in the process of atherogenesis (Opsahl, W. P., DeLuca, D. J. & Ehrhart, L. A. Accelerated rates of collagen synthesis in atherosclerotic arteries quantified in vivo. *Arteriosclerosis* 1987; 7, 470-476). Plaque rupture or fissuring (either spontaneously or following balloon angioplasty) results in exposure of collagen fibrils to the flowing blood.

The invention teaches for the first time that such subendothelial collagens are the major trigger of arterial thrombus formation and reveal an unexpected function of the collagen receptor GPVI in platelet recruitment to the injured vessel wall. The processes of platelet tethering and slow surface translocation under conditions of elevated shear are known to largely depend on GPIbα interaction with immobilized vWF. This interaction is, however, not sufficient to establish initial platelet-vessel wall interactions in vivo as functional GPVI is also required (FIGS. 2 and 3). Thus, both GPIbα and GPVI must act in concert to recruit platelets to the subendothelium. During platelet tethering, ligation of GPVI can shift $\alpha_{IIb}\beta_3$ and $\alpha_2\beta_1$ integrins from a low to a high affinity state. Both $\alpha_{IIb}\beta_3$ and $\alpha_2\beta_1$ then act in concert to promote subsequent stable arrest of platelets on collagen, while $_{IIb-3}$ is essential for subsequent aggregation of adherent platelets. Thus, ligation of GPVI during the initial contact between platelets and subendothelial collagen provides an activation signal that is essential for subsequent stable platelet adhesion and aggregation. Importantly, occupation or lateral clustering of GPIbα (during GPIbα-dependent surface translocation), which induced low levels of $\alpha_{IIb}\beta_3$ integrin activation in vitro (Kasirer-Friede, A. et al. Lateral clustering of platelet GP Ib-IX complexes leads to up-regulation of the adhesive function of Integrin αIIbβ3. *J. Biol. Chem.* 2002; Vol 277: 11949-11956), is not sufficient to promote platelet adhesion in vivo.

The invention therefore has identified an essential receptor for inhibiting platelet attachment to the subendothelium. An antibody which blocks the interaction of GPVI with exposed collagen can specifically inhibit all major phases of thrombus formation, i.e. platelet tethering, firm adhesion, and aggregation at sites of arterial injury (e.g. during acute coronary syndromes). The very profound protection that was achieved by inhibition or depletion of GPVI establishes the importance of selective pharmacological modulation of GPVI-collagen interactions to control the onset and progression of pathological atherosclerotic lesions.

Following rupture of the atherosclerotic plaque, exposure of subendothelial collagen is the major trigger that initiates platelet adhesion and aggregation at the site of injury, followed by arterial thrombosis (1; 24; 25). The platelet glycoprotein GPVI, which has been cloned recently (5; 6), has been identified by the invention to be the major platelet collagen receptor (4), mediating platelet adhesion both in vitro (22) and under (patho-)physiological conditions in vivo (3). Therefore, inhibition of GPVI prevents platelet recruitment and arterial thrombosis in patients with advanced atherosclerosis as shown by the present invention by the inhibitory activities of the specific fusion protein Fc-GPVI-nt on platelet adhesion in vitro and in vivo.

The Fc-GPVI-nt fusion protein is expressed in HELA cells using an adenoviral expression system to obtain soluble Fc-GPVI-nt. Characterization of the soluble forms of GPVI revealed that Fc-GPVI-nt is secreted as dimer with a molecular mass of approximately 160 kDa. Consistently, Miura and co-workers recently reported that GPVI-Fc-dimer is present as a dimer, in which two GPVI-Fc-dimer molecules are cross-linked by disulfide bonds formed from the Cys in the Fc domain of each molecule (21). Importantly, only the dimeric form of GPVI, but not monomers of the extracellular domain of GPVI, has been reported to exhibit collagen binding affinity and to attenuate collagen-induced platelet aggregation (21).

Binding assays were performed to define GPVI-Fc-dimer-collagen interaction. Soluble GPVI binds to immobilized collagen in a saturable manner. GPVI-Fc-dimer binding to fibrillar collagen was highly specific, since it did not occur to immobilized vWF or BSA. Further, GPVI binding to immobilized collagen could be inhibited by soluble collagen. High concentrations of soluble collagen were required to block GPVI-Fc-dimer binding, indicating the fusion protein binds immobilized collagen with high affinity. Correspondingly, a high association and dissociation constant ($K_D$ approximately $5.8 \times 10^{-7}$ M) has been reported for the GPVI-collagen interaction (21).

Soluble Fc-GPVI-nt has been demonstrated earlier to attenuate platelet activation and aggregation in response to collagen or convulxin, a snake toxin, which binds to GPVI with high affinity (6; 21; 27). Apart from platelet aggregation, GPVI is critically involved in the process of platelet adhesion to collagen (3; 22). In the present study, we, therefore, tested the effects of Fc-GPVI-nt on platelet adhesion under physiological flow conditions in vitro. We show that soluble Fc-GPVI-nt dose-dependently inhibits platelet adhesion under low and high shear conditions in vitro. In the presence of Fc-GPVI-nt, but not of control Fc peptide, aggregation of adherent platelets was virtually absent, indicating that GPVI contributes to the processes of both platelet adhesion and subsequent activation by immobilized collagen. GPVI confers collagen responses (i.e. adhesion and aggregation) in a receptor density-dependent fashion (22). Correspondingly, it has been reported that a more than 50% reduction in GPVI expression transfected RBL-2H3 cells is associated with a lack of collagen-induced aggregation in these cells (8; 22). Since a low variability in the GPVI receptor density has been reported albeit in a small sample population (22), one might expect that inhibition of approx. 50% of collagen-GPVI bonds is sufficient to attenuate platelet recruitment to exposed collagen. In the present study doses of 1 mg/kg Fc-GPVI-nt were required to induce significant inhibition of platelet adhesion under flow, supporting the notion that multiple GPVI binding sites are available in each collagen fibril. Similar amounts of a function blocking anti-GPVI antibody were required to attenuate platelet-vessel wall injury in vivo (3).

Fibrillar collagen is a major constituent of the normal vessel wall but also of atherosclerotic lesions (28). Rupture or fissuring of the atherosclerotic plaque results in exposure of collagen fibrils to circulating platelets. As reported earlier, GPVI-collagen interactions are essentially involved in arterial thrombus formation following vascular injury (3). Here we demonstrate the in vivo effects of soluble Fc-GPVI-nt on platelet recruitment after arterial injury. Endothelial denudation was induced by reversible ligation of that carotid artery and the dynamic process of platelet attachment was monitored by intravital videofluorescence microscopy as described (3). We demonstrate for the first time in vivo that soluble Fc-GPVI-nt attenuates stable platelet tethering, adhesion and platelet aggregation following endothelial denudation. Inhibition of platelet recruitment by Fc-GPVI-nt was dose-dependent. Apart from preventing stable arrest of platelets, Fc-GPVI-nt significantly reduced initial platelet tethering/slow surface translocation at sites of endothelial denudation. We have demonstrated earlier that inhibition of GPIbα or of GPVI attenuate platelet tethering to a similar extent (3), supporting that GPVI and GPIbα interaction need to act in contact to promote platelet tethering to subendothelial collagen (2; 29-31). In fact, the high "on"- and "off"-rates reported for the GPVI-ligand interaction (22) are consistent with the role of GPVI as a tethering receptor.

The present invention identifies Fc-GPVI-nt as an active ingredient of a medicament to attenuate arterial thrombosis following vascular injury. This concept is further supported by the observation that Fc-GPVI-nt is targeted to the exposed subendothelium at the site of vascular injury, as demonstrated by immunohistochemistry. This implicates that inhibition of GPVI-collagen interactions are likely to be restricted to the site of vascular injury, while a prolonged systemic inhibition of platelet function is limited by the expected short half-life of unbound Fc-GPVI-nt. In contrast, administration of monoclonal antibodies directed against GPVI inevitably leads to systemic inhibition of GPVI on all circulating platelets. In addition, Fc-GPVI-nt administration did not affect platelet counts. In contrast, anti-GPVI mAbs may eventually induce immune thrombocytopenia or a complete loss of GPVI on circulating platelets (14; 32), hampering their use in clinical practice. Accordingly, Fc-GPVI-nt therapy will likely be associated with a lower risk of clinical hemorrhage, compared to anti-GPVI mAb-based strategies.

Platelet adhesion and aggregation at sites of vascular injury is crucial for hemostasis but may lead to arterial occlusion in the setting of atherosclerosis and precipitate diseases such as coronary thrombosis and myocardial infarction. The use of intravenous GPIIb-IIIa receptor inhibitors, has significantly improved the clinical success of patients undergoing coronary stenting (33-35). However, severe bleeding complications have been reported to hamper the outcome of patients treated with abciximab (36). The present invention demonstrates that inhibition of GPVI-collagen interactions by Fc-GPVI-nt was sufficient to significantly reduce platelet adhesion both in vitro and in vivo; however, the soluble form of GPVI only moderately prolonged tail bleeding times. Similarly, mild bleeding disorders have been reported in patients with GPVI-deficient platelets (37), indicating that coagulation and hemostasis are effective even in the complete absence of GPVI. In part this discrepancy may be due to the fact that inhibition or absence of GPVI does not interfere with platelet aggregation in response to platelet agonists other than collagen, e.g. ADP, tissue factor or thrombin. In contrast, direct inhibition of GPIIb-IIIa, e.g. by 7E3 or its humanized derivative, blocks fibrinogen binding to platelets, a process which is essential for platelet aggregation, and substantially attenuates platelet aggregation to most platelet agonist known thus far. Accordingly, Fc-GPVI-nt therapy are associated with a lower risk of clinical hemorrhage, compared to anti-GPIIb-IIIa-based strategies.

In conclusion, the present invention provides the first in vivo evidence that Fc-GPVI-nt attenuates platelet adhesion under flow in vitro and following endothelial denudation in the carotid artery of mice in vivo. This further supports the concept that GPVI-collagen interactions play a central role in all major phases of thrombus formation, i.e. platelet tethering, firm adhesion, and aggregation at sites of arterial injury (e.g. during acute coronary syndromes). The present invention further supports the concept that GPVI plays a major role in the progression of atherosclerosis. Moreover, the present invention shows for the first time the causal connection between GPVI and diabetes.

This specification includes by reference the entire content of all of U.S. patent application Ser. No. 10/489,053, U.S. patent application Ser. No. 11/009,106 and International patent application No PCT/EP2004/013779 (WO 2005/054294), from all of which priority is claimed. Included herein by reference are therefore all the examples, drawings and sequences of said applications, In this respect, the examples, drawings and sequence numbers of this specification correspond to those of said applications as follows:

Examples 1 to 23 correspond to Examples 1 to 23 of U.S. patent application Ser. Nos. 10/489,053, and 11/009,106; Examples 24 to 34 correspond to text following the heading "Materials and Methods of PCT/EP2004/013779 but include some additional matter;

FIGS. 1 to 18 correspond to FIGS. 1 to 18 of U.S. patent application Ser. Nos. 10/489,053, and 11/009,106; FIGS. 19 to 27 correspond to FIGS. 1 to 9 of PCT/EP2004/013779; FIGS. 20 to 32 correspond to FIGS. 11 to 15 of PCT/EP2004/013779;

SEQ ID NOs: 147 and 148 correspond to SEQ ID NOs: 1 and 2 of U.S. patent application Ser. No. 10/489,053; SEQ ID NOs: 149 and 152 correspond to SEQ ID NOs: 8 to 11 PCT/EP2004/013779. The sequences of the prior applications are incorporated by reference herein.

The invention will now be described in further detail with reference to the following specific examples.

The following methods and examples represent a way of producing or obtaining an agent of the present invention. It will be apparent to the skilled person that alternative methods are available to obtain the agent of the invention.

EXAMPLES

Animals. Specific pathogen-free C57BL6/J mice were obtained from Charles River (Sulzfeld, Germany). For experiments, 12-weeks-old male mice were used. All experimental procedures performed on animals were approved by the German legislation on protection of animals.

Monoclonal antibodies. Monoclonal antibody (mAb) anti GPVI (JAQ1) and anti GPIb_(p0p/B) and Fab fragments from JAQ and p0p/B were generated as described (Bergmeier, W., Rackebrandt, K., Schroder, W., Zirngibl, H. & Nieswandt, B. Structural and functional characterization of the mouse von Willebrand factor receptor GPIb-IX with novel monoclonal antibodies. *Blood* 2000; 95, 886-893; Nieswandt, B., Bergmeier, W., Rackebrandt, K., Gessner, J. E. & Zirngibl, H. Identification of critical antigen-specific mechanisms in the development of immune thrombocytopenic purpura in mice. Blood 2000; 96, 2520-2527). Irrelevant control rat IgG was obtained from Pharmingen (Hamburg, Germany).

Generation of GPVI-Deficient Mice.

To generate mice lacking GPVI, C57BL6/J wild-type mice were injected with 100_g JAQ1 i.c. Animals were used for in vivo assessment of platelet adhesion on day 5 after mAb injection. Absence of GPVI expression on platelets was verified by Western blot analysis and flow cytometry.

Flow Cytometry

Heparinized whole blood, obtained from wild type C57BL6/J mice or GPVI-depleted mice was diluted 1:30 with modified Tyrodes-HEPES buffer (134 mM NaCl, 0.34 mM $Na_2HPO_4$, 2.9 mM KCl, 12 mM $NaHCO_3$, 20 mM HEPES, 5 mM glucose, and 1 mM $MgCl_2$, pH 6.6). The samples were incubated with fluorophor-labeled mAb anti-GPVI (JAQ1) and anti-CD41 for 10 min at room temperature and directly analyzed on a FACScan™ (Becton Dickinson).

Cloning, viral expression and purification of soluble human and murine GPVI. To generate a soluble form of human GPVI, the extracellular domain of human GPVI was cloned and fused to the human immunoglobin Fc domain according to the following examples 1 to 3. Adenoviral constructs coding for the GPVI-Fc-fusion protein or control Fc were prepared to generate the recombinant protein. GPVI-Fc and control Fc were expressed as secreted soluble proteins using the human HELA cell line to prevent misfolding and non-glycosylation of the expressed proteins.

Example 1

Cloning of the Immunoadhesin of GP VI (Fc-GPVI-Nt)

We generated an immunoadhesin of the GP VI receptor by generating a recombinant fusion protein of the n-terminal part of GP VI—which encodes the extracellular domain of GPVI—together with the Fc part of an IgG. The Fc was amplified from a human heart cDNA library (Clonetech, Palo Alto, Calif.) by PCR using the forward primer 5'-cgcggggcg-gccgcgagt-ccaaatcttgtgacaaaac-3' and the reverse primer 5'-gcgggaagctttcatttacccggagacagggag-3'. The PCR reaction was performed at 58° C. annealing temperature and 20 cycles with the Expand High Fidelity PCR Sytem (Roche Molecular Biochemicals, Mannheim, Germany). The PCR fragment was cloned in the plasmid pADTrack CMV with NotI/HindIII and the sequence was checked by sequencing (MediGenomix, Martinsried, Germany).

For cloning of the extracellular domain of the human GPVI RNA from cultured megakaryocytes was isolated (RNeasy Mini Kit; Qiagen, Hilden, Germany) according to the manufacters protocol and reverse transcription was performed (Omniscript RT Kit; Qiagen) with 2 μg RNA at 37° C. overnight. 100 ng of the reaction was used as a template in PCR amplification of the hGPVI with the primer 5'-gcggggagatc-taccaccatgtctccatccccgacc-3' and 5'-cgcggggcggccgccgttgc-ccttggtgtagtac-3'. The PCR reaction was performed at 54° C. annealing temperature and 24 cycles with the Expand High Fidelity PCR Sytem (Roche Molecular Biochemicals, Mannheim, Germany). The PCR fragment was cloned in the plasmid pDATrack CMV Fc with BglII/NotI and the sequence was checked by sequencing.

Construction of a Monomeric Fusion Protein Based on Fc-GPVI-Nt

The Fc monomer fragment was amplified by PCR using the primer pair 5'-cgcggggcggccgcccagcacctgaactcctg-3' and 5'-cgcggggatatctcatttacccggagacagggag-3' and pADTrack CMV gpVI-Fc as a template. The PCR reaction was performed at 58° C. annealing temperature and 20 cycles with the Expand High Fidelity PCR Sytem (Roche Molecular Biochemicals, Mannheim, Germany). The Fc monomer PCR fragment (NotI/EcoRV) and the gpVI fragment from pADTrack CMV gpVI-Fc (BglII/NotI) were cloned as described above.

Example 2

Generation of the Adenovirus for Fc-GPVI-Nt (Ad-Fc-GPVI-Nt)

The plasmid pADTrack CMV Fc-GPVI-nt was linearized with PmeI (New England Biolabs, Beverly, Mass.) overnight, dephosphorylated and purified (GFX DNA and Gel Purification Kit; Amersham Pharmacia Biotech, Uppsala, Sweden). For recombination electrocompetent *E. coli* BJ5183 (Stratagene, La Jolla, Calif.) were cotransformed with 1 μg of the linearized plasmid and 0.1 μg pAdeasyl at 2500 V, 200☐ and 25 μFD (*E. coli*-pulser; Biorad, Heidelberg, Germany), plated and incubated overnight at 37° C. The colonies were checked after minipreparation of the plasmid-DNA with PacI and the positive clones were retransformed in *E. coli* DH5_.

For transfection (Effectene Transfection reagent; Qiagen, Hilden, Germany) of 293 cells plasmid-DNA was digested with PacI. The cells were cultured for 7 days and harvested by scraping and centrifugation. The pellet was resuspended in Dulbecco's PBS and the cells were lysed by four repetitive freezing (−80° C.) and thawing (37° C.) cycles. Cell debris was removed by centrifugation and the lysate stored at −80° C.

For plaque selection of recombinant virus 293 cells are infected in Dulbeccos PBS for 1 hour at room temperature under gentle agitation with different serial dilutions of lysate from transfection. Following the infection, the cells are overlayed with growth medium containing 0.5% agarose (1:1 mix of modified Eagles medium 2x, Gibco Life Technologies # 21935, supplemented with 20% serum, 2× Penicillin/Streptomycin, 2×L-glutamin and agarose in water 1%, Seacam). 5-14 days post infection the cell layer was monitored for formation of plaques which were picked using a pasteur pipett, resuspended in 0.5 ml Dulbeccos PBS and stored at −80° C. The plaques were used for further amplification rounds on 293 cells.

Construction of Human gpVI-Fc Monomer Expressing Stable Cho

The monomer expressing cells were generated in accordance with example 2.

Example 3

Fc-GPVI-Nt Protein and Fc Control Immunoadhesin Purification

The culture supernatant of Ad-Fc-GPVI-nt-infected Hela cells was collected 2 days after infection, centrifugated (3800 g, 30 min, 4° C.) and filtrated (0.45 μm). The immunoadhesin was precipitated by addition of 1 vol. ammonium sulfate (761 g/l) and stirred overnight at 4° C. The proteins were pelleted by centrifugation (3000 g, 30 min, 4° C.), dissolved in 0.1 Vol PBS and dialysed in PBS overnight at 4° C. The protein solution was clarified by centrifugation (3000 g, 30 min, 4° C.) and loaded on a protein A column (HiTrap™ protein A HP, Amersham Pharmacia Biotech AB, Uppsala, Sweden). The column was washed with binding buffer (20 mM sodium phosphate buffer pH 7.0, 0.02% $NaN_3$) until $OD_{280}$ ☐0.01 and eluted with elution buffer (100 mM glycine pH 2.7). The eluted fractions were neutralized with neutralisation buffer (1 M Tris/HCl pH 9.0, 0.02% $NaN_3$), pooled, dialysed in PBS overnight at 4° C., aliquotated and frozen at −20° C.

The molecular mass of Fc-GPVI-nt protein was ~80 kDa under reducing conditions in SDS-PAGE, as detected by Coomassie blue stain or by immunoblotting with peroxidase-conjugated goat anti-human Fc antibody or by the anti-GPVI mAb 5C4 (FIG. 1a, upper and middle panel). In contrast, a ~160 kDa protein was identified under non-reducing conditions (FIG. 1a, lower panel), supporting the notion that GPVI-Fc is obtained solely as dimer (21).

Example 4

GP VI Inhibitor Screening Assay

ELISA plates (Immulon2 HB, Dynx Technologies, Chantilly, Va.) were coated overnight at 4° C. with 1 μg/well collagen (type I bovine; BD Bioscience, Bedford, Mass.) in 100 μl 50 mM Tris/HCl pH 8.0. The plate was washed with 250 μl/well PBS/0.05% Tween 20 (PBST) twice and blocked with 250 μl/well Roti-Block (Roth, Karlsruhe, Germany) overnight. The plate was washed with 250 μl/well PBST twice, 100 μl Fc-GPVI-nt in PBST was added (optimal 2 μg/well) and the plate was incubated for 1 h at room temperature. After 5-fold washing with 250 μl PBST 100 μl peroxidase-conjugated goat anti-humanIgG antibody (Dianova, Hamburg, Germany) was added in a dilution of 1:10000 and incubated for 1 h at room temperature. After repeated washing with 250 μl PBST 100 μl detection reagent (BM Blue POD Substrate; Roche, Mannheim, Germany) was added and incubated for 15 min. The reaction was stopped by the addition of 100 μl 1 M $H_2SO_4$ and the plate was measured at 450 nm against the reference wavelength 690 nm. To screen for potential inhibitors, test compounds are added to the incubation in 100 μl PBST at various concentrations.

Example 5

Platelet Aggregation and Luminometry

Platelet aggregation ex vivo and in vitro was evaluated by optical aggregometry in citrated blood samples at 37° C. using a two channel Chronolog aggregometer (Nobis, Germany). Platelet-rich plasma was prepared from citrated whole blood by centrifugation (200 g for 20 min). The final platelet count was adjusted to $2\times10^8$ platelets/ml with autologous plasma. After adjustment of the baseline, collagen (type I, bovine) from 0.2 to 4 μg/ml was added and aggregation was recorded for 5 min. Simultaneously, release of ATP was recorded using the firefly luminometer method. Incubation with the monoclonal GP VI antibody JAQ 1 was performed for 15 min with 50 μg/ml antibody.

Example 6

In Vitro Platelet Adhesion Assay for GP VI/Collagen Interaction

From ACD (20% final concentration) blood platelet rich plasma was prepared and adjusted to a final concentration of 108 platelets/ml by Hepes Tyrode (pH 6.5). Coverslips were coated with monolayers of various adhesive proteins (Collagen, vWF) at different concentrations. Perfusion studies were carried out in a perfusion chamber generated from glass coverslips. Perfusion was performed at shear rates of 500/s representing low-medium flow and 2000/s representing high shear rates. Adhesion was measured at 37° C. for 20 minutes and then drawn through the chamber at fixed wall shear rates for 5 minutes using an automated syringe pump. After perfusion the coverslips were gently washed with Hepes Tyrode, taken from the chamber. Coverslips were repeatedly washed with Hepes Tyrode to completely remove adhesive platelets. The platelets in suspension were quantitatively analysed by FACS measurements. The analysis of the functional status of platelets was further assessed by analysis of surface marker expression (CD 41; CD 61 and CD 62 P) according to the standard flow cytometry protocol.

Example 7

Preparation of Platelets for Intra Vital Microscopy

Platelets (wild type, or GPVI-deficient) were isolated from whole blood as described (Massberg, S. et al. Platelet-endothelial cell interactions during ischemia/reperfusion: the role of P-selectin. Blood 1998; 92, 507-515) and labeled with 5-carboxyfluorescein diacetat succinimidyl ester (DCF). The DCF-labeled platelet suspension was adjusted to a final concentration of $200\times10^6$ platelets/250 μl. Where indicated, fluorescent wild type platelets were preincubated with 50 μg/ml anti-GPVI (JAQ1) Fab fragments, or anti GPIb (p0p/B) Fab fragments for 10 min. Subsequently, the pretreated platelets together with the Fab fragments were infused into wild type recipient mice and platelet adhesion was assessed prior to and after carotid injury by in vivo video microscopy, as described below.

Example 8

Assessment of Platelet Adhesion and Aggregation by Intravital Microscopy

Wild type C57BL6/J or GPVI-deficient mice were anesthetized by intraperitoneal injection of a solution of midazolame (5 mg/kg body weight, Ratiopharm, Ulm, Germany), medetomidine (0.5 mg/kg body weight, Pfizer, Karlsruhe, Germany), and fentanyl (0.05 mg/kg body weight, CuraMed Pharma GmbH, Munich, Germany). Polyethylene catheters (Portex, Hythe, England) were implanted into the right jugular vein and fluorescent platelets ($200 \times 10^6/250$ µl) were infused intravenously. The right common carotid artery was dissected free and ligated vigorously near the carotid bifurcation for 5 min to induce vascular injury. Prior to and following vascular injury, the fluorescent platelets were visualized in situ by in vivo video microscopy of the right common carotid artery. Platelet-vessel wall interactions were monitored using a Zeiss Axiotech microscope (20× water immersion objective, W 20×/0.5, Zeiss) with a 100 W HBO mercury lamp for epi-illumination. All video-taped images were evaluated using a computer-assisted image analysis program (Cap Image 7.4, Dr. Zeintl, Heidelberg, Germany). Transiently adherent platelets were defined as cells crossing an imaginary perpendicular through the vessel at a velocity significantly lower than the centerline velocity; their numbers are given as cells per $mm^2$ endothelial surface. The number of adherent platelets was assessed by counting the cells that did not move or detach from the endothelial surface within 10 seconds. The number of platelet aggregates at the site of vascular injury was also quantified and is presented per $mm^2$.

Example 9

Scanning Electron Microscopy

Following intravital videofluorescence microscopy, the carotid artery was perfused with PBS (37° C.) for 1 min, followed by perfusion fixation with phosphate-buffered glutaraldehyde (1% vol/vol). The carotid artery was excised, opened longitudinally, further fixed by immersion in 1% PBS-buffered glutaraldehyde for 12 hours, dehydrated in ethanol, and processed by critical point drying with $CO_2$. Subsequently, the carotid artery specimens were oriented with the lumen exposed, mounted with carbon paint, sputter coated with platinum, and examined using a field emission scanning electron microscope (JSM-6300F, Jeol Ltd., Tokyo, Japan).

Example 10

Assessment of fc-GPVI-nt binding to immobilized collagen. The binding of Fc-GPVI-nt to immobilized collagen was determined. ELISA plates (Immulon2 HB, Dynx Technologies, Chantilly, Va.) were coated over night at 4° C. with 1 µg collagen (typI bovine; BD Bioscience, Bedford, Mass.) in 100 µl coating buffer (1.59 g/l $Na_2CO_3$, 2.93 g/l $NaHCO_3$, 0.2 g/l $NaN_3$, pH 9.6). The plates were washed with 250 µl/well PBS/0.05% Tween 20 (PBST) twice and blocked with 250 µl/well Roti-Block (Roth, Karlsruhe, Germany) over night. The plates were washed with 250 µl/well PBST twice, then 3.0, 6.0, 12.5, 25.0, 50.0 or 100 µg/ml Fc-GPVI-nt in PBST was added and the plate was incubated for 1 hr at room temperature. Where indicated, Fc-GPVI-nt (20 µg/ml) was preincubated for 10 min with soluble collagen. After incubation the plates were washed 5 times with 250 µl PBST and peroxidase-conjugated goat anti-human IgG antibody Fc_fragment specific (109-035-098; Dianova, Hamburg, Germany) was added in a dilution of 1:10.000 and incubated for 1 hr at room temperature. After 5 fold washing with 250 µl PBST 100 µl detection reagent (BM Blue POD Substrate; Roche, Mannheim, Germany) was added and incubated up to 10 min. The reaction was stopped by the addition of 100 µl 1 M $H_2SO_4$ and the plate was measured at 450 nm against reference wavelength 690 nm.

Fc-GPVI-nt showed a dose-dependent and saturable binding to immobilized collagen (FIG. 9b). Half maximal collagen binding was observed at a final Fc-GPVI-nt concentration of 6.0 µg/ml. Binding of GPVI-Fc did not occur to BSA, vWF (FIG. 9c, left panel) or Poly-L-Lysin (not shown), supporting the specificity of Fc-GPVI-nt binding. Moreover, we did not detect any significant binding of the control Fc protein lacking the external GPVI domain under identical conditions (FIG. 9c, right panel).

To further address the specificity of GPVI-binding, we the ability of solubilized fibrillar collagen to compete with immobilized collagen for the association with Fc-GPVI-nt was tested. Soluble collagen inhibited Fc-GPVI-nt-binding to immobilized collagen in a dose-dependent manner (FIG. 9d). A concentration of 100 µg/ml soluble collagen was required to reduce Fc-GPVI-nt binding by more than 50%. Together, these data indicated that Fc-GPVI-nt binding to collagen is specific and characterized by high affinity.

Example 11

Generation of monoclonal antibody against human GPVI. Monoclonal antibodies were generated essentially as described (17). Lou/C rats were immunized with the adenovirally expressed human Fc-GPVI-nt fusion protein. Screening of hybridoma supernatants was performed in a solid-phase immunoassay using Fc-GPVI-nt or FC lacking the GPVI domain. Screening identified the supernatant of hybridoma 5C4 to bind specifically to Fc-GPVI-nt but not to Fc lacking the external GPVI domain. The immunoglobulin type was determined with rat Ig class (anti-IgM) and IgG subclass-specific mouse mAbs. The monoclonal antibodies were purified using Protein G-Sepharose columns. Antibody specificity of 5C4 was verified by immunoblotting against Fc-GPVI-nt and control Fc. 5C4 monoclonal antibody detected adenovirally expressed Fc-GPVI-nt but not control Fc. Furthermore, human GPVI was recovered in lysates obtained from human platelets. In addition, 5C4 binds specifically to the surface of platelets but not of leukocytes or red blood cells, as demonstrated using flow cytometry (not shown).

Example 12

FACS measurement of CD62 P externalisation. Human citrate blood was collected from volunteers. Platelet rich plasma (PRP) was generated after centrifugation and washing procedures (PBS 1×; pH 7.2) with 2000 rµm at 4° C. and resuspension. PRP diluted in staining buffer (1×PBS (w/o $Ca^{2+}$ and $Mg^+$) with 0.1% sodium azide and 2% fetal bovine serum (FBS), 2 mM CaCl) was incubated with equine collagen type 1 (0; 2; 5 and 10 µg/ml; Nobis) in the presence of Fc-GPVI-nt (100 µg/ml) or equimolar concentrations control Fc. Anti CD 62P antibodies labelled with the fluorophor peroxidase (Immunotech) were added. FACS measurement was performed with an Becton Dickenson FACScalibur device.

Increasing concentrations of collagen led to platelet secretion from alpha granules indicated by CD 62P externalisation. Co-incubation of collagen with Fc-GPVI-nt blunted the CD62 P externalisation determined by FACS (FIG. 10).

Example 13

Platelet aggregation and ATP release. PRP was generated as described above. Aggregation was determined in a Whole- Blood-Aggregometer 500VS (Chrono-Log Corporation). Platelet cell number from PRP was adjusted to $1.0 \times 10^8$ cells/ml by Thyrodes-HEPES buffer (2.5 mmol/l HEPES, 150 mmol/l NaCl, 12 mmol/l NaHCO$_3$, 2,5 mmol/l KCl, 1 mmol/l MgCl$_2$, 2 mmol/l CaCl$_2$, 5,5 mmol D-Glucose, 1 mg/ml BSA, pH 7.4). Chrono-Lume #395 (Chrono-Log Corporation) was added for ATP measurement. Agonists were added to the platelets, pipetted into the aggregometer and aggregation was started under defined stirring conditions. Aggregation was determined by change of light transmission due to coagulating platelets and normalised to an internal standard. ATP release is determined at the characteristic wavelength of Chrono-Lume for ATP and normalised to an internal standard according to the manufacturer's instructions.

Platelet aggregation and ATP release was specifically inhibited by Fc-GPVI-nt for collagen mediated agonist stimulation (FIG. 11 a & b). ADP- and thrombin-mediated (TRAP 10 μM) platelet aggregation and ATP release was unaffected by Fc-GPVI-nt.

Example 14

PDGF release from human platelets. PRP from human volunteers was prepared as described above. PDGF release from human platelets was determined with a kit system (R & D Systems #DHD00B) according to the manufacturer's instructions. PDGF release was stimulated with collagen type 1 (20 μg/ml; Nobis) under control conditions and in the presence of Fc-GPVI-nt (100 μg/ml) or equimolar concentrations of control Fc. PDGF release is normalised to the manufacturer's standard probe.

PDGF release as an indicator for release of endogenous transmitters from alpha granules of platelets was also blunted after collagen stimulation. (FIG. 11c)

Example 15

Effect of Fc-GPVI-nt on bleeding time from human whole blood in vitro. In vitro bleeding time was determined with an PFA-100 device (Dade-Behring). 800 μl of human whole blood was injected in the PFA-100 device. Bleeding time was measured with ADP/collagen and epinephrine/collagen coated measuring cells according to the manufacturer's instructions.

There was no significant prolongation of bleeding time in vitro (PFA-100 device) with increasing concentrations of Fc-GPVI-nt after different agonist stimulations. In contrast, therapeutically relevant concentrations of ReoPro maximally prolonged bleeding time in the PFA-100 device (FIG. 12)

Example 16

Effect of soluble GPVI on platelet adhesion to immobilized collagen under flow. Human platelets were isolated from ADC-anticoagulated whole blood as described (18). Washed platelets were resuspended in Tyrodes-HEPES buffer (2.5 mmol/l HEPES, 150 mmol/l NaCl, 12 mmol/l NaHCO$_3$, 2,5 mmol/l KCl, 1 mmol/l MgCl$_2$, 2 mmol/l CaCl$_2$, 5.5 mmol D-Glucose, 1 mg/ml BSA, pH 7.4) to obtain a platelet count of $2 \times 10^8$ cells/ml. Adhesion of platelets to plates coated with immobilized collagen was determined in a parallel plate flow chamber in the presence of 200_g/ml Fc-GPVI-nt or control Fc.

GPVI plays a crucial role in the process of platelet recruitment to immobilized collagen in vitro (22). We determined the effect of Fc-GPVI-nt on adhesion of human platelets to immobilized collagen under shear conditions in vitro. As reported by others earlier (23), platelets adhered firmly to immobilized collagen at both low (500 sec$^{-1}$) and high (1000 sec$^{-1}$) shear rates forming thrombi (FIG. 13). Soluble Fc-GPVI-nt, but not control Fc lacking the external GPVI domain, significantly attenuated platelet adhesion on immobilized collagen by 37 and 44% at shear rates of 500 sec$^{-1}$ and 1000 sec$^{-1}$, respectively (FIG. 13). Inhibition was specific since Fc-GPVI-nt did not affect platelet adhesion to immobilized vWF.

Example 17

Determination of Fc-GPVI-nt plasma concentrations was carried out with an IMMUNO-TEK ELISA system for the quantitative determination of human IgG (ZeptoMetrix Corporation; Cat # 0801182). Specific peroxidase conjugated goat anti-human IgG antibodies against the Fc part of the Fc-GPVI-nt are used (Dianova). After several washing steps with PBS-T according to the manufacturer's specifications peroxidase substrate (BM Blue POD, Roche) is added and measured at the characteristic 450 nm wavelength in an ELISA assay reader (Tecan Sunrise). The Fc-GPVI-nt concentration is quantified by comparison to an internal human IgG standard. Fc-GPVI-nt showed favourable in vivo pharmacokinetics. After single intraperitoneal injection in mice high plasma levels were measurable after 24 hours and the half life of the fusion protein exceeded 96 hours (FIG. 14a). Repeated intraperitoneal injection was leading to blood accumulation of the fusion protein (FIG. 14b) suggesting favourable kinetics for long term application for the treatment of chronic diseases. After single intravenous injection of Fc-GPVI-nt with increasing doses, dose-dependent plasma concentrations of Fc-GPVI-nt were detectable over 5 to 60 minutes up to 14 hours (FIG. 14c).

Example 18

Preparation of murine platelets for intravital fluorescence microscopy. Murine platelets were isolated from whole blood and labeled with 5-carboxyfluorescein diacetate succinimidyl ester (DCF) as reported earlier (19). The DCF-labeled platelet suspension was adjusted to a final concentration of $200 \times 10^6$ platelets/250 μl. Adhesion of murine platelets was assessed prior to and after carotid injury by in vivo video microscopy, as described below.

Example 19

Carotid ligation and assessment of platelet adhesion and aggregation by intravital microscopy. Platelet recruitment following endothelial denudation was performed as reported earlier (3). In brief, wild type C57BL6/J mice were anesthetized by intraperitoneal injection of a solution of midazolame (5 mg/kg body weight, Ratiopharm, Ulm, Germany), medetomidine (0.5 mg/kg body weight, Pfizer, Karlsruhe, Germany), and fentanyl (0.05 mg/kg body weight, CuraMed Pharma GmbH, Munich, Germany). Where indicated, Fc-GPVI-nt (1 or 2 mg/kg body weight) or control Fc in an amount equimolar to 2 mg/kg Fc-GPVI-nt was administered intravenously. Thereafter, endothelial denudation was induced near the carotid bifurcation by vigorous ligation for 5 min. Following induction of vascular injury fluorescent platelets ($200 \times 10^6$/250 μl) were infused intravenously via polyethylene catheters (Portex, Hythe, England) implanted into the right jugular vein. The fluorescent platelets were visualized in situ by in vivo video microscopy of the right common carotid artery using a Zeiss Axiotech microscope (20× water immersion objective, W 20×/0.5, Zeiss) with a 100 W HBO mercury lamp for epi-illumination. All video-taped images were evaluated using a computer-assisted image analysis program (Cap Image 7.4, Dr. Zeintl, Heidelberg, Germany (19; 20)). Tethered platelets were defined as all cells establishing initial contact with the vessel wall, followed by slow surface translocation (at a velocity significantly lower than the centerline velocity) or by firm adhesion; their numbers are given as cells per mm² endothelial surface. The number of adherent platelets was assessed by counting the cells that did not move or detach from the endothelial surface within 10 seconds. The number of platelet aggregates at the site of vascular injury was also quantified and is presented per mm². In addition, the total thrombus area was assessed using Cap Image 7.4.

Example 20

Scanning electron microscopy. Following intravital videofluorescence microscopy, the carotid artery was perfused with PBS (37° C.) for 1 min in three animals per group, followed by perfusion fixation with phosphate-buffered glutaraldehyde (1% vol/vol). The carotid artery was excised, opened longitudinally, further fixed by immersion in 1% PBS-buffered glutaraldehyde for 12 hours, dehydrated in ethanol, and processed by critical point drying with $CO_2$. Subsequently, the carotid artery specimens were oriented with the lumen exposed, mounted with carbon paint, sputter coated with platinum, and examined using a field emission scanning electron microscope (JSM-6300F, Jeol Ltd., Tokyo, Japan).

Example 21

Assessment of in vivo Fc-GPVI-nt binding by immunohistochemistry. Carotid arteries obtained from mice treated with Fc-GPVI-nt were shock frozen and embedded in cryoblocks (medite, Medizintechnik GmbH, Burgdorf, Germany). The binding of Fc-GPVI-nt to the endothelium and subendothelium was determined on 5 μm cryostat sections, stained with peroxidase-conjugated goat anti-human IgG antibody Fc_fragment specific (109-035-098; Dianova, Hamburg, Germany). Carotid arteries obtained from Fc-treated mice served as controls.

Example 22

Effect of soluble GPVI on platelet counts, bleeding time and platelet adhesion in vivo. Animals were treated with 2 mg/kg or 4 mg/kg Fc-GPVI-nt or equimolar doses of control Fc lacking the external GPVI domain. Infusion of Fc-GPVI-nt or control Fc even at the highest dose of 4 mg/kg had not significant effects on peripheral platelet counts. Moreover, the Fc-GPVI-nt fusion protein, did not induce any significant prolongation of tail bleeding times compared to control animals (FIG. 15a). The absolute bleeding times were 1.9±0.9 in PBS treated mice and 2.9±1.9 min and 4.6±0.6 min in mice treated with 2 mg/kg or 4 mg/kg Fc-GPVI-nt. In contrast, bleeding times were prolonged considerably (42.6±21.6) in Integrilin-treated animals (0.2 mg per kg IV).

Figure 15D:
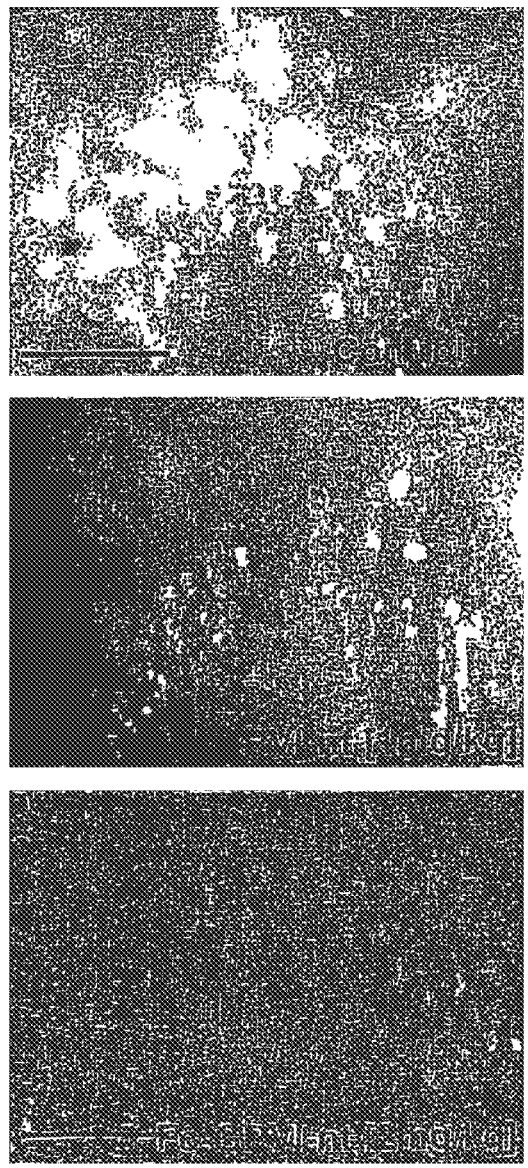

The effects of Fc-GPVI-nt on platelet recruitment in a mouse model of carotid injury may be studied using intravital fluorescence microscopy. Animals were treated with 1 mg/kg or 2 mg/kg Fc-GPVI-nt or an equimolar amount of control Fc lacking the external GPVI domain as described above. After infusion of Fc-GPVI-nt or control Fc endothelial denudation of the mouse carotid artery was induced by vigorous ligation as reported previously (3). Ligation of the carotid artery consistently caused complete loss of the endothelial cell layer. Platelet adhesion was directly visualized and quantified using in vivo fluorescence microscopy (19; 20) (FIG. 15 d). In control (Fc-treated) mice numerous platelets were tethered to the vascular wall within the first minutes after endothelial denudation (12.026±1.115 tethered platelets/mm²). Platelets establishing contact with the subendothelium exhibited initially a slow surface translocation, which is frequently followed by subsequent firm platelet adhesion and platelet aggregation (5.494±874 adherent platelets/mm² and 114±17 platelet thrombi/mm²). In contrast, in the presence of Fc-GPVI-nt platelet recruitment to the site of vascular injury was dramatically attenuated. Platelet tethering was reduced by 65 and 71% compared to Fc-treated animals following pretreatment with 1 mg/kg or 2 mg/kg Fc-GPVI-nt ($P<0.05$ vs. control). In parallel, firm platelet adhesion was reduced in a dose-dependent manner (by 49 and 65% following administration of 1 mg/kg or 2 mg/kg Fc-GPVI-nt, respectively; $P<0.05$ vs. control). Likewise, aggregation of adherent platelets was virtually absent in animals treated with 2 mg/kg Fc-GPVI-nt fusion protein ($P<0.05$ vs. control Fc, FIG. 15b-d). Scanning electron microscopy also clearly demonstrated that platelet adhesion and aggregation following endothelial denudation of the common carotid artery were virtually absent in Fc-GPVI-nt treated, but not in FC-pretreated mice (FIG. 15e). To confirm the presence of Fc-GPVI-nt at the site of injury, the carotid arteries were excised following in vivo microscopy and processed further for immunohistochemistry using peroxidase-conjugated goat anti-human IgG antibodies. In Fc-GPVI-nt-treated mice Fc-GPVI-nt was detected on at the luminal aspect of the site of vascular damage (FIG. 15 f). Together, these data demonstrate that Fc-GPVI-nt specifically binds to sites of vascular injury in vivo and prevents subsequent platelet recruitment.

Effect of soluble GPVI on atherosclerosis. 4 weeks old apoE−/− mice (The Jackson Laboratory) consumed a 0.25% cholesterol diet (Harlan Research diets) for 6 weeks. After 2 weeks 4 apoE−/− mice were injected with Fc-GPVI-nt 200 μg per mouse twice weekly with continuos cholesterol diet. 4 apoE−/− mice with the similar protocol were injected with the control Fc protein (200 μg) twice weekly and served as control mice. For assessment of plaque formation the animals were killed and the vascular tree was carefully dissected from the animals. The whole preparations of the aortae and carotids were flushed with 0.9% sodium chloride and fixed. The complete vascular preparation was stained with SUDAN III red to assess plaque formation and viewed under a microscope. Treatment of atherosclerosis prone apoE−/− knockout mice with Fc-GPVI-nt over 4 weeks significantly attenuated atheroprogression. (FIG. 16).

Example 23

FACS measurement of CD61 and CD32 surface expression on platelets from diabetic patients. Human citrate blood was collected from 111 patients suffering from diabetes or from 363 non-diabetic patients. Platelet rich plasma (PRP) was generated after centrifugation and washing procedures (PBS 1×, pH 7.2) with 2000 rpm at 4° C. and resuspension. Anti CD61 and anti CD32 antibodies labelled with the fluorophor peroxidase (Immunotech) were added or the anti monoclonal anti-GPVI antibody 4C9 labelled with FITC. FACS measurement was performed with an Becton Dickenson FACScalibur device. Surface expression was quantified by fluorescence. Correlation of CD32 fluorescence and 4C9 fluorescence was calculated with the correlation coefficient r=0.516.

Statistical Analysis. Comparisons between group means were performed using Mann-Whitney Rank Sum Test. Data represent mean±s.e.m. A value of P<0.05 was regarded as significant.

Example 24

Generation of monoclonal antibodies against human GPVI. Monoclonal antibodies were generated essentially as described (Kremmer, E., Kranz, B. R., Hille, A., Klein, K., Eulitz, M., Hoffmann-Fezer, G., Feiden, W., Herrmann, K., Delecluse, H. J., Delsol, G., Bornkamm, G. W., Mueller-Lantzsch, N., Grassert, F. A. (1995) Rat monoclonal antibodies differentiating between the Epstein-Barr virus nuclear antigens 2A (EBNA2A) and 2B (EBNA2B). *Virology* 208, 336-342). Lou/C rats were immunized with human dimeric Fc-GPVI-nt fusion protein having the amino acid sequence as shown in FIG. 10. Screening of hybridoma supernatants was performed in a solid-phase immunoassay using dimeric Fc-GPVI-nt or Fc lacking the GPVI domain. Screening identified the supernatant of hybridoma different antibodies to bind specifically to dimeric Fc-GPVI-nt but not to Fc lacking the external GPVI domain. The immunoglobulin type was determined with rat Ig class (anti-IgM) and IgG subclass-specific mouse mAbs. The monoclonal antibodies were purified using Protein G-Sepharose columns. Antibody specificity of hGP 5C4 was verified by immunoblotting against dimericFc-GPVI-nt and control Fc. hGP 5C4 monoclonal antibody detected recombinant dimeric Fc-GPVI-nt but not control Fc (see FIG. 19a, top). Furthermore, hGP 5C4 binds specifically to the surface of human platelets (see FIG. 19a, bottom).

Example 25

Generation of Fab-fragments of monoclonal IgG antibodies. Complete IgG antibodies were digested to generate Fab-fragments of anti-GPVI antibodies with ImmunoPure Fab Kit (Pierce Biotechnology, Inc., Rockford, Ill., USA) according to the manufacturer's instructions. Accordingly, IgG molecules were digested into Fab fragments and Fc fragments by using immobilized papain. After digestion, the fragments were purified on an immobilized Protein A column. Detailed instructions allow for flexibility in the protocol for hard to digest antibodies. The success of Fab-fragment generation was tested by comparing molecular size of both antibody formats in SDS gels and staining with Coomassie blue (see FIG. 19b).

Example 26

Cloning of the fully human fusion protein of GPVI (Fc-GPVI-nt). To generate a soluble form of human GPVI, the extra-cellular domain of human GPVI was cloned and fused to the human immunoglobin Fc-domain. The Fc was amplified from a human heart cDNA library (Clonetech, Palo Alto, Calif.) by PCR using the forward primer 5'-cgcggggcggccgc-gagt-ccaaatcttgtgacaaaac-3' and the reverse primer 5'-gcgg-gaagctttcatttacccggagacagggag-3'. The PCR reaction was performed at 58° C. annealing temperature and 20 cycles with the Expand High Fidelity PCR System (Roche Molecular Biochemicals, Mannheim, Germany). The PCR fragment was cloned in the plasmid pADTrack CMV with NotI/HindIII and the sequence was checked by sequencing (MediGenomix, Martinsried, Germany).

For cloning of the extracellular domain of the human GPVI RNA from cultured megakaryocytes was isolated (RNeasy Mini Kit; Qiagen, Hilden, Germany) according to the manufacturer's protocol and reverse transcription was performed (Omniscript RT Kit; Qiagen) with 2 μg RNA at 37° C. overnight. 100 ng of the reaction was used as a template in PCR amplification of the hGPVI with the primer 5'-gcggggagatc-taccaccatgtctccatccccgacc-3' and 5'-cgcggggcggccgccgttgc-ccttggtgtagtac-3'. The PCR reaction was performed at 54° C. annealing temperature and 24 cycles with the Expand High Fidelity PCR System (Roche Molecular Biochemicals, Mannheim, Germany). The PCR fragment was cloned in the plasmid pADTrack CMV Fc with BglII/NotI and the sequence was checked by sequencing.

Example 27

Cloning of stable Fc-GPVI-nt-CHO-Flp-in cells for expression and secretion of Fc-GPVI-nt The human Fc-GPVI-nt was amplified from the plasmid pADTrackCMV human Fc-GPVI-nt by PCR using the forward primer 5'-gcggggctagcaccaccatgtctccatccccgac-3' and the reverse primer 5'-cgcggggatcctcatttacccggagacagggag-3'. The PCR reaction was performed at 58° C. annealing temperature and 24 cycles with the Expand High Fidelity PCR System (Roche Molecular Biochemicals, Mannheim, Germany). The PCR fragment was cloned in the plasmid pREP4 (Invitrogen, Carlsbad, Calif.) with NheI/BamHI and the sequence of the resulting plasmid pREP4 human Fc-GPVI-nt was checked by sequencing (MediGenomix, Martinsried, Germany). CHO K1 cells (DSMZ, Braunschweig, Germany) were transfected with the plasmid pREP4 human FC-GPVI-NT using effect-ene transfection reagent (Qiagen, Hilden, Germany). 48 hours after transfection the cells were split in medium containing 200 μg/ml hygromycin. Single colonies were picked and the expression was tested by precipitation of the recombinant protein with Protein-A-sepharose (Amersham Pharmacia Biotech AB, Uppsala, Sweden) from 1 ml culture supernatant. After SDS-PAGE the proteins were detected with peroxidase-conjugated goat anti-human IgG antibody (Fc-fragment specific; 109-035-098; Dianova, Hamburg, Germany). Fc-GPVI-nt and control Fc were expressed as secreted soluble proteins using the CHO cell line to prevent misfolding and non-glycosylation of the expressed proteins.

Example 28

Generation of stable GPVI-expressing GPVI-CHO-Flp-In cells. The Flp-in system (Invitrogen, Karlsruhe, Germany) was used to generate a stable GPVI expressing GPVI-CHO-Flp-In cell line. In brief, full length human GPVI was cloned into the pcDNA5/FRT vector. Thereafter, 0.9 μg of GPVI-pcDNA5/FRT were co-transfected with 10 μg of pOG44, encoding the Flp recombinase, into the CHO-Flp-On cells using LipofectAMINE™ together with the Plus™ reagent (Invitrogen). Transfected cells were selected in medium containing 0.1 mg/ml hygromycin B. Expression of human GPVI was confirmed by FACS analysis using anti-GPVI monoclonal antibodies. Non-transfected CHO-Flp-In cells served as controls.

Example 29

Fc-GPVI-nt protein and Fc control fully human fusion protein purification. The culture supernatant of Fc-GPVI-nt CHO cells was collected, then applied onto two sequential tangential flow filtration devices using hollow fibre modules at a perfusion/recirculation rate of 10 l/min. A first purification was achieved via a filter from MembraPure, Bodenheim, #5421534 (Typ Minikross, PEF, 0.5 μm pore width; 4000 ca$^m$ area). Then, the filtrate was concentrated 10-fold via a second module (MembraPure #5422532; 50 kDa pore width; 3900 cm²). The Fc-GPVI-nt fusion protein was centrifuged (3800 g, 30 min, 4° C.) filtrated (0.45 µm) and precipitated by addition of 1 vol. ammonium sulphate (761 g/l) and stirred overnight at 4° C. The proteins were pelleted by centrifugation (3000 g, 30 min, 4° C.), dissolved in 0.1 Vol. PBS and dialysed in PBS overnight at 4° C. Benzonase™ (Merck, cat. no 101695) is added at a concentration of 5 ng/ml to the concentrated and filtrated supernatant to brake down chromosomal DNA into oligonucleotides. The protein solution was clarified by centrifugation (3000 g, 30 min, 4° C.) and loaded on a protein A column MabSelect (Amersham Pharmacia Biotech AB, Uppsala, Sweden). Some column volumes (cv) of elution buffer, 100 mM Na-citrate pH 3.2-4.2 are run into the column mainly to be sure that there is no residual protein left from previous runs in the column. The sample is applied at a flow rate of 5 ml/min corresponding to a linear flow of 150 cm/h. The column was washed with binding buffer (20 mM sodium phosphate buffer pH 7.0, 0.02% NaN₃) until $OD_{280}$ 0.01 and eluted with elution buffer (100 mM glycine pH 2.7). The eluted fractions were neutralized with neutralisation buffer (1 M Tris/HCl pH 9.0, 0.02% NaN₃). Thereafter, an additional chromatographic column with a cation exchange column, Source 30 µm (Amersham BioSciences, cat. no 17-1273-01) was introduced. With an increasing salt gradient (10-15 cv) Fc-GPVI-nt is eluted out of the column. Fractions of 1 ml are collected and appropriately pooled, dialysed in PBS overnight at 4° C., aliquoted and frozen at −20° C.

Example 29

Assessment of dimeric Fc-GPVI-nt binding to immobilized collagen. The binding of dimeric Fc-GPVI-nt to immobilized collagen was determined. ELISA plates (Immulon2 HB, Dynx Technologies, Chantilly, Va.) were coated over night at 4° C. with 1 µg collagen (type I bovine; BD Bioscience, Bedford, Mass.) in 100 µl coating buffer (1.59 g/l Na₂CO₃, 2.93 g/l NaHCO₃, 0.2 g/l NaN₃, pH 9.6). The plates were washed with 250 µl/well PBS/0.05% Tween 20 (PBST) twice and blocked with 250 µl/well Roti-Block (Roth, Karlsruhe, Germany) over night. The plates were washed with 250 µl/well PBST twice, then Fc-GPVI-nt in PBST was added and the plate was incubated for 1 hr at room temperature. Where indicated, Fc-GPVI-nt (20 µg/ml) was pre-incubated for 10 min with different Fab fragments of antibodies e.g. hGP 5C4 Fab (20 µg/ml) to determine inhibition of collagen-GPVI interaction. After incubation the plates were washed 5 times with 250 µl PBST and peroxidase-conjugated goat anti-human IgG antibody Fc_fragment specific (#109-035-098; Dianova, Hamburg, Germany) was added in a dilution of 1:10.000 and incubated for 1 hr at room temperature. After 5 fold washing with 250 µl PBST 100 µl detection reagent (BM Blue POD Substrate; Roche, Mannheim, Germany) was added and incubated up to 10 min. The reaction was stopped by the addition of 100 µl 1 M H₂SO₄ and the plate was measured at 450 nm against reference wavelength 690 nm.

Example 30

FACS measurement for antibody binding to GPVI-expressing CHO cells or native human platelets. GPVI-expressing CHO cells were generated as described above. Human citrate blood was collected from volunteers Platelet rich plasma (PRP) was generated after centrifugation and washing procedures (PBS 1x; pH 7.2) with 2000 rpm at 4° C. and resuspension. GPVI-expressing CHO or control CHO cells were incubated with different antibodies where appropriate. Similarly, human platelets where incubated with different antibodies. Thereafter, secondary anti rat IgG antibodies labelled with peroxidase (Immunotech) were added. FACS measurement was performed and specific mean peroxidase fluorescence was counted with a Becton Dickenson FACS-calibur device.

Example 31

FACS measurement for stimulation of different activation markers on platelets. Human citrate blood was collected from volunteers. PRP was generated as described and diluted in staining buffer (1×PBS (w/o $Ca^{2+}$ and $Mg^+$) with 0.1% sodium azide and 2% fetal bovine serum (FBS), 2 mM $CaCl_2$) was incubated with bovine collagen type 1 (0; 2; 5 and 10 µg/ml; Nobis). For determination of antibody effects, PRP was incubated with various antibodies in staining buffer. Thereafter, stimulation with bovine collagen (10 µg/ml) or ADP (20 µmol/l) or TRAP (10 mmol/L) was followed. Anti CD 62P antibodies or anti PAC-1 antibodies labelled with the fluorophor peroxidase (Immunotech) were added. FACS measurement was performed with a Becton Dickenson FAC-Scalibur device.

Example 32

Platelet aggregation and ATP release. Platelet aggregation ex vivo and in vitro was evaluated by optical aggregometry in citrated blood samples at 37° C. using a two-channel Chronolog aggregometer (Nobis, Germany). PRP was prepared as described and the final platelet count was adjusted to 2×10⁸ platelets/ml by Thyrodes-HEPES buffer (2.5 mmol/l HEPES, 150 mmol/l NaCl, 12 mmol/l NaHCO₃, 2.5 mmol/l KCl, 1 mmol/l MgCl₂, 2 mmol/l CaCl₂, 5.5 mmol D-Glucose, 1 mg/ml BSA, pH 7.4). Chrono-Lume #395 (Chrono-Log Corporation) was added for ATP measurement. For determination of antibody effects, PRP was incubated with various antibodies in different concentrations as indicated. Thereafter, agonists were added to the platelets, pipetted into the aggregometer and aggregation was started under defined stirring conditions. Aggregation was determined by change of light transmission due to coagulating platelets and normalised to an internal standard. ATP release is determined at the characteristic wavelength of Chrono-Lume for ATP and normalised to an internal standard according to the manufacturer's instructions.

Effect of various antibodies on bleeding time of human whole blood ex vivo. In vitro bleeding time was determined with a PFA-100 device (Dade-Behring). 800 µl of human whole blood was injected in the PFA-100 device. Bleeding time was measured with ADP/collagen and epinephrine/collagen coated measuring cells according to the manufacturer's instructions.

Effect of Antibodies on Bleeding Time of Human Blood Ex Vivo (PFA-100).

Bleeding times as the major side-effect of platelet inhibition was assessed in human whole blood ex vivo. Human platelets were stimulated with ADP/collagen or epinephrine/collagen-coated plates in a PFA-100 device. Incubation of human whole blood with hGP 5C4 Fab (5 µg/ml) had no effects on bleeding time ex vivo. In contrast, comparable and therapeutically relevant doses of ReoPro$^R$ (5 µg/ml) markedly prolonged bleeding time beyond the maximum of 300 sec in the PFA-100 device (see FIG. 27a). Different anti-GPVI-antibodies in different antibody formats were also tested for the prolongation of bleeding time. hGP 5C4 Fab (1 µg/ml and 5 µg/ml) did not show any prolongation of bleeding time, whereas the IgG format of hGP 5C4 prolonged bleeding time in low concentrations (1 µg/ml). In contrast, 4C9 markedly prolonged bleeding time both as Fab and as IgG antibody (Please see FIG. 27b). These data further support the safety of hGP 5C4 Fab for the treatment of patients with potent antiplatelet effect without the serious side effect of bleeding complications.

Example 33

Specificity of Antigen Binding of hGP 5C4

The recognition of GPVI as an antigen for hGP 5C4 was investigated. Recombinant GPVI protein as dimeric fusion protein of the extracellular domain of the GPVI receptor and the Fc part of a human IgG1 as a linker was generated as described. Soluble GPVI protein was secreted from Fc-GPVI-nt expressing CHO cells as dimer and purified. The identity of Fc-GPVI-nt was tested in a SDS gel with Coomassie stain for proteins and with an antibody directed against the Fc part of Fc-GPVI-nt (see FIG. 19a, top). hGP 5C4 recognised the Fc-GPVI-nt specifically as purified protein in a Western blot. Under reducing conditions hGP 5C4 recognized a protein with approximately 80 kDalton (see FIG. 19a). A specific protein was also recognised from platelet lysates with approximately 65 kDalton. There was no cross reaction to the control protein Fc-control. Generation of Fab fragments of the IgG antibody hGP 5C4 was tested with SDS-PAGE and Coomassie staining (see FIG. 19b).
Inhibition of Collagen Interaction with GPVI To further address the characteristics of the anti-GPVI antibodies, we tested the ability of various antibodies to compete with immobilized collagen for the association with dimeric Fc-GPVI-nt. Only hGP 5C4 Fab inhibited Fc-GPVI-nt-dimer binding to immobilized collagen (see figure. 20). A concentration of 20 µg/ml antibody was required to reduce Fc-GPVI-nt-dimer binding. The antibody 4C9 Fab had no influence on collagen interactions with Fc-GPVI-nt. Together these data indicate that the novel antibody Fab fragment hGP 5C4 specifically inhibits Fc-GPVI-nt-dimer binding to collagen in vitro.
Specific Binding of Anti-GPVI Antibodies to GPVI Expressed on Cho Cells and Native GPVI on Human Platelets Binding of various anti-GPVI antibodies to GPVI-expressing CHO cells was tested. To further substantiate the specificity of anti-GPVI antibodies, we generated the GPVI-expressing GPVI-Flp-In-CHO cell line. Platelets and GPVI-CHO transfectants expressed GPVI at roughly the same density as determined by flow cytometry (not shown). GPVI-transfectants but not control CHO cells avidly bound the antibodies 4C4; hGP 5C4 and 4C9 (see FIG. 1'). The antibody clones 14E11 and CD3 did not show specific binding to GPVI-expressing CHO cells. Moreover, antibody binding to native GPVI on human platelets was tested with different anti-GPVI antibodies. In accordance, hGP 5C4 showed strong binding to native platelets with weaker binding of 4C4 and 4C9. 14E11 and CD3 did not show increased binding to platelets compared to the control antibody (see FIG. 22). This further supports the concept that hGP 5C4 shows specific binding to native GPVI on the surface of either GPVI-expressing CHO cells or native human platelets.

Example 34

Inhibition of Platelet Activation by Anti-GPVI Antibodies Determined by FACS

The inhibition of human platelet activation by various anti-GPVI antibodies was determined by FACS measurement of activation specific platelet markers. PAC-1 activation in human platelets was determined in presence of 4C9 Fab and hGP 5C4 Fab. hGP 5C4 Fab had no intrinsic activity for PAC-1 expression in unstimulated human platelets, whereas 4C9 Fab leads to a small activation of PAC-1 (see FIG. 23a). Stimulation with bovine collagen (10 µg/ml) activated PAC-1, which could be abolished by hGP 5C4 (20 µg/ml) but not by 4C9 Fab. Collagen (bovine type I; 10 µg/ml) typically activates human platelets and leads to increased surface expression of CD 62-P. Different anti-GPVI antibodies were tested and 4C4 Fab and hGP 5C4 Fab inhibited the collagen-mediated CD 62P activation (please see FIG. 23b). In contrast 4C9 had a potent activating effect on CD 62P in human platelets. Thus, hGP 5C4 inhibits collagen-mediated platelet activation without intrinsic activity.

Specificity of antibodies was tested for ADP-mediated and TRAP-mediated platelet activation determined by FACS. ADP (20 µmol/L) and TRAP (25 µmol/l) stimulated both CD 62P (see FIG. 24a) and PAC-1 (see FIG. 24b). Increasing concentrations of hGP 5C4 Fab (0.5 µg/ml to 5 µg/ml) had no effect on both ADP- and TRAP-mediated CD 62 P— and PAC-1-expression. Moreover, specificity of hGP 5C4 Fab for activation of CD63 was determined (see FIG. 6c). Whereas hGP 5C4 inhibited collagen-mediated CD63 activation, ADP- and TRAP-mediated CD63 was unaffected. This further supports the notion of specific inhibition of collagen-mediated platelet activation by hGP 5C4 leaving other important platelet stimulation pathways unaltered. Moreover, unchanged basal activity underlines the absence of intrinsic activity of 5C9.
Inhibition of Human Platelet Aggregation and ATP Release by hGP 5C4 Fab.

Human platelets were pre-incubated with increasing concentrations of hGP 5C4 Fab (0.1 µg/ml to 2.0 µg/ml). Aggregation of platelets was induced by bovine collagen type I (3 µg/ml) and determined with an aggregometer under stirring conditions (for details see Material and Methods). hGP 5C4 Fab potently inhibited human platelet aggregation [in % of internal standard] ex vivo with an IC50 value of $1.2 \times 10^{-7}$ g/ml (see FIG. 25a). In parallel ATP release [in % of control ATP release] was also induced by collagen and potently inhibited by hGP 5C4 Fab (0.1 µg/ml to 2.0 µg/ml) (see FIG. 25b). In contrast ADP- (5 µM) or TRAP- (10 µM) mediated platelet aggregation was not affected by preincubation with significantly higher hGP 5C4 Fab concentrations (2 µg/ml and 6 µg/ml) (see FIG. 26a). hGP 5C4 inhibited collagen-mediated ATP release but had no effect on thrombin/TRAP-mediated ATP release even at higher concentrations (2 µg/ml and 6 µg/ml). ADP-mediated ATP release, however, was also inhibited by the maximal hGP 5C4 Fab concentrations (6 µg/ml) (see FIG. 26b). This also underlines the specificity of inhibition of collagen-mediated platelet aggregation of hGP 5C4 Fab. Moreover, the release of potent mediator substances from intracellular stores was also potently and selectively inhibited by hGP 5C4.

The method of this example may be modified by using as an immunogen another ligand disclosed herein e.g. a peptide moiety (a) in particular one which includes lysine 27 for example are represented by SEQ ID NOs: 9 to 14.

Deposit: A hybridoma cell line producing hGP 5C4 antibody has been deposited under terms of the Budapest Treaty as hGP 5C4 with DSMZ-Deutsche Sammlung von Mikroorganismen and Zellkulturen GmbH (Inhoffenstr. 7 B, 38124 Braunschweig, GERMANY) on Nov. 25, 2003 and has been given Accession No. 2631.

Example 35

Epitope Mapping Studies Using hGP 5C4 Monoclonal Antibody and GPVI

Peptide Libraries:

A peptide library (peptide scan format 13/11, 131 peptides) was scanned using the antibody hGP 5C4. All N-termini were acetylated. The peptide library comprised the extracellular domain of human Glycoprotein VI, including the signal sequence. Since the fusion protein, PR-15 was used, peptide SEQ ID NO: 131 contains terminal amino acids GGRE which do not occur in the native GPVI protein.

PepSpot-Analysis:

The peptides were synthesized on a cellulose membrane in a stepwise manner resulting in a defined arrangement (peptide array) and are covalently bound to the cellulose membrane. Binding assays were performed directly on the peptide array. In general an antigen peptide array is incubated with blocking buffer for several hours to reduce non-specific binding of proteins or antibodies. It follows the incubation with a primary (antigen peptide-binding) antibody in blocking buffer and an incubation with a horseradish peroxidase (HRP)-labelled secondary antibody, which binds selectively the primary antibody. Alternatively a HRP-labelled primary antibody in blocking buffer can be used.

A short T(Tween)-TBS-buffer washing directly after the incubation of the antigen peptide array with the secondary protein or antibody or the HRP-labelled primary antibody followed by the first chemiluminescence experiment is made to get an first overview which antigen peptides do bind the primary antibody. Several buffer washing steps follow (T-TBS- and TBS-buffer) to reduce false positive binding (unspecific antibody binding to the cellulose membrane itself). After these washing steps the final chemiluminescence analysis is performed. The data were analysed with an imaging system showing the signal intensity (Light units, LU) as single measurements for each peptide. In order to evaluate non-specific binding of secondary antibodies, incubations using the secondary antibody have to be performed in the absence of the primary antibody as control incubation.

Control Incubation with Secondary Antibody:

In order to evaluate non-specific binding of secondary antibodies, incubations have to be performed in the absence of the primary antibody as control incubation. In this case, the control incubation with anti-rat-HRP (Sigma A9037) showed no signals as observable in table 1 and FIG. 34 (used concentration of secondary antibody 1 µg/mL).

The following antibody against human GPVI was used for epitope mappings:

| | |
|---|---|
| Primary antibody | 5C4 |
| Format | |
| Lot | — |
| Conc. of primary protein applied | 5 µg/mL |
| Secondary antibody | anti-rat-HRP (Sigma A9037) |
| Label | horseradish peroxidase (HRP) |
| Conc. of secondary antibody applied | 1 µg/mL |

The primary antibody was hGP 5C4. The secondary antibody was anti-rat HRP antibody and was used as control.

Results

General:

The binding data for the antigen peptide scan is listed in tables 1 and 2 and shown in FIGS. 33 and 34. The most intense signals in each table are shown in bold. Signals with lower intensities but still above background are shown in italics.

The definition of "most intense" and "still above background" is correlated to the signal to noise ratio of all measured signals of each peptide array and is individual for every chemiluminescence analysis.

Example 36

Incubation of Antigen Peptide Library with Antibody 5C4

It was found that the antibody hGP 5C4 recognizes three binding sites. The most intense signals and the corresponding peptide sequences are listed below. The numbers relate to the peptide number. Overlapping amino acid sequences are marked bold:

```
     8          LGRVPAQSGPLPK
     9           RVPAQSGPLPKPS
    10            PAQSGPLPKPSLQ
    11             QSGPLPKPSLQAL
    12              GPLPKPSLQALPS
    13               LPKPSLQALPSSL
    14                KPSLQALPSSLVP

37          LFIPAMKRSLAGR
    38           IPAMKRSLAGRYR

54          ATGVFAKPSLSAQ
    55            GVFAKPSLSAQPG
    56              FAKPSLSAQPGPA
```

All signals below 500 LU for this epitope mapping are considered as background.

Analyzing the results of the incubation of the antigen (GPVI) peptide library with antibodies hGP 5C4 the antibody seems to recognize 3 binding sites. The most intensive signals for antibody hGP 5C4 are recognizable on peptides #11, #37 and #54 (SEQ ID NOs: 11, 37 and 54). The signal to noise ratio for the binding in the region of peptide #11 is much better (approx. 20:1) compared to the other recognizable binding sites on peptides #37 and #54 (approx 4:1).

TABLE 1

CONTROL INCUBATION
Binding data of control incubation, (peptide scan 13/11) with antibody Anti-rat-HRP
The signals obtained were quantified and LU (Light Units) are listed.
Table 1

| peptide | sequence | anti-rat-HRP |
|---|---|---|
| 1 | MSPSPTALFCLGL | 53 |
| 2 | PSPTALFCLGLCL | 18 |
| 3 | PTALFCLGLCLGR | 56 |
| 4 | ALFCLGLCLGRVP | 61 |
| 5 | FCLGLCLGRVPAQ | 2 |
| 6 | LGLCLGRVPAQSG | 56 |
| 7 | LCLGRVPAQSGPL | 239 |
| 8 | LGRVPAQSGPLPK | 206 |
| 9 | RVPAQSGPLPKPS | 223 |
| 10 | PAQSGPLPKPSLQ | 216 |

TABLE 1-continued

CONTROL INCUBATION
Binding data of control incubation, (peptide scan 13/11) with antibody Anti-rat-HRP
The signals obtained were quantified and LU (Light Units) are listed.
Table 1

| peptide | sequence | anti-rat-HRP |
|---|---|---|
| 11 | QSGPLPKPSLQAL | 212 |
| 12 | GPLPKPSLQALPS | 168 |
| 13 | LPKPSLQALPSSL | 189 |
| 14 | KPSLQALPSSLVP | 158 |
| 15 | SLQALPSSLVPLE | 214 |
| 16 | QALPSSLVPLEKP | 200 |
| 17 | LPSSLVPLEKPVT | 71 |
| 18 | SSLVPLEKPVTLR | 77 |
| 19 | LVPLEKPVTLRCQ | 50 |
| 20 | PLEKPVTLRCQGP | 89 |
| 21 | EKPVTLRCQGPPG | 126 |
| 22 | PVTLRCQGPPGVD | 40 |
| 23 | TLRCQGPPGVDLY | 87 |
| 24 | RCQGPPGVDLYRL | 87 |
| 25 | QGPPGVDLYRLEK | 57 |
| 26 | PPGVDLYRLEKLS | 49 |
| 27 | GVDLYRLEKLSSS | 104 |
| 28 | DLYRLEKLSSSRY | 171 |
| 29 | YRLEKLSSSRYQD | 224 |
| 30 | LEKLSSSRYQDQA | 217 |
| 31 | KLSSSRYQDQAVL | 203 |
| 32 | SSSRYQDQAVLFI | 240 |
| 33 | SRYQDQAVLFIPA | 204 |
| 34 | YQDQAVLFIPAMK | 193 |
| 35 | DQAVLFIPAMKRS | 327 |
| 36 | AVLFIPAMKRSLA | 338 |
| 37 | LFIPAMKRSLAGR | 280 |
| 38 | IPAMKRSLAGRYR | 155 |
| 39 | AMKRSLAGRYRCS | 62 |
| 40 | KRSLAGRYRCSYQ | 63 |
| 41 | SLAGRYRCSYQNG | 158 |
| 42 | AGRYRCSYQNGSL | 102 |
| 43 | RYRCSYQNGSLWS | 96 |
| 44 | RCSYQNGSLWSLP | 88 |
| 45 | SYQNGSLWSLPSD | 77 |
| 46 | QNGSLWSLPSDQL | 55 |
| 47 | GSLWSLPSDQLEL | 93 |
| 48 | LWSLPSDQLELVA | 170 |
| 49 | SLPSDQLELVATG | 197 |
| 50 | PSDQLELVATGVF | 313 |
| 51 | DQLELVATGVFAK | 252 |
| 52 | LELVATGVFAKPS | 263 |
| 53 | LVATGVFAKPSLS | 240 |
| 54 | ATGVFAKPSLSAQ | 190 |
| 55 | GVFAKPSLSAQPG | 254 |
| 56 | FAKPSLSAQPGPA | 267 |
| 57 | KPSLSAQPGPAVS | 250 |
| 58 | SLSAQPGPAVSSG | 174 |
| 59 | SAQPGPAVSSGGD | 101 |
| 60 | QPGPAVSSGGDVT | 92 |
| 61 | GPAVSSGGDVTLQ | 192 |
| 62 | AVSSGGDVTLQCQ | 67 |
| 63 | SSGGDVTLQCQTR | 127 |
| 64 | GGDVTLQCQTRYG | 97 |
| 65 | DVTLQCQTRYGFD | 26 |
| 66 | TLQCQTRYGFDQF | 253 |
| 67 | QCQTRYGFDQFAL | 332 |
| 68 | QTRYGFDQFALYK | 182 |
| 69 | RYGFDQFALYKEG | 187 |
| 70 | GFDQFALYKEGDP | 201 |
| 71 | DQFALYKEGDPAP | 195 |
| 72 | FALYKEGDPAPYK | 204 |
| 73 | LYKEGDPAPYKNP | 216 |
| 74 | KEGDPAPYKNPER | 211 |
| 75 | GDPAPYKNPERWY | 196 |
| 76 | PAPYKNPERWYRA | 230 |
| 77 | PYKNPERWYRASF | 263 |
| 78 | KNPERWYRASFPI | 177 |
| 79 | PERWYRASFPIIT | 183 |
| 80 | RWYRASFPIITVT | 176 |
| 81 | YRASFPIITVTAA | 285 |

TABLE 1-continued

CONTROL INCUBATION
Binding data of control incubation, (peptide scan 13/11) with antibody Anti-rat-HRP
The signals obtained were quantified and LU (Light Units) are listed.
Table 1

| peptide | sequence | anti-rat-HRP |
|---|---|---|
| 82 | ASFPIITVTAAHS | 221 |
| 83 | FPIITVTAAHSGT | 210 |
| 84 | IITVTAAHSGTYR | 187 |
| 85 | TVTAAHSGTYRCY | 83 |
| 86 | TAAHSGTYRCYSF | 53 |
| 87 | AHSGTYRCYSFSS | 74 |
| 88 | SGTYRCYSFSSRD | 162 |
| 89 | TYRCYSFSSRDPY | 111 |
| 90 | RCYSFSSRDPYLW | 158 |
| 91 | YSFSSRDPYLWSA | 270 |
| 92 | FSSRDPYLWSAPS | 280 |
| 93 | SRDPYLWSAPSDP | 232 |
| 94 | DPYLWSAPSDPLE | 267 |
| 95 | YLWSAPSDPLELV | 357 |
| 96 | WSAPSDPLELVVT | 377 |
| 97 | APSDPLELVVTGT | 382 |
| 98 | SDPLELVVTGTSV | 230 |
| 99 | PLELVVTGTSVTP | 262 |
| 100 | ELVVTGTSVTPSR | 216 |
| 101 | VVTGTSVTPSRLP | 355 |
| 102 | TGTSVTPSRLPTE | 286 |
| 103 | TSVTPSRLPTEPP | 268 |
| 104 | VTPSRLPTEPPSS | 252 |
| 105 | PSRLPTEPPSSVA | 247 |
| 106 | RLPTEPPSSVAEF | 227 |
| 107 | PTEPPSSVAEFSE | 204 |
| 108 | EPPSSVAEFSEAT | 199 |
| 109 | PSSVAEFSEATAE | 215 |
| 110 | SVAEFSEATAELT | 285 |
| 111 | AEFSEATAELTVS | 303 |
| 112 | FSEATAELTVSFT | 353 |
| 113 | EATAELTVSFTNK | 323 |
| 114 | TAELTVSFTNKVF | 373 |
| 115 | ELTVSFTNKVFTT | 437 |
| 116 | TVSFTNKVFTTET | 382 |
| 117 | SFTNKVFTTETSR | 377 |
| 118 | TNKVFTTETSRSI | 354 |
| 119 | KVFTTETSRSITT | 261 |
| 120 | FTTETSRSITTSP | 236 |
| 121 | TETSRSITTSPKE | 397 |
| 122 | TSRSITTSPKESD | 377 |
| 123 | RSITTSPKESDSP | 364 |
| 124 | ITTSPKESDSPAG | 344 |
| 125 | TSPKESDSPAGPA | 372 |
| 126 | PKESDSPAGPARQ | 346 |
| 127 | ESDSPAGPARQYY | 311 |
| 128 | DSPAGPARQYYTK | 316 |
| 129 | PAGPARQYYTKGN | 347 |
| 130 | GPARQYYTKGNGG | 343 |
| 131 | ARQYYTKGNGGRE | 389 |

TABLE 2

Overview of binding data, (peptide scan 15/12) GPVI with antibody hGP 5C4
The signals obtained were quantified and LU (Light Units) are listed.

| peptide | sequence | ab 5C4 | |
|---|---|---|---|
| 1 | MSPSPTALFCLGL | 149 | (SEQ ID NO: 1) |
| 2 | PSPTALFCLGLCL | 79 | (SEQ ID NO: 2) |
| 3 | PTALFCLGLCLGR | 74 | (SEQ ID NO: 3) |
| 4 | ALFCLGLCLGRVP | 5 | (SEQ ID NO: 4) |
| 5 | FCLGLCLGRVPAQ | 26 | (SEQ ID NO: 5) |
| 6 | LGLCLGRVPAQSG | 91 | (SEQ ID NO: 6) |
| 7 | LCLGRVPAQSGPL | 292 | (SEQ ID NO: 7) |
| 8 | LGRVPAQSGPLPK | 794 | (SEQ ID NO: 8) |
| 9 | RVPAQSGPLPKPS | 1099 | (SEQ ID NO: 9) |
| 10 | PAQSGPLPKPSLQ | 1334 | (SEQ ID NO: 10) |
| 11 | QSGPLPKPSLQAL | 3544 | (SEQ ID NO: 11) |
| 12 | GPLPKPSLQALPS | 2984 | (SEQ ID NO: 12) |
| 13 | LPKPSLQALPSSL | 2052 | (SEQ ID NO: 13) |
| 14 | KPSLQALPSSLVP | 1418 | (SEQ ID NO: 14) |
| 15 | SLQALPSSLVPLE | 74 | (SEQ ID NO: 15) |

TABLE 2-continued

Overview of binding data, (peptide scan 15/12) GPVI with antibody hGP 5C4
The signals obtained were quantified and LU (Light Units) are listed.

| peptide | sequence | ab 5C4 | |
|---|---|---|---|
| 16 | QALPSSLVPLEKP | 80 | (SEQ ID NO: 16) |
| 17 | LPSSLVPLEKPVT | 160 | (SEQ ID NO: 17) |
| 18 | SSLVPLEKPVTLR | 219 | (SEQ ID NO: 18) |
| 19 | LVPLEKPVTLRCQ | 157 | (SEQ ID NO: 19) |
| 20 | PLEKPVTLRCQGP | 175 | (SEQ ID NO: 20) |
| 21 | EKPVTLRCQGPPG | 128 | (SEQ ID NO: 21) |
| 22 | PVTLRCQGPPGVD | 76 | (SEQ ID NO: 22) |
| 23 | TLRCQGPPGVDLY | 76 | (SEQ ID NO: 23) |
| 24 | RCQGPPGVDLYRL | 28 | (SEQ ID NO: 24) |
| 25 | QGPPGVDLYRLEK | 56 | (SEQ ID NO: 25) |
| 26 | PPGVDLYRLEKLS | 101 | (SEQ ID NO: 26) |
| 27 | GVDLYRLEKLSSS | 100 | (SEQ ID NO: 27) |
| 28 | DLYRLEKLSSSRY | 179 | (SEQ ID NO: 28) |
| 29 | YRLEKLSSSRYQD | 169 | (SEQ ID NO: 29) |
| 30 | LEKLSSSRYQDQA | 184 | (SEQ ID NO: 30) |
| 31 | KLSSSRYQDQAVL | 211 | (SEQ ID NO: 31) |
| 32 | SSSRYQDQAVLFI | 319 | (SEQ ID NO: 32) |
| 33 | SRYQDQAVLFIPA | 259 | (SEQ ID NO: 33) |
| 34 | YQDQAVLFIPAMK | 125 | (SEQ ID NO: 34) |
| 35 | DQAVLFIPAMKRS | 186 | (SEQ ID NO: 35) |
| 36 | AVLFIPAMKRSLA | 125 | (SEQ ID NO: 36) |
| 37 | LFIPAMKRSLAGR | 1120 | (SEQ ID NO: 37) |
| 38 | IPAMKRSLAGRYR | 1031 | (SEQ ID NO: 38) |
| 39 | AMKRSLAGRYRCS | 134 | (SEQ ID NO: 39) |
| 40 | KRSLAGRYRCSYQ | 139 | (SEQ ID NO: 40) |
| 41 | SLAGRYRCSYQNG | 8 | (SEQ ID NO: 41) |
| 42 | AGRYRCSYQNGSL | 41 | (SEQ ID NO: 42) |
| 43 | RYRCSYQNGSLWS | 64 | (SEQ ID NO: 43) |
| 44 | RCSYQNGSLWSLP | 9 | (SEQ ID NO: 44) |
| 45 | SYQNGSLWSLPSD | 12 | (SEQ ID NO: 45) |
| 46 | QNGSLWSLPSDQL | 1 | (SEQ ID NO: 46) |
| 47 | GSLWSLPSDQLEL | 79 | (SEQ ID NO: 47) |
| 48 | LWSLPSDQLELVA | 47 | (SEQ ID NO: 48) |
| 49 | SLPSDQLELVATG | 91 | (SEQ ID NO: 49) |
| 50 | PSDQLELVATGVF | 38 | (SEQ ID NO: 50) |
| 51 | DQLELVATGVFAK | 73 | (SEQ ID NO: 51) |
| 52 | LELVATGVFAKPS | 148 | (SEQ ID NO: 52) |
| 53 | LVATGVFAKPSLS | 359 | (SEQ ID NO: 53) |
| 54 | ATGVFAKPSLSAQ | 1208 | (SEQ ID NO: 54) |
| 55 | GVFAKPSLSAQPG | 810 | (SEQ ID NO: 55) |
| 56 | FAKPSLSAQPGPA | 759 | (SEQ ID NO: 56) |
| 57 | KPSLSAQPGPAVS | 128 | (SEQ ID NO: 57) |
| 58 | SLSAQPGPAVSSG | 110 | (SEQ ID NO: 58) |
| 59 | SAQPGPAVSSGGD | 155 | (SEQ ID NO: 59) |
| 60 | QPGPAVSSGGDVT | 88 | (SEQ ID NO: 60) |
| 61 | GPAVSSGGDVTLQ | 71 | (SEQ ID NO: 61) |
| 62 | AVSSGGDVTLQCQ | 49 | (SEQ ID NO: 62) |
| 63 | SSGGDVTLQCQTR | 2 | (SEQ ID NO: 63) |
| 64 | GGDVTLQCQTRYG | 6 | (SEQ ID NO: 64) |
| 65 | DVTLQCQTRYGFD | 26 | (SEQ ID NO: 65) |
| 66 | TLQCQTRYGFDQF | 82 | (SEQ ID NO: 66) |
| 67 | QCQTRYGFDQFAL | 62 | (SEQ ID NO: 67) |
| 68 | QTRYGFDQFALYK | 84 | (SEQ ID NO: 68) |
| 69 | RYGFDQFALYKEG | 78 | (SEQ ID NO: 69) |
| 70 | GFDQFALYKEGDP | 3 | (SEQ ID NO: 70) |
| 71 | DQFALYKEGDPAP | 29 | (SEQ ID NO: 71) |
| 72 | FALYKEGDPAPYK | 35 | (SEQ ID NO: 72) |
| 73 | LYKEGDPAPYKNP | 33 | (SEQ ID NO: 73) |
| 74 | KEGDPAPYKNPER | 8 | (SEQ ID NO: 74) |
| 75 | GDPAPYKNPERWY | 95 | (SEQ ID NO: 75) |
| 76 | PAPYKNPERWYRA | 78 | (SEQ ID NO: 76) |
| 77 | PYKNPERWYRASF | 97 | (SEQ ID NO: 77) |
| 78 | KNPERWYRASFPI | 51 | (SEQ ID NO: 78) |
| 79 | PERWYRASFPIIT | 119 | (SEQ ID NO: 79) |
| 80 | RWYRASFPIITVT | 184 | (SEQ ID NO: 80) |
| 81 | YRASFPIITVTAA | 141 | (SEQ ID NO: 81) |
| 82 | ASFPIITVTAAHS | 149 | (SEQ ID NO: 82) |
| 83 | FPIITVTAAHSGT | 75 | (SEQ ID NO: 83) |
| 84 | IITVTAAHSGTYR | 87 | (SEQ ID NO: 84) |
| 85 | TVTAAHSGTYRCY | 14 | (SEQ ID NO: 85) |
| 86 | TAAHSGTYRCYSF | 58 | (SEQ ID NO: 86) |
| 87 | AHSGTYRCYSFSS | 93 | (SEQ ID NO: 87) |
| 88 | SGTYRCYSFSSRD | 64 | (SEQ ID NO: 88) |

TABLE 2-continued

Overview of binding data, (peptide scan 15/12) GPVI with antibody hGP 5C4 The signals obtained were quantified and LU (Light Units) are listed.

| peptide | sequence | ab 5C4 | |
|---|---|---|---|
| 89 | TYRCYSFSSRDPY | 46 | (SEQ ID NO: 89) |
| 90 | RCYSFSSRDPYLW | 65 | (SEQ ID NO: 90) |
| 91 | YSFSSRDPYLWSA | 67 | (SEQ ID NO: 91) |
| 92 | FSSRDPYLWSAPS | 110 | (SEQ ID NO: 92) |
| 93 | SRDPYLWSAPSDP | 107 | (SEQ ID NO: 93) |
| 94 | DPYLWSAPSDPLE | 63 | (SEQ ID NO: 94) |
| 95 | YLWSAPSDPLELV | 120 | (SEQ ID NO: 95) |
| 96 | WSAPSDPLELVVT | 210 | (SEQ ID NO: 96) |
| 97 | APSDPLELVVTGT | 147 | (SEQ ID NO: 97) |
| 98 | SDPLELVVTGTSV | 141 | (SEQ ID NO: 98) |
| 99 | PLELVVTGTSVTP | 202 | (SEQ ID NO: 99) |
| 100 | ELVVTGTSVTPSR | 114 | (SEQ ID NO: 100) |
| 101 | VVTGTSVTPSRLP | 211 | (SEQ ID NO: 101) |
| 102 | TGTSVTPSRLPTE | 160 | (SEQ ID NO: 102) |
| 103 | TSVTPSRLPTEPP | 50 | (SEQ ID NO: 103) |
| 104 | VTPSRLPTEPPSS | 91 | (SEQ ID NO: 104) |
| 105 | PSRLPTEPPSSVA | 33 | (SEQ ID NO: 105) |
| 106 | RLPTEPPSSVAEF | 2 | (SEQ ID NO: 106) |
| 107 | PTEPPSSVAEFSE | 71 | (SEQ ID NO: 107) |
| 108 | EPPSSVAEFSEAT | 12 | (SEQ ID NO: 108) |
| 109 | PSSVAEFSEATAE | 69 | (SEQ ID NO: 109) |
| 110 | SVAEFSEATAELT | 71 | (SEQ ID NO: 110) |
| 111 | AEFSEATAELTVS | 136 | (SEQ ID NO: 111) |
| 112 | FSEATAELTVSFT | 100 | (SEQ ID NO: 112) |
| 113 | EATAELTVSFTNK | 135 | (SEQ ID NO: 113) |
| 114 | TAELTVSFTNKVF | 226 | (SEQ ID NO: 114) |
| 115 | ELTVSFTNKVFTT | 143 | (SEQ ID NO: 115) |
| 116 | TVSFTNKVFTTET | 224 | (SEQ ID NO: 116) |
| 117 | SFTNKVFTTETSR | 472 | (SEQ ID NO: 117) |
| 118 | TNKVFTTETSRSI | 336 | (SEQ ID NO: 118) |
| 119 | KVFTTETSRSITT | 287 | (SEQ ID NO: 119) |
| 120 | FTTETSRSITTSP | 250 | (SEQ ID NO: 120) |
| 121 | TETSRSITTSPKE | 186 | (SEQ ID NO: 121) |
| 122 | TSRSITTSPKESD | 195 | (SEQ ID NO: 122) |
| 123 | RSITTSPKESDSP | 91 | (SEQ ID NO: 123) |
| 124 | ITTSPKESDSPAG | 66 | (SEQ ID NO: 124) |
| 125 | TSPKESDSPAGPA | 25 | (SEQ ID NO: 125) |
| 126 | PKESDSPAGPARQ | 119 | (SEQ ID NO: 126) |
| 127 | ESDSPAGPARQYY | 101 | (SEQ ID NO: 127) |
| 128 | DSPAGPARQYYTK | 66 | (SEQ ID NO: 128) |
| 129 | PAGPARQYYTKGN | 139 | (SEQ ID NO: 129) |
| 130 | GPARQYYTKGNGG | 255 | (SEQ ID NO: 130) |
| 131 | ARQYYTKGNGGRE | 289 | (SEQ ID NO: 131) |

The present disclosure further includes the subject matter of the following paragraphs:

1. Fusion protein comprising
   (a) the extracellular domain of glycoprotein VI or a variant thereof that is functional for binding to collagen and
   (b) the Fc domain of an immunoglobulin or a function-conservative part thereof, characterised by an amino acid sequence as shown in FIG. 7, whereby the fusion protein is obtainable by
   (a) collecting 2 days after infection the culture supernatant of Hela cells infected with an adenovirus for Fc-GPVI-nt coding for an amino acid sequence as shown in FIG. 7;
   (b) centrifuging (3800 g, 30 min, 4° C.) the supernatant of step (a);
   (c) filtrating (0.45 µm) the supernatant of step (b);
   (d) precipitating the immunoadhesin by addition of 1 vol. ammonium sulfate (761 g/l) and stirring overnight at 4° C.;
   (e) pelletizing the proteins by centrifugation (3000 g, 30 min, 4° C.),
   (f) dissolving the pelletized proteins of step (e) in 0.1 Vol PBS and dialysing in PBS overnight at 4° C.;
   (g) clarifying the protein solution by centrifugation (3000 g, 30 min, 4° C.);
   (h) loading the solution of step (g) on a protein A column (HiTrap™ protein A HP, Amersham Pharmacia Biotech AB, Uppsala, Sweden);
   (i) washing the column with binding buffer (20 mM sodium phosphate buffer pH 7.0, 0.02% NaN$_3$) until OD$_{280}$<0.01;
   (k) eluting fractions with elution buffer (100 mM glycine pH 2.7);
   (l) neutralizing the eluted fractions with neutralisation buffer (1 M Tris/HCl pH 9.0, 0.02% NaN$_3$);
   (m) pooling the fractions;
   (n) dialysing the pooled fractions in PBS overnight at 4° C.,
   (o) aliquoting the dialysed product and freezing at −20° C.

2. Nucleic acid sequence selected from the following group:
   (i) the nucleic acid sequence of SEQ ID NO: 148 or a variant thereof that codes for the same polypeptide according to the degeneracy of the genetic code;
   (ii) a nucleic acid sequence coding for a polypeptide that has at least 70% sequence homology to the polypeptide encoded by SEQ ID NO: 148;
   (iii) a nucleic acid coding for a polypeptide of at least 300 amino acids, whereby a segment of at least 100 amino acids is functional for binding to collagen and a segment of at least 200 amino acids is functional as an Fc domain; and (iv) a nucleic acid sequence coding for the fusion protein of claim 10.

3. Use of the fusion protein as defined by claim 1 for the preparation of a medicament for the prevention of intraarterial thrombosis in a patient characterized by
   (i) having suffered from an acute coronary or carotid syndrome and
   (ii) having active intraarterial lesions.

4. The use according to paragraph 3, wherein the patient is further characterized by suffering from unstable atherosclerotic plaque.

5. The use according to paragraph 3, wherein the patient is further characterized by suffering from chronic progression of atherosclerosis.

6. The use according to any one of paragraphs 3, 4 or 5, wherein the medicament is administered parenterally, preferably in a dosage form containing 0.5 to 5.0 mg/kg.

7. Method of in vivo screening for an inhibitor of GPVI mediated adhesion of platelets to active intravascular lesions, said method comprising the steps of
   (i) providing an in Vivo model for active intravascular lesions;
   (ii) measuring the adhesion of platelets to an active intravascular lesion in the presence of a test compound; and
   (iii) identifying the test compound as an inhibitor of GPVI when the adhesion of platelets to the active intravascular lesion is less in the presence of the test compound as compared to the absence of the test compound.

8. The method of paragraph 7, wherein the model is a mouse model.

9. The method of paragraph 7 or 8 wherein the adhesion of platelets to an active intravascular lesion is carried out by using in vivo fluorescence microscopy.

10. The method of paragraph 9, wherein fluorescent platelets are introduced to the model prior to measuring the adhesion of platelets to an active intravascular lesion in the presence of a test compound.

11. Method of in vitro screening for an inhibitor of GPVI mediated adhesion of platelets to active intravascular lesions, said method comprising the steps of
    (i) providing a surface exposing collagen;
    (ii) contacting the surface with platelets under predetermined conditions allowing for an adhesion of the platelets to the collagen;
    (iii) measuring the adhesion of platelets in the presence of a test compound;
    (iv) identifying the test compound as an inhibitor of GPVI when the adhesion of platelets to collagen is less in the presence of the test compound as compared to the absence of the test compound; and
    (v) optionally determining the functional effect of said inhibitor on platelet aggregation and/or platelet activation.

12. Medicament for the prevention or treatment of intraarterial thrombosis, whereby the medicament comprises the fusion protein of paragraph 1 or the nucleic acid as defined in paragraph 2 in a viral vector.

13. Method of in vitro screening for inhibitors of binding of glycoprotein VI to collagen, comprising
    (i) providing a surface that exposes collagen;
    (ii) contacting a portion of said surface with the fusion protein of paragraph 1 under predetermined conditions that allow binding of said fusion protein to said surface;
    (iii) contacting another portion of said surface with said fusion protein in the presence of a test compound under conditions as in step (ii);
    (iv) determining the amount of said fusion protein bound to said surface in the absence and in the presence of said test compound;
    (v) identifying a test compound as inhibitor if binding of said fusion protein to said surface is less in the presence of said test compound as compared to the absence of the test compound; and
    (vi) optionally determining the functional effect of said inhibitor on platelet aggregation and/or platelet activation.

14. The method of paragraph 13, wherein said fusion protein carries a fluorescent label.

15. Method of treating a patient suffering from an acute coronary or carotid syndrome, said method comprising for avoiding intravascular thrombosis the steps of administering to the patient the fusion protein of paragraph 1, or the nucleic acid as defined in paragraph 2 in a viral vector.

16. Use of a fusion protein comprising
    (a) the extracellular domain of glycoprotein VI or a variant thereof that is functional for binding to collagen and
    (b) the Fc domain of an immunoglobulin or a function-conservative part thereof, for the manufacture of a medicament for the treatment of diabetes.

17. The use according to paragraph 16, wherein the medicament is manufactured for the treatment of acute complications of diabetes.

18. The use according to any one of paragraphs 16 to 20, wherein the medicament is administered intravenously, preferably in a dosage form containing 0.5 to 5.0 mg/kg of the fusion protein.

19. The use according to paragraph 16, wherein the medicament is manufactured for the treatment of chronic progression of atherosclerosis in diabetic patients.

20. The use according to any one of paragraphs 16 to 19, wherein the medicament is administered subcutaneously or intraperitoneally, preferably in a dosage form containing 1 to 6.0 mg/kg of the fusion protein.

21. The use according to any one of paragraphs 16 to 20, wherein the fusion protein is as defined in claim 1.

22. The use according to any one of paragraphs 16 to 20 wherein the fusion protein is a dimeric fusion protein.

23. Use of the fusion protein according to paragraph 1 for the manufacture of a medicament for the treatment or prevention of atherosclerosis.

24. The use according to paragraph 22, wherein the medicament is administered subcutaneously or intraperitoneally, preferably in a dosage form containing 1 to 6.0 mg/kg of the fusion protein.

25. A method for the preparation of a fusion protein as defined by paragraph 1, which comprises the following steps:
    (a) collecting 2 days after infection the culture supernatant of Hela cells infected with an adenovirus for Fc-GPVI-nt coding for an amino acid sequence as shown in FIG. 7;
    (b) centrifuging (3800 g, 30 min, 4° C.) the supernatant of step (a);
    (c) filtrating (0.45 μm) the supernatant of step (b);
    (d) precipitating the immunoadhesin by addition of 1 vol. ammonium sulfate (761 g/l) and stirring overnight at 4° C.;
    (e) pelletizing the proteins by centrifugation (3000 g, 30 min, 4° C.),
    (f) dissolving the pelletized proteins of step (e) in 0.1 Vol PBS and dialysed in PBS overnight at 4° C.;

(g) clarifying the protein solution by centrifugation (3000 g, 30 min, 4° C.);
(h) loading the solution of step (g) on a protein A column (HiTrap™ protein A HP, Amersham Pharmacia Biotech AB, Uppsala, Sweden);
(i) washing the column with binding buffer (20 mM sodium phosphate buffer pH 7.0, 0.02% NaN$_3$) until OD$_{280}$<0.01;
(k) eluting fractions with elution buffer (100 mM glycine pH 2.7);
(l) neutralizing the eluted fractions with neutralisation buffer (1 M Tris/HCl pH 9.0, 0.02% NaN$_3$);
(m) pooling the fractions;
(n) dialysing the pooled fractions in PBS overnight at 4° C.,
(o) aliquoting the dialysed product and freezing at −20° C.

26. An agent that binds specifically to domain 1 of GP VI.

27. An agent that binds to a ligand, the ligand consisting of one or a combination of:
   (a) a peptide moiety of 5 to 15 amino acid residues including a sequence of contiguous amino acid residues selected from the sequence of contiguous amino acids from position 15 to position 39 of human GP VI protein as shown in FIG. 35;
   (b) a peptide moiety of 5 to 15 amino acid residues including a sequence of contiguous amino acid residues selected from the sequence of contiguous amino acids from position 73 to position 87 of human GP VI protein as shown in FIG. 35;
   (c) a peptide moiety of 5 to 15 amino acid residues including a sequence of contiguous amino acid residues selected from the sequence of contiguous amino acids from position 107 to position 121 of human GP VI protein as shown in FIG. 35.

28. An agent as claimed in paragraph 27, wherein peptide moiety (a) has 6 to 15, particularly 13, more particularly 11, most particularly 9 amino acid residues.

29. An agent as claimed in paragraph 2 or paragraph 3, wherein the peptide moiety (a) is selected from one of the following sequences of contiguous amino acids of human GP VI as shown in FIG. 35:
   (i) position 15 to position 27
   (ii) position 17 to position 29
   (iii) position 19 to position 31
   (iv) position 17 to position 29
   (v) position 21 to position 33
   (vi) position 23 to position 35
   (vii) position 25 to position 37
   (viii) position 27 to position 39
   (ix) position 21 to position 29

30. An agent as claimed in paragraph 27 or paragraph 28, wherein the peptide moiety (a) is selected from one of the following sequences of contiguous amino acids of human GP VI as shown in FIG. 35:
   (i) position 21 to position 27
   (ii) position 21 to position 29
   (iii) position 21 to position 31
   (iv) position 21 to position 29
   (v) position 21 to position 33
   (vi) position 21 to position 35
   (vii) position 21 to position 37
   (viii) position 21 to position 39

31. An agent as claimed in any of paragraphs 26 to 30, wherein the peptide moiety (a) is selected from one of the following amino acid sequences:
   SEQ ID NO: 8
   SEQ ID NO: 9
   SEQ ID NO: 10
   SEQ ID NO: 11
   SEQ ID NO: 12
   SEQ ID NO: 13
   SEQ ID NO: 14

32. An agent as claimed in any of paragraphs 26 to 31, wherein the ligand includes a peptide moiety (a) which has amino acid residue 27 as part of the contiguous sequence of said peptide moiety.

33. An agent as claimed in paragraph 32 which binds at amino acid residue 27 comprised in the ligand.

34. An agent as claimed in paragraph 32 or paragraph 33, wherein amino acid residue 27 is replaced by a basic amino acid other than Lysine.

35. An agent as claimed in any of paragraphs 26 to 34, wherein the peptide moiety (b) has 6, 7, 8, 9, 10, 11, 12, 13, 14 or 15, particularly 13, more particularly 11, most particularly 9 amino acid residues.

36. An agent as claimed in any of paragraphs 26 to 35, wherein the peptide moiety (b) is selected from the contiguous sequence of amino acids from position 75 to position 85 of human GP VI as shown in FIG. 35.

37. An agent as claimed in any of paragraphs 26 to 36, wherein the peptide moiety (b) is selected from one of the following amino acid sequences:
   SEQ ID NO: 37
   SEQ ID NO: 38

38. An agent as claimed in any of paragraphs 26 to 37, wherein the peptide moiety (c) has 6, 7, 8, 9, 10, 11, 12, 13, 14 or 15, particularly 13, more particularly 11, most particularly 9 amino acid residues.

39. An agent as claimed in any of paragraphs 26 to 38, wherein the peptide moiety (c) is selected from the contiguous sequence of amino acids from position 111 to position 119 of human GP VI as shown in FIG. 18.

40. An agent as claimed in any of paragraphs 26 to 39, wherein the peptide moiety (c) is selected from one of the following amino acid sequences:
   SEQ ID NO: 54
   SEQ ID NO: 55

41. An agent as claimed in any of paragraphs 26 to 40, which is an antibody or fragment thereof, an aptamer, a compound, a fusion protein or a protein, a peptide or a combination thereof.

42. An agent as claimed in paragraph 41, wherein the antibody or fragment thereof is a Fab fragment or a scFv.

43. An agent as claimed in paragraph 41 or paragraph 42, wherein the antibody or fragment thereof is a monoclonal antibody, a polyclonal antibody, a chimeric antibody, a human antibody or a humanized antibody and the fragment is a fragment of such an antibody.

44. A nucleic acid comprising a nucleic acid sequence, which sequence encodes an agent as claimed in any preceding claim when the agent is an antibody, a fusion protein, a peptide or a protein.

45. An expression vector comprising a nucleic acid of paragraph 44 and associated regulatory sequences necessary for expression of a protein or polypeptide in a host cell.

46. A host cell comprising a nucleic acid of paragraph 44 or a vector of paragraph 45.

47. A hybridoma cell which expresses a monoclonal antibody of paragraph 43.

48. A ligand consisting of one or more of:
   (a) a peptide moiety of between 5 to 15 amino acid residues including a sequence of contiguous amino acid residues is comprised in the sequence of contiguous amino acids from position 15 to position 39 of human GP VI protein as shown in FIG. 19;

(b) a peptide moiety of 5 to 15 amino acid residues including a sequence of contiguous amino acid residues is comprised in the sequence of contiguous amino acids from position 73 to position 87 of human GP VI protein as shown in FIG. 35;

(c) a peptide moiety of 5 to 15 amino acid residues including a sequence of contiguous amino acid residues is comprised in the sequence of contiguous amino acids from position 107 to position 121 of human GP VI protein as shown in FIG. 35.

49. A ligand as claimed in paragraph 48 which is further defined by any of the features recited in paragraphs 26 to 40.

50. A ligand as claimed in paragraph 49 which is a peptide.

51. A ligand as claimed in any of paragraphs 48 to 50 which is a fusion protein.

52. An array of ligands as claimed in any of paragraphs 48 to 50.

53. A humanized antibody comprising the complementarity determining regions of an antibody that binds e.g. specifically binds the ligand of paragraph 48 and a human framework region, or a conservative substitution thereof 1, 2, 3, 4 or 5 residues of the complementarity determining regions, wherein the antibody retains substantially the binding affinity to the ligand of paragraph 48 or has a greater affinity.

54. An antibody as claimed in paragraph 26, comprising the complementarity determining regions of hGP 5C4 antibody or a conservative substitution thereof of 1, 2, 3, 4 or 5 residues of the complementarity determining regions of hGP 5C4.

55. A fragment of the humanized antibody of paragraph 53 or paragraph 54 that binds e.g. specifically binds the ligand of paragraph 48.

56. The humanized antibody or antibody fragment of paragraph 53, 54 or 55, wherein binding affinity of the antibody for D1 may be greater than $10^{-6}$M, preferably greater than $10^{-7}$M, $10^{-8}$M, $10^{-9}$ M, $10^{-10}$ M, $10^{-11}$ M, $10^{-12}$ M.

57. An agent according to any of paragraphs 26 to 40, a ligand according to paragraphs 48 to 51 or a humanised antibody according to any of paragraph 53 to 56 for use as a pharmaceutical.

58. A pharmaceutical formulation comprising an agent as claimed in any of paragraphs 26 to 40, a ligand as claimed in any of paragraph 48 to 51, or a humanised antibody according to any of paragraph 53 to 56.

59. A pharmaceutical formulation comprising a ligand as claimed in any of paragraphs 48 to 51.

60. A method of making an antibody comprising immunising an animal with a ligand of any paragraph 48 to 51.

61. A method of making an antibody comprising using any of ligands as defined in any of paragraph 48 to 51 as an immunogen.

62. A method of identifying an agent for binding to GP VI comprising contacting a candidate agent with a ligand as defined in any of paragraphs 48 to 51.

63. A method of humanising antibodies comprising using a ligand as claimed in any of paragraphs 52 to 55.

64. The use of a ligand of any of paragraphs 48 to 51 in a binding assay for identifying an agent capable of binding GP VI.

65. A method for inhibiting platelet aggregation in a subject, comprising administering to a subject a therapeutically effective amount of an agent of any of paragraphs 26 to 40 or an antibody of paragraph 53 to 56.

66. A method for inhibiting platelet aggregation, comprising contacting platelets with an effective amount of the agent of any of paragraphs 26 to 40 or an antibody of any of paragraph 53 to 56.

67. A method as claimed in paragraph 66, wherein the platelets are in vitro.

68. A method as claimed in paragraph 66, wherein the platelets are in vivo.

69. A method for treating therapeutic or prophylactic a disease or disorder selected from therapeutic or prophylactic cardiovascular conditions, thrombosis, arterial thrombosis, heart attack, stroke, intermittent coagulation, conditions with disseminated intravascular coagulation, thrombocytopenic purpura, haemolytic uraemic syndrome, damage to blood vessel wall resulting from surgery or therapy, collagen-induced inflammation, homozygous sickle disease, kidney damage by platelet and fibrin disposition on the glomerular member and micro-angiopathic vasculitides comprising administering an agent of any of any of paragraphs 26 to 40, to a subject with the disease or disorder or at risk of developing the disease or disorder.

70. The use of an agent according to any of paragraphs 26 to 40 for the manufacture of a medicament to treat or prevent of a disease or disorder selected from cardiovascular conditions, thrombosis, heart attack, stroke, intermittent coagulation, conditions with disseminated intravascular coagulation, thrombocytopenic purpura, haemolytic uraemic syndrome, damage to blood vessel wall resulting from surgery or therapy, collagen-induced inflammation, homozygous sickle disease, kidney damage by platelet and fibrin disposition on the glomerular member and micro-angiopathic vasculitides 71. An agent of any of paragraphs 26 to 43 which is not monoclonal antibody hGP 5C4 or a fragment thereof other than a Fab', a (Fab')$_2$, Fv or dsFv fragment.

72. An agent of any of paragraphs 26 to 45 which is not hGP 5C4 or a fragment thereof.

73. An agent of any of paragraphs 26 to 43 which is a Fab', a (Fab')$_2$, Fv or dsFv fragment of hGP 5C4 or humanised hGP 5C4, or is a humanised Fab', a humanised (Fab')$_2$, a humanised Fv or a humanised dsFv fragment of hGP 5C4.

74. An agent of any of paragraphs 26 to 43 which is not monoclonal antibody hGP 5C4, humanised hGP 5C4, a fragment of hGP 5C4, a humanised fragment of hGP 5C4, or a fragment of humanised hGP 5C4, other than a humanised or unhumanised Fab', a (Fab')$_2$, Fv or dsFv fragment.

75. An agent of any of paragraphs 26 to 43 which is not monoclonal antibody hGP 5C4, humanised hGP 5C4, a fragment of hGP 5C4, a humanised fragment of hGP 5C4, or a fragment of humanised hGP 5C4.

76. The subject matter of any of paragraphs 57 to 59 and 65 to 70 wherein the agent is as defined in any of claims 70 to 76.

77. Monoclonal antibody hGP 5C4 or function-conservative fragments or variants thereof, which specifically bind to glycoprotein VI.

78. The monoclonal antibody hGP 5C4 or function-conservative fragments or variants thereof according to paragraph 77, which specifically bind to human glycoprotein VI.

79. The monoclonal antibody according to paragraph 77, which is purified from an antibody producing cell deposited as hGP 5C4 with DSMZ-Deutsche Sammlung von Mikroorganismen und Zellkulturen under Accession No. 2631, or progeny thereof.

80. The monoclonal antibody or function-conservative fragment or variant thereof according to paragraph 77, 78 or 79, which inhibits collagen-binding to human glycoprotein VI.

81. Fab fragment of the monoclonal antibody according to any one of paragraphs 77 to 80, which is hGP 5C4 Fab obtainable by papain digestion of hGP 5C4.

82. Humanized antibody specifically binding to glycoprotein VI, which comprises a function conservative fragment or variant of the monoclonal antibody hGP 5C4.

83. Fusion protein specifically binding to glycoprotein VI, which comprises an amino acid sequence of the antibody hGP 5C4 or of function-conservative fragments or variants thereof.

84. Conjugate comprising an effector moiety and the monoclonal antibody hGP 5C4 or function-conservative fragments or variants thereof, which specifically bind to glycoprotein VI as defined in any one of paragraphs 77 to 81, or the humanized antibody of paragraph 82 or the fusion protein as defined in paragraph 83.

85. A hybridoma cell line deposited as hGP 5C4 with DSMZ-Deutsche Sammlung von Mikroorganismen und Zellkulturen under Accession number 2631, or a progeny thereof.

86. A nucleic acid coding for monoclonal antibody hGP 5C4 Fab or function-conservative fragments or variants thereof, wherein said nucleic acid is obtainable from the hybridoma cell line according to paragraph 85.

87. A nucleic acid coding for a polypeptide comprising at least 5 consecutive amino acids of the monoclonal antibody hGP 5C4 Fab and binding specifically to human glycoprotein VI.

88. A composition comprising an excipient and an inhibitor selected from
(a) the antibody, the function-conservative fragment or variant thereof according to any one of paragraphs 77 to 81, or
(b) the humanized antibody according to paragraph 82,
(c) the fusion protein according to paragraph 83, and
(d) the conjugate according to paragraph 84.

89. Use of an inhibitor selected from
(a) the antibody, the function-conservative fragment or variant thereof according to any one of paragraphs 77 to 81, or
(b) the humanized antibody according to paragraph 82, or
(c) the fusion protein according to paragraph 83, or
(d) the conjugate according to paragraph 84, for the prevention or treatment of acute or chronic vascular diseases associated with intraarterial and/or intravenous thrombosis.

90. The use according to 89, wherein the medicament is for parenteral administration.

91. A process for producing monoclonal antibody hGP 5C4 or function-conservative fragments thereof, said process comprising
(i) culturing hybridomAn hGP 5C4 according to paragraph 85, or progeny thereof in medium under conditions conducive to expression of antibody therefrom and;
(ii) obtaining antibody hGP 5C4 from the culture medium and optionally;
(iii) preparing a Fab fragment of antibody hGP 5C4 by enzymatic digestion.

92. A process for the preparation of hGP 5C4 Fab, said process comprising the step of digesting hGP 5C4 antibodies and isolating the Fab fragments.

93. The process according to paragraph 92, wherein hGP 5C4 is digested by using papain or a derivative thereof.

94. Protein containing an amino acid sequence of SEQ ID NO: 8 or SEQ ID NO: 10 or a function conservative fragment or variant thereof, which protein shows hGP 5C4 or hGP 5C4 Fab activity in vivo.

95. The protein according to paragraph 94, which is a monoclonal antibody, fragment or variant thereof, Fab fragment, or single chain antibody.

96. A nucleic acid encoding a protein according to paragraph 94 or 95.

97. The nucleic acid according to paragraph 96, which comprises a sequence according to SEQ ID NO: 9 or SEQ ID NO: 11 or a variant thereof based on the degeneracy of the genetic code.

98. A vector comprising a nucleic acid according to paragraph 96 or 97.

99. A host cell containing the vector according to paragraph 98 and/or a nucleic acid according to paragraph 96 or 97.

100. A process for preparing a pharmaceutical composition for treating thrombotic disorders comprising:
(a) providing a plurality of compounds;
(b) screening the plurality by a method which utilises a ligand disclosed herein to determine whether a compound binds to GPVI at an epitope identified hereinto obtain IC50 values for each compound;
(c) selecting a compound with an IC50 of less than 500 nm from the series;
(d) synthesising the selected compound; and
(e) incorporating the synthesized compound into a pharmaceutical composition.

101. A process for preparing a pharmaceutical composition for treating thrombotic disorders comprising:
(a) screening a plurality of compounds by a method which utilises a ligand disclosed herein to determine whether a compound binds to GPVI at an epitope identified hereinto obtain IC50 values for each compound;
(b) selecting from the plurality a compound having a binding affinity of greater than a predetermined amount, e.g. having an IC50 of less than 500 nm;
(c) synthesising the selected compound; and
(d) incorporating the synthesized compound into a pharmaceutical composition.

102. A method of treating or preventing a cardiovascular disorder comprising use of a compound as selected by the method of claim 101.

REFERENCE LIST

1. Baumgartner, H. R. 1977. Platelet interaction with collagen fibrils in flowing blood. I. Reaction of human platelets with alpha chymotrypsin-digested subendothelium. *Thromb Haemost* 37:1-16.
2. Clemetson, K. J. and Clemetson, J. M. 2001. Platelet collagen receptors. *Thromb. Haemost.* 86:189-197.
3. Massberg, S., Gawaz, M., Grüner, S., Schulte, V., Konrad, I., Zohlnhöfer, D., Heinzmann, U., and Nieswandt, B. 2003. A crucial role of glycoprotein VI for platelet recruitment to the injured arterial wall in vivo. *J. Exp. Med.* 197:41-49.
4. Moroi, M., lung, S. M., Okuma, M., and Shinmyozu, K. 1989. A patient with platelets deficient in glycoprotein VI that lack both collagen-induced aggregation and adhesion. *J. Clin. Invest* 84:1440-1445.
5. Clemetson, J. M., Polgar, J., Magnenat, E., Wells, T. N., and Clemetson, K. J. 1999. The platelet collagen receptor glycoprotein VI is a member of the immunoglobulin superfamily closely related to FcalphaR and the natural killer receptors. *J. Biol. Chem.* 274:29019-29024.
6. Jandrot-Perrus, M., Busfield, S., Lagrue, A. H., Xiong, X., Debili, N., Chickering, T., Le Couedic, J. P., Goodearl, A., Dussault, B., Fraser, C. et al., 2000. Cloning, characterization, and functional studies of human and mouse glycoprotein VI: a platelet-specific collagen receptor from the immunoglobulin superfamily. *Blood* 96:1798-1807.

7. Gibbins, J. M., Okuma, M., Farndale, R., Barnes, M., and Watson, S. P. 1997. Glycoprotein VI is the collagen receptor in platelets which underlies tyrosine phosphorylation of the Fc receptor gamma-chain. *FEBS Lett.* 413:255-259.
8. Zheng, Y. M., Liu, C., Chen, H., Locke, D., Ryan, J. C., and Kahn, M. L. 2001. Expression of the platelet receptor GPVI confers signaling via the Fc receptor gamma-chain in response to the snake venom convulxin but not to collagen. *J. Biol. Chem.* 276:12999-13006.
9. Suzuki-Inoue, K., Tulasne, D., Shen, Y., Bori-Sanz, T., Inoue, O., Jung, S. M., Moroi, M., Andrews, R. K., Berndt, M. C., and Watson, S. P. 2002. Association of Fyn and Lyn with the proline rich domain of GPVI regulates intracellular signalling. *J Biol. Chem.*
10. Barnes, M. I., Knight, C. G., and Farndale, R. W. 1998. The collagen-platelet interaction. *Curr. Opin. Hematol.* 5:314-320.
11. Falet, H., Barkalow, K. L., Pivniouk, V. I., Barnes, M. I., Geha, R. S., and Hartwig, J. H. 2000. Roles of SLP-76, phosphoinositide 3-kinase, and gelsolin in the platelet shape changes initiated by the collagen receptor GPVI/FcR gamma-chain complex. *Blood* 96:3786-3792.
12. Pasquet, J. M., Gross, B., Quek, L., Asazuma, N., Zhang, W., Sommers, C. L., Schweighoffer, E., Tybulewicz, V., Judd, B., Lee, J. R. et al. 1999. LAT is required for tyrosine phosphorylation of phospholipase cgamma2 and platelet activation by the collagen receptor GPVI. *Mol. Cell. Biol.* 19:8326-8334.
13. Berlanga, O., Tulasne, D., Bori, T., Snell, D. C., Miura, Y., Jung, S., Moroi, M., Frampton, J., and Watson, S. P. 2002. The Fc receptor gamma-chain is necessary and sufficient to initiate signalling through glycoprotein VI in transfected cells by the snake C-type lectin, convulxin. *Eur. J. Biochem.* 269:2951-2960.
14. Sugiyama, T., Okuma, M., Ushikubi, F., Sensaki, S., Kanaji, K., and Uchino, H. 1987. A novel platelet aggregating factor found in a patient with defective collagen-induced platelet aggregation and autoimmune thrombocytopenia. *Blood* 69:1712-1720.
15. Sugiyama, T., Ishibashi, T., and Okuma, M. 1993. Functional role of the antigen recognized by an antiplatelet antibody specific for a putative collagen receptor in platelet-collagen interaction. *Int J. Hematol.* 58:99-104.
16. Schulte, V., Snell, D., Bergmeier, W., Zirngibl, H., Watson, S. P., and Nieswandt, B. 2001. Evidence for two distinct epitopes within collagen for activation of murine platelets. *J. Biol. Chem.* 276:364-368.
17. Kremmer, E., Kranz, B. R., Hille, A., Klein, K., Eulitz, M., Hoffmann-Fezer, G., Feiden, W., Herrmann, K., Delecluse, H. J., Delsol, G. et al. 1995. Rat monoclonal antibodies differentiating between the Epstein-Barr virus nuclear antigens 2A (EBNA2A) and 2B (EBNA2B). *Virology* 208: 336-342.
18. Dickfeld, T., Lengyel, E., May, A. E., Massberg, S., Brand, K., Page, S., Thielen, C., Langenbrink, K., and Gawaz, M. 2001. Transient interaction of activated platelets with endothelial cells induces expression of monocyte-chemoattractant protein-I via a p38 mitogen-activated protein kinase mediated pathway. Implications for atherogenesis. *Cardiovasc. Res.* 49:189-199.
19. Massberg, S., Enders, G., Leiderer, R., Eisenmenger, S., Vestweber, D., Krombach, F., and Messmer, K. 1998. Platelet-endothelial cell interactions during ischemia/reperfusion: the role of P-selectin. *Blood* 92:507-515.
20. Massberg, S., Enders, G., Matos, F. C., Tomic, L. I., Leiderer, R., Eisenmenger, S., Messmer, K., and Krombach, F. 1999. Fibrinogen deposition at the postischemic vessel wall promotes platelet adhesion during ischemia-reperfusion in vivo. *Blood* 94:3829-3838.
21. Miura, Y., Takahashi, T., Jung, S. M., and Moroi, M. 2002. Analysis of the interaction of platelet collagen receptor glycoprotein VI (GPVI) with collagen. A dimeric form of GPVI, but not the monomeric form, shows affinity to fibrous collagen. *J. Biol. Chem.* 277:46197-46204.
22. Chen, H., Locke, D., Liu, Y., Liu, C., and Kahn, M. L. 2002. The platelet receptor GPVI mediates both adhesion and signaling responses to collagen in a receptor density-dependent fashion. *J. Biol. Chem.* 277:3011-3019.
23. Savage, B., Almus-Jacobs, F., and Ruggeri, Z. M. 1998. Specific synergy of multiple substrate-receptor interactions in platelet thrombus formation under flow. *Cell* 94:657-666.
24. van Zanten, G. H., de Graaf, S., Slootweg, P. J., Heijnen, H. F., Connolly, T. M., de Groot, P. G., and Sixma, J. J. 1994. Increased platelet deposition on atherosclerotic coronary arteries. *J. Clin. Invest* 93:615-632.
25. Baumgartner, H. R., Muggli, R., Tschopp, T. B., and Turitto, V. T. 1976. Platelet adhesion, release and aggregation in flowing blood: effects of surface properties and platelet function. *Thromb. Haemost* 35:124-138.
27. Jandrot-Perrus, M., Lagrue, A. H., Okuma, M., and Bon, C. 1997. Adhesion and activation of human platelets induced by convulxin involve glycoprotein VI and integrin alpha2beta1. *J. Biol. Chem.* 272:27035-27041.
28. Rekhter, M. D. 1999. Collagen synthesis in atherosclerosis: too much and not enough. *Cardiovasc. Res.* 41:376-384.
29. Ruggeri, Z. M. 1997. Mechanisms initiating platelet thrombus formation. *Thromb. Haemost.* 78:611-616.
30. Goto, S., Ikeda, Y., Saldivar, E., and Ruggeri, Z. M. 1998. Distinct mechanisms of platelet aggregation as a consequence of different shearing flow conditions. *J. Clin. Invest.* 101:479-486.
31. Sixma, J. J., van Zanten, G. H., Banga, J. D., Nieuwenhuls, H. K., and de Groot, P. G. 1995. Platelet adhesion. *Semin. Hematol* 32:89-98.
32. Nieswandt, B., Schulte, V., Bergmeier, W., Mokhtari-Nejad, R., Rackebrandt, K., Cazenave, J. P., Ohlmann, P., Gachet, C., and Zirngibl,H.2001. Long-term antithrombotic protection by in vivo depletion of platelet glycoprotein VI in mice. *J Exp Med* 193:459-469.
33. Lincoff, A. M., Califf, R. M., and Topol, E. J. 2000. Platelet glycoprotein IIb/IIIa receptor blockade in coronary artery disease. *J. Am. Coll. Cardiol.* 35:1103-1115.
34. Neumann, F. I. and Schömig, A. 1998. Glycoprotein IIb/IIIa receptor blockade with coronary stent placement. *Semin. Interv. Cardiol.* 3:81-90.
35. Bertrand, M. E., Rupprecht, H. J., Urban, P., Gershlick, A. H., and Investigators, f. 2000. Double-blind study of the safety of clopidogrel with and without a loading dose in combination with aspirin compared with ticlopidine in combination with aspirin after coronary stenting: the clopidogrel aspirin stent international cooperative study (CLASSICS). *Circulation* 102:624-629.
36. Foster, R. H. and Wiseman, L. R. 1998. Abciximab. An updated review of its use in ischaemic heart disease. *Drugs* 56:629-665.
37. Arai, M., Yamamoto, N., Moroi, M., Akamatsu, N., Fukutake, K., and Tanoue, K. 1995. Platelets with 10% of the normal amount of glycoprotein VI have an impaired response to collagen that results in a mild bleeding tendency. *Br. J Haematol.* 89:124-130

The invention claimed is:

1. A pharmaceutical formulation comprising
a monoclonal antibody secreted by the hGP 5C4 cell line deposited with DSMZ-Deutsche Sammlung von Mikroorganismen und Zellkulturen under Accession No. 2631, a humanized form of the monoclonal antibody, or an antigen binding fragment of the monoclonal antibody, wherein the monoclonal antibody, humanized form or antigen binding fragment specifically binds to glycoprotein VI; and
a pharmaceutically acceptable excipient.

2. The pharmaceutical formulation according to claim 1, wherein glycoprotein VI is a human glycoprotein VI.

3. The pharmaceutical formulation according to claim 1, comprising the monoclonal secreted by the hGP 5C4 cell line deposited with DSMZ-Deutsche Sammlung von Mikroorganismen und Zellkulturen under Accession No. 2631.

4. The pharmaceutical formulation according to claim 1 comprising the antigen binding fragment of the monoclonal antibody.

5. The pharmaceutical formulation comprising the antigen binding fragment of the monoclonal antibody according to claim 4, wherein the antigen binding fragment is a Fab.

6. The pharmaceutical formulation according to claim 1, comprising the humanized form of the monoclonal antibody.

7. A pharmaceutical formulation comprising a conjugate comprising an effector moiety and the monoclonal antibody, antigen binding fragments or humanized form of the monoclonal antibody, according to claim 1, and a pharmaceutically acceptable excipient.

8. A hybridoma cell line deposited with DSMZ-Deutsche Sammlung von Mikroorganismen and Zellkulturen under Accession number 2631.

9. A method of treating thrombosis in a subject, comprising administering to the subject a therapeutically effective amount of the pharmaceutical formulation of claim 1 or a pharmaceutical formulation comprising a conjugate of the antibody secreted by the hGP 5C4 cell line deposited with DSMZ-Deutsche Sammlung von Mikroorganismen and Zellkulturen under Accession No. 2631, a humanized form of the monoclonal antibody, or an antigen binding fragment of the monoclonal antibody and an effector molecule,
thereby treating the thrombosis in the subject.

10. The method of claim 9, wherein the pharmaceutical formulation is formulated for parenteral administration.

11. An isolated monoclonal antibody comprising a heavy chain and a light chain variable domain, or an antigen binding fragment thereof or a humanized form thereof,
wherein the heavy chain comprises a heavy chain complementarity determining region (HCDR) 1 comprising Kabat position 31 to 35b of the amino acid sequence set forth as SEQ ID NO: 151, a HCDR2 comprising Kabat position 50 to 65, 95 to 102 of the amino acid sequence set forth as SEQ ID NO: 151, a HCDR3 comprising Kabat position 95 to 102 of the amino acid sequence set forth as SEQ ID NO: 151;
and wherein the light chain comprises light chain complementarity determining region (LCDR) 1 comprising Kabat position 24 to 34 of the amino acid sequence set forth as SEQ ID NO: 149, a LCDR 2 comprising Kabat position 50 to 56 of the amino acid sequence set forth as SEQ ID NO: 149, and a LCDR 3 comprising Kabat position 95-102 of the amino acid sequence set forth as SEQ ID NO: 149, and wherein the monoclonal antibody, the antigen binding fragment, and the humanized form specifically bind human glycoprotein IV.

12. The monoclonal antibody, the antigen binding fragment, or humanized form according to claim 11, wherein the heavy chain variable domain comprises the amino acid sequence set forth as SEQ ID NO: 151, and wherein the light chain variable domain comprises the amino acid sequence set forth as SEQ ID NO: 149.

13. A pharmaceutical composition comprising the monoclonal antibody, the antigen binding fragment, or the humanized form according to claim 11.

14. The humanized form of the monoclonal antibody according to claim 11.

15. A monoclonal antibody produced by the hybridoma cell of claim 8, an antigen binding fragment thereof or a humanized form thereof, wherein the monoclonal antibody, antigen binding fragment and humanized form specifically bind human glycoprotein IV.

16. An isolated monoclonal antibody secreted by the hGP 5C4 cell line deposited-with DSMZ-Deutsche Sammlung von Mikroorganismen and Zellkulturen under Accession No. 2631, a humanized form of the monoclonal antibody, or an antigen binding fragment of the monoclonal antibody, wherein the monoclonal antibody, humanized form or antigen binding fragment specifically binds to human glycoprotein VI.

17. The humanized form of the isolated monoclonal antibody according to claim 16.

18. The antigen binding fragment of the isolate monoclonal antibody according to claim 16.

19. The antigen binding fragment according to claim 16, wherein the antigen binding fragment is a Fab fragment.

20. A conjugate comprising the monoclonal antibody, antigen binding fragment or humanized form according to claim 16 and an effector molecule.

21. The conjugate according to claim 20, wherein the effector molecule is a label.

22. A method of inhibiting the aggregation and/or activation of human platelets, comprising
contacting the human platelets with an effective amount of the monoclonal antibody, humanized form, or antigen binding fragment according to claim 16,
thereby inhibiting the aggregation and/or activation of the human platelets.

23. A method of inhibiting the aggregation and/or activation of human platelets, comprising
contacting the human platelets with an effective amount of the pharmaceutical composition according to claim 1,
thereby inhibiting the aggregation and/or activation of the human platelets.

24. A method of inhibiting the aggregation and/or activation of human platelets, comprising
contacting the human platelets with an effective amount of the pharmaceutical composition according to claim 11,
thereby inhibiting the aggregation and/or activation of the human platelets.

25. The method of claim 24, comprising
contacting the human platelets with an effective amount of the monoclonal antibody, humanized form or antigen binding fragment according to claim 11 ex vivo.

26. A method of treating thrombosis in a subject, comprising
administering to the subject a therapeutically effective amount of the monoclonal antibody, humanized form or antigen binding fragment according to claim 11,
thereby treating the thrombosis in the subject.

27. A method of treating thrombosis in a subject, comprising
administering to the subject a therapeutically effective amount of the monoclonal antibody, humanized form or antigen binding fragment according to claim 16,
thereby treating the thrombosis in the subject.

* * * * *

UNITED STATES PATENT AND TRADEMARK OFFICE
CERTIFICATE OF CORRECTION

PATENT NO. : 8,119,135 B2
APPLICATION NO. : 12/355689
DATED : February 21, 2012
INVENTOR(S) : Götz Münch et al.

It is certified that error appears in the above-identified patent and that said Letters Patent is hereby corrected as shown below:

On the Title Page, Item (73) Assignees:
Page 1, left column, at Assignees: "Helmhotz Zentrum Munchen," should read --Helmholtz Zentrum Munchen--.
Page 1, left column, at Assignees: "(Martinsreid, DE)," should read --(Martinsried, DE)--.

On the Title Page, Item (56) OTHER PUBLICATIONS:
Page 2, right column, at Vinik et al., "1479-141485," should read --1479-1485--.

In the Specification:
Column 4, line 20, "(2001) Evidence" should read --(2001): Evidence--.
Column 5, line 65, "meditor" should read --mediator--.
Column 14, line 52, "form its" should read --from its--.
Column 18, line 23, "compound" should read --compound;--.
Column 19, line 21, "this methods" should read --this method--.
Column 19, line 54, "4° C.)," should read --4° C.);--.
Column 20, line 44, "(Fab')$_2$" should read --F(ab')$_2$--.
Column 23, line 4, "a Fab." should read --a Fab--.
Column 25, line 33, "cell can" should read --cell and can--.
Column 25, line 58, "pure." should read --pure--.
Column 30, lines 27-28, "obtained (PRP) obtained" should read --(PRP) obtained--.
Column 30, line 29, "mm3" should read --mm$^3$--.
Column 30, line 32, "37 C" should read --37° C--.
Column 32, line 60, "GPVI determined." should read --GPVI is determined.--.

Signed and Sealed this
Fourteenth Day of August, 2012

David J. Kappos
*Director of the United States Patent and Trademark Office*

CERTIFICATE OF CORRECTION (continued)
U.S. Pat. No. 8,119,135 B2

Column 37, line 28, "translocation is." should read --translocation.--.

Column 40, line 38, "continuos" should read --continuous--.

Column 43, line 30, "given in" should read --in--.

Column 43, line 52, "149)" should read --149).--.

Column 43, line 54, "150)" should read --150).--.

Column 43, line 56, "151)" should read --151).--.

Column 43, line 58, "152)" should read --152).--.

Column 43, line 60, "collagen" should read --collagen.--.

Column 43, line 62, "agonist)" should read --agonist).--.

Column 43, line 64, "aggregation" should read --aggregation.--.

Column 47, line 31, "Constant Region" should read --Constant Region:--.

Column 52, line 38, "(1999)" should read --(1999).--.

Column 53, line 25, "isolated. CDR" should read --isolated CDR--.

Column 53, line 27, "fragments" should read --fragments;--.

Column 53, line 32, "(PCT/US92/09965)" should read --(PCT/US92/09965);--.

Column 53, line 61, "1996)." should read --1996)--.

Column 54, line 67, "of An" should read --of an--.

Column 55, line 7, "of An" should read -- of an--.

Column 55, line 10, "as An" should read --as an--.

Column 61, line 9, "Fab as appear" should read --Fab appear--.

Column 62, line 5, "additional" should read --an additional--.

Column 62, line 6, "from An" should read --from an--.

Column 64, line 40, "in deed" should read --indeed--.

Column 65, lines 21-22, "deposited with deposited with" should read --deposited with--.

Column 66, line 32, "pure, as" should read --pure as--.

Column 72, line 60, "there is ability" should read --the ability--.

Column 72, line 61, "also ability" should read --also the ability--.

Column 73, line 54, "at least 100 compounds, at least 100 compounds or at least" should read --at least 100 compounds, at least 1,000 compounds or at least--.

Column 77, line 62, "treating therapeutic or prophylactic a disease" should read --treating therapeutically or prophylactically a disease--.

Column 87, line 16, "aspolyoxyl" should read --as Polyoxyl--.

Column 88, line 5, "vehicles" should read --vehicles.--.

Column 90, line 65, "$\alpha_2\alpha_1$" should read --$\alpha_2\beta_1$--.

CERTIFICATE OF CORRECTION (continued)
U.S. Pat. No. 8,119,135 B2

Column 91, line 30, "vWF-GPIb_-interaction" should read --vWF-GPIbα-interaction--.

Column 91, line 40, "GPIb_" should read --GPIbα--.

Column 100, line 49, "rµm" should read --rpm--.

Column 101, line 34, "stimulation. (FIG. 11c)" should read --stimulation (FIG. 11c)."--.

Column 101, line 49, "(FIG. 12)" should read --(FIG. 12).--.

Column 104, lines 31-32, "detected on at the" should read --detected at the--.

Column 104, line 40, "continuos" should read --continuous--.

Column 105, line 65, "For cloning of the" should read --For cloning the--.

Column 107, line 42, "over night" should read --overnight--.

Column 121, line 7, "claim 1" should read --paragraph 1--.

Column 121, line 25, "in Vivo" should read --in vivo--.

Column 122, lines 17-18, "comprising for avoiding" should read --comprising avoiding--.

Column 124, line 65, "is comprised" should read --that is comprised--.

Column 125, line 2, "residues is" should read --residues that is--.

Column 125, line 7, "residues is" should read --residues that is--.

Column 126, line 40, "(Fab')$_2$" should read --F(ab')$_2$--.

Column 126, line 41, "(Fab')$_2$" should read --F(ab')$_2$--.

Column 126, line 47, "(Fab')$_2$" should read --F(ab')$_2$--.

Column 126, line 53, "claims 70 to 76" should read --paragraphs 71 to 75--.

Column 128, line 17, "hereinto" should read --herein to--.

Column 128, line 28, "hereinto" should read --herein to--.

Column 128, line 38, "claim 101" should read --paragraph 101--.